United States Patent [19]

Katakami et al.

[11] Patent Number: 5,008,267
[45] Date of Patent: Apr. 16, 1991

[54] PYRIMIDINEDIONE COMPOUNDS, METHOD OF PRODUCING THE SAME AND ANTIARRYTHMIC AGENTS CONTAINING THE SAME

[75] Inventors: Tsutomu Katakami, Kamakura; Tatsuro Yokoyama, Yokohama; Michihiko Miyamoto, Yokohama; Haruki Mori, Yokohama; Nobuya Kawauchi, Yokohama; Tadahito Nobori, Yokohama; Kunio Sannohe, Yokohama; Joji Kamiya, Mobara; Masaaki Ishii, Mobara; Kanji Yoshihara, Mobara, all of Japan

[73] Assignee: Mitsui Toatsu Chemicals, Incorporated, Tokyo, Japan

[21] Appl. No.: 425,730

[22] Filed: Oct. 24, 1989

[30] Foreign Application Priority Data

| Oct. 29, 1988 | [JP] | Japan | 63-271992 |
|---|---|---|---|
| Dec. 6, 1988 | [JP] | Japan | 63-306840 |
| Dec. 6, 1988 | [JP] | Japan | 63-306841 |
| Apr. 18, 1989 | [JP] | Japan | 1-096416 |
| Apr. 18, 1989 | [JP] | Japan | 1-096417 |
| Apr. 18, 1989 | [JP] | Japan | 1-096418 |
| Sep. 6, 1989 | [JP] | Japan | 1-229272 |
| Sep. 25, 1989 | [JP] | Japan | 1-246317 |
| Sep. 25, 1989 | [JP] | Japan | 1-246318 |

[51] Int. Cl.$^5$ .............. A61K 31/495; A61K 31/505; C07D 403/04; C07D 239/54

[52] U.S. Cl. .................. 514/269; 514/252; 514/274; 514/821; 544/295; 544/310; 544/311; 544/312

[58] Field of Search ............ 544/310, 311, 312, 295; 514/269, 274, 821, 252

[56] References Cited

U.S. PATENT DOCUMENTS

4,216,314  8/1980  Raabe et al. .................. 544/310

FOREIGN PATENT DOCUMENTS

2329399  2/1975  Fed. Rep. of Germany ...... 544/310
2819629  11/1978  Fed. Rep. of Germany ...... 544/310

OTHER PUBLICATIONS

Hartlebon et al., Chem. Abst. 82-171026k (1975).
Raab et al. Chem. Abst. 90-121636d (1979).
Cassella Farbwerke Mainkur A-G, Chem. Abst. 90-121639g (1979).
E. M. Vaughan Williams, Advances in Drug Research, vol. 9, pp. 69-101 (1974), "Electrophysiological Basis for a Rational Approach to Antidysrhythmic Drug Therapy".

*Primary Examiner*—Cecilia Shen
*Attorney, Agent, or Firm*—Nixon & Vanderhye

[57] ABSTRACT

A pyrimidinedione derivative compound has a basic backbone in which a phenyl group part and a pyrimidinedione part are linked by a structure comprising an alkyl chain containing at least two nitrogen atoms. The pyrimidinedione derivative is useful for a medical treatment of cardiac arrhythmias.

12 Claims, No Drawings

PYRIMIDINEDIONE COMPOUNDS, METHOD OF PRODUCING THE SAME AND ANTIARRYTHMIC AGENTS CONTAINING THE SAME

BACKGROUND OF THE INVENTION

1. Field of the Invention

This invention relates to novel pyrimidinedione derivatives and acid addition salts thereof, to methods of producing the same and to pharmaceutical agents containing the same, which are effective for the treatment of cardiac dysfunctions such as arrhythmia and cardiac insufficiency.

2. Description of the Prior Art

The mechanism of the occurrence of arrhythmia is complicated. Abnormalities in stimulation production and disorders in the conducting system or combinations thereof are considered to be responsible.

As to disorders in excitation conduction, the re-entry theory is representative.

One of the conditions of occurrence of arrhythmia is irregularity in the refractory period in various parts of the heart. In addition, one-directional block, shortened refractory period, delay in conduction, the presence of circus movement are complicatedly involved.

Conventionally, varieties of antiarrythmic agents have been used for the treatment of arrhythmia.

The antiarrythmic agents are classified into four groups according to their mode of action.

Namely, E. M. Vaughan Williams (Vaughn Williams E. M.; "Advances in drug research, vol. 9", ed. by Harper N. J., Simmonds A. B., Academic Press, London, 1974; pages 69–101) classified the antiarrythmic agents into the following four groups according to their action against the action potential of cardiac muscle or against the ionic current which generates the action potential.

Class I: Sodium channel depressors

These agents are efficacious in repressing a sodium current. However, these agents have no or only minute effects on the retention time of the normal action potential and decrease the maximum rising velocity ($V_{max}$) of the sodium current. The antiarrythmic agents which belong to this class have a high antiarrythmic activity but at the same time strongly repress cardiac functions. Careful consideration is required in administering to patients with cardiac failure or hypotension.

Class II: Beta-blocking agents

The agents in this class, represented by propranolol, are efficacious in the beta-blocking action and are useful in treating patients with arrhythmia in which the sympathetic nerve is involved. However, the care must be taken for use since these agents have side-effects caused by the beta-blocking action, such as depression of cardiac functions, induction of bronchial asthmatic attach and hypoglycemic seizures.

Class III: Pharmaceutical agents for prolonging the retention time of the action current.

These agents are efficacious in remarkably prolonging the retention time of the action current of the cardiac muscle and in prolonging an effective refractory period. Re-entry arrhythmia is considered to be suppressed by the action of the pharmaceutical agents of Class III. The medicaments of this Class III include amiodarone and bretylium. However, all the agents have severe side effects; therefore, careful consideration is required for use.

Class IV: Calcium antagonists

These agents control a calcium channel and suppress arrhythmia due to automatic sthenia of sinoatrial nodes and to ventricular tachycardia in which atrial nodes are contained the re-entry cycle.

Among these antiarrythmic agents, pharmaceutical agents of the Class III type are considered to be particularly important and the most efficacious, and known to be effective on ventricular arrhythmia, the most fatal of all symptoms.

SUMMARY OF THE INVENTION

Various medicinal agents have been developed and used as antiarrythmic agents.

Search for ideal antiarrythmic agents has been pursued for treatment of arrhythmia which has complicated generating mechanisms and requires administration of such agents for a long period of time. However, satisfactory results have not been achieved.

The present invention has been accomplished in view of the present situation regarding antiarrythmic agents. Thus, an object of the present invention is to provide a novel compound which is useful as a Class III type antiarrythmic agent and to provide a process for producing the same.

Another object of the present invention is to provide a novel compound which is effective in improving cardiac dysfunction such as cardiac insufficiency and a process for the preparation of the same.

Another object of the present invention is to provide a pharmaceutical agent, which contains the novel compound as an effective component, for the treatment of cardiac dysfunctions such as arrythmic and cardiac insufficiency.

In the course of the intensive study to solve the above-mentioned problems, the present inventors discovered compounds of the general formula (1) shown below and acid addition salts thereof, and then investigated the pharmacological properties of these compounds. As a result, the present inventors found that these compounds have pharmacological characteristics to markedly prolong the retention time of the action potential of cardiomuscular cells and to markedly prolong the ventricular refractory period; and thus completed the present invention.

Furthermore, the present inventors found that the compounds of the present invention have a positive inotropic action and are useful as therapeutic agents for cardiac insufficiency.

DETAILED DESCRIPTION OF PREFERRED EMBODIMENTS

Compounds according to the present invention is those of the general formula (1) shown below and acid addition salts thereof. More specifically, the compounds are described in Examples thereinafter as preferred embodiments.

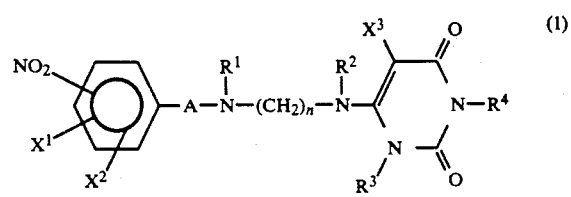

In the formula, A represents —(CH$_2$)$_m$—, —B—(CH$_2$)$_k$—, —D—(CH$_2$)$_l$—,

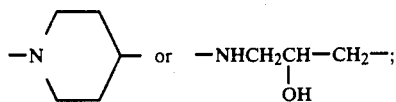

B represents an oxygen or a sulfur atom,

D represents

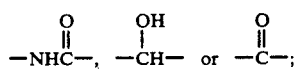

$R^1$ and $R^2$ each independently represent a hydrogen atom, a lower alkyloxycarbonyl group, an unsaturated lower alkyl group or a lower alkyl group, any one of the hydrogen atoms of said alkyl groups may be substituted by a group selected from the group consisting of a hydroxy group; a lower monoalkylamino group; a lower dialkylamino group; a lower alkyloxy group; a lower alkanoyloxy group; a benzoyloxy group; a benzoyloxy group substituted by a halogen atom or a lower alkyloxy group; a phenyl group; a phenyl group substituted by a halogen atom or a lower alkyloxy group; and a lower alkyloxycarbonyl group, or $R^1$ and $R^2$ may be so linked as to form an alkylene chain and thus form a heterocyclic structure;

$R^3$ and $R^4$ each independently represent a hydrogen atom or a lower alkyl group;

$X^1$ and $X^2$ each independently represent a hydrogen atom, —CO—$R^6$, a halogen atom, a lower alkyl group, a halogen-substituted lower alkyl group, a hydroxy group, a lower alkyloxy group, a lower alkylthio group, a lower alkyloxycarbonyl, group a carboxyl group, a cyano group, an amino group, a lower alkanoyloxy group, a lower alkanoylamino group, a lower alkylsulfonamido group, a lower mono- or dialkylamino group, a phenyl-substituted lower alkylamino group or an unsaturated lower alkyloxy group;

$X^3$ represents a hydrogen atom, a nitro group, a methyl group or a cyano group; $R^5$ represents a hydrogen atom, a lower alkanoyl group, a lower alkylsulfonyl group or a lower alkyl group, or $R^1$ and $R^5$ may be so linked as to form an alkylene chain and thus form a heterocyclic structure;

$R^6$ represents a lower alkyl group, a cycloalkyl group or a phenyl group, said phenyl group may be substituted by either one or two of groups independently selected from a halogen atom, a lower alkyl group, a hydroxy group and a lower alkyloxy group, or a heterocyclic ring;

n represents an integral number 2 or 3; m represents an integral number, 0, 1, 2, 3 or 4 ; k represents an integral number, 2, 3, or 4; and l represents an integral number, 0, 1, 2, 3 or 4.

In the above formula (1), examples of the unsaturated lower alkyl group include vinyl, allyl and propargyl groups.

Examples of the lower alkyl group include linear- or branched alkyl groups having 1-5 carbon atoms, such as methyl, ethyl, propyl, butyl, isopropyl, isobutyl, tertiary-butyl and secondary-butyl groups.

Examples of the lower alkyl group substituted by a hydroxyl group include 2-hydroxyethyl, 3-hydroxypropyl, 2-hydroxypropyl and 4-hydroxy-butyl groups.

Examples of the lower alkyl group substituted by a lower monoalkylamino group include 2-(methylamino)ethyl, 3-(methylamino)propyl and 2-(ethylamino)ethyl groups.

Examples of the lower alkyl group substituted by a lower dialkylamino group include 2-(dimethylamino)ethyl, 2-(diethylamino)ethyl and 3-(dimethylamino)propyl groups.

An example of the lower alkyloxy group is an oxygen atom substituted by a lower alkyl group described above.

Examples of the lower alkanoyloxy group include acetyloxy, propionyloxy, butyryloxy, isobutyryloxy and pivaloyloxy groups.

Examples of the lower alkyl group substituted by a benzoyloxy group include 2-benzoyloxyethyl, 3-benzoyloxypropyl, 2-benzoyloxypropyl and 2-benzoyloxy-1-methylethyl groups.

Examples of the lower alkyl group substituted by a phenyl group include benzyl, 2-phenylethyl and 3-phenylpropyl groups.

An example of the lower alkyl group in the lower alkyloxycarbonyl group is that identical with the lower alkyl group described above.

Examples of the halogen atom include fluorine, chlorine, bromine and iodine atoms.

No limitation is required of substitution sites in the halogen-substituted lower alkyl group; the lower alkyl group substituted by a substituting group selected from the group consisting of the lower alkyloxy group, the lower alkanoyloxy group, the benzoyloxy group substituted by a halogen atom or a lower alkyloxy group, the phenyl group substituted by a halogen atom or a lower alkyloxy group and the lower alkyloxycarbonyl group; the benzoyloxy group substituted by a halogen atom or a lower alkyloxy group; and the phenyl group substituted by a halogen atom or a lower alkyloxy group.

Examples of the lower alkylthio group include sulfur atoms substituted by the lower alkyl group mentioned above.

Examples of the lower alkanoylamino group include acetylamino and propionylamino groups.

Examples of the lower alkylsulfonamido group include methanesulfonamido and ethanesulfonamido groups.

Examples of the mono- or di-lower alkylamino group include methylamino, ethylamino, dimethylamino and diethylamino groups.

Examples of the phenyl group-substituted lower alkylamino group include the above-mentioned alkylamino groups which are further substituted by phenyl group. No limitation is required in this substitution.

Examples of the unsaturated lower alkyloxy group include vinyloxy, allyloxy and propargyloxy groups.

Examples of the alkyl chain to link $R^1$ and $R^2$ or $R^1$ and $R^5$ include ethylene and propylene chains.

Examples of the lower alkanoyl group include formyl, acetyl, propionyl and butyryl and pivaloyl groups.

Examples of the lower alkylsulfonyl group include methanesulfonyl and ethanesulfonyl groups.

Examples of the cycloalkyl group include cyclopentyl and cyclohexyl groups.

Examples of the heterocyclic group as $R^6$ include pyridyl, pyrazolyl, pyrimidinyl, thienyl, furyl and pyrrolyl groups.

No limitation is required of the substitution sites in the phenyl group substituted by a substituting group in $R^6$.

The expression "pharmaceutically acceptable" as used to describe the pharmaceutically acceptable acid addition salts in the compounds of the general formula (1) described above means not to have remarkable side effects or absence of toxicity and not to reduce the pharmaceutical activities, when administered to man. These acid addition salts can be produced by neutralization of the corresponding free bases.

Examples of the acids from which these pharmaceutically acceptalbe salts can be prepared include organic acids or inorganic acids, such as hydrochloric acid, hydrobromic acid, phosphoric acid, sulfuric acid, nitric acid, methanesulfonic acid, maleic acid, oxalic acid, malonic acid, succinic acid, fumaric acid, tartaric acid, citric acid, lactic acid, and benzenesulfonic acid.

The concrete examples of the compounds of the general formula (1) include the following compounds.

1. 1,3-dimethyl-6-[2-(4-nitroanilino)ethylamino]-2,4-(1H,3H)-pyrimidinedione
2. 1,3-dimethyl-6-[3-(4-nitroanilino)propylamino]-2,4-(1H,3H)-pyrimidinedione
3. 1,3-dimethyl-6-[4-(4-nitrophenyl)piperazin-1-yl]-2,4(1H,3)-pyrimidinedione
4. 1,3-dimethyl-6-[N-ethyl-2-(4-nitroanilino)ethylamino]-2,4(1H,3H)-pyrimidinedione
5. 1,3-dimethyl-6-[2-(N-methyl-4-nitroanilino)ethylamino)]-2,4(1H,3H)-pyrimidinedione
6. 1,3-dimethyl-6-[4-(nitrophenyl)homopiperazin-1-yl]-2,4(1H,3H)-pyrimidinedione
7. 1,3-dimethyl-6-[2-(4-nitrobenzylamino)ethylamino]-2,4(1H,3H)-pyrimidinedione
8. 1,3-dimethyl-6-[3-(4-nitrobenzylamino)propylamino)]-2,4(1H,3H)-pyrimidinedione
9. 1,3-dimethyl-6-[4-(4-nittrobenzyl)piperazin-1-yl]-2,4(1H,3H)-pyrimidinedione
10. 1,3-dimethyl-6-[N-propyl-2-(4-nitrobenzylamino)ethylamino]-2,4-(1H,3H)-pyrimidinedione
11. 1,3-dimethyl-6-[2-(N-ethyl-4-nitrobenzylamino)ethylamino)]-2,4(1H,3H)-pyrimidinedione
12. 1,3-dimethyl-6-{2-[N-(2-hydroxyethyl)-4-nitrobenzylamino]ethylamino}-2,4(1H,3H)-pyrimidinedione
13. 1,3-dimethyl-6-{2-[2-(4-nitrophenyl)ethylamino]ethylamino}-2,4(1H,3H)-pyrimidinedione
14. 1,3-dimethyl-6-{3-[2-(4-nitrophenyl)ethylamino]propylamino{-2,4(1H,3H)-pyrimidinedione
15. 1,3-dimethyl-6-{N-(2-hydroxyethyl)-2-[2-(4-nitrophenyl)ethylamino]ethylamino}-2,4(1H,3H)-pyrimidinedione
16. 1,3-dimethyl-6-{N-ethyl-2-(4-nitrophenyl)ethylamino]ethylamino}-2,4(1H,3H)-pyrimidinedione
17. 1,3-dimethyl-6-{2[N-(2-hydroxyethyl)-2-(4nitrophenyl)ethylamino]ethylamino}-2,4(1H,3H)-pyrimidinedione
18. 1,3-dimethyl-6-{4-[2-nitrophenyl)ethyl]piperazin-1-yl}-2,4(1H,3H)-pyrimidinedione
19. 1,3-dimethyl-6-{4-[2-(4-nitrophenyl)ethyl]homopiperazin-1-yl}-2,4(1H,3H)-pyrimidinedione
20. 1,3-dimethyl-6-{2-[N-(2-acetoxyethyl)-2-(4-nitrophenyl)ethylamino]ethylamino}-2,4(1H ,3H)-pyrimidinedione
21. 1,3-dimethyl-6-{2-[N-(3-hydroxypropyl)-2-(4-nitrophenyl)ethylamino]ethylamino}-2,4(1H,3H)-pyrimidinedione
22. 1,3-dimethyl-6-{2-[N-(3-benzoyloxypropyl)-2-(4-nitrophenyl)ethylamino]ethylamino}-6-{2-[N-(3-benzoyloxypropyl)-2-(4-nitrophenyl)ethylamino]ethylamino}-2,4(1H,3H)-pyrimidinedione
23. 1,3-dimethyl-6-{4-[2-(3-nitrophenyl)ethyl]piperazin-1-yl}-2,4(1H,3H)-pyrimidinedione
24. 1,3-dimethyl-6-{4-[2-(2-nitrophenyl)ethyl]piperazin-1-yl}-2,4(1H,4H)-pyrimidinedione
25. 3-methyl-6-{4-[2-(4-nitrophenyl)ethyl]piperazin-1-yl}-2,4(1H,3H)-pyrimidinedione
26. 1-methyl-6-{4-nitrophenyl)ethyl]piperazin-1-yl}-2,4(1H,3H)-pyrimidinedione
27. 1,3-diethyl-6-{2-[N-(2-hydroxyethyl)-2(4-nitrophenyl)ethylamino]ethylamino}-2,4-(1H,3H)-pyrimidinedione
28. 1,3-diisopropyl-6-{2-[N-(2-hydroxyethyl)-2-(4-nitrophenyl)ethylamino]ethylamino}-2,4(1H,3H)-pyrimidinedione
29. 1,3-dimethyl-6-{2[3-(4-nitrophenyl)propylamino]ethylamino}-2,4(1H,3H)-pyrimidinedione
30. 1,3-dimethyl-6-{3-[3-(4-nitrophenyl)proipylamino]propylamino}-2,4(1H,3H)-pyrimidinedione
31. 1,3-dimethyl-6-{N-methyl-2-[3-(4-nitrophenyl)propylamino]ethylamino}-2,4(1H,3H)-pyrimidinedione
32. 1,3-dimethyl-6-{N-ethyl-2-[3-(4-nitrophenyl)propylamino]ethylamino}-2,4(1H,3H)-pyrimidinedione
33. 1,3-dimethyl-6-{N-propyl-2-[3-(4-nitriphenyl)propylamino]ethylamino}-2,4(1H,3H)-pyrimidinedione
34. 1,3-dimethyl-6-{N-(2-hydroxyethyl)-2-[3-(4-nitrophenyl]propylamino]ethylamino}-2,4(1H,3H)-pyrimidinedione
35. 1,3-dimethyl-6-{N-(2-hydroxypropyl)-2-[3-(4-nitroiphenyl)propylamino]ethylamino}-2,4(1H,3H)-pyrimidinedione
36. 1,3-dimethyl-6-{N-(2-hydroxy-1-methylethyl)-2-[3-(4-nitrophenyl)propylamino]ethylamino}-2,4-(1H,3H)-pyrimidinedione
37. 1,3-dimethyl-6-{N-(2-acetoxyethyl)-2-[3-(4-nitrophenyl)propylamino]ethylamino}-2,4(1H,3H)-pyramidinedione
38. 1,3-dimethyl-6-{N-(methoxycarbonylmethyl-2-[3-(4nitrophenyl)propylamino]ethylamino}-2,4(1H,3H)-pyrimidinedione
39. 1,3-dimethyl-6-{N-(2-phenylethyl)-2-[3-(4-nitrophenyl)propylamino]ethylamino)-2,4-(1H,3H)-pyrimidinedione
40. 1,3-dimethyl-6-{2-[N-methyl-3-(4-nitrophenyl)propylamino]ethylamino)-2,4(1H,3H)-pyrimidinedione
41. 1,3-dimethyl-6-{2-<N-ethyl-N-[3-(4-nitrophenyl)propyl]amino>ethylamino}-2,4(1H,3H)-pyrimidinedione
42. 1,3-dimethyl-6-{2-[N-propyl-3-(4-nitrophenyl)propylamino]ethylamino}-2,4(1H,3H)-pyrimidinedione
43. 1,3-dimethyl-6-{2-[N-(1-methylethyl)-3-(4-nitrophenyl)propylamino]ethylamino)-2,4-(1H,3H)-pyrimidinedione
44. 1,3-dimethyl-6-{2-[N-butyl-3-(4-nitrophenyl)propylamino]ethylamino)-2,4(2,4(1H,3H)-pyrimidinedione 45. 1,3-dimethyl-6-{2-[N-(tert-butyl)-3(4-nitrophenyl)propylamino]ethylamino}-2,4(1H,3H)-pyrimidinedione
46. 1,3-dimethyl-6-{2-<N-(2-hydroxyethyl)-N-[3-(4-nitrophenyl)propyl]amino>ethylamino]-2,4(1H,3H)-pyrimidinedione
47. 1,3-dimethyl-6-{2-[N-(3-hydroxypropyl)-3-(4-nitrophenyl)propylamino]ethylamino}-2,4(1H,3H)-pyrimidinedione
48. 1,3-dimethyl-6-{2-[N-(2-hydroxy-1-methylethyl)-3-(4-nitrophenyl)propylamino]ethylamino}-2,4(1H,3H)-pyrimidinedione
49. 1,3-dimethyl-6-{2-[N-(2-hydroxypropyl)-3-(4-nitrophenyl)propylamino]ethylamino)-2,4(1H,3H)-pyrimidinedione
50. 1,3-dimethyl-6-{2-[N-(4-hydroxybutyl)-3-(4-nitrophenyl)propylamino]ethylamino}-2,4(1H,3H)-pyrimidinedione
51. 1,3-dimethyl-6-{2-[N-(2-acetoxyethyl)-3-(4-nitrophenyl)propylamino]ethylamino}-2,4(1H-3H)-pyrimidinedione
52. 1,3-dimethyl-6-{2-[N-(2-formyloxyethyl)-3-(4-nitrophenyl)propylamino]ethylamino}-2,4(1H,3H)-pyrimidinedione
53. 1,3-dimethyl-6-{2-[N-(2-propionyloxyethyl)-3-(4-nitrophenyl)propylamino]ethylamino}-2,4(1H,3H)-pyrimidinedione
54. 1,3-dimethyl-6-{2-[N-(2-isobutyryloxyethyl)-3,4-nitrophenyl)propylamino]ethylamino}-2,4(1H,3H)-pyrimidinedione
55. 1,3-dimethyl-6-{2-[N-(2-pivaloyloxyethyl)-3-(4-nitrophenyl)propylamino]ethylamino}-2,4(1H,3H)-pyrimidinedione
56. 1,3-dimethyl-6-{2-[N-(2-acetoxypropyl)-3-(4-nitrophenyl)propylamino]ethylamino}-2,4(1H,3H)-pyrimidinedione
57. 1,3-dimethyl-6-{2-[N-(2-acetoxy-1-methylethyl)-3-(4-nitrophenyl)propylamino]ethylamino}-2,4(1H,3H)-pyrimidinedione
58. 1,3-dimethyl-6-{2-[N-(2-benzoyloxyethyl)-3-(4-nitrophenyl)propylamino]ethylamino}-2,4(1H,3H)-pyrimidinedione
59. 1,3-dimethyl-6-{2-<N-[2-(4-fluorobenzoyloxy)ethyl]-3-(4-nitrophenyl)propylamino>ethylamino}-2,4(1H,3H)-pyrimidinedione
60. 1,3-dimethyl-6-{2-<N-[2(4-methoxybenzoyloxy)ethyl]-3-(4-nitrophenyl)propylamino>ethylamino-2,4(1H,3H)-pyrimidinedione
61. 1,3-dimethyl-6-{2-<N-[2-(2-chlorobenzoyloxy)ethyl]-3-(4-nitrophenyl)propylamino>ethylamino}-2,4(1H,3H)-pyrimidinedione
62. 1,3-dimethyl-6-{2-<N-[2-(3,5-dimethoxybenzoyloxy)ethyl]-3-(4-nitrophenyl)propylamino>ethylamino}-2,4(1H,3)-pyrimidinedione
63. 1,3-dimethyl-6-{2-<N-[2-[3,4-dibromobenzoyloxy)ethyl]-3-(4-nitrophenyl)propylamino>ethylamino)-2,4(1H,3H)-pyrimidinedione
64. 1,3-dimethyl-6-{2-[N-(2-methoxyethyl)-3-(4-nitrophenyl)propylamino]ethylamino}-2,4(1H,3H)-pyrimidinedione
65. 1,3-dimethyl-6-{2-[N-(2-propyloxyethyl)-3-(4-nitrophenyl)propylamino]ethylamino}-2,4(1H,3H)-pyrimidinedione
66. 1,3-dimethyl-6-{2-[N-benzyl-3-(4-nitrophenyl)propylamino]ethylamino}-2,4(1H,3H)-pyrimidinedione
67. 1,3-dimethyl-6-{2-[N-(4-methoxybenzyl)-3-(4-nitrophenyl)propylamino]ethylamino}-2,4(1H,3H)-pyrimidinedione
68. 1,3-dimethyl-6-{2-[N-(3,4,5-trimethoxybenzyl)-3-(4-nitrophenyl)propylamino]ethylamino}-2,4(1H,3H)-pyrimidinedione
69. 1,3-dimethyl-6-{2-[N-(2-chlorobenzyl)-3-(4-nitrophenyl)propylamino]ethylamino}-2,4(1H,3H)-pyrimidinedione
70. 1,3-dimethyl-6-{2-[N-(2-phenylethyl)-3-(4-nitrophenyl)propylamino]ethylamino}-2,4(1H,3H)-pyrimidinedione
71. 1,3-dimethyl-6-{2-[N-vinyl-3-(4-nitrophenyl)propylamino]ethylamino}-2,4-(1H,3H)-pyrimidinedione
72. 1,3-dimethyl-6-{2-[N-allyl-3-(4-nitrophenyl)propylamino]ethylamino}-2,4(1H,3H)-pyrimidinedione
73. 1,3-dimethyl-6-{2-[N-propargyl-3-(4-nitrophenyl)propylamino]ethylamino}-2,4(1H,3H)-pyrimidinedione
74. 1,3-dimethyl-6-{2-[N-ethoxycarbonylmethyl-3-(4-nitrophenyl)propylamino]ethylamino)-2,4(1H,3H)-pyrimidinedione
75. 1,3-dimethyl-6-{2-[N-tert-butoxycarbonylmethyl-3-(4-nitrophenyl)propylamino]ethylamino)-2,4(1H,3H)-pyrinidinedione
76. 1,3-dimethyl-6-{2-[N-(2-methoxycarbonylethyl)-3-(4-nitrophenyl)propylamino]ethylamino}-2,4(1H,3)-pyrimidinedione
77. 1,3-dimethyl-6-{N-methyl-2-[N-methyl-3-(4-nitrophenyl)propylamino]ethylamino}-2,4(1H,3H)-pyrimidinedione
78. 1,3-dimethyl-6-{N-ethyl-2-[N-(2-hydroxyethyl)-3-(4-nitrophenyl)propylamino]ethylamino}-2,4(1H,3H)-pyrimidinedione
79. 1,3-dimethyl-6-{2-<N-ethyl-N-[3-(3-nitrophenyl)propyl]amino>ethylamino}-2,4(1H,3H)-pyrimidinedione
80. 1,3-dimethyl-6-{2-[N-methoxycarbonyl-3-(4-nitrophenyl)propylamino]ethylamino}-2,4(1H,3H)-pyrimidinedione
81. 1,3-dimethyl-6-{2-[N-(tert-butyoxycarbonyl)-3-(4-nitrophenyl)propylamino]ethylamino}-2,4(1H,3H)-pyrimidinedione
82. 1,3-dimethyl-6-{2-<N-[2-(N-methylamino)ethyl]-3-(4-nitrophenyl)propylamino>ethylamino}-2,4(1H,3H)-pyrimidinedione
83. 1,3-dimethyl-6-{2-<N-[2-(N,N-dimethylamino)ethyl]-3-(4-nitrophenyl)propylamino]ethylamino}-2,4-(1H,3H)-pyrimidinedione
84. 1,3-dimethyl-6-{2-<N-[2-(N,N-diethylamino)ethyl]-3-(2-nitrophenyl)propylamino>ethylamino)-2,4(1H,3H)-pyrimidinedione
85. 1,3-dimethyl-6-{2-[N-(2-hydroxyethyl)-3-(2-nitrophenyl)propylamino]ethylamino}2,4(1H,3H)-pyrimidinedione
86. 1,3-dimethyl-6-{4-[3-(4-nitrophenyl)propyl]piperazin-1-yl}-2,4(1H,3H)-pyrimidinedione
87. 1,3-dimethyl-6-{4-[3-(4-nitrophenyl)propyl]homopiperazin-1-yl}-2,4(1H,3H)-pyrimidinedione
88. 3-methyl-6-{4-[3-(4-nitrophenyl)propyl]piperazin-1-yl}-2,4(1H,3H)-pyrimidinedione
89. 1-propyl-6-(2-[N-(2-hydroxyethyl)-3-(4-nitrophenyl)propylamino]ethylamino}-2,4(1H,3)-pyrimidinedione 90. 6-(2-[N-ethyl-3-(4-nitrophenyl)propylamino]ethylamino}-1,3,5-trimethyl-2,4(1H,3H)-pyrimidinedione
91. 6-{2-[N-(2-hydroxyethyl)-3-(4-nitrophenyl)propylamino]ethylamino}-1,3,5-trimethyl]-2,4(1H,3H)-pyrimidinedione
92. 1,3-dimethyl-6-{2-[N-(ethyl-3-(4-nitrophenyl)propylamino]ethylamino}-5-nitro-2,4(1H,3H)-pyrimidinedione
93. 1,3-dimethyl-6-{2-[N-(2-hydroxyethyl)-3-(4-nitrophenyl)propylamino]ethylamino}-5-nitro-2,4(1H,3H)-pyrimidinedione
94. 1,3-dimethyl-6-{2-[N-(methoxycarbonylmethyl)-3-(4-nitrophenyl)propylamino]ethylamino}-5-cyano-2,4(1H,3)-pyrimidinedione
95. 1,3-dimethyl-6-{2-[N-(2-hydroxyethyl)-3-(4-nitrophenyl)propylamino]ethylamino}-5-cyano-2,4(1H,3H)-pyrimidinedione
96. 1,3-dimethyl-6-{2-[4-(4-nitrophenyl)butylamino]ethylamino}-2,4(1H,3H)-pyrimidinedione
97. 6-{N-ethyl-N<2-[4-(4-nitrophenyl)butylamino]ethyl>amino}-1,3dimethyl-2,4(1H,3H)-pyrimidinedione
98. 1,3-dimethyl-6-{N-(2-hydroxyethyl)-2-[4-(4-nitrophenyl)butylamino]ethylamino}-2,4(1H,3H)-pyrimidinedione
99. 1,3-dimethyl-6-{N-methoxycarbonylmethyl-2-(4-(4-nitrophenyl)butylamino]ethylamino}-2,4(1H,3H)-pyrimidinedione
100. 1,3-dimethyl-6-{2-[N-ethyl-4-(4-nitrophenyl)butylamino]ethylamino}-2,4(1H,3H)-pyrimidinedione
101. 1,3-dimethyl-6-{2-[N-tert-butyl)-4-(4-nitrophenyl)butylamino]ethylamino}-2,4(1H,3H)-pyrimidinedione
102. 1,3-dimethyl-6-{2-[N-(2-hydroxyethyl)-4-(4-nitrophenyl)butylamino]ethylamino}-2,4(1H,3H)-pyrimidinedione
103. 1,3-dimethyl-6-{2-[N-(3-hydroxypropyl)-4-(4-nitrophenyl)butylamino]ethylamino}-2,4(1H,3H)-pyrimidinedione
104. 1,3-dimethyl-6-{2-[N-(2-acetoxyethyl)-4-(4-nitrophenyhl)butylamino]ethylamino}-2,4(1H,3H)-pyrimidinedione
105. 1,3-dimethyl-6-{2-[N-(2-methoxyethyl)-4-(4-nitrophenyl)butylamino]ethylamino}-2,4(1H,3H)-pyrimidinedione
106. 1,3-dimethyl-6-{2-[N-benzyl-4-(4-nitrophenyl)butylamino]ethylamino}-2,4(1H,3H)-pyrimidinedione
107. 1,3-dimethyl-6-{2-[N-allyl-4-(4-nitrophenyl)butylamino]ethylamino}-2,4(1H,3H)-pyrimidinedione
108. 1,3-dimethyl-6-{2-[N-ethoxycarbonylmethyl-4-(4-nitrophenyl)butylamino]ethylamino}-2,4(1H,3H)-pyrimidinedione
109. 1,3-dimethyl-6-{N-methyl-2[N-methyl-4-(4-nitrophenyl)butylamino]ethylamino}-2,4(1H,3H)-pyrimidinedione
110. 1,3-dimethyl-6-{2-<N-[2-(N,N-diethylamino)ethyl]-4-(4-nitrophenyl)butylamino>ethylamino}-2,4(1H,3H)-pyrimidinedione
111. 1,3-dimethyl-6-{4-[4-(4-nitrophenyl)butyl]piperazin-1-yl}-2,4(1H,3H)-pyrimidinedione
112. 6-{2-[N-ethyl-4-(4-nitrophenyl)butylamino]ethylamino}-1,3,5-trimethyl-2,4(1H,3H)-pyrimidinedione
113. 1,3-dimethyl-6-{2-[b 2-(4-nitrophenoxy)ethylamino]ethylamino-2,4(1H,3H)-pyrimidinedione
114. 1,3-dimethyl-6-{N-ethyl-2-[2-(4-nitroiphenoxy)ethylamino]ethylamino}-2,4(1H,3H)-pyrimidinedione
115. 1,3-dimethyl-6-{4-[2-(4-nitrophenoxy)ethyl]piperazin-1-yl}-2,4(1H,3H)-pyrimidinedione
116. 1,3-dimethyl-6-{2-[3-(4-nitrophenoxy)propylamino]ethylamino)-2,4(1H,3H)-pyrimidinedione
117. 1,3-dimethyl-6-{N-ethyl-2-[3-(4-nitrophenoxy)propylamino]ethylamino}-2,4(1H,3H)-pyrimidinedione
118. 1,3-dimethyl-6-{2-[N-ethyl-3-(4-nitrophenoxy)propylamino]ethylamino}-2,4(1H,3H)-pyrimidinedione
119. 1,3-dimethyl-6-{2-[N-(2-hydroxyethyl)-3-(4-nitrophenoxy)propylamino]ethylamino}-24(1H,3H)-pyrimidinedione
120. 1,3-dimethyl-6-{2-[N-(2-acetoxyethyl)-3-(4-nitrophenoxy)propylamino]ethylamino}-2,4(1H,3H)-pyrimidinedione
121. 1,3-dimethyl-6-{N-methyl-2-[N-methyl-3-(4-nitrophenoxy)propylamino]ethylamino}-2,4(1H,3H)-pyrimidinedione
122. 1,3-dimethyl-6-{4-[3-(4-nitrophenboxy)propyl]piperazin-1-yl}-2,4(1H,3H)-pyrimidinedione
123. 3-methyl-6-{4[3-(4-nitrophenoxy)propyl]piperazin-1-yl}-2,4(1H,3H)-pyrimidinedione
124. 1,3-dimethyl-6-{4-[3-(3-nitrophenoxy)propyl]piperazin-1-yl}2,4(1H,3H)-pyrimidinedione
125. 1,3-dimethyl-6-{4-[3-(2-nitrophenoxy)propyl]piperazin-1-yl}-2,4(1H,3H)-pyrimidinedione
126. 1,3-dimethyl-6-{2-[4-(4-nitrophenoxy)butylamino]ethylamino}-2,4(1H,3H)-pyrimidinedione
127. 1,3-dimethyl-6-{N-methyl-2[N-methyl-4-(4-nitrophenoxy)butylamino]ethylamino}-2,4(1H,3H)-pyrimidinedione
128. 1,3-dimethyl-6-{4-[4-(4-nitrophenoxy)butyl]piperazin-1-yl}-2,4(1H,3H)-pyrimidinedione
129. 1,3-dimethyl-6-{N-ethyl-2-(4-nitrophenylthio)ethylamino]ethylamino}-2,4(1H,3H)-pyrimidinedione
130. 1,3-dimethyl-6-{2-[N-(2-hydroxyethyl)-3-(4-nitrophenylthio)propylamino]ethylamino}-2,4(1H,3H)-pyrimidinedione
131. 1,3-dimethyl-6-{4-[3-(4-nitrophenylthio)propyl]piperazin-1-yl}-2,4(1H,3H)-pyrimidinedione
132. 1,3-dimethyl-6-{N-methyl-2-[N-methyl-4-(4-nitrophenylthio)butylamino]ethylamino}-2,4(1H,3H)-pyrimidinedione
133. 1,3-dimethyl-6-[4-(4-nitrophenacyl)piperazin-1-yl]-2,4(1H,3H)-pyrimidinedione
134. 1,3-dimethyl-6-{4-[2-(4-nitrobenzoyl)ethyl]piperazin-1-yl}-2,4(1H,3H)-pyrimidinedione
135. 1,3-dimethyl-6-{N-methyl-2-[N-methyl-4-(4-nitrophenylthio)butylamino]ethylamino}-2,4(1H,3H)-pyrimidinedione
136. 1,3-dimethyl-6-{4-[2-hydroxy-2-(4-nitrophenyl)ethyl]piperazin-1-yl}-2,4(1H,3H)-pyrimidinedione
137. 1,3-dimethyl-6-{4-[2-(4-nitrobenzoyloxy)ethyl]piperazin-1-yl}-2,4(1H,3H)-pyrimidinedione
138. 1,3-dimethyl-6-{2-[N-ethyl-3-(4-nitrobenzoyloxy)propylamino]ethylamino}-2,4(1H,3H)-pyrimidinedione
139. 1,3-dimethyl-6-[2-(4-nitrobenzoylamino)ethylamino]-2,4(1H,3H)-pyrimidinedione 140. 1,3-dimethyl-6-{4-[2-(4-nitrobenzoylamino)ethyl]-piperazin-1-yl}-2,4(1H,3H)-pyrimidinedione
141. 1,3-dimethyl-6-{4-[N-4-nitrophenyl)carbamoylmethyl]piperazin-1-yl}-2,4(1H,3H)-pyrimidinedione
142. 1,3-dimethyl-6-{4-[N-(4-nitrophenyl)carbamoylethyl]homopiperazin-1-yl}-2,4(1H,3H)-pyrimidinedione
143. 1,3-dimethyl-6-{4-[3-(4-nitroanilino)-2-hydroxypropyl]piperazin-1-yl}-2,4(1H,3H)-pyrimidinedione
144. 1,3-dimethyl-6-{4-<4-[N-(4-nitrophenyl)carbamoyl]butyl>piperazin-1-yl}-2,4(1H,3H)-pyrimidinedione
145. 1,3-dimethyl-6-{N-methyl-2[N-methyl-2-(4-nitroanilino)ethylamino]ethylamino}-2,4(1H,3H)-pyrimidinedione
146. 1,3-dimethyl-6-{N-methyl-2-[N-(2hydroxyethyl)-2-(4-nitroanilino)ethylamino]ethylamino}-2,4(1H,3H)-pyrimidinedione
147. 1,3-dimethyl-6-{2-[N-ethyl-2-(4-nitroanilino)ethylamino]ethylamino}-2,4(1H,3H)-pyrimidinedione
148. 1,3-dimethyl-6-{3-[N-propyl-2-(4-nitroanilino)ethylamino]propylamino}-2,4(1H,3H)-pyrimidinedione
149. 1,3-dimethyl-6-{N-methyl-2-[N-methyl-2-(N-methyl-4-nitroanilino)ethylamino]ethylamino}-2,4(1H,3H)-pyrimidinedione
150. 1,3-dimethyl-6-{N-methyl-3-[N-methyl-2-(4-nitroanilino)ethylamino]propylamino}-2,4(1H,3H)-pyrimidinedione
151. 1,3-dimethyl-6-{2-[N-ethyl-3-(4-nitroanilino)propylamino]ethylamino}-2,4(1H,3H)-pyrimidinedione
152. 1,3-dimethyl-6-{2-[N-(2-hdyroxyethyl)-3-(4-nitroanilino)propylamino]propylamino}-2,4(1,3H)-pyrimidinedione
153. 1,3-dimethyl-6-{2-[N-methoxycarbonylmethyl-3-(4-nitroanilino)propylamino]ethylamino}-2,4(1H,3H)-pyrimidinedione
154. 1,3-dimethyl-6-{4-[3-(4-nitroanilino)propyl]piperazin-1-yl}-2,4(1H,3H)-pyrimidinedione
155. 1,3-dimethyl-6-{4-[3-(N-methyl-4-nitroanilino)propyl]piperazin-1-yl}-2,4(1H,3H)-pyrimidinedione
156. 1,3-dimethyl-6-{4-[3-(N-propyl-4-nitroanilino)propyl]piperazin-1yl}-2,4(1H,3H)-pyrimidinedione
157. 1,3-dimethyl-6-{4-[3-(N-methanesulfonyl-4-nitroanilino)propyl]piperazin-1yl}-2,4(1H,3H)-pyrimidinedione
158. 1,3-dimethyl-6-{4-[3-(N-ethanesulfonyl-4-nitroanilino)propyl]piperazin-1-yl}-2,4(1H,3H)-pyrimidinedione
159. 1,3-dimethyl-6-{4-[3-(N-acetyl-4-nitroanilino)propyl]piperazin-1-yl}-2,4(1H,3H)-pyrimidinedione
160. 1,3-dimethyl-6-{4-[3-(N-propionyl-4-nitroanilino)propyl]piperazin-1-yl}-2,4(1H,3H)-pyrimidinedione
161. 1,3-dimethyl-6-{2-<[1-(4-nitrophenyl)piperidine-4-yl]amino>ethylamino}-2,4(1H,3H)-pyrimidinedione
162. 1,3-dimethyl-6-{2-[4-(4-nitrophenyl)piperazin-1yl]ethylamino}-2,4(1H,3H)-pyrimidinedione
163. 1,3-dimethyl-6-{3-[4-(4-nitrophenyl)piperazin-1-yl]propylamino}-2,4(1H,3H)-pyrimidinedione
164. 1,3-dimethyl-6-{N-(2-hydroxyethyl)-2-[4-(4-nitrophenyl)piperazin-1-yl]-ethylamino}-2,4(1H,3H)-pyrimidinedione
165. 1,3-dimethyl-6-{N-methyl-2-[4-(4-nitrophenyl)piperazin-1-yl]ethylamino}-2,4(1H,3H)-pyrimidinedione
166. 1,3-dimethyl-6-{4-[3-(2-acetyl-4-nitrophenyl)propyl]piperazin-1-yl}-2,4(1H,3H)-pyrimidinedione
167. 1,3-dimethyl-6-{2-[N-ethyl-2-(2-benzoyl-4-nitrophenyl)ethylamino]ethylamino}-2,4(1H,3H)-pyrimidinedione
168. 1,3-dimethyl-6-[4-(3-acetyl-4-nitrophenyl)piperazin-1-yl]-2,4(1H,3H)-pyrimidinedione
169. 1,3-dimethyl-6-{4-[4-(2-acetyl-4-nitrophenoxy)butyl]piperazin-1-yl}-2,4(1H,3H)-pyrimidinedione
170. 1-methyl-6-{4-[3-(2-acetyl-4-nitrophenoxy)propyl]piperazin-1-yl}-2,4(1H,3H)-pyrimidinedione
171. 1,3-dimethyl-6-{4-<3-[2-nitro-4-(2-pyridinecarbonyl)phenoxy]propyl>piperazin-1-yl}-2,4(1H,3H)-pyrimidinedione
172. 1,3-dimethyl-6-{2-[N-(2-hdyroxyethyl)-3-(4-benzoyl-2-nitrophenoxy)propylamino]ethylamino}-2,4(1H,3H)-pyrimidinedione
173. 1,3-dimethyl-6-{4-[3-(2-acetyl-4-nitroanilino)propyl]piperazin-1-yl}-2,4(1H,3H)-pyrimidinedione
174. 1,3-dimethyl-6-{4-[3-(2-cyclopentanecarbonyl-4-nitroanilino)propyl]piperazin-1-yl}-2,4(1H,3H)-pyrimidinedione
175. 1,3-dimethyl-6-{4-<3-[2-(2-chlorobenzoyl)-4-nitroanilino]propyl>piperazin-1-yl}-2,4(1H,3H)-pyrimidinedione
176. 1,3-dimethyl-6-{4-<3-[2-(2-pyridinecarbonyl)-4-nitroanilino]propyl>piperazin-1-yl}-2,4(1H,3H)-pyrimidinedione
177. 1,3-dimethyl-6-{4-<3-[2-(4-pyridinecarbonyl)-4-nitroanilino]propyl>piperazin-1-yl}-2,4(1H,3H)-pyrimidinedione
178. 1,3-dimethyl-6-{4-[3-(4-acetyl-2-nitroanilino)propyl]piperazin-1-yl}-2,4(1H,3H)-pyrimidinedione
179. 1,3-dimethyl-6-{4-[3-(4-propanoyl-2-nitroanilino)propyl]piperazin-1-yl}-2,4(1H,3H)-pyrimidinedione
180. 1,3-dimethyl-6-{4-[3-(4-benzoyl-2-nitroanilino)propyl]piperazin-1-yl}-2,4(1H,3H)-pyrimidinedione
181. 1,3-dimethyl-6-{4[3-(3-acetyl-4-nitroanilino)propyl]piperazin-1-yl}2,4(1H,3H)-pyrimidinedione
182. 1,3-dimethyl-6-{2-[3-(4-acetyl-2-nitroanilino)propylamino]ethylamino}-2,4(1H,3H)-pyrimidinedione
183. 1,3-dimethyl-6-{3-[N-(2-hydroxyethyl)-3-(4-propanoyl-2-nitroanilino)propylamino]propylamino}-2,4(1H,3H)-pyrimidinedione
184. 1,3-dimethyl-6-{4-[3-(2-benzoyl-4-nitroanilino)propyl]piperazin-1-yl}-2,4(1H,3H)-pyrimidinedione
185. 3-methyl-6-{4-[3-(2-benzoyl-4-nitroanilino)propyl]piperazin-1-yl}-2,4(1H,3H)-pyrimidinedione
186. 1,3-dimethyl-6-{N-ethyl-2-[3-(2-formyl-4-nitroanilino)propylamino]ethylamino}-2,4(1H,3H)-pyrimidinedione
187. 1,3-dimethyl-6-{4-[3-(3-fluoro-4-nitrophenoxy)propyl]piperazin-1-yl}-2,4(1H,3H)-pyrimidinedione
188. 1,3-dimethyl-6-{4-[3-(3-fluoro-4-nitroanilino)propyl]piperazin-1-yl}-2,4(1H,3H)-pyrimidinedione
189. 1,3-dimethyl-6-{4-[3-(3,5-difluoro-4-nitrophenoxy)propyl]piperazin-1-yl}-2,4(1H,3H)-pyrimidinedione
190. 1,3-dimethyl-6-{4-[3-difluoro-4-nitroanilino)propyl]piperazin-1-yl}-2,4(1H,3H)-pyrimidinedione
191. 1,3-dimethyl-6-{4-[3-(2-fluoro-4-nitroanilino)propyl]piperazin-1-yl}-2,4(1H,3H)-pyrimidinedione
192. 1,3-dimethyl-6-{2-[3-(2-methoxy-4-nitrophenoxy)propylamino]ethylamino}-2,4(1H,3H)-pyrimidinedione 193. 1,3-dimethyl-6-{3-[N-ethyl-3-(3-trifluoromethyl-4-nitroanilino)propylamino]propylamino}-2,4(1H,3H)-pyrimidinedione
194. 1,3-dimethyl-6-{2-[4-(2-acetyloxy-4-nitrophenoxy)butylamino]ethylamino}-2,4(1H,3H)-pyrimidinedione
195. 1,3-dimethyl-6-{4-[3-(2-dimethylamino-4-nitroanilino)propyl]homopiperazin-1-yl}-2,4(1H,3H)-pyrimidinedione
196. 1,3-dimethyl-6-{2-[2-(2-diethylamino-4-nitroanilino)ethylamino]ethylamino}-2,4(1H,3H)-pyrimidinedione
197. 3-methyl-6-{2-[3-(2-hydroxy-4-nitrophenoxy)propylamino]ethylamino}-2,4(1H,3H)-pyrimidinedione
198. 1-ethyl-6-{4-[3-(2-bromo-4-nitroanilino)propyl]piperazin-1-yl}-2,4(1H,3H)-pyrimidinedione
199. 6{4-[2-(2-ethyl-4-nitroanilino)ethylamino]piperazin-1-yl}-2,4(1H,3H)-pyrimidinedione
200. 1,3-dimethyl-6-{4-[N-(3-fluoro-4-nitroiphenyl)carbamoylmelthyl]piperazin-1-yl}-2,4(1H,3H)-pyrimidinedione
201. 1,3-dimethyl-6-{2-[3-(2-ethoxy-4-nitrophenylthio)propylamino]ethylamino}-2,4(1H,3H)-pyrimidinedione
202. 1,3-dimethyl-6-{4-[3-2-ethanesulfonamido-4-nitrophenoxy)propyl]piperazin-1yl}-2,4(1H,3H)-pyrimidinedione
203. 1,3-dimethyl-6-{4-[2-(3-fluoro-4-nitrophenyl)ethyl]piperazin-1-yl}-2,4(1H,3H)-pyrimidinedione
204. 1,3-dimethyl-6-{2-[N-ethyl-3-(3-fluoro-4-nitrophenyl)propylamino]ethylamino}-2,4(1H,3H)-pyrimidinedione
205. 1,3-dimethyl-6-{3-[N-(2-hydroxyethyl)-4-(3,5-difluoro-4-nitrophenyl)propylamino]propylamino}-2,4(1H,3H)-pyrimidinedione
206. 1,3-dimethyl-6-{2-[N-(2-acetoxyethyl)-3-(2-diemthylamino-4-nitrophenyl)propylamino]ethylamino}-2,4(1H,3H)-pyrimidinedione
207. 1,3-dimethyl-6-{2-[N-ethyl-3(2-ethoxy-4-nitrophenyl)propylamino]ethylamino}-2,4-(1H,3H)-pyrimidinedione
208. 1,3-dimethyl-6-{3-[N-(2-acetoyloxyethyl)-3-(2-ethanesulfonamido-4-nitrophenyl)propylamino]propylamino}-2,4(1H,3H)-pyrimidinedione
209. 1,3-dimethyl-6-[4-(3-methyl-4-nitrobenzyl)piperazin-1-yl]-2,4(1H,3H)-pyrimidinedione
210. 1,3-dimethyl-6-{2-[N-(2-hydroxyethyl)-3-(3-methoxy-4-nitrophenyl)propylamino]ethylamino}-2,4-(1H,3H)-pyrimidinedione
211. 1,3-dimethyl-6-{2-[N-(3-(2-ethoxycarbonyl-4-nitrophenyl)propylamino]ethylamino]-2,4(1H,3H)-pyrimidinedione
212. 1,3-dimethyl-6-{4-[3-(2-acetyl-4-nitrophenoxy)propyl]piperazin-1-yl}-2,4(1H,3H)-pyrimidinedione
213. 1,3-dimethyl-6-{4-[3-(4-acetyl-2-nitrophenoxy)propyl]piperazin-1-yl}-2,4(1H,3H)-pyrimidinedione
214. 1,3-dimethyl-6-{4-[3-(4-benzoyl-2-nitrophenoxy)propyl]piperazin-1-yl}-2,4(1H,3H)-pyrimidinedione
215. 1,3-dimethyl-6-{4-[3-(3-acetyl-4-nitrophenoxy)propyl]piperazin-1yl}-2,4(1H,3H)-pyrimidinedione
216. 1,3-dimethyl-6-{4-[3-(2-benzoyl-4-nitrophenoxy)propyl]piperazin-1-yl}-2,4(1H,3H)-pyrimidinedione
217. 1,3-dimethyl-6-{4-<3-[2-(4-bromobenzoyl]-4-nitrophenoxy]propyl>piperazin-1-yl}-2,4(1H,3H)-pyrimidinedione
218. 1,3-dimethyl-6-{4-<3-[2-(3-pyrazolylcarbonyl)-4-nitrophenoxy]propyl>piperazin-1-yl}-2,4(1H,3H)-pyrimidinedione
219. 1,3-dimethyl-6-{4-<3-[2-(2-pyridinecarbonyl)-4-nitrophenboxy]propyl>piperazin-1-yl}-2,4(1H,3H)-pyrimidinedione
220. 1,3-dimethyl-6-{4-<3-[2-(3-pyridinecarbonyl)-4-nitrophenoxy]propyl>piperazin-1-yl}-2,4(1H,3H)-pyrimidinedione
221. 1,3-dimethyl-6-{4-<3-[2-(4-pyridinecarbonyl)-4-nitrophenoxy]propyl>piperazin-1-yl}-2,4(1H,3H)-pyrimidinedione
222. 1,3-dimethyl-6-{4-<3-[2-(2-pyrimidinedinylcarbonyl)-4-nitrophenoxy]propyl>piperazin-1-yl}-2,4(1H,3H)-pyrimidinedione
223. 1,3-dimethyl-6-{4-[2-(2-acetyl-4-nitrophenoxy)ethyl]piperazin-1-yl}-2,4(1H,3H)-pyrimidinedione
224. 1,3-dimethyl-6-{4-[2-(2-benzoyl-4-nitrophenoxy)ethyl]piperazine-1-yl}-2,4(1H,3H)-pyrimidinedione
225. 1,3-dimethyl-6-{4-<2-[2-(4-bromobenzoyl)-4-nitrophenoxy]ethyl>piperazin-1-yl}-2,4(1H,3H)-pyrimidinedione
226. 1,3-dimethyl-6-{4-[2-(3-acetyl-4-nitrophenyl)ethyl]piperazin-1-yl}-2,4(1H,3H)-pyrimidinedione
227. 1,3-dimethyl-6-{4-[2-(2-nitro-4-acetyl)ethyl]piperazin-1-yl}-2,4(1H,3H)-pyrimidinedione
228. 1,3-dimethyl-6-{4-[2-(2-nitro-4-benzoyl)ethyl]piperazin-1-yl}-2,4(1H,3H)-pyrimidinedione
229. 1,3-dimethyl-6 {4-<3-[2-(2-hydroxybenzoyl)-4-nitrophenoxy]propyl>piperazin-1-yl}-2,4(1H ,3H)-pyrimidinedione
230. 1,3-dimethyl-6-{4-<3-[2-(2-chlorobenzoyl)-4-nitrophenoxy]propyl>piperazin-1-yl}-2,4(1H,3H)-pyrimidinedione
231. 1,3-dimethyl-b-{4-<3-[4-nitro-2-(2-pyridinecarbonyl)phenylthio]propyl>piperazin-1-yl}-2,4(1H,3H)-pyrimidinedione
232. 3-methyl-6-{4-[3-(4-nitro-2-benzoylphenoxy)propyl]piperazin-1-yl}-2,4(1H,3H)-pyrimidinedione
233. 1,3-dimethyl-6-{2-[3-(2-benzoyl-4-nitrophenoxy)propylamino]ethylamino}-2,4(1H,3H)-pyrimidinedione
234. 1,3-dimethyl-6-{2-[N-ethyl-3-(4-benzoyl-2-nitrophenoxy)propylamino]ethylamino-2,4(1H,3H)-pyrimidinedione
235. 1,3-dimethyl-6-{4-[2-(2-benzoyl-4-nitrophenylthio)ethyl]piperazin-1-yl}-2,4(1H,3H)-pyrimidinedione
236. 1,3-dimethyl-6-[4-(2-benzoyl-4-nitrophenyl)piperazin-1-yl]-2,4(1H,3H)-pyrimidinedione
237. 1,3-dimethyl-6-{3-[4-nitro-2-(3-pyridinecarbonyl)phenylamino]propylamino}-2,4(1H,3H)-pyrimidinedione
238. 1,3-dimethyl-6-[3-(2-benzoyl-4-nitrophenylamino)propylamino]-2,4(1H,3H)-pyrimidinedione
239. 1,3-dimethyl-6-[2-(2-benzoyl-4-nitrophenylamino)ethylamino]-2,4(1H,3H)-pyrimidinedione
240. 1,3-dimethyl-6-{2-[4-nitro-2-(3-pyridinecarbonyl)phenylamino]ethylamino}-2,4(1H,3H)-pyrimidinedione
241. 1,3-dimethyl-6-{4-[2-(2-benzoyl-4-nitrophenyl)ethyl]piperazin-1-yl}-2,4(1H,3H)-pyrimidinedione
242. 1,3-dimethyl-6-{4-[(2-benzoyl-4-nitrophenyl)methyl]piperazin-1-yl}-2,4(1H,3H)-pyrimidinedione
243. 1,3-dimethyl-6-{2-[(2-benzoyl-4-nitrophenyl)methylamino]ethylamino}-2,4(1H,3H)-pyrimidinedione
244. 1,3-dimethyl-6-{4-[3-(4-benzoyl-2-nitrophenyl)propyl]piperazin-1-yl}-2,4(1H,3H)-pyrinidinedione 245. 1,3-dimethyl-6-{4-[2-(4-benzoyl-2-nitrophenyl)ethyl]piperazin-1-yl}-2,4(1H,3H)-pyrimidinedione
246. 1,3-dimethyl-6-{4-[3-(3-methyl-4-nitrophenyloxy)propyl]piperazin-1-yl}-2,4(1H,3H)-pyrimidinedione
247. 1,3-dimethyl-6-{4-[3-(4-chloro-2-nitrophenyloxy)propyl]piperazin-1-yl}-2,4(1H,3H)-pyrimidinedione
248. 1,3-dimethyl-6-{4-[3-(2-chloro-4-nitrophenyloxy)propyl]piperazin-1-yl}-2,4(1H,3H)-pyrimidinedione
249. 1,3-dimethyl-6-{4-[3-(4-methanesulfonamido-2-nitrophenyloxy)propyl]piperazin-1-yl}-2,4(1H,3H)-pyrimidinedione
250. 1,3-dimethyl-6-{4-[3-(4-acetamido-2-nitrophenyloxy)propyl]piperazin-1-yl}-2,4(1H,3H)-pyrimidinedione
251. 1,3-dimethyl-6-{4-[3-(2-hydroxy-5-nitrophenyloxy)propyl]piperazin-1-yl}-2,4(1H,3H)-pyrimidinedione
252. 1,3-dimethyl-6-{4-[3-(2-allyloxy-5-nitrophenyloxy)propyl]piperazin-1-yl}-2,4(1H,3H)-pyrimidinedione
253. 1,3-dimethyl-6-{4-[3-(4-methylthio-2-nitrophenyloxy)propyl]piperazin-1-yl}-2,4(1H,3H)-pyrimidinedione
254. 1,3-dimethyl-6-{4-<3-[2-(α-hydroxybenzyl)-4-nitrophenyloxy]propyl>piperazin-1-yl}-2,4(1H,3H)-pyrimidinedione
255. 1,3-dimethyl-6-{4-[3-(3-trifluoromethyl-4-nitrophenyloxy)propyl]piperazin-1-yl}-2,4(1H,3H)-pyrimidinedione
256. 1,3-dimethyl-6-{4-[3-(2-methoxycarbonyl-4-nitrophenylxoy)propyl]piperazin-1-yl}-2,4(1H,3H)-pyrimidinedione
257. 1,3-dimethyl-6-{4-[3-(2-carboxy-4-nitrophenyloxy)propyl]piperazin-1-yl}-2,4(1H,3H)-pyrimidinedione
258. 1,3-dimethyl-6-{4-[3-(2-amino-4-nitrophenylxoy)propyl]piperadin-1-yl}-2,4(1H,3H)-pyrimidinedione
259. 1,3-dimethyl-6-{4-[3-(4-methoxycarbonyl-2-nitrophenyloxy)propyl]piperazin-1-yl}-2,4(1H,3H)-pyrimidinedione
260. 1,3-dimethyl-6-{4-[3-(2-cyano-4-nitrophenyloxy)propyl]piperazin-1-yl}-2,4(1H,3H)-pyrimidinedione
261. 1,3-dimethyl-6-{4-[3-(2-cyano-4-nitrophenylamino)propyl]piperazin-1-yl}-2,4(1H,3H)-pyrimidinedione
262. 1,3-dimethyl-6-{4-[3-(2-chloro-4-nitrophenylamino)propyl]piperazin-1-yl}-2,4(1H,3H)-pyrimidinedione
263. 1,3-dimethyl-6-{4-[3-(2-methoxy-5-nitrophenyloxy)propyl]piperazin-1-yl}-2,4(1H,3H)-pyrimidinedione
264. 1,3-dimethyl-6-{4-[3-(2-allyloxy-4-nitrophenyloxy)propyl]piperazin-1-yl}-2,4(1H,3H)-pyrimidinedione
265. 1,3-dimethyl-6-{4-[3-(2hydroxy-4-nitrophenyloxy)propyl]piperazin-1-yl}-2,4(1H,3H)-pyrimidinedione
266. 1,3-dimethyl-6-{4-[3-(2-benzylamino-4-nitrophenyloxy)proipyl]piperazin-1-yl}-2,4(1H,3H)-pyrimidinedione
267. 1,3-dimethyl-6-{4-[3-(2-melthoxy-4-nitrophenyloxy)propyl]piperazin-1-yl}-2,4(1H,3)-pyrimidinedione
268. 1,3-dimethyl-6-{4-[3-(2,6-dichloro-4-nitrophenyloxy)propyl]piperazin-1-yl}-2,4(1H,3H)-pyrimidinedione As shown in the general formula (1) above, compounds of the present invention have a basic backbone in which the phenyl and pyrimidinedione parts are linked by a structure comprising mainly an alkyl chain containing at least two nitrogen atoms. This basic backbone structure is believed to be responsible for the pharmaceutical effects.

When the compounds shown by the general formula (1) above were applied to the following arrhythmia pathological models, all the compounds demonstrated efficacy.

Atrial fibrillation model

Atrial fibrillation model animals were made according to the method of A. L. Goldberger et al. (International Journal of Cardiology, 13, 47–55, 1986) by anesthetizing adult mongrel dogs with pentobarbital sodium (30 mg/kg, intravenously). Using these atrial fibrillation model animals, the effects of the compounds of the present invention on the atrial fibrillation model were investigated by administering the compounds intravenously at a dose of 0.1–10 mg/kg. As a result, all of the compounds according to the present invention were confirmed to have therapeutic effects on atrial fibrillation.

Ventrical tachycardia model

Adult mongrel dogs were anesthetized with pentobarbital sodium (30 mg/kg. intravenously). A left thoracotomy was performed in the fourth intercostal space under artificial respiration, and the left anterior descending coronary artery was ligated at the border of the atrial appendage. The blood was recirculated for 120 minutes after the ligation so that an cardiac infarction lesion was formed to readily induce tachycardia in each animal.

Thereafter, the ventricular tachycardia model animals were made by inducing ventricular tachycardia according to the method of Lynch (Journal of Cardiovascular Pharmacology, 6, 1132–1141, 1984).

Using these model animals, the compounds of the present invention were confirmed to have therapeutic effects on ventricular tachycardia when administered intravenously at a dose of 0.1–3 mg/kg.

The compounds according to the present invention have marked therapeutic effects on the arrhythmia pathology model, i.e. atrial fibrillation model and ventricular tachycardia model; thus they are useful for the treatment and prevention of arrhythmia.

Furthermore, the effects of the compounds of the present invention on cardiac functions were experimentally investigated and the following results were obtained.

Mongrel dogs (body weights: 8–15 kg) were anesthetized with pentobarbital sodium (30 mg/kg, intravenously). A microsensor catheter was inserted through the common carotid artery into the left ventricle of each animal so that primary differential values (dp/dt) of the inner pressure of the left ventricle and electrocardiograms were recorded. The compounds of the present invention were administered intravenously to the dogs (1 mg/kg) and changes in the dp/dt and electrocardiograms were investigated.

As a result, it was revealed that the compounds of the present invention significantly increased the values of dp/dt max and significantly extended QTc on the electrocardiograms.

Consequently, the compounds according to the present invention were confirmed to have an antiarrythmic action and particularly to be useful as Class III type antiarrythmic agents. Furthermore, the significant increase in dp/dt max demonstrated that the compounds according to the present invention have a positive inotropic action and accordingly they are useful as therapeutic agents for cardiac insufficiency.

As mentioned above, in general, most of patients with arrhythmia have deficiency in cardiac functions. In the case where, for example, antiarrythmic agents classified in Class I or II are given to such patients, the greatest care has to be taken for use because these agents exert more or less antiarrythmic action as well as a negative inotropic action (action to further repress cardiac functions) (Eivind S. Platous, Journal of Cardiovascular Pharmacology, 8(3), 459, 1986).

On the contrary, as mentioned above, the compounds according to the present invention have a positive inotropic action to significantly increase the dp/dt max, as well as an antiarrythmic action. Accordingly, they are expected to provide satisfactory results to the patients with arrhythmia, whose cardiac functions are depressed.

Representative examples of processes for the production of the compounds of the general formula (1) according to the present invention will be demonstrated hereinafter; however, these examples are not to be construed to limit the scope of the invention.

Among the compounds of the general formula (1) described above, a compound of the following general formula (2) can be produced according to a method containing the following step (a).

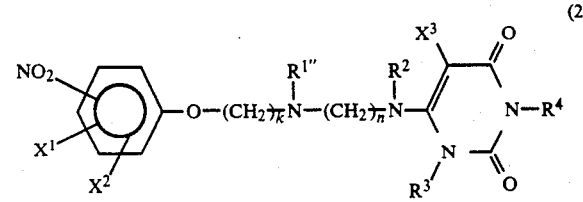

(2)

[In the formula (2), $R^{1''}$ and $R^2$ each independently represents a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group), or $R^{1''}$ and $R^2$ may be so linked as to make an alkylene chain and thus form a heterocyclic structure; and $X^1$, $X^2$, $R^2$, $R^3$, $R^4$, k and n are defined as in the formula (1).

Step (a)

A compound of the following general formula (9)

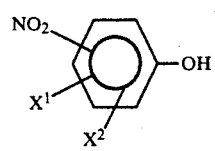

(9)

[in which $X^1$ and $X^2$ are defined as in the general formula (1) above]
and a compound of the following general formula (10)

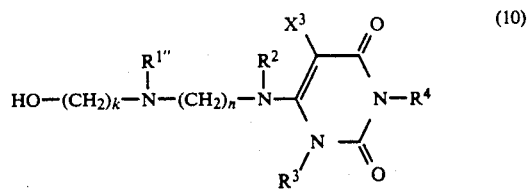

(10)

[in which $R^{1''}$ is defined as in the general formula (2) above and $R^2$, $R^3$, $R^4$, $X^3$, n and k are defined as in the general formula (1) above]
are allowed to react in the presence of a dehydratecondensing agent in a solution using an appropriate solvent or in a suspension using an appropriate dispersing agent (Application of Mitunobu reaction; O. Mitunobu, Synthesis, 1–28, 1981), thereby the compound of the general formula (2) above being obtained.

The reaction is carried out at or below the reflux temperature of the solvent or dispersing agent used for the reaction. For example, the temperature in the range $-10°$ to $80°$ C. is selected.

Examples of the dehydratecondensing agent to be used in this reaction include various dehydratecondensing agents used ordinarily for ether bond formation. Among them, mixed condensing agents of diethylazodicarboxylate and triphenylphosphine are preferably used.

Any solvent or dispersing agent can be used for the reaction provided it is inactive to the reaction. For example, tetrahydrofuran, dimethylformamide, chloroform, dichloromethane or dioxane can be used.

Next, among the compounds of the general formula (1) above, a compound of the following general formula (4) can be produced according to a method containing the following step (b).

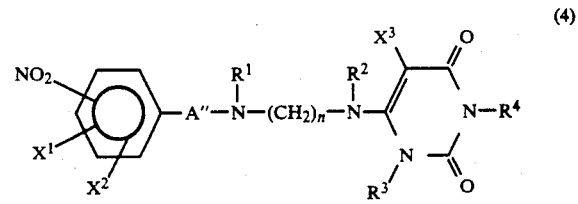

(4)

[In the formula (4), A'' represents $—B''—(CH_2)_k—$ or

in which B'' represents an oxygen or sulfur atom or

$R^5$ represents a hydrogen atom, a lower alkanoyl, lower alkylsulfonyl or lower alkyl group, or $R^1$ and $R^5$ may be so linked as to make an alkylene chain and thus form a heterocyclic structure;

k represents an integral number, 2, 3 or 4; and $X^1$, $X^2$, $R^1$, $R^2$, $R^3$, $R^4$, $X^3$ and n are defined as in the formula (1) above].

Step (b)

A compound of the following general formula (11)

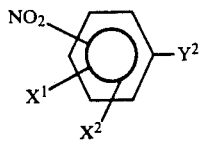
(11)

[in which $Y^2$ represents a halogen atom and $X^1$ and $X^2$ are defined as in the general formula (1) above]
and a compound of the following general formula (12)

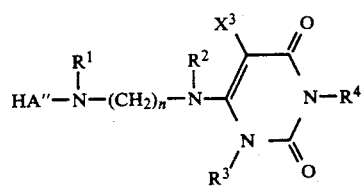
(12)

[in which A" is defined as in the general formula (4) above and $R^1$, $R^2$, $R^3$, $R^4$, $X^3$ and n are defined as in the general formula (1) above]
are allowed to react by mixing without a solvent, dissolving using an appropriate solvent or suspending using an appropriate dispersing agent, thereby the compound of the general formula (4) above being obtained.

The reaction is carried out at a temperature in the range from room temperature to the reflux temperature of the reaction mixture. For example, a temperature in the range between 20°–150° C. is preferably selected.

The reaction can be more preferably conducted in the presence of a base in the reaction mixture.

Any solvent or dispersing agent can be used for the reaction provided it is inactive to this reaction. For example, alcohols such as methanol and ethanol, tetrahydrofuran, dimethylformamide, chloroform, dichloromethane, dioxane, benzene and dimethylsufonoxide can be used.

Furthermore, examples of the base effective to facilitate this reaction include triethylamine, pyridine, potassium carbonate, sodium carbonate and sodium hydroxide.

Next, among the compounds of the general formula (1) above, a compound of the following general formula (3) can be produced according to a method containing the following step (c).

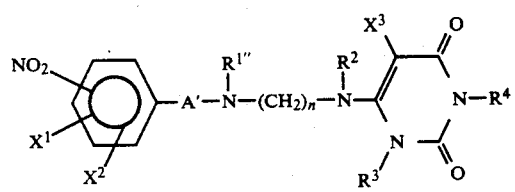
(3)

[In the formula (3), A' represents —(CH$_2$)$_m$—, —B'—(CH$_2$)$_k$— or

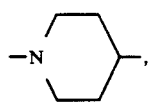, in which B' represents an oxygen or sulfur atom or

;

$R^{5'}$ represents a hydrogen atom, a lower alkanoyl, lower alkylsulfonyl or lower alkyl group (but does not form a heterocyclic structure with $R^{1''}$);
m represents an integral number, 0, 1, 2, 3 or 4;
k represents an integral number, 2, 3 or 4;
$R^{1''}$ is defined as in the general formula (2) above; and $R^2$, $R^3$, $R^4$, $X^1$, $X^2$, $X^3$ and n are defined as in the general formula (1) above.

Step (c)
A compound of the following general formula (13)

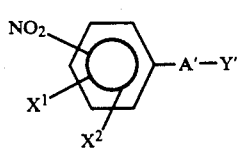
(13)

[in which $Y^1$ represents a halogen atom or a substituting group that can be an eliminating group in the reaction with a compound of the general formula (14) below, $X^1$ and $X^2$ are defined as in the general formula (1) above, and A' is defined as in the general formula (3) above]
and a compound of the following general formula (14)

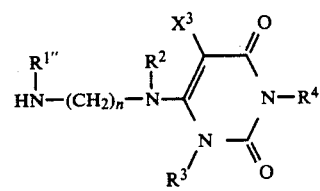
(14)

[in which $R^{1''}$ is defined as in the general formula (2) above and $R^2$, $R^3$, $R^4$, $X^3$ and n are as defined in the general formula (1) above]
are allowed to react by mixing without a solvent, dissolving using an appropriate solvent or suspending using an appropriate dispersing agent, thereby the compound of the general formula (3) above being obtained.

The reaction is carried out at a temperature in the range from room temperature to the reflux temperature of the reaction mixture. For example, a temperature in the range between 20° and 170° C. is preferably selected.

The reaction can be more preferably conducted in the presence of a base in the reaction mixture.

Any solvent or dispersing agent can be unlimitedly used for the reaction provided it is inactive to this reaction. For example, any of those exemplified in the step (b) above can be used.

Furthermore, examples of the base effective to facilitate this reaction include those exemplified in the step (b) above.

The compounds of the general formula (1) above can also be produced according to a method containing the following step (d):

A compound of the following general formula (15)

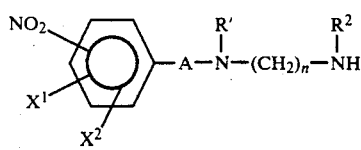
(15)

[in which A, $X^1$, $X^2$, $R^1$, $R^2$ and n are defined as in the general formula (1) above]
and a compound of the following general formula (16)

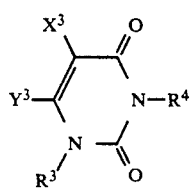
(16)

[in which $Y^3$ is a halogen atom or a substituting group that can be an eliminating group in the reaction with the compound of the general formula (15) above and $R^3$, $R^4$ and $X^3$ are defined as in the general formula (1) above]
are allowed to react by mixing without a solvent, dissolving using an appropriate solvent or suspending using an appropriate dispersing agent, thereby the compound of the general (1) above being obtained.

The reaction can be carried out at a temperature in the range from room temperature to the reflux temperature of the reaction mixture. For example, a temperature in the range between 20° and 150° C. is preferably selected.

The reaction can be more preferably conducted in the presence of a base in the reaction mixture.

Any solvent or dispersing agent can be used for the reaction provided it is inactive to this reaction. For example, any of those exemplified in the step (b) above can be used.

Furthermore, examples of the base useful to facilitate this reaction include those exemplified in the step (b) above.

Next, among the compounds of the general formula (1) above, a compound of the following general formula (5) can be produced according to a method containing the following step (e).

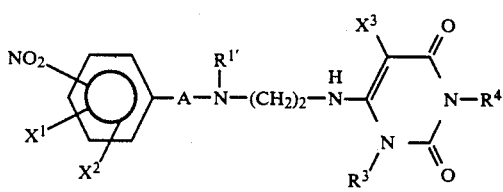
(5)

[In the formula (5), A represents —(CH$_2$)$_m$—, —B—(CH$_2$)$_k$—, —D—(CH$_2$)$_l$—,

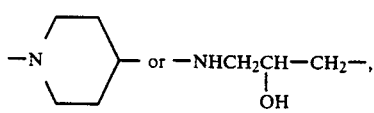

wherein B represents an oxygen or sulfur atom,

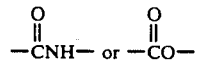

and D represents

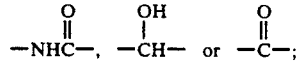

$R^{1'}$ represents a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group), or may be so linked with $R^5$ as to make an alkylene chain and thus form a heterocyclic structure but not linked with any of other sites to form heterocyclic structure;

$R^5$ represents a hydrogen atom, a lower alkanoyl, lower alkylsulfonyl or lower alkyl group; and $X^1$, $X^2$, $X^3$, $R^3$ and $R^4$ are defined as in the formula (1) above.

Step (e)
A compound of the following general formula (17)

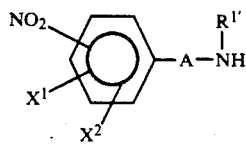
(17)

[in which $X^1$ and $X^2$ are defined as in the general formula (1) above and A and $R^{1'}$ are defined as in the general formula (5) above]
and a compound of the following general formula (18)

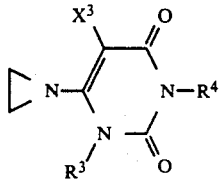
(18)

[in which $R^3$, $R^4$ and $X^3$ are defined as in the general formula (1) above]
are allowed to react by mixing without a solvent, dissolving using an appropriate solvent or suspending using an appropriate dispersing agent, thereby the compound of the general formula (5) above being obtained.

The reaction is carried out at a temperature in the range from room temperature to the reflux temperature of the reaction mixture. For example, a temperature in the range between 20° C. and 180° C. is preferably selected.

Furthermore, the reaction can be more preferably conducted in the presence of an acid catalyst in the reaction mixture.

Any solvent or dispersing agent can be used for the reaction provided it is inactive to this reaction. For example, any of those exemplified in the step (b) above can be used.

Furthermore, examples of the above-mentioned acid catalyst include p-toluenesulfonic acid and an acidic ion exchange resin (for example, Amberlist ® (Rhome and Haas, USA, e.g., Amberlist 15 ®)).

Among the compounds of the general formula (1) above, a compound of the following general formula (7) can also be produced according to a method containing the following step (f).

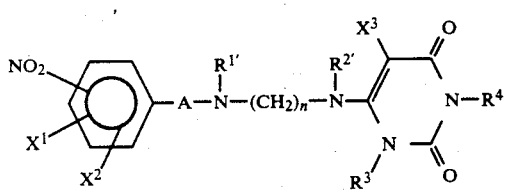
(7)

[In the formula (7), A represents $-(CH_2)_m-$, $-B-(CH_2)_k-$, $-D-(CH_2)_l-$,

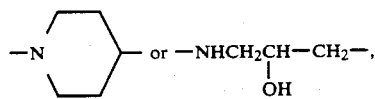

wherein B represents an oxygen or sulfur atom

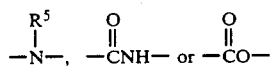

and D represents

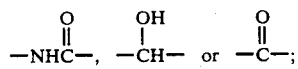

$R^{1'}$ and $R^{2'}$ each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group);

$R^5$ represents a hydrogen atom, a lower alkanoyl, lower alkylsulfonyl or lower alkyl group; or $R^{1'}$ and $R^5$ may be so linked as to make an alkylene chain and thus form a heterocyclic structure; and $X^1$, $X^2$, $X^3$, $R^3$, $R^4$, m, k, l and n are defined as in the general formula (1) above].

Step (f)

A compound of the general formula (17) above and a compound of the following general formula (19)

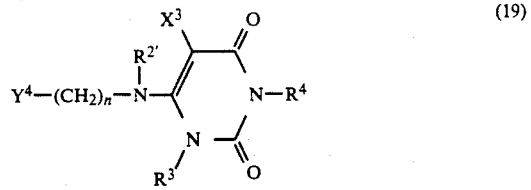
(19)

[in the formula (19), $R^{2'}$ represents a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group) and is not so linked with $R^{1'}$ to form any heterocyclic ring;

$R^3$, $R^4$, $X^3$ and n are defined as in the general formula (1) above; and $Y^4$ represents a halogen atom or a substituting group that can be an eliminating group in the reaction with a compound of the general formula (17) above]

are treated in the same manner as in the step (c) above, thereby the compound of the general formula (7) above being obtained.

Among the compounds of the general formula (1) above, a compound of the following general formula (8) can also be produced according to a method containing the following step (g).

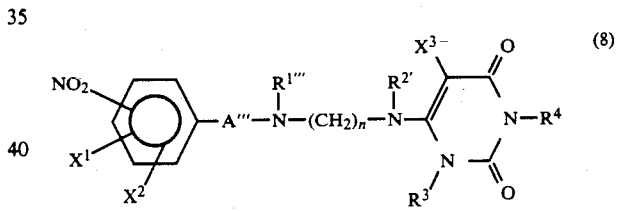
(8)

[in the formula (8), A''' represents $-(CH_2)_m-$, $-B'''-(CH_2)_k-$, $-D-(CH_2)_l-$,

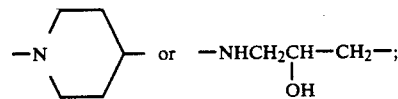

B''' represents an oxygen or sulfur atom,

D represents

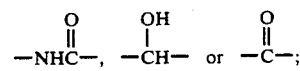

$R^{1'''}$ and $R^{2'}$ each independently represent a hydrogen atom, a lower alkyloxycarbonyl, unsaturated lower alkyl or lower alkyl group (any one of the hydrogen atoms of said alkyl groups may be replaced by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group and a lower alkyloxycarbonyl group), $R^{1'''}$ does not link to other sites including $R^{2'}$ or $R^{5'}$;

$R^{5'}$ is defined as in the general formula (3) above; and $X^1$, $X^2$, $X^3$, A, $R^3$, $R^4$ and n are defined as in the formula (1) above].

Step (g)

A compound of the following general formula (20)

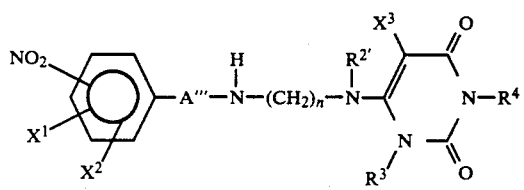

[in which A''' and $R^{2'}$ are defined as in the general formula (8) above; and $X^1$, $X^2$, $X^3$, $R^3$, $R^4$ and n are defined as in the general formula (1) above]
and a compound of the following general formula (21)

$$R^{1'''}—Y^4 \qquad (21)$$

[in which $Y^4$ represents a halogen atom or a substituting group that can be eliminated in the reaction with a compound of the general formula (20) above and $R^{1'''}$ is defined as in the general formula (8) above]
are treated in the same manner as in the step (c) above; thereby the compound of the general formula (8) above being obtained.

Further, for $Y^1$, $Y^3$ and $Y^4$ in the compounds to be used in the production steps above, examples of the substituting group that can be an eliminating group include arylsulfonyloxy group such as p-toluenesulfonyloxy group and alkylsulfonyloxy group such as methanesulfonyloxy group.

The relationships among $R^1$, $R^{1'}$, $R^{1''}$, $R^{1'''}$, $R^2$, $R^{2'}$, $R^5$ and $R^{5'}$ can be summarized as follows:

$R^1$ may link to $R^2$ or $R^5$ as to form a heterocyclic structure. $R^{1'}$, may link only to $R^5$. $R^{1''}$ may link only to $R^2$. $R^{1'''}$, $R^{2'}$, and $R^{5'}$ form no linkage, i.e., no heterocyclic structure with other sites.

$R^1$, $R^{1'}$, $R^{1''}$, & $R^{1'''}$, $R^2$ & $R^{2'}$ and $R^5$ & $R^{5'}$ are synonymously defined except their above relationships.

A compound of the general formula (18) above can be produced according to a method containing the following step (h).

Step (h)

A compound of the general formula (16) above and 2-aminoethanol are treated in the same manner as in the step (d) above so that a compound of the following general formula (22) can be prepared.

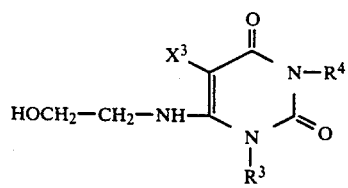

[In the formula (21), $X^3$, $R^3$ and $R^4$ are as defined as in the general formula (1) above].

The resultant compound is either sulfonated using methanesulfonyl chloride, p-toluenesulfonyl chloride or the like, or halogenized using thionyl chloride or phosphorus tribromide. The compound thus obtained is mixed in the presence of a base such as sodium hydroxide or sodium hydride and in a solvent such as acetonitrile, chloroform, benzene dimethylsulfonoxide and methanol at room temperature or under heating, thereby a compound of the general formula (18) above being obtained.

A pharmaceutically acceptable acid addition salt of a compound of the general formula (1) above can be produced by allowing the compound of the general formula (1) above to react in water or an organic solvent or the mixture thereof, for example, with an inorganic or organic acid such as hydrochloric acid, hydrobromic acid, phosphoric acid, sulfuric acid, acetic acid, citric acid, maleic acid, fumaric acid, oxalic acid or methanesulfonic acid.

When the compounds of the general formula (1) above according to the present invention and the acid addition salts thereof are used as a therapeutic agent to treat patients with cardiac malfunctions such as arrhythmia and cardiac insufficiency, the amount and form of doses are different depending on the properties of the compound of the present invention to be used as an active ingredient and on the symptoms of the patients to be treated. For example, the amount in the range from 10 to 1,000 mg/day, preferably 10–500 mg/day for an adult can be orally administered in forms such as tablets, granules, powders, suspensions and capsules, or parenterally in forms of depositories, injections, fluids for infusion, inhalations or plasters. Daily doses by injection for adults, in particular phleboclysis, may range from 1–1,000 mg, preferably 1–300 mg.

General processes for producing pharmaceutical compositions of the present invention include a method in which the compound of the present invention is dissolved in an appropriate amount in an oil selected from the group consisting of cotton seed oil, corn oil, peanut oil, olive oil and the like so as prepare non-aqueous injections; a method in which the compound of the present invention is either suspended or emulsified in water in the presence of an appropriate surfactant so as to prepare aqueous injections; or a method in which the compound of the present invention is prepared in a tablet form by adding lactose, crystallized cellulose, corn starch or the like and finally adding magnesium stearate. However, the pharmaceutical preparations of the present invention can be prepared by any ordinary method in addition to the methods exemplified above.

Useful antiarrythmic agents, therapeutic agents for cardiac insufficiency can be provided by the compounds of the present invention.

The following Examples demonstrate the present invention more in detail; however, it should be understood that they are not intended to limit the invention.

EXAMPLE 1

Preparation of 1,3-dimethyl-6-[4-(4-nitrophenyl)piperazin-1-yl]-2,4(1H,3H)-pyrimidinedione (compound 1):

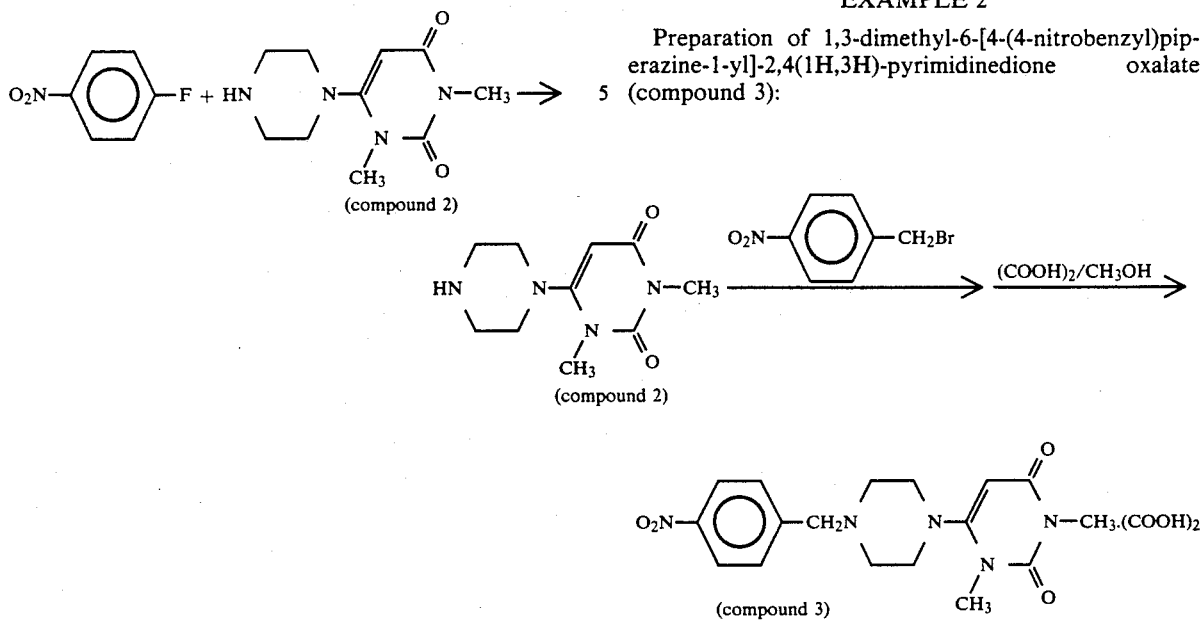

EXAMPLE 2

Preparation of 1,3-dimethyl-6-[4-(4-nitrobenzyl)piperazine-1-yl]-2,4(1H,3H)-pyrimidinedione oxalate (compound 3):

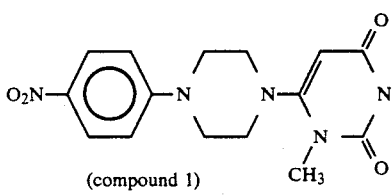

First, 0.48 g of 4-nitrobenzyl bromide, 0.5 g of 1,3-dimethyl-6-(piperazin -1-yl)-2,4(1H,3H)-pyrimidinedione (compound 2) and 0.5 ml of triethylamine were suspended in 5 ml of isopropanol, and the resulting suspension was then heated under reflux for 8 hours. Afterward, the used solvent was removed from the resulting reaction mixture by distillation under reduced pressure, and the residue was dissolved in chloroform and was then washed with water. The washed organic layer was dried over anhydrous sodium sulfate. Furthermore, the dried organic layer was subjected to distillation under reduced pressure so as to remove the solvent therefrom, and the residue was then purified through a silica gel column chromatograph (chloroform/methanol=50/1 to 20/1 in terms of volume ratio) in order to obtain 0.88 g of 1,3-dimethyl-6-[4-(4-nitrobenzyl)piperazin-1-yl]-2,4(1H,3H)-pyrimidinedione.

Analytical results of the pyrimidinedione derivative thus obtained:

NMR (CDCl$_3$), δppm: 2.6 (m, 2H), 3,0 (m, 2H), 3.22, 3.34 (Sx2, 3Hx2), 3.36 (S, 2H), 5.14 (S, 1H) 7.55, 8.17 (dx2, 2Hx2)

Next, this pyrimidinedione derivative was treated with an oxalic acid/methanol solution in an ordinary manner, thereby preparing 1,3-dimethyl-6-[4-(4-nitrobenzyl)piperazin-1-yl]-2,4(1H,3H)-pyrimidinedione oxalate (compound 3).

Analytical results of the crystalline compound 3 thus obtained:

Melting point: 211°–212° C. (decomposed)

IR$\nu$KBr$_{max}$ (cm$^{-1}$): 2950, 1720, 1670, 1650 1620, 1520, 1360, 760

Values of elemental analysis [as C$_{17}$H$_{21}$N$_5$O$_4$·(COOH)$_2$]

Calcd. (%): C 50.78; H 5.16; N 15.58

Found (%): C 50.70; H 5.44; N 15.77

EXAMPLE 3

Preparation of 1,3-dimethyl-6-{2-<N-ethyl-N-[3-(4-nitrophenyl)propyl]amino>ethylamino}-2,4(1H,3H)-pyrimidinedione hydrochloride (compound 4):

In the first place, 0.36 ml of 4-fluoronitrobenzene, 1 g of sodium bicarbonate and 0.5 g of 1,3-dimethyl-6-(piperazin-1-yl)-2,4(1H,3H)-pyrimidinedione (compound 2) were added to 5 ml of dimethyl sulfoxide, and reaction was then performed at 100° C. for 3 hours. Afterward, the reaction mixture was poured into 50 ml of water and was then extracted with chloroform.

Next, the chloroform extract was washed with water and was then dried over anhydrous magnesium sulfate, and the used solvent was distilled off under reduced pressure. The resulting residue was then purified with a silica gel column chromatograph (chloroform/methanol=40:1 in terms of volume ratio) in order to obtain 0.44 g of 1,3-dimethyl-6-[4-(4-nitrophenyl)piperazin-1-yl]-2,4(1H,3H)-pyrimidinedione (compound 1).

Analytical results of the resulting crystalline compound 1:

Melting point: 249°–250° C.

IR$\nu$KBr$_{max}$ (cm$^{-1}$): 1700, 1660, 1610, 1530 1340, 840

NMR (d$_6$-DMSO), δppm: 8.13, 6.98 (dx2, 2Hx2), 5.23 (s, 1H), 3.23, 3.36 (Sx2, 3Hx2), 3.0 (m, 8H)

Values of elemental analysis (as C$_{16}$H$_{19}$N$_5$O$_4$)

Calcd. (%): C 55.65; H 5.55; N 20.28

Found (%): C 55.34; H 5.76; N 20.46

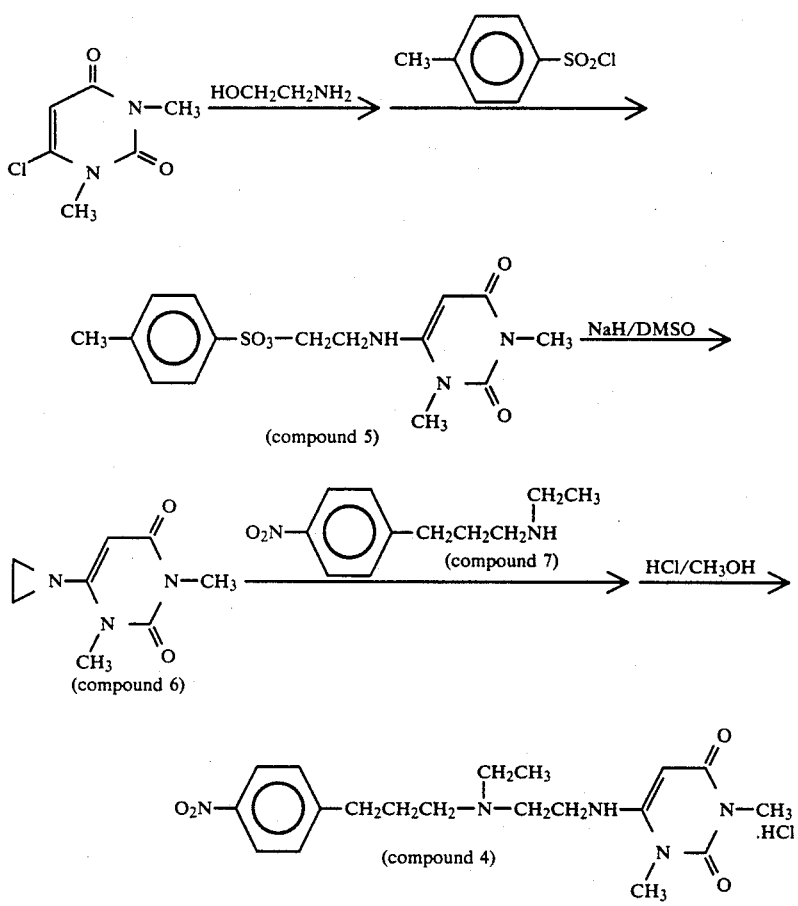
(compound 5)

(compound 6)

(compound 4)

(1) Preparation of 1,3-dimethyl-6-[2-(p-toluenesulfonyloxy)ethylamino]-2,4(1H,3H)-pyrimidinedione (compound 5):

First, 35.0 g of 2-amino-ethanol was heated up to 90° C. and then taken out from the oil bath, and 50.0 g of 6-chloro-1,3-dimethyl-2,4(1H,3H)-pyrimidinedione was added thereto, so that reaction was performed therebetween. In this case, the addition was carried out at such a velocity that the reaction temperature was maintained in the range of to 110° C. After completion of the addition, the reaction mixture was stirred for 10 minutes, and 300 ml of dioxane/methanol (which was 10/1 in terms of volume ratio) was then added thereto. Afterward, the mixture was allowed to stand overnight. The resulting crystals were then washed with a small amount of dioxane, followed by drying to obtain 49.0 g of white crystals of 1,3-dimethyl-6-(2-hydroxyethylamino)-2,4(1H,3H)-pyrimidinedione.

Next, 200 ml of a pyridine suspension containing 49.0 g of the above-mentioned white crystals was cooled to −5° C., and 40.0 g of p-toluenesulfonyl chloride was then added thereto at such a velocity that the reaction temperature does not rise up to 5° C. or more. In order for the suspension of the reaction mixture to disappear completely, 51.0 g of p-toluenesulfonyl chloride was further used.

Moreover, the reaction mixture was then poured into 1.5 liters of ice water containing 70 g of potassium carbonate and was then allowed to stand overnight. The resulting crystals were collected by filtration, then washed with water, and dried under reduced pressure, thereby preparing 50.5 g of light yellow crystals of 1,3-dimethyl-6-[2-((p-toluenesulfonyloxy)ethylamino]-2,4(1H,3H)-pyrimidinedione (compound 5).

Analytical results of the crystalline compound 5 thus obtained:

Melting point: 146.0°–149.0° C.

IR$\nu$KBr$_{max}$ (cm$^{-1}$): 3270, 1682, 1615, 1550, 1480, 1435, 1360, 1190, 1178, 1010, 903, 780

(2) Preparation of 6-(1-aziridinyl)-1,3-dimethyl-2,4(1H,3H)-pyrimidinedione (compound 6):

To 150 ml of an anhydrous dimethyl sulfoxide solution containing 47.2 g of the above prepared compound 5 was slowly added 6.24 g of sodium hydride (60% dispersion in mineral oil) at room temperature. The resulting liquid mixture was then stirred vigorously at room temperature for hours and was cooled, and a small amount of water was then added thereto in order to bring the reaction to an end. Afterward, this mixture was poured into 1 liter of water containing 70 g of potassium carbonate and was then extracted with 200 ml of chloroform three times. The combined organic layers were then dried over anhydrous sodium sulfate and was concentrated, and 300 ml of ether was added to the resulting concentrate. Afterward, the mixture was allowed to stand overnight.

Light yellow crystals which had been deposited by the overnight standing were collected by filtration and were then washed with ether, followed by drying under reduced pressure to obtain 15.2 g of 6-(1-aziridinyl)-1,3-dimethyl-2,4(1H,3H)-pyrimidinedione (compound 6).

Analytical results of the crystalline compound 6 thus obtained:

Melting point: 126.0°–126.5° C.

IRνKBr$_{max}$ (cm$^{-1}$): 1705, 1650, 1612, 1470, 1440, 1305, 1160, 783, 490

$^1$H-NMR (CDCl$_3$), δppm: 2.34 (s, 4H), 3.35 (s, 3H), 3.56 (s, 3H), 5.25 (s, 1H)

(3) Preparation of 1,3-dimethyl-6-{2-<N-ethyl-N-[3-(4nitrophenyl)propyl]amino>ethylamino}-2,4(1H,3H)pyrimidinedione hydrochloride (compound 4):

In 5 ml of chloroform were dissolved 1.28 g of N-ethyl-N-[3-(4-nitrophenyl)propyl]amine (compound 7) and 1.11 g of the above prepared 6-(1-aziridinyl)-1,3-dimethyl-2,4(1H,3H)-pyrimidinedione (compound 6), and the resulting mixture was then concentrated under reduced pressure. Afterward, 10 mg of Amberlist 15 (made by Rohm & Haas Co.) was added to the residue (concentrate), and the mixture was then heated at 80° C. for 1 hour.

Next, the resulting reaction mixture was dissolved in 20 ml of ethyl acetate, and the Amberlist was removed therefrom by filtration. Afterward, 30 ml of n-hexane was added to the filtrate.

The solution was allowed to stand overnight, and the deposited light yellow crystals were then collected by filtration. After washing with ether, the crystals were dried under reduced pressure to obtain 2.20 g of 1,3-dimethyl-6-2- N-ethyl-N-[3-(4-nitrophenyl)propyl]amino-ethylamino-2,4(1H,3H)-pyrimidinedione.

This product was further recrystallized from ethyl acetate and n-hexane, followed by filtering, washing and drying in order to obtain 1.85 g of light yellow crystals.

Analytical results of the crystalline pyrimidinedione derivative thus obtained:

IRνKBr$_{max}$ (cm$^{-1}$): 3310, 2940, 1692, 1620, 1600, 1545, 1515, 1345, 1205, 770, 755

$^1$H-NMR (CDCl$_3$), δppm: 1.07 (t, 3H, J=7.5 Hz), 1.90 (m, 2H), 2.17-3.27 (m, 10H), 3.37 (s, 3H), 3.44 (s, 3H), 4.90 (s, 1H), 5.64 (brs, 1H), 7.47 (m, 2H), 8.30 (m, 2H)

Values of elemental analysis (as C$_{19}$H$_{27}$N$_5$O$_4$)
Calcd. (%): C 58.60; H 6.99; N 17.98
Found (%): C 58.61; H 7.41; N 17.57

Moreover, the light yellow crystals which had been recrystallized from ethyl acetate and n-hexane were treated with hydrochloric acid/methanol in a usual manner in order to obtain an amorphous powder of 1,3-dimethyl-6-{2-<N-ethyl-N-[3-(4-nitrophenyl)-propyl]amino)ethylamino<ethylamino}-2,4(1H,3H)-pyrimidinedione hydrochloride (compound 4).

Analytical results of the amorphous powder of the compound 4:

IRνKBr$_{max}$ (cm$^{-1}$): 3450, 1705, 1608, 1513, 1345
Values of elemental analysis (as C$_{19}$H$_{27}$N$_5$O$_4$·HCl)
Calcd. (%): C 53.58; H 6.63; N 16.44; Cl 8.33
Found (%): C 53.11; H 53.11; H 6.81; N 16.12; Cl 7.95

EXAMPLE 4

Preparation of 1,3-dimethyl-6-{2-<N-(2-hydroxyethyl)-N-[3-(4-nitrophenyl)propyl]amino>ethylamino}-2,4(1H,3H)-pyrimidinedione fumarate (compound 8):

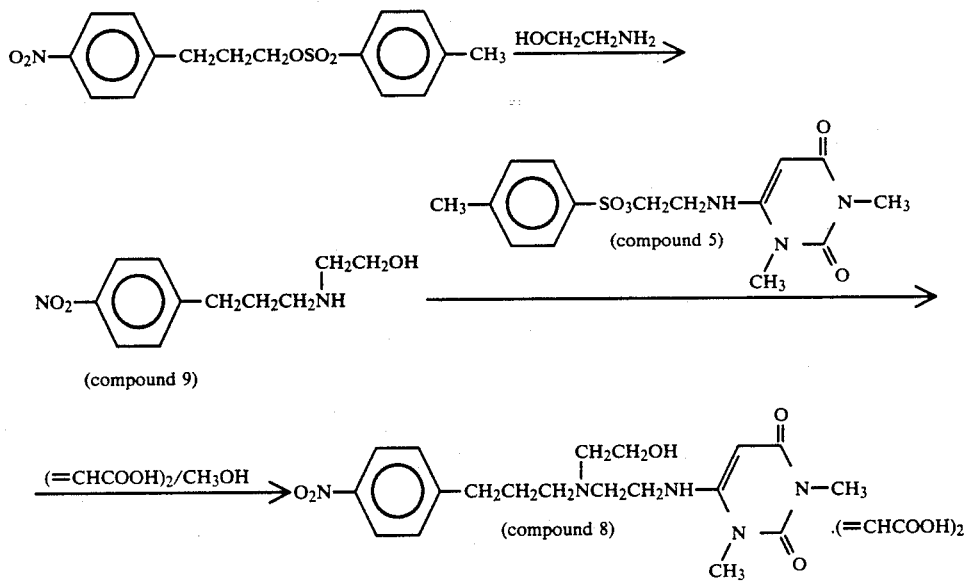

(1) Preparation of N-(2-hydroxyethyl)-N-[3-(4-nitrophenyl)propyl]amine (compound 9):

A mixture of 37.5 g of 3-(4-nitrophenyl)propyl p-toluene sulfonate, 125 g of aminoethanol and 65 ml of dioxane was heated with stirring at a temperature of 90 to 100° C. for 3 hours. Thereafter, the used solvent was distilled off from the mixture under reduced pressure, and the residue was dissolved in 800 ml of chloroform and the solution was then washed with 1 liter of water. The washed organic layer was further washed with a 0.5 N sodium hydroxide solution and then with water, followed by drying over anhydrous sodium sulfate. The dried organic layer was then treated under reduced pressure to distill off the solvent therefrom, and the residue was recrystallized from benzene/hexane (which was 2/1 in terms of volume ratio). The obtained crystals were collected by filtration, washed and dried, thereby preparing 21 g of N-(2-hydroxyethyl)-N-[3-(4-nitrophenyl)propyl]amine (compound 9).

Analytical results of the crystalline compound 9 thus obtained:

Melting point: 80.5°-81° C.

(2) Preparation of 1,3-dimethyl-6-{2-(N-(2-hydroxyethyl)-N-[3-(4-nitrophenyl)propyl]amino>ethylamino}-2,4-(1H,3H)-pyrimidinedione fumarate (compound 8):

In 350 ml of methanol was dissolved 23.2 g of 1,3-dimethyl-6-[2-(p-toluenesulfonyloxy)ethylamino]-2,4(1H,3H)-pyrimidinedione (compound 5) synthesized in Example 3-(1), and 2.76 g of sodium hydroxide was further added thereto slowly. The resulting mixture was stirred at a temperature of 50° to 60° C. for 1 hour, and the solvent was then distilled off from the reaction mixture. Afterward, 120 ml of chloroform was added to the residue, and insoluble materials were removed by filtration therefrom. To the filtrate were added 17 g of N-(2-hydroxyethyl)-N-[3-(4-nitrophenyl)propyl]amine (compound 9) and 0.66 g of p-toluene-sulfonic acid, and the reaction mixture was then treated under reduced pressure to distill off the solvent therefrom. The solvent-free residue was heated and stirred at 80° C. for 1 hour and was then dissolved in 480 ml of chloroform, and the reaction mixture was extracted twice with 300 ml of 0.5 N hydrochloric acid. Afterward, potassium carbonate was added to the extract (hydrochloric acid solution) with the intention of making the latter alkaline, and the liquid mixture was then stirred at room temperature for 1 hour. The resulting crystals were then collected by filtration.

The crystals were dried, recrystallized from ethanol, collected by filtration, washed and dried in order to obtain 22.1 g of 1,3-dimethyl-6-{2-(N-(2-hydroxyethyl)-N-[3-(4-nitrophenyl)propyl]amino>ethylamino}-2,4(1H,3H)-pyrimidinedione.

Analytical results of the crystalline pyrimidinedione derivative thus obtained:

Melting point: 117.5°-118.5° C.

$^1$H-NMR (CDCl$_3$), δppm: 1.86 (m, 2H), 2.48-3.00 (m, 11H), 3.00-3.26 (m, 2H), 3.27 (s, 3H), 3.39 (s, 3H), 3.71 (m, 2H), 4.78 (s, 1H), 6.06 (m, 1H), 7.38 (d, 2H), 8.18 (d, 2H)

This pyrimidinedione derivative was treated with a fumaric acid/methanol solution in a usual manner to obtain 1,3-dimethyl-6-{2-(N-(2-hydroxyethyl)-N-[3-(4-nitrophenyl)propyl]amino>ethylamino}-2,4(1H,3H)-pyrimidinedione fumarate (compound 8).

Analytical results of the prepared crystalline compound 8:

Melting point: 152.5°-153.5° C.

IRνKBr$_{max}$ (cm$^{-1}$): 3400, 2960, 1700, 1630, 1600, 1555, 1520, 1450, 1355, 1250, 1070, 990, 780

(3) Preparation of 1,3-dimethyl-6-{2-<N-(2-hydroxyethyl)-N-[3-(4-nitrophenyl)propyl]amino>ethylamino}-2,4(1H,3H)-pyrimidinedione hydrochloride (compund 8')

1,3-Dimethyl-6-{2-<N-(2-hydroxyethyl)-N-[3-(4-nitrophenyl)propyl]amino>ethylamino}2,4(1H,3H)-pyrimidinedione (free from of compound 8) (2.6 g) was dissolved in 26 ml methanol under heating and to the resulting solution was added 2.7 ml 13% (w/w) of HCl/methanol solution drop by drop, while the temperature of the mixture was maintained at 40° C.

The resulting mixture was cooled on ice and was left overnight. Crystals thus formed were collected by filtration and dried in vacuum; thus, 1,3-dimethyl-6-{2-<N-(2-hydroxyethyl)-N-[3-(4-nitrophenyl)propyl]amino>ethylamino}-2,4(1H,3H)-pyrimidinedione hydrochloride (compound 8') was obtained.

Analytical results of the crystalline 8' thus obtained:

Melting point: 172°-174° C.

IRνKBr$_{max}$ (cm$^{-1}$): 3230, 1640, 1605, 1540, 1340, 1240

EXAMPLE 5

Preparation of 1,3-dimethyl-6-{4-[2-(2-nitrophenyl)ethyl]piperazin-1yl}-2,4(1H,3H)-pyrimidinedione oxalate (compound 10):

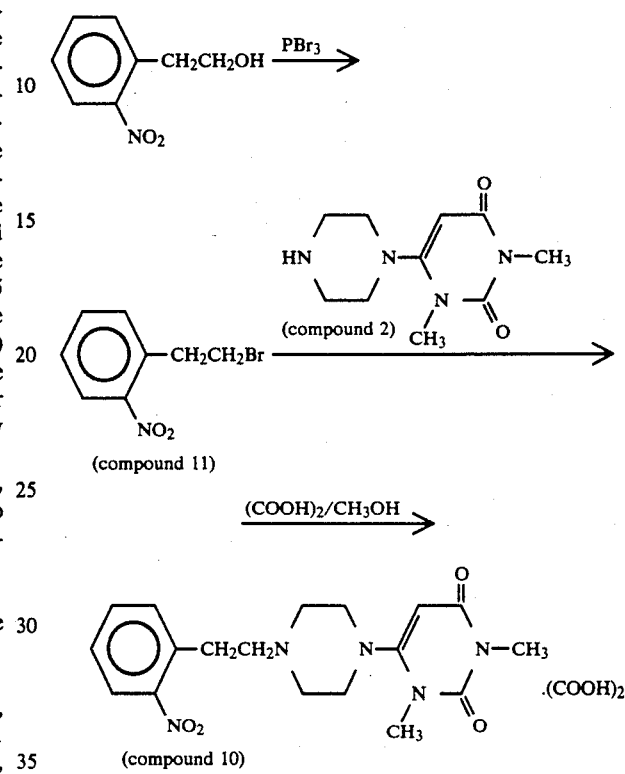

(compound 10)

(1) Preparation of 2-(2-nitrophenyl)ethyl bromide (compound 11):

First, 2.5 ml of 2-(2-nitrophenyl)ethanol and 5.4 ml of PBr$_3$ were mixed and stirred at 0° C. for 30 minutes to perform reaction therebetween, and the resulting reaction mixture was diluted with 30 ml of benzene and was then poured into 30 ml of water. Afterward, the separated organic layer was collected, dried over anhydrous sodium sulfate, and then treated under reduced pressure to distill off the solvent therefrom, thereby preparing 3 g of a crude product, 2-(2-nitrophenyl)ethyl bromide (compound 11).

(2) Preparation of 1,3-dimethyl-6-{4-[2-(2-nitrophenyl)ethyl]piperazin-1-yl}-2,4(1H,3H)-pyrimidinedione oxalate (compound 10):

To 15 ml of isopropanol were added 3.0 g of the above prepared compound 11, 3.2 g of 1,3-dimethyl-6-(piperazine-1-yl)-2,4(1H,3H)-pyrimidinedione (compound 2) and 4.2 ml of triethylamine, and the resulting mixture was then treated by the same procedure as in Example 2 in order to obtain 2.2 g of 1,3-dimethyl-6-{4-[2-(2-nitrophenyl)ethyl]piperazin-1-yl}-2,4(1H,3H)-pyrimidinedione.

Analytical results of the pyrimidinedione derivative thus obtained:

NMR (CDCl$_3$), δppm: 2.7-3.0 (m, 12H), 3.39 (s, 3H), 3.41 (s, 3H), 5.11 (s, 1H), 7.53 (m, 3H), 7.96 (m, 1H)

Furthermore, this pyrimidinedione derivative was treated with an oxalic acid/methanol solution in a usual manner, thereby preparing 1,3-dimethyl-6-{4-[2-(2-nitrophenyl)ethyl]piperazin-1-yl}-2,4(1H,3H)-pyrimidinedione oxalate (compound 10).

Analytical results of the prepared crystalline compound 10:

Melting point: 212°–214° C.

Values of elemental analysis (as $C_{18}H_{23}N_5O_4$ $(COOH)_2 \cdot \frac{1}{2}H_2O$)

Calcd. (%): C 50.85; H 5.55; N 14.82
Found (%): C 50.57; H 5.54; N 14.44

IR$\nu$KBr$_{max}$ (cm$^{-1}$): 3050, 2940, 1720, 1680, 1630, 1550, 1380, 770

EXAMPLE 6

Preparation of 1,3-dimethyl-6-[2-(4-nitroanilino)ethylamino]-2,4(1H,3H)-pyrimidinedione (compound 12):

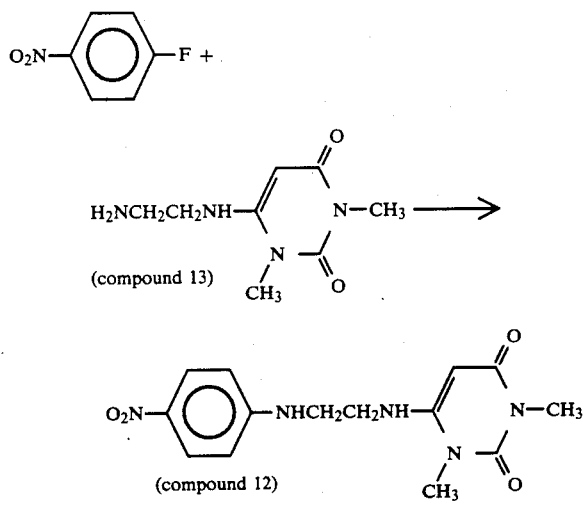

The same procedure as in Example 1 was repeated with the exception that 1,3-dimethyl-6-(piperazin-1-yl)-2,4(1H,3H)-pyrimidinedione (compound 2) was replaced with 0.45 g of 6-(2-aminoethylamino)-1,3-dimethyl-2,4(1H,3H)-pyrimidinedione (compound 13), in order to obtain 0.5 g of 1,3-dimethyl-6-[2-(4-nitroanilino)ethylamino]-2,4(1H,3H)-pyrimidinedione (compound 12).

Analytical results of the crystalline compound 12 thus obtained:

Melting point: 308° C. (decomposed)

IR$\nu$KBr$_{max}$(cm$^{-1}$): 1690, 1660, 1600, 1550, 1320, 850

NMR (DMSO-d$_6$), δppm: 2.9 (m, 2H), 3.1 (m, 2H), 3.29 (s, 3H), 3.38 (s, 3H), 5.09 (s, 1H), 7.04 (d, 2H), 8.09 (d, 2H)

Values of elemental analysis (as $C_{14}H_{17}N_5O_4$)

Calcd. (%): C 52.66; H 5.37; N 21.93
Found (%): C 52.55; H 5.34; N 21.82

EXAMPLE 7

Preparation of 1,3-dimethyl-6-{4-[2-(4-nitrophenyl)ethyl]piperazin-1-yl}-2,4(1H,3H)-pyrimidinedione hydrochloride (compound 14):

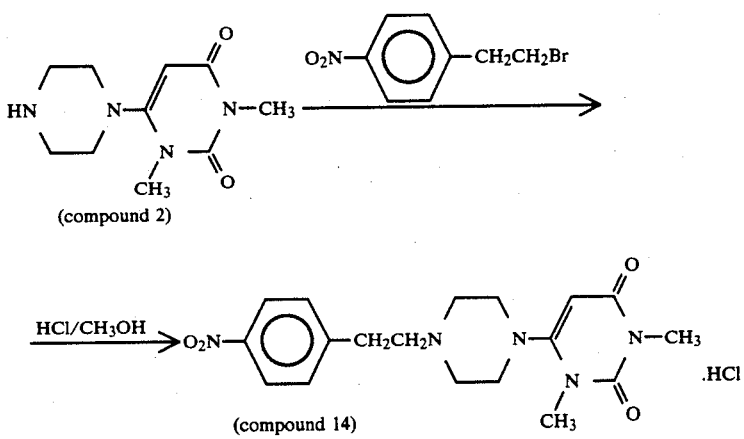

The same procedure as in Example 2 was repeated with the exception that 4-nitrobenzyl bromide was replaced with 0.51 g of 4-nitrophenethyl bromide, in order to obtain 1,3-dimethyl-6-{4-[2-(4-nitrophenyl)ethyl]piperazin -1-yl}-2,4(1H,3H)-pyrimidinedione.

Analytical results of the pyrimidinedione derivative thus obtained:

NMR (CDCl$_3$), δppm: 2.8 (m, 12H), 3.22 (s, 3H), 3.36 (s, 3H), 5.19 (s, 1H), 7.36 (d, 2H), 8.12 (d, 2H)

Moreover, this pyrimidinedione derivative was treated with a hydrochloric acid/methanol solution in a usual manner to obtain 1,3-dimethyl-6-{4-[2-(4-nitrophenyl)ethyl]piperazin-1-yl}-2,4(1H,3H)-pyrimidinedione hydrochloride (compound 14).

Analytical results of the crystalline compound 14 thus obtained:

Melting point: 263°–266° C. (decomposed)

Values of elemental analysis (as $C_{18}H_{23}N_5O_4 \cdot HCl \cdot 0.5H_2O$)

Calcd. (%): C 51.61; H 6.02; N 16.72; Cl 8.46
Found (%): C 51.78; H 6.28; N 16.93; Cl 8.60

IR$\nu$KBr$_{max}$ (cm$^{-1}$): 2950, 2500, 1700, 1690, 1630, 1520, 1350, 805

EXAMPLE 8

Preparation of 1,3-dimethyl-6-[2-(4-nitrobenzylamino)ethylamino]-2,4(1H,3H)-pyrimidinedione oxalate (compound 15)

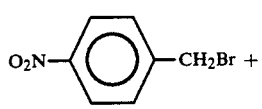

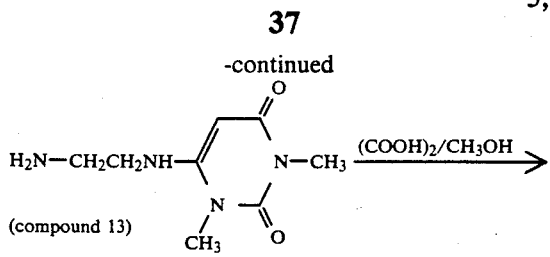

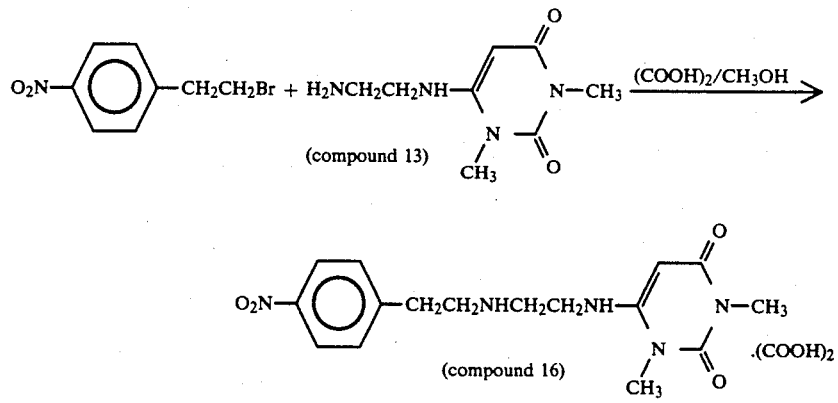

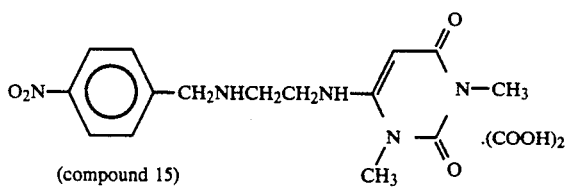

The same procedure as in Example 2 was repeated with the exception that 1,3-dimethyl-6-(piperazin-1-yl)-2,4-(1H,3H)-pyrimidinedione (compound 2) was replaced with 0.45 g of 6-(2-aminoethylamino)-1,3-dimethyl-2,4(1H,3H)-pyrimidinedione (compound 13), in order to obtain 1,3-dimethyl-6-[2-(4-nitrobenzylamino)ethylamino]-2,4(1H,3H)-pyrimidinedione.

Analytical results of the prepared pyrimidinedione derivative:

NMR (CDCl₃:DMSO-d₆=1:1), δppm: 2.9 (m, 2H), 3.2 (m, 2H), 3.30 (s, 3H), 3.38 (s, 3H), 3.60 (m, 2H), 5.07 (s, 1H), 7.42 (d, 2H), 8.06 (d, 2H)

Moreover, this pyrimidinedione derivative was treated with an oxalic acid/methanol solution in a usual manner to obtain crystals of 1,3-dimethyl-6-[2-(4-nitrobenzylamino)ethylamino]-2,4(1H,3H)-pyrimidinedione oxalate (compound 15).

Analytical results of the crystalline compound 15 thus obtained:

Melting point: 203°-205° C. (decomposed)

IRνKBr$_{max}$ (cm$^{-1}$): 3150, 2900, 1710, 1650, 1640, 1630, 870

Values of elemental analysis [as C₁₅H₁₉N₅O₄·(COOH)₂·0.5H₂O]

Calcd. (%): C 47.22; H 5.13; N 16.20
Found (%): C 47.04; H 4.40; N 16.61

EXAMPLE 9

Preparation of 1,3-dimethyl-6-{2-[2-(4-nitrophenyl)ethylamino]ethylamino}-2,4(1H,3H)-pyrimidinedione oxalate (compound 16)

The same procedure as in Example 2 was repeated with the exception that 4-nitrobenzyl bromide and 1,3-dimethyl-6-piperazin-1-yl)-2,4-(1H,3H)-pyrimidinedione (compound 2) were replaced with 0.51 g of 2-(4-nitrophenyl)ethyl bromide and 0.45 g of 6-(2-aminoethylamino)-1,3-dimethyl-2,4(1H,3H)-pyrimidinedione (compound 13), respectively, in order to obtain 1,3-dimethyl-6-{2-[2-(4-nitrophenyl)ethylamino]ethylamino}-2,4(1H,3H)-pyrimidinedione.

Analytical results of the pyrimidinedione derivative thus obtained:

NMR (CDCl₃), δppm: 2.7-3.2 (m, 6H), 3.29 (s, 3H), 3.37 (s, 3H), 3.51 (t, 2H), 5.01 (s, 1H), 8.13 (d, 2H), 8.43 (d, 2H)

Furthermore, this pyrimidinedione derivative was treated with an oxalic acid/methanol solution in a usual manner, thereby preparing crystals of 1,3-dimethyl-6-2-[2-(4-nitrophenyl)ethylamino]ethylamino -2,4(1H,3H)-pyrimidinedione oxalate (compound 16).

Analytical results of the crystalline compound 16 thus obtained:

Melting point: 200°-202° C. (decomposed)

Values of elemental analysis (as C₁₆H₂₁N₅O₄·(COOH)2·½H₂O)

Calcd. (%): C 48.43; H 5.42; N 15.69
Found (%): C 48.52; H 5.16; N 16.25

IR KBr$_{max}$ (cm$^{-1}$): 3100, 2900, 1710, 1640, 1620, 1560, 1360, 850

EXAMPLE 10

Preparation of 1,3-dimethyl-6-{N-methyl-2-[N-methyl-3-(4-nitrophenyl)propylamino]ethylamino}-2,4(1H,3H)-pyrimidinedione oxalate (compound 17)

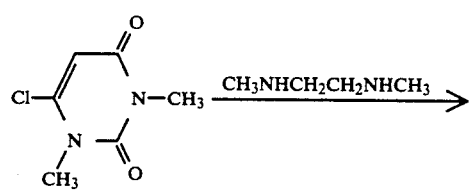

-continued

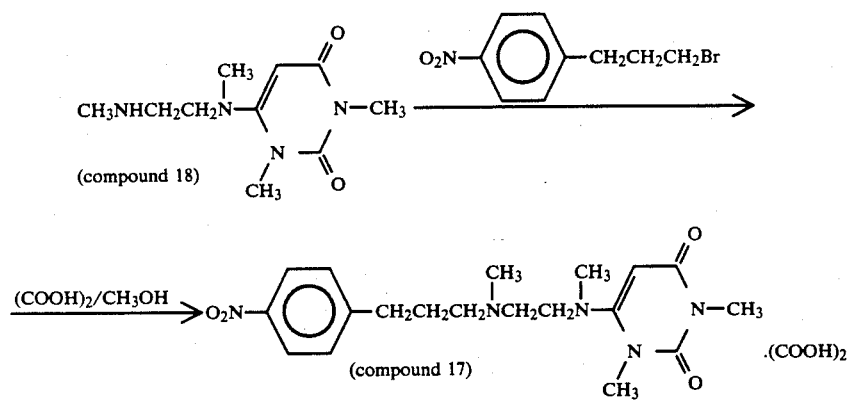

(1) Preparation of 1,3-dimethyl-6-{N-methyl-N-[2-(methylamino)ethyl]amino}-2,4(1H,3H)-pyrimidinedione (compound 18)

In 200 ml of chloroform were dissolved 50 g of N,N'-dimethylethylenediamine and 19.8 g of 6-chloro-1,3-dimethyl-2,4(1H,3H)-pyrimidinedione, and the reaction mixture was then heated with stirring under reflux for 5 hours.

The reaction mixture was washed with water, and a separated organic layer was then dried over anhydrous sodium sulfate. Furthermore, the dried organic layer was treated under reduced pressure to distill off the solvent, and ether was then added to the resulting residue so as to deposit crystals. The latter were then collected by filtration, washed and dried in order to obtain 10 g of 1,3-dimethyl-6-{N-methyl-N-[2-(methylamino)ethyl]amino}-2,4(1H,3H)-pyridinedione (compound 18).

Analytical results of the crystalline compound 18 thus obtained:

NMR (CDCl$_3$), δppm: 2.7 (s, 3H), 2.5-3.3 (m, 4H), 3.25 (s, 3H), 3.3 (s, 3H), 3.33 (s, 3H), 5.25 (s, 1H)

(2) Preparation of 1,3-dimethyl-6-{N-methyl-2-[N-methyl-3-(4-nitrophenyl)propylamino]ethylamino}-2,4(1H,3H)-pyrimidinedione oxalate (compound 17)

To 60 ml of isopropanol were added 5.0 g of the above compound 18, 5.5 g of 3-(4-nitrophenyl)propyl bromide and 6 ml of triethylamine, and the resuting mixture was then treated by the same procedure as in Example 2 in order to obtain 8.1 g of 1,3-dimethyl-6-{N-methyl-2-[N-methyl-3-(4-nitrophenyl)propylamino]ethylamino}-2,4(1H,3H)-pyrimidinedione.

Analytical results of the pyrimidinedione derivative thus obtained:

NMR (CDCl$_3$), δppm: 1.5-2.2 (m, 2H), 2.25 (s, 3H), 2.25-3.2 (m, 8H), 3.3 (s, 3H), 3.35 (s, 3H), 5.25 (s, 1H), 7.3 (d, 2H), 8.15 (d, 2H)

Moreover, this pyrimidinedione derivative was treated with an oxalic acid/methanol solution in a usual manner to obtain crystals of 1,3-dimethyl-6-{N-methyl-2-[N-methyl-3-(4-nitrophenyl)propylamino]ethylamino}-2,4(1H,3H)-pyrimidinedione oxalate (compound 17).

Analytical results of the prepared crystalline compound 17:

Values of elemental analysis [as $C_{19}H_{27}N_5O_4 \cdot (COOH)_2$]

Calcd. (%): C 52.60; H 6.10; N 14.61
Found (%): C 52.41; H 6.33; N 14.21

EXAMPLE 11

The same procedure as in Example 3-(3) was repeated with the exception that N-ethyl-N-[3-(4-nitrophenyl)propyl]amine (compound 7) was replaced with each amino compound in which the ethyl group portion ($R^{1'}$) and the number (m) of carbon atoms in an alkyl chain of the compound 7 were as shown in Table 1, in order to obtain compounds 19 to 24.

Physical properties of these compounds are set forth in Table 1.

TABLE 1

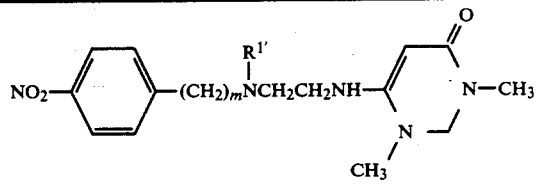

| Comp. No. | m | $R^{1'}$ | m.p. (°C.) | IR ν KBr$_{max}$(cm$^{-1}$) | Molecular Formula | Calcd. (Found) (%) C | H | N |
|---|---|---|---|---|---|---|---|---|
| 19 | 4 | —H | amorphous | 3430, 3300, 1692 1620, 1550, 1347 | $C_{18}H_{25}N_5O_4$ $(CO_2H)_2$ | | | |
| 20 | 1 | —C$_2$H$_5$ | 164.0–165.5 | 3250, 1745, 1688 1630, 1520, 1460 1352, 1232, 740 | $C_{17}H_{23}N_5O_4$ $(CO_2H)_2 \cdot \frac{1}{2}H_2O$ | 49.56 (49.89) | 5.69 (6.01) | 15.21 (14.69) |
| 21 | 2 | —C$_2$H$_5$ | 127.5–130.0 | 3360, 1693, 1625, 1553, 1420, 1350, 1240, 783 | $C_{18}H_{25}N_5O_4$ $(CO_2H)_2 \cdot \frac{1}{2}H_2O$ | 50.63 (50.43) | 5.95 (5.58) | 14.76 (15.43) |
| 22 | 4 | —C$_2$H$_5$ | 165.5–170.0 | 3400 (br), 1685, 1640, 1518, 1348 | $C_{20}H_{29}N_5O_4$ $(CO_2H)_2$ | 53.54 (53.28) | 6.33 (6.29) | 14.19 (14.08) |
| 23 | 4 | —CH$_2$CH$_2$OH | 99.5–102.0 | 3240 (br), 1692, | $C_{20}H_{29}N_5O_5$ | 49.25 | 6.39 | 13.05 |

TABLE 1-continued

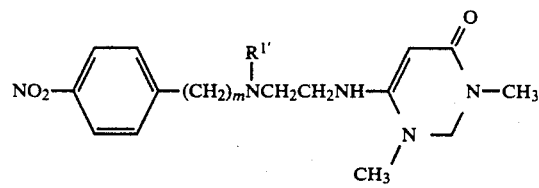

| Comp. No. | m | R¹' | m.p. (°C.) | IR ν KBr$_{max}$(cm$^{-1}$) | Molecular Formula | Calcd. (Found) (%) | | |
|---|---|---|---|---|---|---|---|---|
| | | | | | | C | H | N |
| | | | | 1625, 1550, 1348, 1248 | (CO$_2$H)$_2$ 1.5H$_2$O | (49.07) | (6.34) | (13.10) |
| 24 | 4 | —CH$_2$CH$_2$N—(CH$_2$CH$_3$)$_2$ | | | C$_{24}$H$_{38}$N$_6$O$_4$ (CO$_2$H)$_2$ | | | |

EXAMPLE 12

Preparation of 1,3-dimethyl-6-{2-<N-ethyl-N-[3-(3-nitrophenyl)propyl]amino>ethylamino}-2,4(1H,3H)-pyrimidinedione hydrochloride (compound 25)

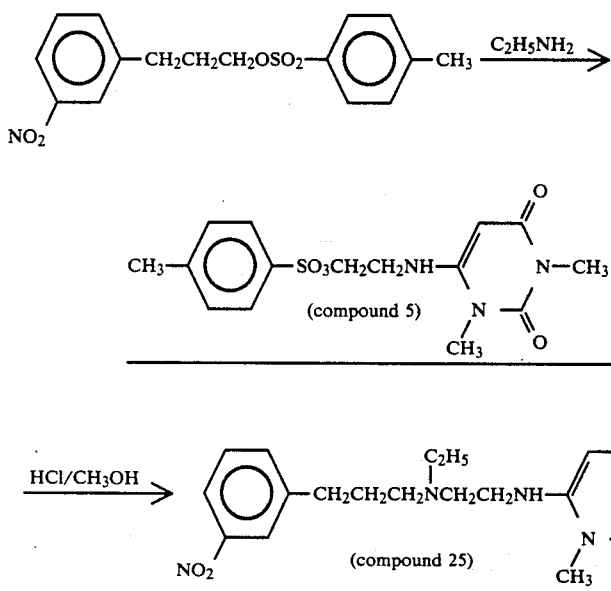

The same procedure as in Example 4 was repeated with the exception that 37.5 g of 3-(3-nitrophenyl)propyl p-toluene sulfonate, 120 g of ethylamine and 188 g of 1,3-dimethyl-6-[2-(p-toluenesulfonyloxy)ethylamino-2,4-(1H,3H)-pyrimidinedione (compound 5) were used as starting materials, in order to obtain crystals of 1,3-dimethyl-6-{2-<N-ethyl-N-[3-(3-nitrophenyl)propyl]amino>ethylamino}-2,4(1H,3H)-pyrimidinedione.

Analytical results of the crystalline pyrimidinedione derivative thus obtained:

NMR (CDCl$_3$), δppm: 1.00 (t, 3H), 1.6-2.0 (m, 2H), 2.4-2.8 (m, 8H), 2.9-3.1 (m, 2H), 3.2 (s, 3H), 3.3 (s, 3H), 4.75 (s, 1H), 5.5 (br, 1H), 7.3-7.4 (m, 2H), 7.8-8.0 (m, 2H)

The thus obtained crystals were treated with a hydrochloric acid/methanol solution in an ordinary manner to obtain crystals of 1,3-dimethyl-6-{2-(N-ethyl-N-[3-(3nitrophenyl)propyl]amino>ethylamino}-2,4(1H,3H)-pyrimidinedione hydrochloride (compound 25).

Analytical results of the crystalline compound 25 thus obtained:

Values of elemental analysis (as C$_{19}$H$_{27}$N$_5$O$_4$·HCl)
Calcd. (%): C 53.58; H 6.63; N 16.44; Cl 8.33
Found (%): C 53.02; H 6.79; N 16.01; Cl 7.98

EXAMPLE 13

Preparation of 1,3-dimethyl-6-{N-ethyl-N-<2-[4-(4-nitrophenyl)butylamino]ethyl>amino}-2,4(1H,3H)-pyrimidinedione oxalate (compound 26)

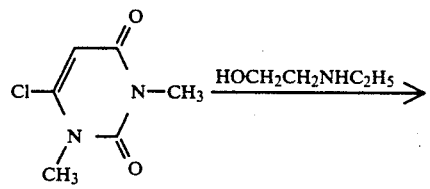

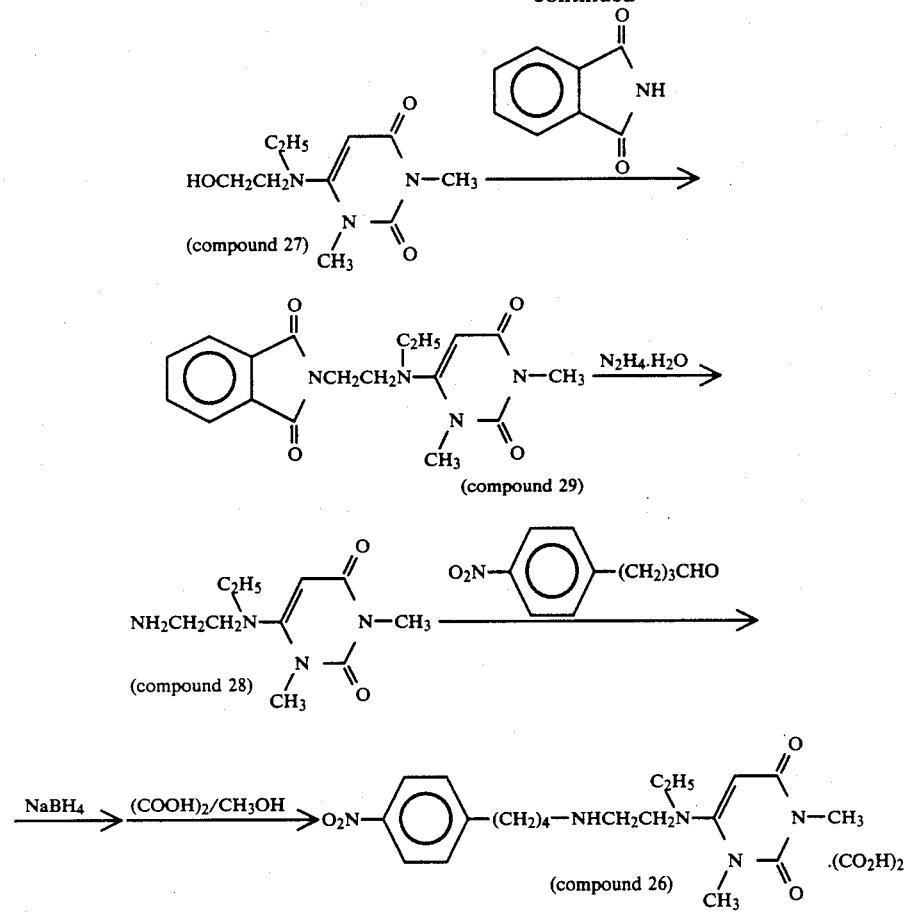

(1) Preparation of 1,3-dimethyl-6-[N-ethyl-N-(2-hydroxyethyl)amino]-2,4(1H,3H)-pyrimidinedione (compound 27)

Up to 100° C., 11 g of N-ethylaminoethanol was heated, and while the above temperature was maintained, 10 g of 6-chloro-1,3-dimethyl-2,4(1H,3H)-pyrimidinedione was added thereto little by little.

The reaction mixture was heated at the same temperature for 1 hour, and 100 ml of dioxane was then added thereto, followed by stirring under ice cooling for 1 hour.

The crystals deposited by the above stirring were removed from the reaction mixture by filtration, and the filtrate was then concentrated. Afterward, the residue (concentrate) was purified through a silica gel column chromatograph (ethyl acetate/methanol=20/1 in terms of volume ratio) to obtain 7.2 g of 1,3-dimethyl-6-[N-ethyl-N-(2-hydroxyethyl)amino]-2,4(1H,3H)-pyrimidinedione (compound 27).

Analytical results of the compound 27 thus obtained:

NMR (CDCl$_3$), δppm: 1.15 (t, 3H), 3.0–3.3 (m, 4H), 3.3 (s, 3H), 3.4 (s, 3H), 3.6–3.9 (m, 2H), 5.35 (s, 1H)

(2) Preparation of 1,3-dimethyl-6-[N-ethyl-N-(2-aminoethyl)amino]-2,4(1H,3H)-pyrimidinedione (compound 28)

In 200 ml of tetrahydrofurane were suspended 16.8 g of the above compound 27, 8.6 g of triphenylphosphine and 11.96 g of phthalimide, and 14.81 g of diethyl azodicarboxylate was further added dropwise to the resulting suspension under ice cooling.

Next, after completion of the addition, the used solvent was distilled off from the reaction mixture under reduced pressure, and the residue was then purified through a silica gel column chromatograph (ethyl acetate) in order to obtain 22.5 g of 6-[N-ethyl-N-(2-phthaloylaminoethyl)amino]-1,3-dimethyl-2,4(1H,3H)-pyrimidinedione (compound 29). The latter compound was then treated with hydrazine monohydrate in ethanol in a usual method to remove the phthaloyl group therefrom, thereby preparing crystals of 1,3-dimethyl-6-[N-ethyl-N-(2-aminoethyl)amino]-2,4(1H,3H)-pyrimidinedione (compound 28).

Analytical results of the crystalline compound 28 thus obtained:

NMR (CDCl$_3$: DMSO-d$_6$ =1:1, v/v), δppm: 1.15 (t, 3H), 2.65 (q, 2H), 2.6–3.3 (m, 4H), 3.3 (s, 3H), 3.4 (s, 3H), 4.8 (s, 1H)

(3) Preparation of 1,3-dimethyl-6-{N-ethyl-N-(2-[4-(4-nitrophenyl)butylamino]ethyl}amino}-2,4(1H,3H)-pyrimidinedione oxalate (compound 26)

In 25 ml of ethanol were dissolved 1.58 g of 1,3-dimethyl-6-[N-ethyl-N-(2-aminoethyl)amino]-2,4(1H,3H)-pyrimidinedione (compound 28) and 1.35 g of 4-(4-nitrophenyl)butanal, and 0.5 g of molecular shieves (3A) (made by Junsei Kagaku Co., Ltd.) was then added to the solution, followed by stirring at room temperature for 3 hours.

To the resulting reaction mixture was added 0.8 g of sodium borohydride, and the mixture was then stirred for 2 hours. A small amount of water was added to the mixture, and the solvent was then distilled off from the mixture under reduced pressure. Afterward, the resulting residue was dissolved in chloroform. The chloroform solution was washed with water, and a separated organic layer was then dried over anhydous sodium sulfate. The solution was treated under reduced pressure so as to distill off the solvent. The resulting residue was purified through a silica gel column chromatograph (chloroform/methanol=30/1 in terms of volume), then recrystallized from ethyl acetate, collected by filtration, washed, and dried in order to obtain 0.78 g of 1,3-dimethyl-6-{N-ethyl-N-[2-[4-(4-nitrophenyl)-butylamino]ethyl]amino}-2,4(1H,3H)-pyrimidinedione.

Analytical results of the obtained crystalline pyrimidinedione derivative:

NMR (CDCl$_3$), δppm: 1.05 (t, 3H), 1.4–1.8 (m, 4H), 2.2–2.8 (m, 8H), 2.9–3.1 (m, 2H), 3.3 (s, 6H), 4.8 (s, 1H), 5.6 (m, 1H), 7.35 (d, 2H), 8.15 (d, 2H)

The thus obtained crystals were treated with an oxalic acid/methanol solution in a usual manner in order to prepare 1,3-dimethyl-6-{N-ethyl-N-[2-[4-(4-nitrophenyl)butylamino]ethyl]amino}-2,4(1H,3H)-pyrimidinedione oxalate (compound 26).

Analytical results of the crystalline compound 26 thus obtained:

Melting point: 164°–166° C.

Values of elemental analysis [as C$_{20}$H$_{29}$N$_5$O$_4$·(COOH)$_2$]

Calcd. (%): C 53.54; H 6.33; N 14.19
Found (%): C 53.21; H 6.32; N 13.98

EXAMPLE 14

Preparation of 1,3-dimethyl-6-[3-(4-nitroanilino)-propylamino]-2,4(1H,3H)-pyrimidinedione oxalate (compound 30)

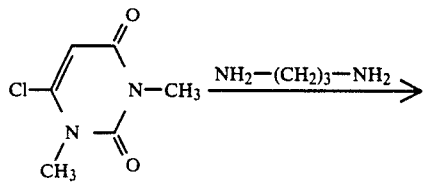

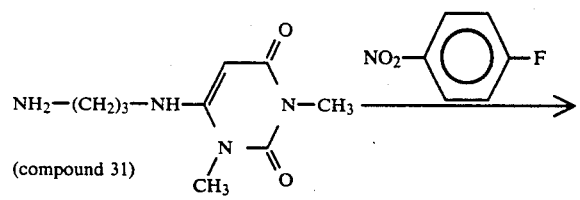

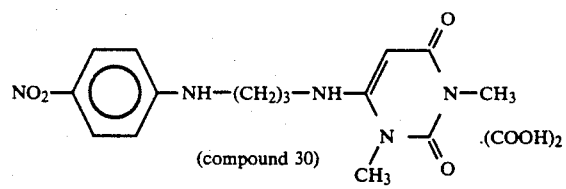

(1) Preparation of 1,3-dimethyl-6-(3-aminopropylamino)-2,4(1H,3H)-pyrimidinedione (compound 31)

The same procedure as in Example 10-(1) was repeated with the exception that N,N'-dimethylethylenediamine was replaced with 50 g of 1,3-diaminopropane, in order to obtain 9.5 g of 1,3-dimethyl-6-(3-aminopropylamino)-2,4(1H,3H)-pyrimidinedione (compound 31).

Analytical results of the compound 31 thus obtained:
NMR (CDCl$_3$), δppm: 1.75–2.10 (m, 2H), 2.75–3.48 (m, 4H), 3.12 (s, 3H), 3.35 (s, 3H), 4.75 (s, 1H)

(2) Preparation of 1,3-dimethyl-6-[3-(4-nitroanilino)-propylamino]-2,4(1H,3H)-pyrimidinedione oxalate (compound 30)

The same procedure as in Example 1 was repeated with the exception that the compound 2 was replaced with 0.5 g of the above compound 31, in order to obtain 1,3-dimethyl-6-[3-(4-nitroanilino)propylamino]-2,4(1H,3H)-pyrimidinedione. The latter compound was further treated with an oxalic acid/methanol solution in a usual manner, thereby preparing 0.45 g of crystalline 1,3-dimethyl-6-[3-(4-nitroanilino)propylamino]-2,4(1H,3H)-pyrimidinedione oxalate (compound 30).

Analytical results of the crystalline compound 30 thus obtained:

Melting point: 213°–214° C. (decomposed)

IRνKBr$_{max}$ (cm$^{-1}$): 2600, 1700, 1640, 1600, 1560, 1320, 840

Values of elemental analysis [as C$_{15}$H$_{19}$N$_5$O$_4$·½(COOH)$_2$]

Calcd. (%): C 50.79; H 5.33; N 18.51
Found (%): C 50.95; H 5.38; N 18.82

EXAMPLE 15

Preparation of 1,3-dimethyl-6-[3-(4-nitrobenzylamino)propylamino]-2,4(1H,3H)-pyrimidinedione oxalate (compound 32)

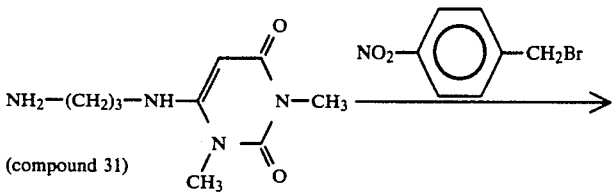

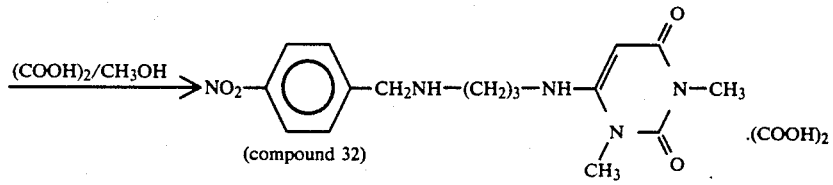

To 20 ml of isopropanol were added 1.45 g of 1,3-dimethyl-6-(3-aminopropylamino)-2,4(1H,3H)-pyrimidinedione (compound 31) obtained in Example 14-(1), 1.44 g of p-nitrobenzyl bromide and 1.5 ml of triethylamine, and the resulting mixture was then treated in the same manner as in Example 2 in order to obtain crystals of 1,3-dimethyl-6-[3-(4-nitrobenzylamino)-propylamino]-2,4(1H,3H)-pyrimidinedione oxalate (compound 32).

Analytical results of the crystalline compound 32 thus obtained:

Melting point: 175°–178° C.
IR$\nu$KBr$_{max}$ (cm$^{-1}$): 2600, 1690, 1620, 1610 1550, 1350, 850
Values of elemental analysis [as C$_{16}$H$_{21}$N$_5$O$_4$·(COOH)2.3H$_2$O]
Calcd. (%): C 43.99; H 5.95; N 14.25
Found (%): C 43.52; H 6.05; N 14.33 order to obtain 1,3-dimethyl-6-{4-[4-(4-nitrophenyl)-butyl]piperazin-1-yl}-2,4(1H,3H)-pyrimidinedione hydrochloride (compound 34).

Physical properties of these compounds were as follows:

(1) 1,3-dimethyl-6-{4-[3-(4-nitrophenyl)propyl]piperazin-1-yl}-2,4(1H,3H)-pyrimidinedione oxalate (compound 33)

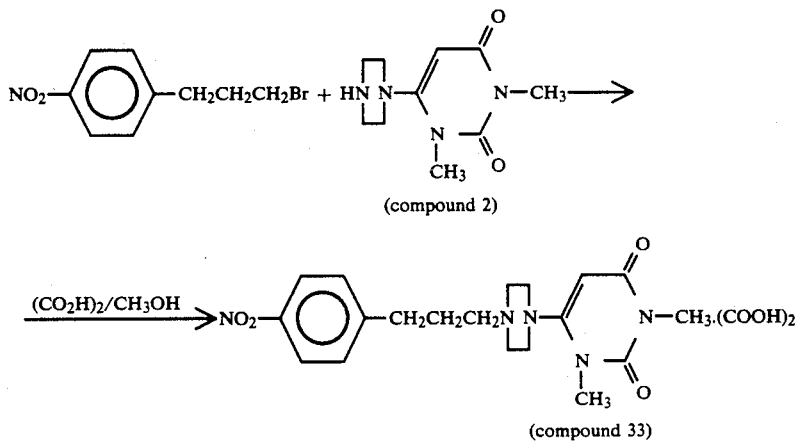

Melting point: 153°–156° C. (decomposed)
IR$\nu$KBr$_{max}$ (cm$^{-1}$): 2550, 1680, 1630, 1600 1590, 1510, 1340, 850
Values of elemental analysis [as C$_{19}$H$_{25}$N$_5$O(-COOH)$_2$·1.5H$_2$O]
Calcd. (%): C 50.00; H 5.99; N 13.88
Found (%): C 50.24; H 5.64; N 13.23

(2) 1,3-dimethyl-6-{4-[4-(4-nitrophenyl)butyl]piperazine-1-yl}-2,4(1H,3H)-pyrimidinedione hydrochloride (compound 34)

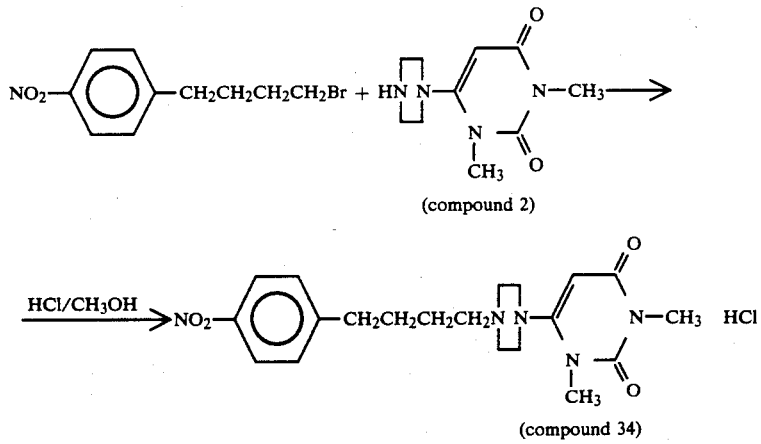

EXAMPLE 16

The same procedure as in Example 2 was repeated with the exception that 4-nitrobenzyl bromide was replaced with 0.51 g of 3-(4-nitrophenyl)propyl bromide, in order to obtain 1,3-dimethyl-6-{4-[3-(4-nitrophenyl)-propyl]piperazin-1-yl}-2,4(1H,3H)-pyrimidinedione oxalate (compound 33).

Furthermore, the same procedure as in Example 2 was repeated with the exception that 4-nitrobenzyl bromide was replaced with 0.55 g of 4-(4-nitrophenyl)-butyl bromide and that the oxalic acid/methanol solution was replaced with hydrochloric acid/methanol, in Melting point: 202°–205.5° C.
IR$\nu$KBr$_{max}$ (cm$^{-1}$): 2920, 2450, 1700, 1650 1615, 1440, 1345, 791, 762, 740
Values of elemental analysis [as C$_{20}$H$_{27}$N$_5$O$_4$·HCl]
Calcd. (%): C 54.85; H 6.44; N 15.99; Cl 8.10
Found (%): C 54.20; H 6.67; N 15.56; Cl 8.95

EXAMPLE 17

Preparation of tablets containing, as an effective component, 1,3-dimethyl-6-[4-(4-nitrobenzyl)piperazin-1- yl]-2,4(1H,3H)-pyrimidinedione oxalate (compound 3) which can be obtained by the process of Example 2

With 20 g of corn starch were mixed 1 g of the above pyrimidinedione derivative oxalate (compound 3) and 123 g of lactose, and the mixture was further mixed with a solution prepared by dissolving 5 g of hydroxypropyl cellulose in 100 ml of water, so as to form grains, followed by drying the grains at 50° C. for 4 hours. Afterward, 1 g of magnesium stearate was added to the dried grains and was then mixed sufficiently. The mixture was then formed into tablets by the use of a tableting machine, the weight of each tablet being 150 mg.

EXAMPLE 18

Preparation of capsules containing, as an effective component, 1,3-dimethyl-6-{2-(N-ethyl-N-[3-(4-nitrophenyl)propyl]amino>ethylamino}-2,4(1H,3H)-pyrimidinedione hydrochloride (compound 4) which can be obtained by the process of Example 3:

With 25 g of corn starch were sufficiently mixed 5 g of the above pyrimidinedione derivative hydrochloride (compound 4) and 120 g of lactose, and hard capsules were filled with the resulting mixture by the use of a capsule filling machine to prepare capsules, the content of the mixture in each capsule being 150 mg.

EXAMPLE 19

(1) Preparation of an injection containing, as an effective component, 1,3-dimethyl-6-{2-(N-(2-hydroxyethyl-N-[3-(4-nitrophenyl)propyl]amino>ethylamino}-2,4(1H,3H)-pyrimidinedione fumarate (compound 8) which can be obtained by the process of Example 4

In distilled water for injection were dissolved 20 mg of the above pyrimidinedione derivative fumarate (compound 8) and 0.85 g of sodium chloride, and the total volume of the liquid was regulated to be 100 ml, thereby preparing an injection.

(2) Preparation of capsules containing, as an effective component, 1,3-dimethyl-6-{2-(N-(2-hydroxyethyl-N-[3-(4nitrophenyl)propyl]amino>ethylamino}-2,4(1H,3H)-pyrimidinedione hydrochloride (compound 8') which can be otained by process of Example 4

With 24 g of corn starch were sufficiently mixed 5 g of the above pyrimidinedione derivative hydrochloride (compound 8') and 120 g of lactose and the resulting mixture and 1 g of magnesium stearate were mixed to prepare the final mixture.

Hard capsules were filled with the resulting final mixture by the use of a capsule filling machine to prepare capsules, the content of the mixture in each capsule being 150 mg.

PHARMACOLOGICAL TEST 1

(1) Influence on myocardial action potential duration time ($APD_{75}$)

To a hybrid adult dog, 30 mg/kg of pentobarbital was administered through a vein, and after being anesthetized, the heart was removed. Afterward, the right ventricular free wall of the heart was cut out in a Tyrode solution.

The right ventricular free wall was fixed in an incubator at 37° C., and a nutritional solution (20 ml of the Tyrode solution) was refluxed.

In this isolated condition, myocardial action potential duration times ($APD_{75}$) were measured before and after the administration of the respective compounds prepared in the above examples in Table 2 and d-sotalol as a control medicine, and $APD_{75}(\%)$ was calculated from the measured results in accordance with the formula:

$$APD_{75}(\%) = (B-A)/A \times 100$$

A: $APD_{75}$ before administration
B: $APD_{75}$ after administration

Here, $APD_{75}$ was measured as follows: A field stimulation of 1 Hz was given to the right ventricular free wall, and any variation of an action potential was depicted on an oscilloscope via a glass microelectrode (10 to 20 MΩ) thrust into a Purkinje fiber of the free wall and via an amplifier. Afterward, a waveform on the oscilloscope was analyzed by the use of a computer, and the time of from a point of the action potential generation to a point of 75% repolarization was measured. This measured time was regarded as the myocardial action potential duration time ($APD_{75}$).

Each of the compounds and d-sotalol shown in Table 2 was separately added to the refluxing nutritional solution (20 ml), and after 20 minutes' incubation, $APD_{75}$ after the administration was calculated from the variation of the myocardial action potential duration time.

Incidentally, this test was carried out in accordance with a Sato et al's method [H. Sato, K. Hashimoto, Arzneimittel Forschung, 34 (1), 3a, 376–380 (1984)].

The results are set forth in Table 2.

(2) Influence on ventricular muscle refractory period

Refractory periods were measured in the following manner before and after each of the compounds and d-sotalol shown in Table 2 was separately administered to a vein or a duodenum, and ERP (%; extensibility of refractory period) was calculated from the measured values:

$$ERP (\%) = (W-Y)/Y \times 100$$

W: Refractory period after administration
Y: Refractory period before administration To a mongrel adult dog, 30 mg/kg of pentobarbital was administered intravenously, and after being anesthetized, a pair of silver-silver chloride electrodes separated by 3 mm was sewn on an opened right ventricule, and electrical stimulation was given at an interval of 400 msec at a duration time of 4 msec under a current twice as much as the threshold. Afterward, a small amount of alcohol was injected into a sinus artery in order to extinguish a pacemaker activity, and the ventricular refractory period (ERP) was measured under ventricule pacing.

That is, each 1 train comprised 10 stimulations having intervals of 400 msec, and an interval between the trains was usually 400 msec. However, this interval was shortened 10 msec by 10 msec at the time of the refractory period measurement, and an interval between the trains at the time when reaction to the first stimulation of the train disappeared was regarded as the refractory period.

In this case, the electrical stimulation was fed in accordance with a program by a heart stimulation device (Diamedical Co., Ltd.; DHM-226-3).

The results are set forth in Table 2.

TABLE 2

| | (results of pharmacological test) | | | | | | | |
|---|---|---|---|---|---|---|---|---|
| Compound | $APD_{75}$ (%) Dose (μg/ml) | | | | ERP (%) Dose (mg/kg, i.v.) | | | |
| No. | 0.3 | 1.0 | 3.0 | 10.0 | 0.1 | 0.3 | 1.0 | 3.0 |
| 1 | — | — | — | — | 3.6 | 3.6 | 10.3 | — |

TABLE 2 -continued

| | (results of pharmacological test) | | | | | | | |
|---|---|---|---|---|---|---|---|---|
| Com-pound No. | APD75 (%) Dose (μg/ml) | | | | ERP (%) Dose (mg/kg, i.v.) | | | |
| | 0.3 | 1.0 | 3.0 | 10.0 | 0.1 | 0.3 | 1.0 | 3.0 |
| 4 | — | 11 | 16 | — | 5.6 | 11.1 | 16.7 | 16.7 |
| 8 | 16 | 22 | 38 | — | 0 | 10.7 | 21.4 | 14.2 |
| 10 | — | — | 2 | 11 | 6.7 | 6.7 | 13.3 | 20 |
| 14 | 18 | 43 | — | — | 14 | 33.5 | — | — |
| 15 | — | — | 6 | 16 | 6.3 | 12.5 | 12.5 | 18.8 |
| 16 | — | — | 22 | — | 6.7 | 13.3 | 13.3 | — |
| 21 | — | 13 | 27 | 37 | 7 | 10 | 14 | 14 |
| 23 | — | 18 | 35 | 39 | — | — | — | — |
| 26 | — | 20 | 30 | 35 | 6.5 | 6.5 | 6.5 | 6.5 |
| 33 | — | 17 | 22 | 31 | 14.3 | 14.3 | 17.9 | 21.4 |
| 34 | — | — | 17 | 25 | 6 | 12 | 12 | 18 |
| d-sota-lol | 0 | 3 | 7.4 | 15.8 | 1.7 | 6.7 | 8.7 | 15.5 |

TOXICITY TEST 1

Each of the compounds prepared in the above-mentioned examples was administered into a mouse (ddY strain, male). In each case, oral administration (p.o.) and intra peritoneal administration (i.p.) were separately carried out in a dose of 300 mg/kg and 250 mg/kg, respectively.

A mortality rate (number of specimens: one group=2 to 4 mice) of the mice 24 hours after the administration was calculated, and the results are set forth in Table 3.

TABLE 3

| | (results of toxicity test) | |
|---|---|---|
| Compound Number | Mortality Rate (%) | |
| | 300 mg/kg (p.o.) | 250 mg/kg (i.p.) |
| 4 | 0 | 0 |
| 8 | 0 | 0 |
| 10 | 0 | — |
| 22 | 0 | 50 |
| 23 | 0 | — |
| 26 | 0 | 50 |

TABLE 3-continued

| | (results of toxicity test) | |
|---|---|---|
| Compound Number | Mortality Rate (%) | |
| | 300 mg/kg (p.o.) | 250 mg/kg (i.p.) |
| 34 | 100 | — |

EXAMPLE 20

Preparation of 1,3-dimethyl-6-{4-[3-(4-nitrophenoxypropyl]piperazin-1-yl}-2,4(1H,3H)-pyrimidinedione hydrochloride (compound 35)

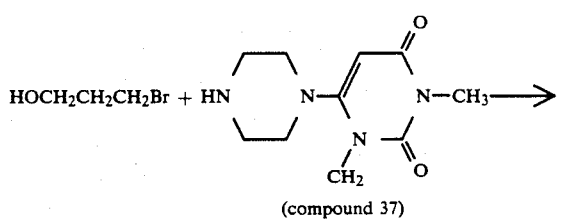
(compound 37)

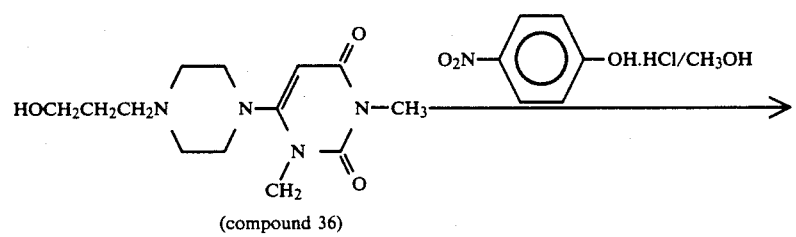
(compound 36)

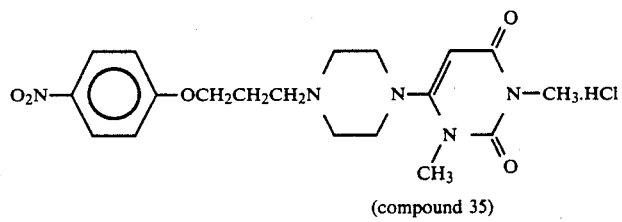
(compound 35)

(1) Preparation of 1,3-dimethyl-6-[4-(3-hydroxypropyl)piperazin-1-yl]-2,4(1H,3H)-pyrimidinedione (compound 36)

To 250 ml of ethanol were added 14.1 g of 1,3-dimethyl-6-(1-piperazinyl)-2,4(1H,3H)-pyrimidinedione (compound 37), 11.7 g of 3-bromo-1-propanol and 13 g of triethylamine, and the mixture was then heated under reflux for 20 hours to perform reaction. After completion of the reaction, the reaction mixture was concentrated to dryness, and the residue was then dissolved in 300 ml of chloroform. The resulting solution was washed with 100 ml of water twice, and the washed orgnaic layer was then dried over anhydrous magnesium sulfate. This organic layer was treated under reduced pressure to distill off the solvent, thereby obtaining 20.5 g of a composition. Afterward, ether was added to this composition, followed by crystallizing, recovering, washing and drying in order to obtain 12.4 g of 1,3-dimethyl-6-[4-(3-hydroxypropyl)piperazin-1-yl]-2,4(1H,3H)-pyrimidinedione (compound 36) (yield 69.8%).

Analytical results of the crystalline compound 36 thus obtained:

Melting point: 119°-121° C.

NMR (CDCl$_3$), δppm: 1.8 (dt, 2H), 2.7 (m, 6H), 3.02 (m, 4H), 3.36 (s, 3H), 3.43 (s, 3H), 3.82 (t, 2H), 4.34 (br, 1H), 5.26 (s, 1H) IR$\nu$KBr$_{max}$ (cm$^{-1}$): 3380, 3180, 2830, 1695, 1650, 1605, 1440, 1213, 1068, 1000, 921, 760

(2) Preparation of 1,3-dimethyl-6-{4-[3-(4-nitrophenoxy)propyl]piperazin-1-yl}-2,4(1H,3H)-pyrimidinedione hydrochloride (compound 35):

In 15 ml of anhydrous tetrahydrofuran were suspended 1.0 g of the above compound 36, 1.1 g of triphenylphosphine and 0.57 g of 4-nitrophenol, and 15 ml of an anhydrous tetrahydrofuran solution containing 0.71 g of diethyl azodicarboxylate was further added to the resulting suspension at room temperature.

Next, the resulting reaction mixture was stirred for 10 minutes and then concentrated to dryness, and the residue was purified through a silica gel column chromatograph (methanol/ethyl acetate=1/15 to 1/7 in the terms of volume ratio) to obtain 1.3 g of 1,3-dimethyl-6-{4-[3-(4-nitrophenoxy)propyl]piperazin-1-yl}-2,4(1H,3H)-pyrimidinedione (yield 80%).

Analytical results of the crystalline pyrimidinedione derivative thus obtained:

Melting point: 167°-170° C.
Values of elemental analysis (as C$_{19}$H$_{25}$N$_3$O$_5$)
Calcd. (%): C 56.57; H 6.25; N 17.36
Found (%): C 56.29; H 6.17; N 17.17

Furthermore, the thus obtained 1,3-dimethyl-6-{4-[3-(4-nitrophenoxy)propyl]piperazin-1-yl}-2,4(1H,3H)-pyrimidinedione was treated with a hydrochloric acid/methanol solution in a usual manner to obtain 1,3-dimethyl-6-{4-[3-(4-nitrophenoxy)propyl]piperazin-1-yl}-2,4(1H,3H)-pyrimidinedione hydrochloride (compound 35).

Analytical results of the crystalline compound 35 thus obtained:

Melting point: 244°-246° C. (decomposed)

EXAMPLE 21

Preparation 1,3-dimethyl-6-{4-[3-(3-nitrophenoxy)propyl]piperazin-1-yl}-2,4(1H,3H)-pyrimidinedione hydrochloride (compound 38)

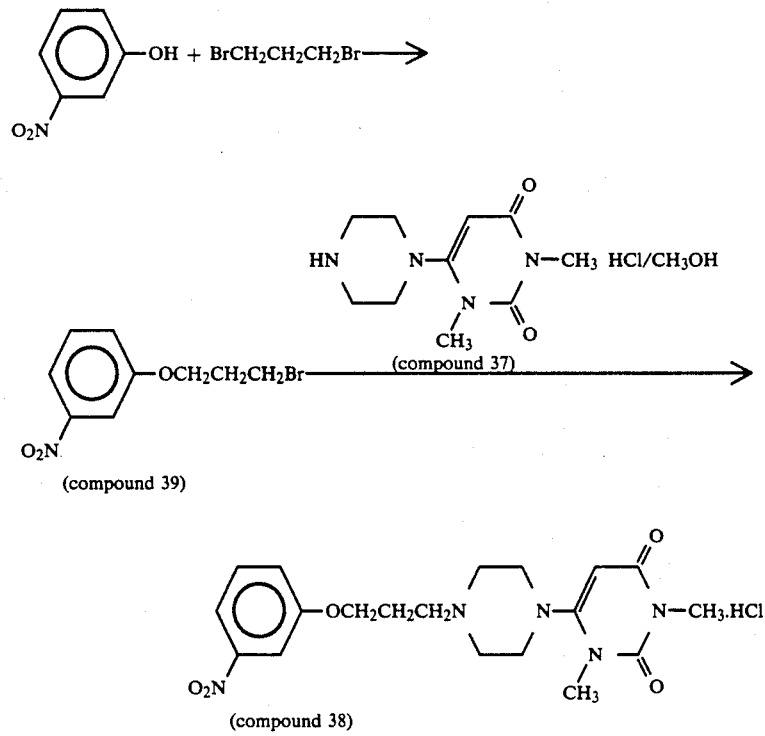

(1) Preparation of 3-(3-nitrophenoxy)propyl bromide (compound 39)

To 100 ml of methyl ethyl ketone were added 13.9 g of 3-nitrophenol, 101 g of 1,3-dibromopropane and 15.2 g of anhydrous potassium carbonate, and the mixture was then heated under reflux for 2 hours to perform reaction. After completion of the reaction, insoluble matters were removed from the reaction mixture by filtration, and the filtrate was then concentrated. Next, the resulting concentrate was dissolved in 300 ml of chloroform, and this chloroform solution was washed with water. Afterward, the washed organic layer was then dried over anhydrous magnesium sulfate. This organic layer was then treated under reduced pressure to distill off the solvent, thereby obtaining 24.6 g of 3-(3-nitrophenoxy)propyl bromide (compound 39) as an oily product. This product could be used in the subsequent reaction without purifying particularly.

(2) Preparation of 1,3-dimethyl-6-{4-[3-(3-nitrophenoxy)propyl]piperazin-1-yl}-2,4(1H,3H)-pyrimidinedione hydrochloride (compound 38)

In 20 ml of dioxane were dissolved 1.69 g of the above oily compound 39, 1.12 g of 1,3-dimethyl-6-(1-piperazinyl)-2,4(1H,3H)-pyrimidinedione (compound 37) and 1 ml of triethylamine, and the solution was then heated under reflux for 4 hours to perform reaction. After completion of the reaction, insoluble matters were removed from the reaction mixture by filtration, the resulting filtrate was then concentrated. The residue (concentrate) was dissolved in chloroform, and the resulting chloroform solution was then washed with water. Afterward, the water-washed organic layer was dried over anhydrous magnesium sulfate and then treated under reduced pressure to distill off the solvent. Furthermore, the residue was purified through a silica gel column chromatograph (chloroform/methanol=100/1 to 25/1 in terms of volume ratio), and the purified material was then recrystallized from methanol. Afterward, the crystals were collected by filtration, washed and dried in order to obtain 1.35 g of 1,3-dimethyl-6-{4-[3-(3-nitrophenoxy)propyl]piperazin-1-yl}-2,4(1H,3H)-pyrimidinedione.

Analytical results of the crystalline pyrimidinedione derivative thus obtained:

Melting point: 164°–165° C.

NMR(CDCl$_3$), δppm: 1.8–2.2 (m, 2H), 2.4–2.8 (m, 6H), 2.8–3.8 (m, 4H), 3.34 (s, 3H), 3.42 (s, 3H), 4.15 (t, 2H), 5.25 (s, 1H), 7.1–8.0 (m, 4H)

Values of elemental analysis (as $C_{19}H_{25}N_5O_5$)

Calcd. (%): C 56.57; H 6.25; N 17.36

Found (%): C 56.27; H 6.69; N 17.21

Next, the thus obtained 1,3-dimethyl-6-4-[3-(3-nitrophenoxy)propyl]piperazin-1-yl -2,4(1H,3H)-pyrimidinedione was treated with a hydrochloric acid/methanol solution to obtain 1,3-dimethyl-6-{4-[3-(3-nitrophenoxy)propyl]piperazin-1-yl}-2,4(1H,3H)-pyrimidinedione hydrochloride (compound 38).

Analytical results of the crystalline compound 38 thus obtained:

IR$\nu$KBr$_{max}$ (cm$^{-1}$): 1690, 1650, 1525, 1345, 1240, 1200, 1025, 980, 790, 760, 740, 670

Values of elemental analysis (as $C_{19}H_{25}N_5O \cdot HCl \cdot MeOH$)

Calcd. (%): C 51.00 H 6.21; N 14.87; Cl 7.53

Found (%): C 50.60; H 6.71; N 14.81; Cl 7.74

EXAMPLE 22

Preparation of 1,3-dimethyl-6-{4-[2-(4-nitrobenzoyloxy)ethyl]piperazin-1-yl}-2,4(1H,3H)-pyrimidinedione oxalate (compound 40)

To 5 ml of tetrahydrofuran were added 0.5 g of 4-nitrobenzoyl chloride, 0.47 g of 1,3-dimethyl-6-[4-(2-hydroxyethyl)piperazin-1-yl]-2,4(1H,3H)-pyrimidinedione (compound 41) and 1.5 ml of triethylamine, and the resulting mixture was stirred at room temperature overnight. Afterward, the used solvent was distilled off under reduced pressure, and the residue was then dissolved in chloroform. The resulting chloroform solution was washed with water, then dried over anhydrous sodium sulfate, and concentrated to dryness, thereby obtaining a crude product. The latter was then purified through a silica gel column chromatograph (chloroform/methanol=40/1 in terms of volume ratio) in order to obtain 1,3-dimethyl-6-{4-[2-(4-nitrobenzoyloxy)ethyl]piperazin-1-yl}-2,4(1H,3H)-pyrimidinedione.

Next, this pyrimidinedione derivative was treated with an oxalic acid/methanol solution in a usual manner to prepare 0.84 g of 1,3-dimethyl-6-{4-[2-(4-nitrobenzoyloxy)ethyl]piperazine-1-yl}-2,4(1H,3H)-pyrimidinedione oxalate (compound 40).

Analytical results of the crystalline compound 40 thus obtained:

Melting point: 171°–173° C. (decomposed)

IR$\nu$KBr$_{max}$ (cm$^{-1}$): 3100, 2550, 1740, 1700, 1660, 1640, 1540, 1360, 850

Values of elemental analysis [as $C_{19}H_{25}N_5O_6$ (COOH)2 2H$_2$O]

Calcd. (%): C 46.24; H 5.73; N 12.84

Found (%): C 46.64; H 5.38; N 12.83

EXAMPLE 23

Preparation of 1,3-dimethyl-6-[4-(4-nitrophenacyl)-piperazin-1-yl]-2,4(1H,3H)-pyrimidinedione hydrochloride (compound 42)

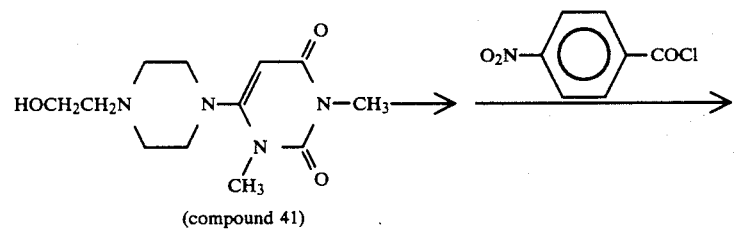

(compound 41)

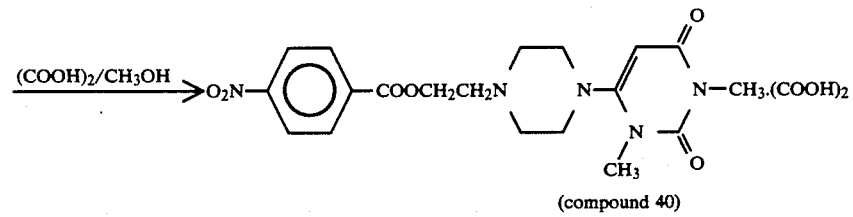

(compound 40)

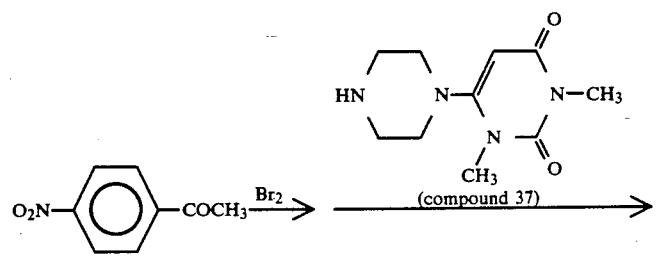

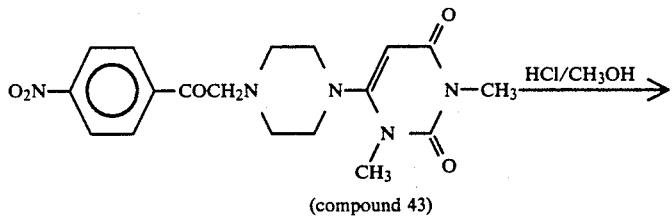

(compound 43)

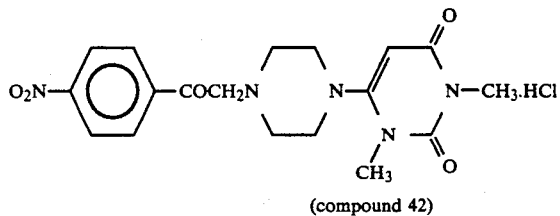

(compound 42)

In 200 ml of chloroform was dissolved 8.25 g of 4-nitroacetophenone, and 20 ml of a chloroform solution containing 8 g of bromine was added dropwise thereto under cooling. The resulting reaction mixture was concentrated, and the residue (concentrate) was recrystallized from chloroform/ether, collected by filtration, washed, and dried to obtain 8.03 g of p-nitrophenacyl bromide.

Next, to 150 ml of dioxane were added 4.88 g of the above prepared p-nitrophenacyl bromide, 4.48 g of 1,3-dimethyl-6-(1-piperazinyl)-2,4(1H,3H)-pyrimidinedione (compound 37) and 4.2 ml of triethylamine, and the solution was heated under reflux for 1 hour. Afterward, the reaction mixture was cooled to deposit crystals, and the latter were collected by filtration, dissolved in chloroform, washed with water, and dried (over anhydrous sodium sulfate). Afterward, the used solvent was distilled off, and methanol was then added to the residue so as to crystallize it. The resulting crystals were then collected by filtration, washed, and dried to obtain 4.02 g of 1,3-dimethyl-6-[4-(4-nitrophenacyl)piperazin-1-yl]-2,4(1H,3H)-pyrimidinedione (compound 43).

NMR (CF$_3$COOH), δppm: 3.63 (s, 3H), 3.73 (s, 3H), 3.7–4.3 (m, 8H), 5.21 (s, 2H), 6.12 (s, 1H), 8.28 (s, 2H), 8.52 (d, 2H)

Furthermore, 0.9 g of the compound 43 was treated with a hydrochloric acid/methanol solution in a usual manner to obtain 0.91 g of 1,3-dimethyl-6-[4-(4-nitrophenacyl)piperazin-1-yl]-2,4(1H,3H)-pyrimidinedione hydrochloride (compound 42).

Analytical results of the crystalline compound 42 thus obtained:

Melting point: 257°–262° C.

IRνKBr$_{max}$ (cm$^{-1}$): 1685, 1630, 1520, 1340, 1190, 960, 845, 790, 740

Values of elemental analysis (as C$_{18}$H$_{21}$N$_5$O$_5$·Hcl·½C-H$_3$OH)

Calcd. (%): C 50.52; H 5.50; N 15.92; Cl 8.06
Found (%): C 50.77; H 5.29; N 15.82; Cl 7.61

EXAMPLE 24

Preparation of 1,3-dimethyl-6-{4-[2-hydroxy-2-(4-nitrophenyl)ethyl]piperazin-1-yl}-2,4-(1H,3H)-pyrimidinedione hydrochloride (compound 44)

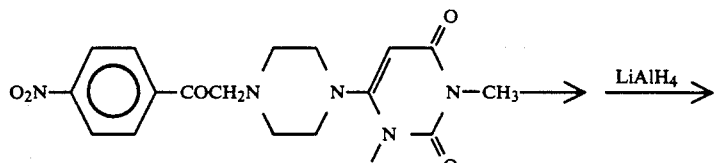

(compound 43)

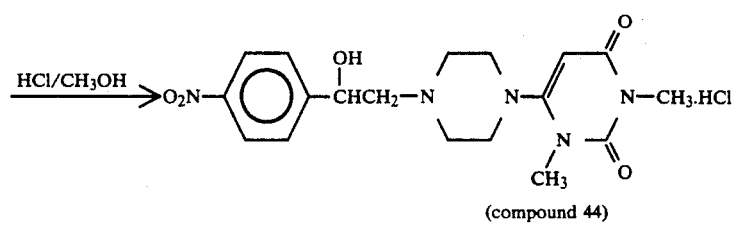

(compound 44)

Analytical results of the crystalline compound 43 thus obtained:

Melting point: 189°–192° C.

Values of elemental analysis (as C$_{18}$H$_{21}$N$_5$O$_5$·½C-H$_3$OH)

Calcd. (%): C 55.08; H 5.75; N 17.36
Found (%): C 54.86; H 5.44; N 17.62

Under ice cooling, 3.46 g of lithium aluminum hydride was added to 700 ml of a dried tetrahydrofuran suspension containing 8.12 g of 1,3-dimethyl-6-[4-(4-nitrophenacyl)piperazin-1-yl]-2,4-(1H,3H)-pyrimidinedione (compound 43), and the mixture was then stirred at the same temperature for 30 minutes, followed by stirring at room temperature for 2 hours.

After completion of the stirring operation, 50 ml of water was added to the reaction mixture under cooling in order to bring the reaction to an end, and insoluble matters were removed therefrom by filtration and the filtrate was then concentrated.

The residue (concentrate) was dissolved in chloroform, washed with water and dried (over anhydrous sodium sulfate), and the resulting organic layer was concentrated to a small amount. Afterward, the concentrate was purified through a silica gel column chromatograph (chloroform/methanol=100:1 to 100:2 in terms of volume ratio), thereby preparing 3.7 g of 1,3-dimethyl-6-{4-[2-hydroxy-2-(4-nitrophenyl)ethyl]piperazin-1-yl}-2,4(1H,3H)-pyrimidinedione.

Analytical results of the crystalline pyrimidinedione derivative thus obtained:

Melting point: 205°–207° C.

NMR (DMSO-$d_6$), δppm: 2.5–2.7 (m, 6H), 2.7–2.95 (m, 4H), 3.06 (s, 3H), 3.20 (s, 3H), 4.79 (t, 1H), 7.47 (d, 2H), 8.04 (d, 2H)

Next, 0.55 g of this pyrimidinedione derivative was treated with a hydrochloric acid/methanol solution in a usual manner in order to obtain 0.53 g of 1,3-dimethyl-6-{4-[2-hydroxy-2-(4-nitrophenyl)ethyl]piperazin-1-yl}-2,4-(1H,3H)-pyrimidinedione hydrochloride (compound 44).

Analytical results of the crystalline compound 44 thus obtained:

Melting point: 250°–265° C. (gradually colored and decomposed)

Values of elemental analysis (as $C_{18}H_{22}N_5O_5 \cdot HCl \cdot \frac{1}{4}H_2O$):

Calcd. (%): C 50.23; H 5.74; N 16.27; Cl 8.24
Found (%): C 50.22; H 6.07; N 16.04; Cl 8.20

IR$\nu$KBr$_{max}$ (cm$^{-1}$): 1700, 1620, 1430, 1340, 1190, 1165, 850, 785

EXAMPLE 25

Preparation of 1,3-dimethyl-6-{4-[2-(4-nitrobenzoylamino)ethyl]piperazin-1-yl}-2,4(1H,3H)-pyrimidinedione hydrochloride (compound 45):

(1) Preparation of 2-(4-nitrobenzoylamino)ethyl bromide (compound 46)

In 30 ml of chloroform were added 3 g of 4-nitrobenzoyl chloride, 3.3 g of 2-aminoethyl bromide hydrobromide and 3.9 ml of pyridine under ice cooling, and they were stirred at the same temperature for 1 hour. The reaction mixture was then washed with water, and the resulting organic layer was concentrated to obtain a crude product of 2-(4-nitrobenzoylamino)ethyl bromide. Afterward, the latter was recrystallized from hexane/ethanol, the resulting crystals were collected by filtration, washed and dried to prepare 2.9 g of 2-(4-nitrobenzoylamino)ethyl bromide (compound 46).

Analytical results of the crystalline compound 46 thus obtained:

Melting point: 104°–108° C.

(2) Preparation of 1,3-dimethyl-6-{4-[2-(4-nitrobenzoylamino)ethyl]piperazin-1-yl}-2,4(1H,3H)-pyrimidinedione hydrochloride (compound 45):

A mixture of 1.3 g of the compound 46 obtained in the paragraph (1), 1.8 g of 1,3-dimethyl-6-(1-piperazinyl)-2,4(1H,3H)pyrimidinedione (compound 37), 1.3 ml of triethylamine and 10 ml of isopropanol was heated under reflux for 3 hours.

Next, the used solvent was distilled off from the resulting reaction mixture, and water was added to the reaction mixture, followed by extracting with chloroform.

Furthermore, a chloroform extract was washed with water, dried over anhydrous sodium sulfate, and concentrated in order to obtain a crude product. Afterward, the latter was recrystallized from hexane/ethanol, and the resulting crystals were collected by filtration, washed and dried in order to obtain 1.77 g of 1,3-dimethyl-6-{4-[2-(4-nitrobenzoylamino)ethyl]piperazin-1-yl}-2,4(1H,3H)-pyrimidinedione.

Analytical results of the crystalline pyrimidinedione derivative thus obtained:

Melting point: 169°–171° C.

IR$\nu$KBr$_{max}$ (cm$^{-1}$): 3000, 2900, 1700, 1640, 1530, 1340, 850, 700

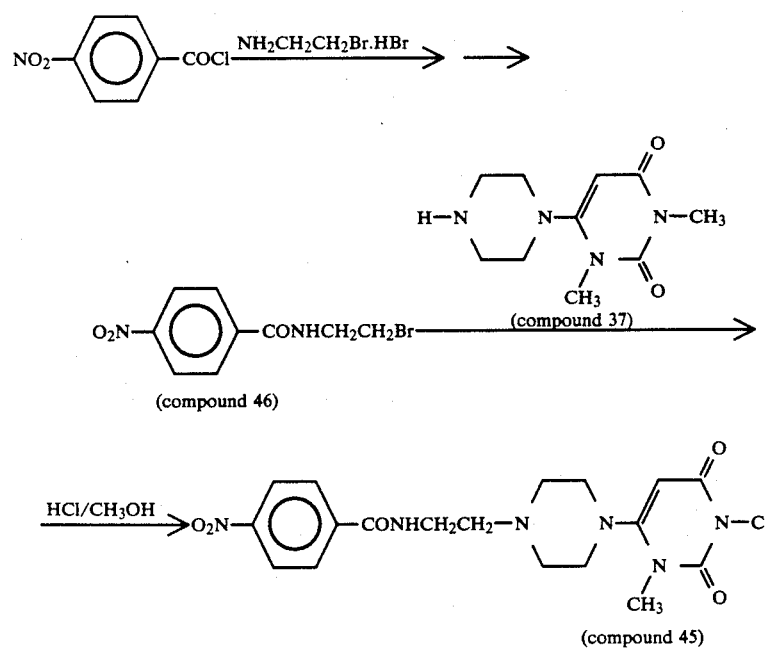

Next, the thus obtained pyrimidinedione derivative crystals were treated with a hydrochloric acid/methanol solution in a usual manner to obtain 1,3-dimethyl-6-{4-[2-(4-nitrobenzoylamino)ethyl]piperazin-1-yl}-2,4(1H,3H)-pyrimidinedione hydrochloride (compound 45).

Analytical results of the crystalline compound 45 thus obtained:
Melting point: 283°–285° C. (decomposed)
Values of elemental analysis (as $C_{19}H_{24}N_6O_5 \cdot 2HCl$):
Calcd. (%): C 46.62; H 5.66; N 17.20; Cl 14.49
Found (%): C 46.45; H 5.79; N 17.01; Cl 14.67

EXAMPLE 26

Preparation of 1,3-dimethyl-6-{4-[N-(4-nitrophenyl)carbamoylmethyl]piperazin-1-yl}-2,4(1H,3H)pyrimidinedione oxalate (compound 47)

ward, the resulting solution was washed with water and dried over anhydrous sodium sulfate.

Afterward, the solvent was distilled off from the dried chloroform solution under reduced pressure, and the residue was purified through a silica gel chromatograph (chloroform/methanol=100/1 to 25/1 in terms of volume ratio) to obtain 0.85 g of 1,3-dimethyl-6-{4-[N-(4-nitrophenyl)carbamoylmethyl]piperazin-1-yl}-2,4(1H,3H)pyrimidinedione.

Analytical results of the crystalline pyrimidine derivative thus obtained:
NMR (DMSO-$d_6$), δppm: 2.5–2.9 (m, 10H), 3.28 (s, 3H), 3.37 (s, 3H), 5.00 (s, 1H), 7.29 (d, 2H), 8.01 (d, 2H)

Next, this pyrimidine derivative was treated with an oxalic acid/methanol solution in a usual manner, thereby preparing 0.81 g of 1,3-dimethyl-6-{4-[N-(4-nitrophenyl)carbamoylmethyl]piperazin-1-yl-

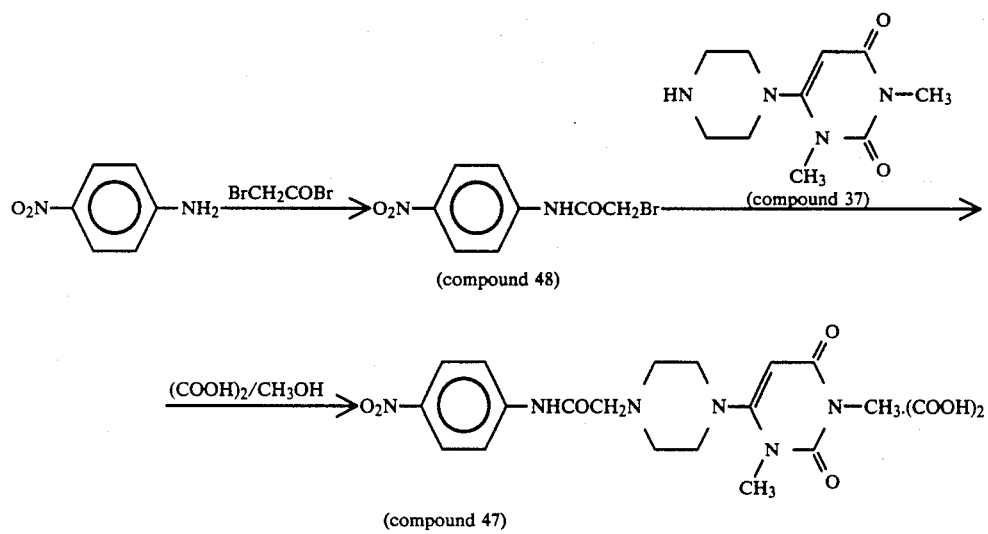

A mixture of 0.8 g of 4-nitroaniline, 0.6 ml of bromoacetyl bromide, 1.5 g of anhydrous potassium carbonate and 10 ml of dimethyl sulfoxide was stirred at 100° C. for 4 hours, and insoluble matters were removed from the mixture by filtration while the latter was hot. The filtrate was cooled to deposit 4-(bromoacetamide)nitrobenzene (compound 48) crystals, and the latter were collected by filtration and then heated under reflux for 16 hours together with 1.3 g of 1,3-dimethyl-6-(1-piperazinyl)-2,4(1H,3H)-pyrimidinedione (compound 37), 1.6 g of triethylamine and 15 ml of isopropanol.

After cooling, the used solvent was distilled off, and the residue was then dissolved in chloroform. After- 2,4(1H,3H)pyrimidinedione oxalate (compound 47).

Analytical results of the crystalline compound 47 thus obtained:
Melting point: 281°–283° C. (decomposed)
Values of elemental analysis (as $C_{18}H_{22}N_6O_5 \cdot (COOH)_2 \cdot H_2O$):
Calcd. (%): C 47.06; H 5.13; N 16.46
Found (%): C 46.90; H 5.34; N 16.37

EXAMPLE 27

Preparation of 1,3-dimethyl-6-{4-[3-(4-nitroanilino)-2-hydroxypropyl]piperazin-1-yl}-2,4(1H,3H)-pyrimidinedione oxalate (compound 49)

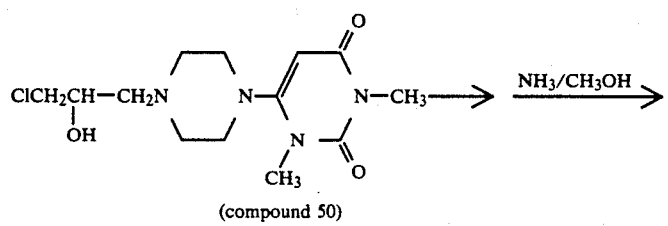

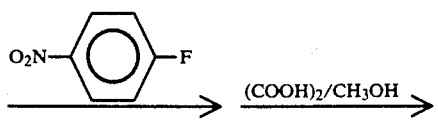

-continued

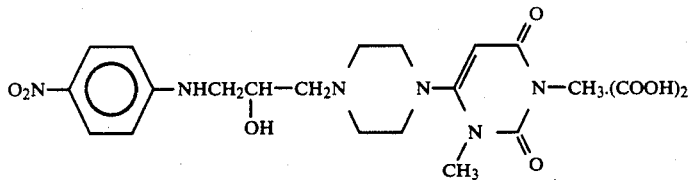

(compound 49)

In the first place, 20 ml (0.1 g/ml) of an ammonic methanol solution containing 2.0 g of 1,3-dimethyl-6-[4-(3-chloro-2-hydroxypropyl)piperazin-1-yl]-2,4(1H,3H)-pyrimidinedione (compound 50) was heated at 90° C. for 8 hours. The reaction mixture was concentrated under reduced pressure, and the residue (concentrate) was mixed with 0.9 g of 4-nitrofluorobenzene and 1 ml of triethylamine and then heated at 90° C. for 2 hours. The resulting reaction mixture was poured into 100 ml of water, and the deposited crystals were then collected by filtration, washed with methanol/ether, and dried in order to obtain 2.15 g of yellow crystalline 1,3-dimethyl-6-{4-[3-(4-nitroanilino)-2-hydroxypropyl]piperazin-1-yl}-2,4(1H,3H)-pyrimidinedione.

Furthermore, the yellow crystals were treated with an oxalic acid/methanol solution in a usual manner to obtain 1,3-dimethyl-6-{4-[3-(4-nitroanilino)-2-hydroxypropyl]piperazin-1-yl}-2,4(1H,3H)-pyrimidinedione oxalate (compound 49).

Analytical results of the crystalline compound 49 thus obtained:

IR$\nu$KBr$_{max}$(cm$^{-1}$): 3375 (br), 1693, 1640, 1600, 1470 (br), 1308, 1113

Values of elemental analysis [as $C_{19}H_{26}N_6O_5 \cdot (CO_2H)_2$]:

Calcd. (%): C 49.60; H 5.55; N 16.53
Found (%): C 50.10; H 5.98; N 16.79

EXAMPLE 28

Preparation of 1,3-dimethyl-6-{4-[3-(4-nitrophenylthio)propyl]piperazin-1-yl}-2,4(1H,3H)-pyrimidinedione oxalate (compound 51)

(1) Preparation of 3-(4-nitrophenylthio)propyl bromide (compound 52)

To 50 ml of a 2-butanone solution containing 5.5 g of 4-nitrothiophenol and 28.3 g of 1,3-dibromopropane was added 9.0 g of anhydrous potassium carbonate, and the solution was then stirred for 30 minutes at room temperature.

Afterward, insoluble matters were removed from the resulting reaction mixture by filtration, and the filtrate was then concentrated. The concentrate was dissolved in chloroform, and the resulting chloroform solution was then washed with water. Furthermore, the water-washed orgnaic layer was dried over anhydrous magnesium sulfate and then treated under reduced pressure to distill off the solvent, thereby preparing 8.0 g of crystalline 3-(4-nitrophenylthio)propyl bromide (compound 52). This product could be used in the subsequent reaction without purifying particularly.

(2) Preparation of 1,3-dimethyl-6-{4-[3-(4-nitrophenylthio)propyl]piperazin-1-yl}-2,4(1H,3H)-pyrimidinedione oxalate (compound 51)

To 30 ml of ethanol were added 2.0 g of the above compound 52, 1.68 g of 1,3-dimethyl-6-(1-piperazinyl)-2,4(1H,3H)-pyrimidinedione (compound 37) and 3 ml of triethylamine, and the solution was then heated with stirring under reflux for 3 hours.

The resulting reaction mixture was concentrated to dryness and then mixed with 100 ml of water. Afterward, the deposited material was collected by filtration and then washed with ethanol.

Furthermore, the thus washed deposit was recrystallized from methanol, collected by filtration, washed and

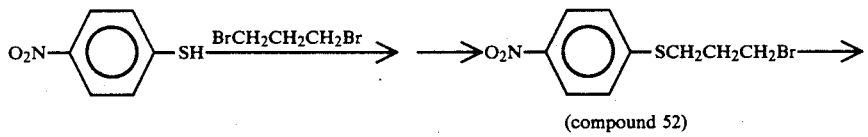

(compound 52)

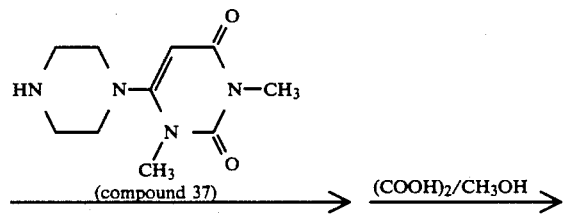

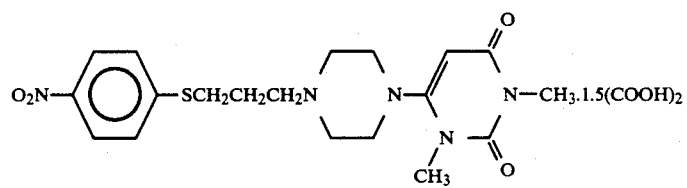

(compound 51)

dried to obtain 2.4 g of 1,3-dimethyl-6-{4-[3-(4-nitrophenylthio)propyl]piperazin-1-yl}-2,4(1H,3H)-pyrimidinedione.

Analytical results of the resulting crystalline pyrimidinedione derivative:

Melting point: 145°–147° C.

In 20 ml of methanol was suspended 2.2 g of the thus obtained crystals, and 2.0 g of oxalic acid dihydrate was added thereto, followed by stirring. After complete dissolution, stirring was further continued for a while. Afterward, 30 ml of ether was added thereto so as to deposit crystals, and the latter was collected by filtration, washed, and dried to obtain 2.0 g of 1,3-dimethyl-6-{4-[3-(4-nitrophenylthio)propyl]piperazin-1-yl}-2,4(1H,3H)pyrimidinedione oxalate (compound 51).

Analytical results of the crystalline compound 51 thus obtained:

Melting point: 164°–168° C. (decomposed)

Values of elemental analysis [as $C_{19}H_{25}N_5O_4S \cdot 1.5\text{-}(COOH)_2 \cdot H_2O$]:

Calcd. (%): C 46.15; H 5.28; N 12.23; S 5.60

Found (%): C 45.89; H 5.25; N 12.16; S 6.12

IR$\nu$KBr$_{max}$ (cm$^{-1}$): 3450, 1700, 1641, 1340, 1222, 978, 851, 745, 722

EXAMPLE 29

Preparation of 1,3-dimethyl-6-{4-[2-(4-nitrophenoxy)ethyl]piperazin-1-yl}-2,4(1H,3H)-pyrimidinedione hydrochloride (compound 53)

To 100 ml of anhydrous tetrahydrofuran were added 5.37 g of 1,3-dimethyl-6-[4-(2-hydroxyethyl)piperazin-1-yl]-2,4(1H,3H)-pyrimidinedione (compound 41), 3.20 g of 4-nitrophenol and 6.03 g of triphenylphosphine, and the resulting mixture was treated in the same manner as in Example 20-(2) to obtain 5.40 g of crystalline 1,3-dimethyl-6-{4-[2-(4-nitrophenoxy)ethyl]piperazin-1-yl}-2,4(1H,3H)-pyrimidinedione.

Analytical results of the crystalline pyrimidinedione derivative thus obtained:

IR$\nu$, KBr$_{max}$ (cm$^{-1}$): 1705, 1663, 1595, 1505, 1340, 1275, 1213, 1180, 1115, 1010, 862, 805, 750

Furthermore, the thus obtained crystals were treated with a hydrochloric acid/methanol solution in a usual manner to obtain 1,3-dimethyl-6-{4-[2-(4-nitrophenoxy)ethyl]piperazin-1-yl}-2,4(1H,3H)-pyrimidinedione hydrochloride (compound 53).

Analytical results of the crystalline compound 53 thus obtained:

IR$\nu$KBr$_{max}$ (cm$^{-1}$): 1705, 1655, 1595, 1435, 1342, 1267, 1112, 860, 755

Values of elemental analysis (as $C_{18}H_{23}N_5O_5 \cdot HCl \cdot 0.5H_2O$):

Calcd. (%): C 49.71; H 5.79; N 16.10; Cl 8.15

Found (%): C 49.17; H 6.05; N 16.20; Cl 8.40

EXAMPLE 30

Preparation of 1,3-dimethyl-6-{4-[4-(4-nitrophenoxy)butyl]piperazin-1-yl}-2,4(1H,3H)-pyrimidinedione

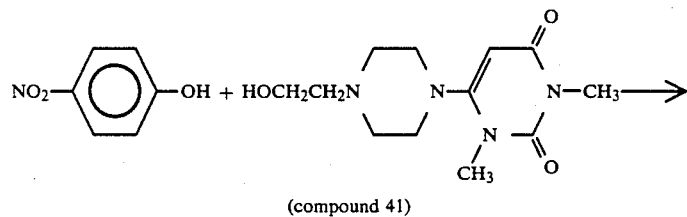

(compound 41)

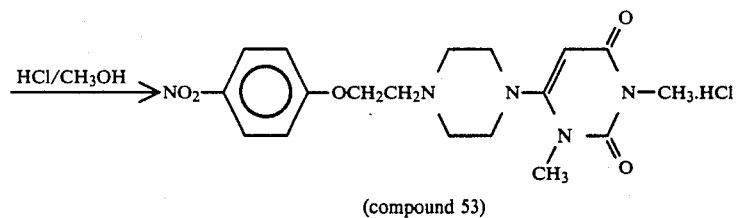

(compound 53)

hydrochloride (compound 54)

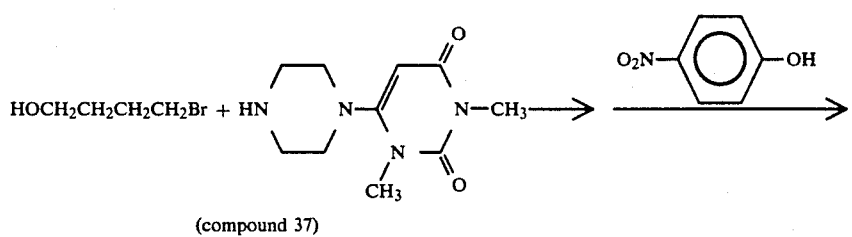

(compound 37)

-continued

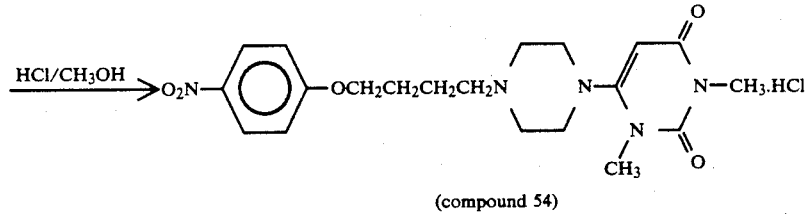

(compound 54)

The same procedure as in Example 20-(1) was repeated with the exception that 3-bromo-1-propanol was replaced with 12.9 g of 4-bromo-1-butanol, in order to obtain 13.1 g of 1,3-dimethyl-6-[4-(4-hydroxybutyl)piperazin-1-yl]-2,4-(1H,3H)-pyrimidinedione.

Furthermore, the same procedure as in Example 20-(2) was repeated with the exception that 1.05 g of this pyrimidinedione derivative was substituted for 1,3-dimethyl-6-[4-(3-hydroxypropyl)piperazin-1-yl]-2,4(1H,3H)-pyrimidinedione (compound 36), in order to prepare 1.2 g of crystals of 1,3-dimethyl-6-{4-[4-(4-nitrophenoxy)butyl]piperazine-1-yl}-2,4(1H,3H)-pyrimidinedione hydrochloride (compound 54).

Analytical results of the crystalline compound 54 thus obtained:
Values of elemental analysis (as $C_{20}H_{27}N_5O_5 \cdot HCl \cdot 0.5H_2O$)
Calcd. (%): C 51.89; H 6.31; N 15.13; Cl 7.66
Found (%): C 52.01; H 6.24; N 15.41; Cl 7.56

EXAMPLE 31

Preparation of 1,3-dimethyl-6-{4-[3-(2-nitrophenoxy)propyl]piperazin-1-yl}-2.4(1H,3H)-pyrimidinedione hydrochloride (compound 55)

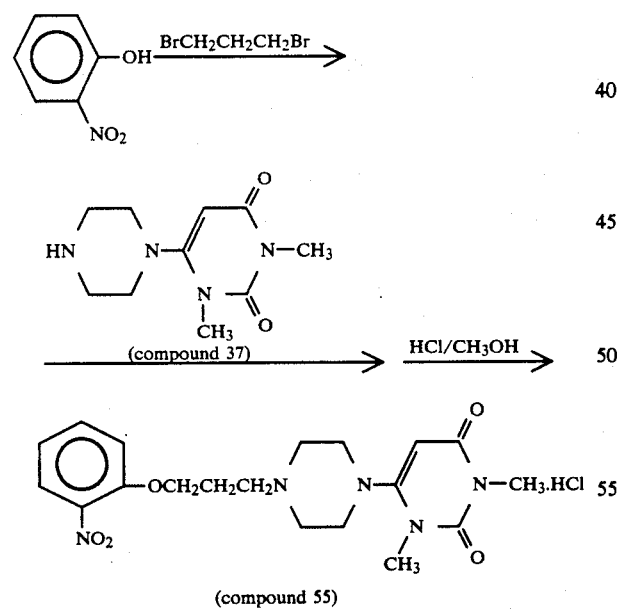

(compound 55)

The same procedure as in Example 21-(1) and 21-(2) was repeated with the exception that 3-nitrophenol was replaced with 13.9 g of 2-nitrophenol, in order to obtain crystals of 1,3-dimethyl-6-4-[3-(2-nitrophenoxy)-propyl]piperazin-1-yl}-2.4(1H,3H)-pyrimidinedione.

Analytical results of the crystalline pyrimidinedione derivative thus obtained:
Melting point: 123.5°-125° C.

Values of elemental analysis (as $C_{19}H_{25}N_5O_5$)
Calcd. (%): C 56.57; H 6.25; N 17.36
Found (%): C 56.74; H 5.85; N 17.46
NMR (CDCl$_3$), δppm: 2.03 (m, 2H), 2.66 (m, 6H), 2.98 (m, 4H), 3.32 (s, 3H), 3.40 (s, 3H), 4.11 (t, 2H), 5.22 (s, 1H), 6.9-7.9 (m, 4H)

The thus obtained crystals were treated with a hydrochloric acid/methanol solution in a usual manner to obtain 1,3-dimethyl-6-{4-[-3-(2-nitrophenoxy)propyl]-piperazin-1-yl}-2,4(1H,3H)-pyrimidinedione hydrochloride (compound 55).

Analytical results of the crystalline compound 55 thus obtained:
Melting point: 251°-252° C. (decomposed)
Values of elemental analysis (as $C_{19}H_{25}N_5O_5 \cdot HCl$)
Calcd. (%): C 51.88; H 5.96; N 15.92; Cl 8.06
Found (%): C 51.29; H 5.84; N 16.06; Cl 7.58

EXAMPLE 32

Preparation of 1,3-dimethyl-6-[2-(4-nitrobenzoylamino)ethylamino]-2,4(1H,3H)-pyrimidinedione (compound 56)

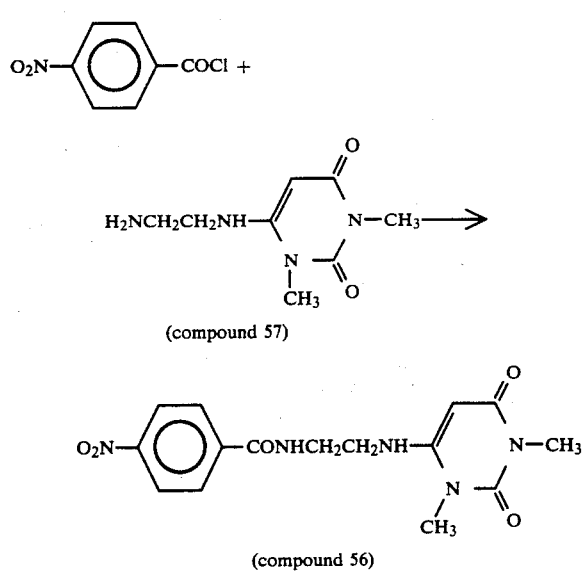

(compound 56)

The same procedure as in Example 22 was repeated with the exception that 1,3-dimethyl-6-[4-(2-hydroxyethyl)piperazin-1-yl]-2,4(1H,3H)-pyrimidinedione (compound 41) was replaced with 0.35 g of 1,3-dimethyl-6-(2-aminoethylamino)-2,4(1H,3H)-pyrimidinedione (compound 57), in order to obtain crystals of 0.49 g of 1,3-dimethyl-6-[2-(4-nitrobenzoylamino)ethylamino]-2,4(1H,3H)-pyrimidinedione (compound 56).

Analytical results of the crystalline compound 56 thus obtained:
Melting point: 284°-285° C. (decomposed)

IRνKBr$_{max}$ (cm$^{-1}$): 1690, 1660, 1640, 1610, 1550, 1360, 860

NMR (DMSO-d$_6$), δppm: 3.3 (m, 4H), 3.36 (s, 3H), 3.28 (s, 3H), 4.98 (s, 1H), 8.18 (d, 2H), 8.41 (d, 2H)

Values of elemental analysis (as C$_{15}$H$_{17}$N$_5$O$_5$)
Calcd. (%): C 51.87; H 4.93; N 20.16
Found (%): C 51.89; H 5.19; N 19.73

EXAMPLE 33

Preparation of tablets containing, as an effective component, 1,3-dimethyl-6-{4-[3-(4-nitrophenoxy)propyl]-piperazin-1-yl}-2,4(1H,3H)-pyrimidine hydrochloride (compound 35) which can be obtained by the process of Example 20

With 20 g of corn starch were mixed 1 g of the above pyrimidinedione derivative hydrochloride (compound 35) and 123 g of lactose, and the mixture was further mixed with a solution prepared by dissolving 5 g of hydroxypropyl cellulose in 100 ml of water, so as to form grains, followed by drying the grains at 50° C. for 4 hours. Afterward, 1 g of magnesium stearate was added to the dried grains and then mixed sufficiently. The mixture was then formed into tablets by the use of a tableting machine, the weight of each tablet being 150 mg.

EXAMPLE 34

Preparation of capsules containing, as an effective component, 1,3-dimethyl-6-{4-[2-(4-nitrobenzoylamino)ethyl]piperazin-1-yl}-2,4(1H,3H)-pyrimidinedione hydrochloride (compound 45) which can be obtained by the process of Example 25

With 25 g of corn starch were sufficiently mixed 5 g of the above pyrimidinedione derivative hydrochloride (compound 45) and 120 g of lactose, and hard capsules were filled with the resulting mixture by the use of a capsule filling machine to obtain capsules, the content of the mixture in each capsule being 150 mg.

EXAMPLE 35

Preparation of an injection containing, as an effective component, 1,3-dimethyl-6-{4-[3-(4-nitrophenyl)-2-hydroxypropyl]piperazin-1-yl}-2,4(1H,3H)-pyrimidinedione oxalate (compound 49) which can be obtained by the process of Example 27

In distilled water for injection were dissolved 20 mg of the above pyrimidinedione derivative oxalate (compound 49) and 0.85 g of sodium chloride, and the total volume of the liquid was regulated to be 100 ml, thereby preparing an injection.

PHARMACOLOGICAL TEST 2

Following the same procedure as in Pharmacological Test 1, APD$_{75}$ and ERP of the respective compounds prepared in the above examples in Table 4 were calculated. The resluts are set forth in Table 4.

TOXICITY TEST 2

Following the same procedure as in Toxicity Test 1, toxicity of the respective compounds prepared in the above examples in Table 5 was tested to calculate a mortality rate of mice.

Administration was made by oral administration (p.o.) in an amount of 300 mg/kg of each compound for one mouse.

TABLE 4

| | (results of pharmacological test) | | | | | | | |
|---|---|---|---|---|---|---|---|---|
| Compound | APD$_{75}$ (%) Dose (μg/ml) | | | | ERP (%) Dose (mg/kg, i.v.) | | | |
| No. | 0.3 | 1.0 | 3.0 | 10.0 | 0.1 | 0.3 | 1.0 | 3.0 |
| 35 | — | 17 | 22 | 30 | 6 | 12 | 15.8 | 25.3 |
| 38 | — | 15 | 34 | — | 0 | 0 | 7 | 14 |
| 42 | — | 2 | 10 | 17 | 4.6 | 9.4 | 11.7 | 18.4 |
| 44 | — | 5 | 13 | 21 | 0 | 7.7 | 19.9 | 27.8 |
| 47 | — | 5 | 11 | 16 | — | — | — | — |
| 51 | — | — | 33 | — | 12.6 | 12.6 | 19.0 | — |
| 53 | — | 8 | 22 | 43 | 8.8 | 23 | 30.1 | — |
| 54 | — | — | 15 | 26 | — | — | — | — |
| 55 | — | — | 18 | 39 | 0 | 0 | 6.8 | 13.6 |
| 56 | — | — | — | — | 6.7 | 6.7 | 6.7 | — |

TABLE 5

| (results of toxicity test) | |
|---|---|
| Compound Number | Mortality Rate (%) |
| 45 | 0 |
| 51 | 0 |
| 54 | 0 |
| 56 | 50 |

EXAMPLE 36

Preparation of 1,3-dimethyl-6-{4-[3-(4-nitroanilino)-propyl]piperazin-1-yl}-2,4(1H,3H)-pyrimidinedione hydrochloride (compound 58)

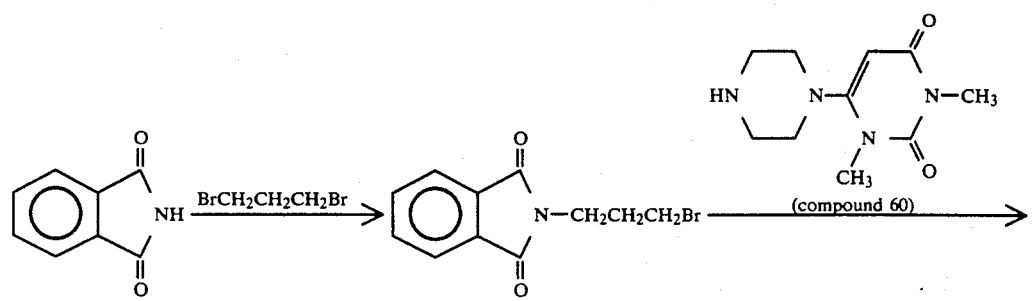

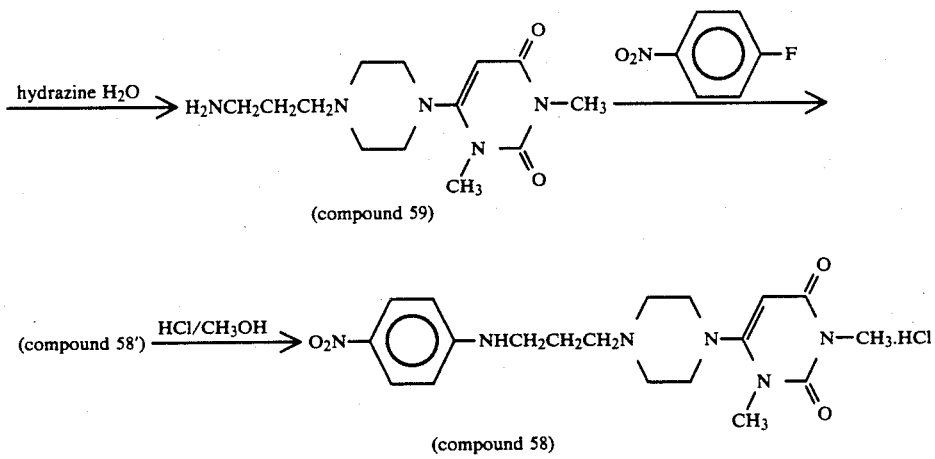

(compound 59)

(compound 58') —HCl/CH₃OH→ (compound 58)

(1) Preparation of 1,3-dimethyl-6-[4-(3-aminopropyl)-piperazin-1-yl]-2,4(1H,3H)-pyrimidinedione (compound 59)

In 100 ml of dimethylformamide were suspended 18.52 g of potassium phthalimide and 200 g of 1,3-dibromopropane, and then this suspension was heated with stirring at 120° C. for 6 hours so as to perform reaction. Next, insoluble matters were removed from the resulting reaction mixture by filtration, and the filtrate was then concentrated to dryness under reduced pressure. The residue was washed with hexane and then recrystallized from ethanol/water, and the resulting crystals were collected by filtration, washed, and dried to obtain 13.8 g of N-(3-bromopropyl)phthalimide.

Afterward, 13.0 g of this N-(3-bromopropyl)phthalimide, 10.3 g of 1,3-dimethyl-6-(1-piperazinyl)-2,4(1H,3H)-pyrimidinedione (compound 60) and 20 g of triethylamine were suspended in 200 ml of dioxane, and the resulting suspension was refluxed for 6 hours.

Furthermore, insoluble matters were removed from the reaction mixture by filtration, and the filtrate was then concentrated to dryness under reduced pressure. The residue (concentrate) was recrystallized from ethyl acetate/n-hexane, and the resulting crystals were collected by filtration, washed, and dried to obtain 12.5 g of 1,3-dimethyl-6-[4-(3-phthaloylaminopropyl)piperazin-1-yl]-2,4(1H,3H)-pyrimidinedione.

Next, 12.5 g of the thus obtained crystals and 6.0 g of hydrazine nomohydrate were suspensed in 200 ml of ethanol, and the suspension was then refluxed for 4 hours. After cooling, the resulting insoluble matters were removed therefrom by filtration, and the filtrate was then concentrated to dryness under reduced pressure. Furthermore, the residue (concentrate) was dissolved in water, and dilute hydrochloric acid was added thereto to adjust a pH to about 3. Insoluble matters which had been formed at this time were then removed therefrom by filtration, and a great deal of potassium carbonate was added to the filtrate, followed by extracting with chloroform. After completion of the extraction, the resulting organic layer was dried over anhydrous sodium sulfate and then subjected to a treatment under reduced pressure so as to distill off the solvent, thereby obtaining 1,3-dimethyl-6-[4-(3-aminopropyl)-piperazin-1-yl]-2,4(1H,3H)-pyrimidinedione (compound 59) as a colorless syrupy. This product was then allowed to stand, whereby it crystallized.

(2) Preparation of 1,3-dimethyl-6-{4-[3-(4-nitroanilino)propyl]piperazin-1-yl}-2,4(1H,3H)-pyrimidinedione hydrochloride (compound 58)

To 20 ml of dimethyl sulfoxide were added 2.50 g of the above obtained compound (compound 59) and 1.90 g of 4-nitrofluorobenzene, and the resulting mixture solution was heated at 80° C. for 3 hours. After cooling, the deposited crystals were collected by filteration, washed, and dried to obtain 2.75 g of 1,3-dimethyl-6-{4-[3-(4-nitroanilino)propyl]piperazin-1-yl}-2,4(1H,3H)-pyrimidinedione (compound 58').

Analytical results of the crystalline compound 58' thus obtained:

IR$\nu$KBr$_{max}$ (cm$^{-1}$): 3280, 1635, 1592, 1450, 1425, 1295, 1105, 990, 840

Values of elemental analysis (as $C_{19}H_{26}N_6O_4$):
Calcd. (%): C 56.70; H 6.51; N 20.88
Found (%): C 56.19; H 6.88; N 20.50

Next, the thus prepared compound 58' was treated with a hydrochloric acid/methanol solution in a usual manner to prepare 1,3-dimethyl-6-{4-[3-(4-nitroanilino)-propyl]piperazin-1-yl}-2,4(1H,3H)-pyrimidinedione hydrochloride (compound 58).

Analytical results of the crystalline compound 58 thus obtained:

Melting point: 270° C. or more
IR$\nu$KBr$_{max}$ (cm$^{-1}$): 3230, 1645, 1595, 1432, 1315, 1105, 837, 745

Values of elemental analysis (as $C_{19}H_{26}N_6O_4 \cdot HCl$):
Calcd. (%): C 51.99; H 6.20; N 19.15; Cl 8.08
Found (%): C 52.30; H 6.56; N 18.91; Cl 8.56

EXAMPLE 37

Preparation of 1,3-dimethyl-6-{2-[[1-(4-nitrophenyl)-piperidin-4-yl]amino]ethylamino}-2,4(1H,3H)-pyrimidinedione oxalate (compound 61)

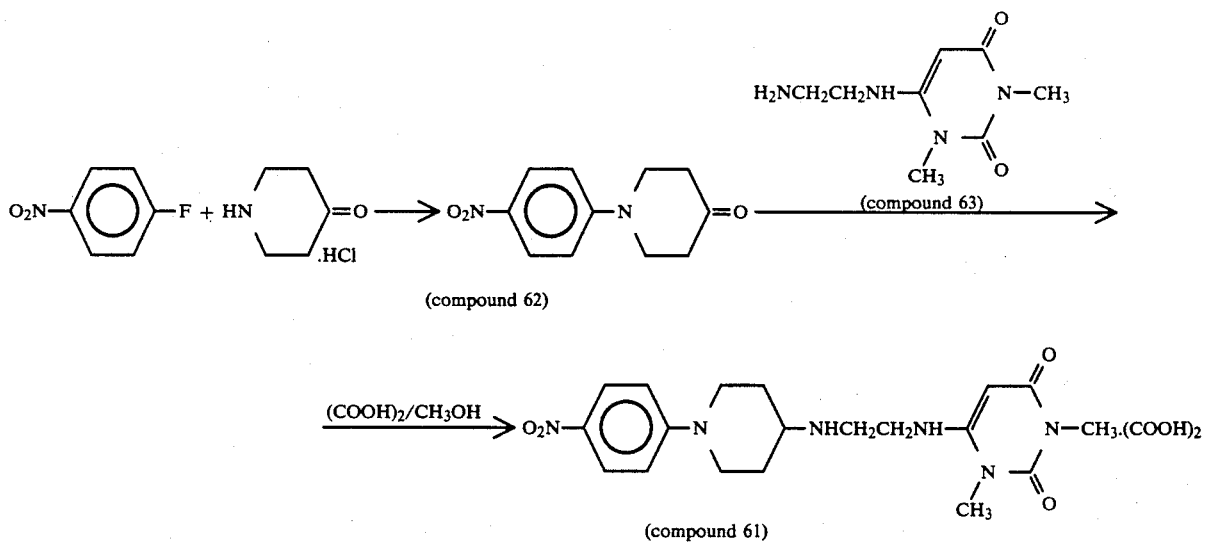

(1) Preparation of 1-(4-nitrophenyl)-4-oxopiperidine (compound 62)

In 20 ml of acetonitrile were dissolved 2.8 g of 4-nitrofluorobenzene, 3 g of 4-piperidone hydrochloride and 6.9 ml of triethylamine, and the solution was then heated under reflux for 6 hours. After cooling, the reaction mixture was poured into 100 ml of water, and the deposited crystals were collected by filtration. The crystals were washed with water and then with ether, and they were recrystallized from isopropanol/hexane (1/1 in terms of volume ratio), collected by filtration, washed, and dried in order to obtain 3.47 g of 1-(4-nitrophenyl)-4-oxopiperidine (compound 62).

(2) Preparation of 1,3-dimethyl-6-{2-[[1-(4-nitrophenyl)piperidin-4-yl]amino]ethylamino}-2,4-(1H,3H)-pyrimidinedione oxalate (compound 61)

In 30 ml of methanol were suspended 0.5 g of the above prepared compound 62 and 1.8 g of 6-(2-aminoethylamino)-1,3-dimethyl-2,4(1H,3H)-pyrimidinedione (compound 63), and 0.58 ml of a 4 N HCl/dioxane solution was added dropwise to the resulting suspension at 0° C., followed by stirring at the same temperature for 1 hour.

Next, the bulk temperature of the reaction mixture was maintained at 0° C., and 0.14 g of sodium cyanoborohydride was added thereto little by little and stirring was then performed at the same temperature for 3 hours.

Then, a small amount of water was added to the reaction mixture, and methanol was distilled off under reduced pressure. The resulting residue was dissolved in 0.5 N hydrochloric acid.

Potassium carbonate was added to this hydrochloric acid solution to make it alkaline, followed by extracting with chloroform.

Afterward, the extract (organic layer) was washed with water and then dried over anhydrous sodium sulfate, and the used solvent was distilled off under reduced pressure. Afterward, the residue was then purified through a silica gel column chromatograph (chloroform/methanol=50/1 to 25/1 in terms of volume ratio), thereby preparing 0.6 g of 1,3-dimethyl-6-{2-[[1-(4-nitrophenyl)piperidin-4-yl]amino]ethylamino}-2,4(1H,3H)-pyrimidinedione.

Analytical results of the crystalline pyrimidinedione derivative thus obtained:

NMR (CDCl$_3$) δppm: 1.5 (m, 4H), 2.2–3.2 (m, 7H), 3.30 (s, 3H), 3.41 (s, 3H), 4.0 (m, 2H), 4.86 (s, 1H), 6.93 (d, 2H), 8.17 (d, 2H)

Next, this pyrimidinedione derivative was treated with an oxalic acid/methanol solution in a usual manner to prepare 0.52 g of 1,3-dimethyl-6-{2-[[1-(4-nitrophenyl)piperidin-4-yl]amino]ethylamino}-2,4(1H,3H)-pyrimidinedione oxalate (compound 61).

Analytical results of the crystalline compound 61 thus obtained:

Melting point: 216°–217° C. (decomposed)

IRνKBr$_{max}$ (cm$^{-1}$): 2500, 1690, 1620, 1600, 1540, 1330, 810

Values of elemental analysis [as $C_{19}H_{26}N_6O_4$ (COOH)$_2$]:

Calcd. (%): C 51.22; H 5.73; N 17.06
Found (%): C 51.08; H 5.69; N 16.58

EXAMPLE 38

Preparation of 1,3-dimethyl-6-{2-[4-(4-nitrophenyl)-piperazin-1-yl]ethylamino}-2,4(1H,3H)-pyrimidinedione oxalate (compound 64):

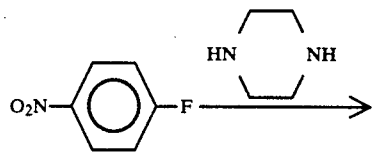

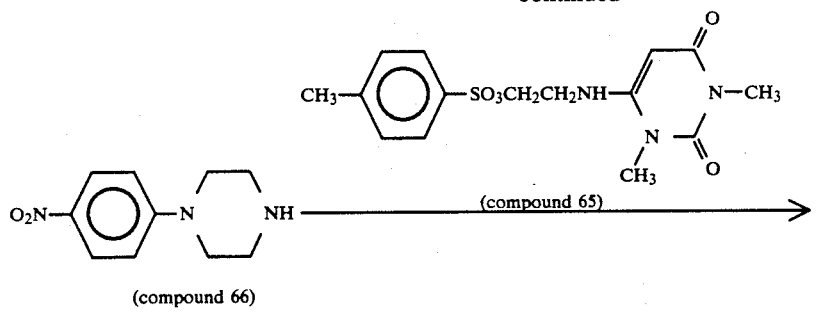

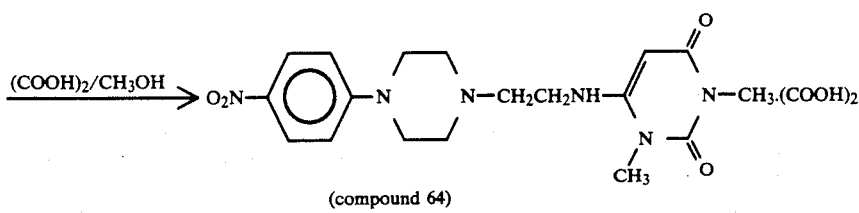

(1) Preparation of 1,3-dimethyl-6-[2-(p-toluenesulfonyloxy)ethylamino]-2,4(1H,3H)-pyrimidinedione (compound 65)

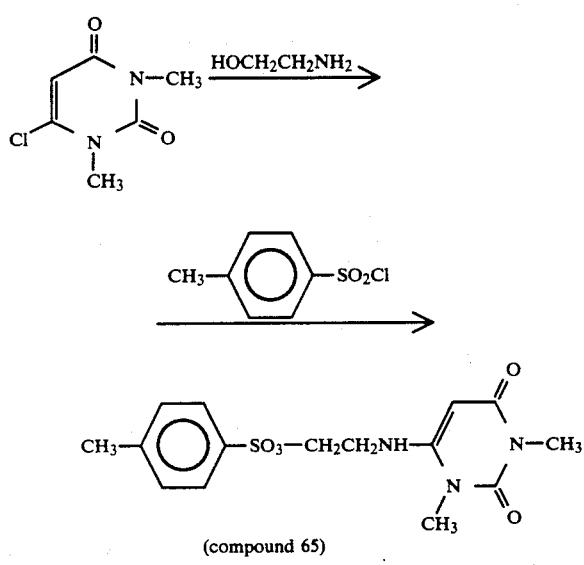

First, 35 g of 2-aminoethanol was heated up to 90° C., and it was then taken out of the oil bath. Afterward, 50.0 g of 6-chloro-1,3-dimethyl-2,4(1H,3H)-pyrimidinedione was added thereto, so that reaction was performed. At this time, a rate of the addition was such that reaction temperature was maintained in the range of 90° to 110° C.

After completion of the addition, the reaction mixture was stirred for 10 minutes, and 300 ml of dioxane/methanol (10/1 in terms of volume ratio) was added thereto, followed by standing onvernight. The resulting crystals were then washed with a small amount of dioxane, and dried to obtain 49.0 g of white crystalline 1,3-dimethyl-6-(2-hydroxyethyl-amino)-2,4(1H,3H)-pyrimidinedione.

Next, 200 ml of a pyridine suspension of this white crystals (49.0 g) was cooled to −5° C., and 40.0 g of p-toluenesulfonyl chloride was added at such a rate that the reaction temperature did not exceed a level of 5° C. Furthermore, 51.0 g of p-toluenesulfonyl chloride was additionally used to completely eliminate the turbidity of the reaction mixture.

Afterward, the reaction mixture was poured into 1.5 liters of ice water containing 70 g of $K_2C_3O$ and then allowed to stand overnight. The resulting crystals were collected by filtration, washed with water, and dried under reduced pressure in order to obtain 50.5 g of light yellow crystalline 1,3-dimethyl-6-[2-(p-toluenesulfonyloxy)ethylamino]-2,4(1H,3H)-pyrimidinedione (compound 65).

Analytical results of the crystalline compound 65 thus obtained:

Melting point: 146.0°–149.0° C.

IR$\nu$KBr$_{max}$ (cm$^{-1}$): 3270, 1682, 1615, 1550, 1480, 1435, 1350, 1190, 1178, 1010, 903, 780

(2) Preparation of 1-(4-nitrophenyl)piperazine (compound 66)

A mixture of 2.8 g of 4-nitrofluorobenzene, 15 g of piperazine and 20 ml of acetonitrile was heated under reflux for 6 hours. After cooling, chloroform was added to the reaction mixture, and the resulting solution was washed with water, dried (over anhydrous sodium sulfate), and concentrated under reduced pressure to obtain N-(4-nitrophenyl)piperazine (compound 66).

(3) Preparation of 1,3-dimethyl-6-{2-[4-(4-nitrophenyl)piperazin-1-yl]ethylamino}-2,4(1H,3H)-pyrimidinedione oxalate (compound 64)

With 0.6 g of the above N-(4-nitrophenyl)piperazine (compound 66) was mixed 0.5 g of 1,3-dimethyl-6-[2-(p-toluenesulfonyloxy)ethylamino]-2,4(1H,3H)-pyrimidinedione (compound 65), and the mixture was then heated at 80° C. for 1 hour. After cooling, the reaction mixture was diluted with 5 ml of acetonitrile.

Next, the diluted solution was then poured into 20 ml of a dilute aqueous sodium hydroxide solution, and the resulting mixture was extracted with chloroform. The resulting organic layer was washed with water, dried (over anhydrous sodium sulfate), and concentrated to dryness.

The residue (concentrate) was purified through a silica gel column chromatograph (chloroform/methanol=30:1 in terms of volume ratio) to obtain 1,3-dimethyl-6-{2-[4-(4-nitrophenyl)piperazin-1-yl]ethylamino}-2,4(1H,3H)-pyrimidinedione.

Analytical results of the pyrimidinedione derivative thus obtained:

NMR (CDCl$_3$) δppm: 2.8–3.8 (m, 12H), 3.36 (s, 3H), 3.41 (s, 3H), 4.86 (s, 1H), 6.87 (d, 2H), 8.16 (d, 2H)

This pyrimidinedione derivative was treated with an oxalic acid/methanol solution in a usual manner to obtain 0.36 g of 1,3-dimethyl-6-{2-[4-(4-nitrophenyl)piperazine-1-yl]ethylamino}-2,4(1H,3H)-pyrimidinedione oxalate (compound 64).

Analytical results of the crystalline compound 6 thus obtained:

IRνKBr$_{max}$(cm$^{-1}$): 1680, 1640, 1600, 1540, 1320, 830

Values of elemental analysis (as C$_{20}$H$_{24}$N$_6$O$_4$·2-(COOH)$_2$·4H$_2$O):

Calcd. (%): C 43.38; H 5.46; N 12.65
Found (%): C 42.91; H 5.19; N 13.24

EXAMPLE 39

Preparation of 1,3-dimethyl-6-{N-methyl-2-[N-methyl-2-(N-methyl-4-nitroanilino)ethylamino]ethylamino}-2,4(1H,3H)-pyrimidinedione oxalate (compound 67)

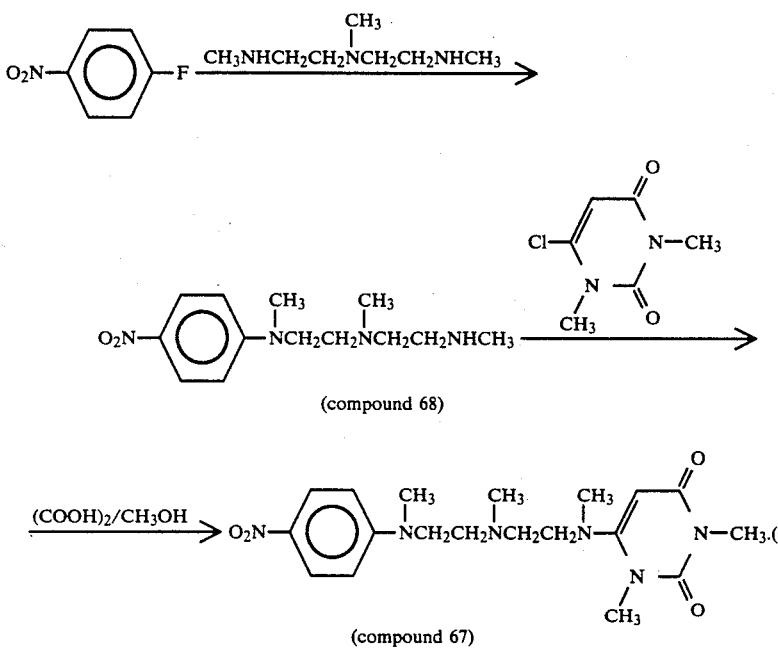

(compound 68)

(compound 67)

(1) Preparation of N,N′, N″-trimethyl-N-(4-nitrophenyl)diethylenetriamine (compound 68)

In 7 ml of dimethyl sulfoxide were dissolved 1.41 g of p-fluoronitrobenzene and 14 g of N,N′,N″-trimethyldiethylenetriamine, and the mixture was then stirred at 120° C. for 3 hours.

The solvent was then distilled off from the reaction mixture under reduced pressure, and the residue was then dissolved in chloroform. This chloroform solution was washed with a small amount of water, and then dried over anhydrous sodium sulfate. The used solvent was distilled off under reduced pressure, so that 2.1 g of N,N′,N″-tri-methyl-N-(4-nitrophenyl)diethylenetriamine (compound 68) was obtained in a yellow oily state.

(2) Preparation of 1,3-dimethyl-6-{N-methyl-2-[N-methyl-2-(N-methyl-4-nitroanilino)ethylamino]ethylamino}-2,4(1H,3H)-pyrimidinedione oxalate (compound 67)

In 10 ml of ethanol were suspended 2.1 g of the above prepared N,N′,N″-trimethyl-N-(4-nitrophenyl)diethylenetriamine (compound 68), 1.22 g of 6-chloro-1,3-dimethyl-2,4(1H,3H)-pyrimidinedione and 2 ml of triethylamine, and the suspension was then heated under reflux for 1 hour. The resulting reaction mixture was then concentrated to dryness, and the residue was purified through a silica gel column chromatograph (chloroform/methanol=50/1 to 25/1, v/v) and then recrystallized from acetone/water (1/1 in terms of volume ratio), thereby preparing 1.87 g of 1,3-dimethyl-6-{N-methyl-2-[N-methyl-2-(N-methyl-4-nitroanilino)ethylamino]ethylamino}-2,4(1H,3H)-pyrimidinedione.

Analytical results of the crystals thus obtained:
Melting point: 65° C.

NMR (CDCl$_3$), δppm: 2.40 (s, 3H), 2.82 (s, 3H), 3.38 (s, 3H), 3.50 (s, 3H), 3.54 (s, 3H), 2.78 (m, 2H), 3.13 (m, 2H), 3.80 (m, 2H), 5.40 (s, 1H), 6.78 (m, 2H), 8.62 (m, 2H)

Values of elemental analysis (as C$_{19}$H$_{28}$N$_6$O$_4$)
Calcd. (%): C 56.42; H 6.98; N 20.78
Found (%): C 56.63; H 7.31; N 19.98

The thus obtained 1,3-dimethyl-6-{N-methyl-2-[N-methyl-2-(N-methyl-4-nitroanilino)ethylamino]ethylamino}-2,4(1H,3H)-pyrimidinedione was treated with an oxalic acid/methanol solution in a usual manner to obtain 1.91 g of 1,3-dimethyl-6-{N-methyl-2-[N-methyl-2-(N-methyl-4-nitroanilino)ethylamino]ethylamino}-2,4(1H,3H)-pyrimidinedione oxalate (compound 67).

Analytical results of the crystalline compound 67 thus obtained:

Melting point: 184°–185° C. (decomposed)
IRνKBr$_{max}$ (cm$^{-1}$): 3460, 1700, 1642, 1545, 1480, 1310, 1200, 1100, 833, 722

Values of elemental analysis (as C$_{19}$H$_{26}$N$_6$O$_4$·(COOH)$_2$·½H$_2$O)

Calcd. (%): C 50.09; H 6.21; N 16.69
Found (%): C 50.29; H 6.29; N 16.11

EXAMPLE 40

Preparation of 1,3-dimethyl-6-{4-[3-(N-methyl-4-nitroanilino)propyl]piperazin-1-yl}-2,4(1H,3H)-pyrimidinedione oxalate (compound 69)

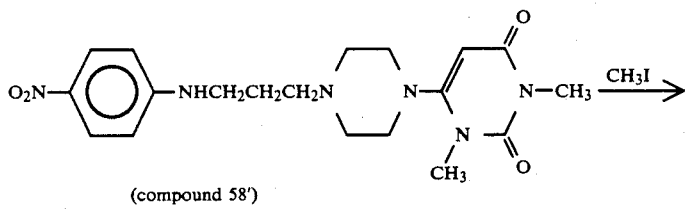

(compound 58')

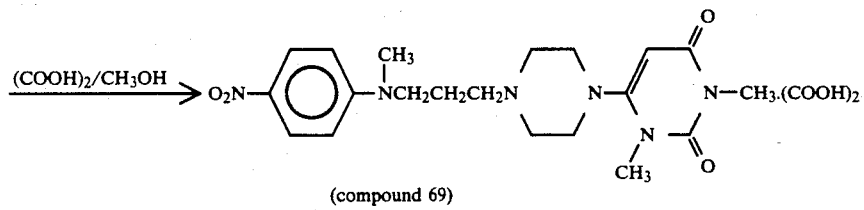

(compound 69)

At room temperature, 0.12 g of sodium hydride (60% dispersion in mineral oil) was added to a suspension obtained by suspending 0.7 g of 1,3-dimethyl-6-{4-[3-(4-nitroanilino)propyl]piperazin-1-yl}-2,4(1H,3H)-pyrimidinedione (compound 58') obtained in Example 36 in 15 ml of anhydrous dimethylformamide, and they were stirred for 30 minutes. Afterward, 0.29 g of methyl iodide was further added thereto.

This mixture was stirred at room temperature for 10 minutes, and a small amount of methanol and then 50 ml of chloroform were added thereto. Afterward, the resulting reaction mixture was poured into 50 ml of water. The separated organic layer was taken out, washed with water, and dried (over anhydrous sodium sulfate). The used solvent was distilled off, and the residue was crystallized from a methanol/ether solution (1/1 in terms of volume ratio), collected by filtration, washed, and dried in order to obtain 0.62 g of 1,3-dimethyl-6-[4-{3-(N-methyl-4-nitroanilino)propylpiperazin-1-yl]-2,4(1H,3H)-pyrimidinedione.

Analytical results of the crystalline pyrimidinedione derivative thus obtained:

IR$v$KBr$_{max}$ (cm$^{-1}$): 1690, 1640, 1588, 1520, 1480, 1425, 1282, 1205, 1101, 815

NMR (d$_6$-DMSO), δppm: 1.82 (m, 2H), 2.13-2.73 (m, 6H), 2.73-3.07 (m, 4H), 3.10 (s, 3H), 3.17 (s, 3H), 3.30 (s, 3H), 3.57 (t, 2H), 5.22 (s, 1H), 6.87 (d, 2H), 8.10 (d, 2H)

Values of elemental analysis (as C$_{20}$H$_{28}$N$_6$O$_4$·2H$_2$O)
Calcd. (%): C 57.13; H 7.67; N 19.99
Found (%): C 57.49; H 7.02; N 20.16

This pyrimidinedione derivative was treated with an oxalic acid/methanol solution in a usual manner to obtain 1,3-dimethyl-6-4-[3-(N-methyl-4-nitroanilino)-propyl]-piperazin-1-yl}-2,4(1H,3H)-pyrimidinedione oxalate (compound 69).

Analytical results of the crystalline compound 69 thus obtained:

Values of elemental analysis (as C$_{20}$H$_{28}$N$_6$O$_4$·(COOH)$_2$·2H$_2$O)
Calcd. (%): C 51.76; H 6.71; N 16.46
Found (%): C 52.05; H 6.08; N 16.56

EXAMPLE 41

Preparation of 1,3-dimethyl-6-{4-[3-(N-methansulfonyl-4-nitroanilino)propyl]piperazin-1-yl}-2,4(1H,3H)-pyrimidinedione oxalate (compound 70)

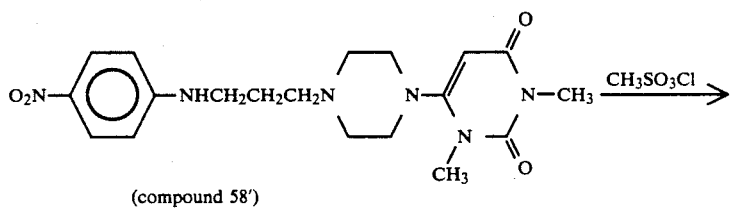

(compound 58')

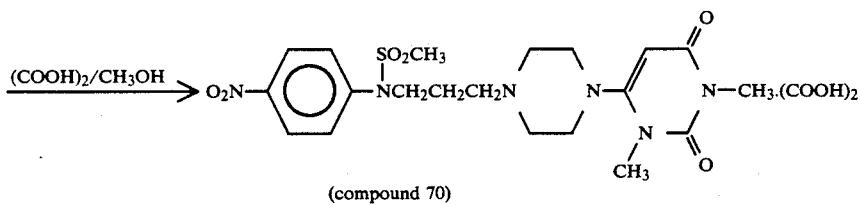

(compound 70)

In 20 ml of chloroform were dissolved 0.4 g of 1,3-dimethyl-6-{4-[3-(4-nitroanilino)propyl]piperazin-1-yl}-2,4(1H,3H)-pyrimidinedione (compound 58') obtained in Example 36 and 0.4 g of triethylamine, and 0.2 g of methanesulfonyl chloride was further added to the resulting solution under ice cooling.

This mixture was allowed to stand overnight at room temperature, and a small amount of water was added thereto, followed by stirring at room temperature for 30 minutes.

Furthermore, 20 ml of a dilute aqueous alkaline solution was added to the reaction mixture, and the separated chloroform layer was washed with water and then dried over anhydrous sodium sulfate. Afterward, the dried chloroform layer was treated under reduced pressure to distill off the solvent. The resulting residue was purified through a silica gel column chromatograph (chloroform/methanol = 100/1 to 25/1 in terms of volume ratio), thereby preparing 0.35 g of 1,3-dimethyl-6-{4-[3-(N-methanesulfonyl-4-nitroanilino)propyl]piperazin-1-yl}-2,4(1H,3H)-pyrimidinedione.

This pyrimidinedione derivative was treated with an oxalic acid/methanol solution in a usual manner to obtain 1,3-dimethyl-6-{4-[3-(N-methanesulfonyl-4-nitroanilino)propyl]piperazin-1-yl}-2,4(1H,3H)-pyrimidinedione oxalate (compound 70).

Analytical results of the crystalline compound 70 thus obtained:

Melting point: 204.0°–204.5° C.

Values of elemental analysis (as $C_{20}H_{28}N_6O_6S\cdot(COOH)_2\cdot 2H_2O$)

Calcd. (%): C 43.56; H 5.65; N 13.85; S 5.29
Found (%): C 43.81; H 5.24; N 13.35; S 5.52

IR$\nu$KBr$_{max}$(cm$^{-1}$): 1780, 1695, 1630 (br), 1350, 1340, 1205, 1155

EXAMPLE 42

Preparation of 1,3-dimethyl-6-{2-[N-ethyl-2-(4-nitroanilino)ethylamino]ethylamino}-2,4(1H,3H)-pyrimidinedione oxalate (compound 71)

Light yellow crystals which had been deposited by the overnight standing were collected by filtration, washed with ether, and dried under reduced pressure in order to obtain 15.2 g of 6-(1-aziridinyl)-1,3-dimethyl-2,4(1H,3H)-pyrimidinedione (compound 72).

Analytical results of the crystalline compound 72 thus obtained:

Melting point: 126.0°–126.5° C.

IR$\nu$KBr$_{max}$ (cm$^{-1}$): 1705, 1650, 1612, 1470, 1440, 1305, 1150, 783, 490

$^1$H-NMR (CDCl$_3$), δppm: 2.34 (s, 4H), 3.35 (s, 3H), 3.56 (s, 3H), 5.25 (s, 3H)

(2) Preparation of 1,3-dimethyl-6-{2-[N-ethyl-2-(4-nitroanilino)ethylamino]ethylamino}-2,4(1H,3H)-pyrimidinedione oxalate (compound 71)

In 5 ml of chloroform were dissolved 1.32 g of N-ethyl-N'-(4-nitrophenyl)ethylenediamine and 1.12 g of the above obtained 6-(1-aziridinyl)-1,3-dimethyl-2,4(1H,3H)-pyrimidinedione (compound 72), and the resulting reaction mixture was concentrated under reduced pressure. To the residue (concentrate) was added 10 mg of Amberlist 15 (trade name; made by Rohm &

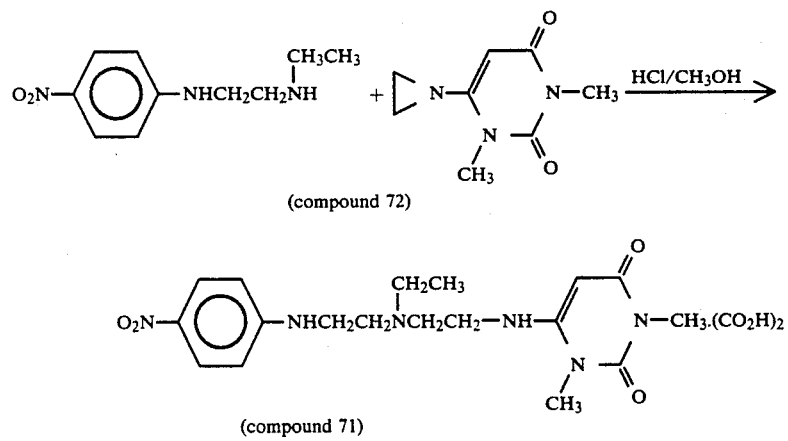

(1) Preparation of 6-(1-aziridinyl)-1,3-dimethyl-2,4(1H,3H)-pyrimidinedione (compound 72)

Haas Co.), and the mixture was then heated at 80° C. for 1 hour.

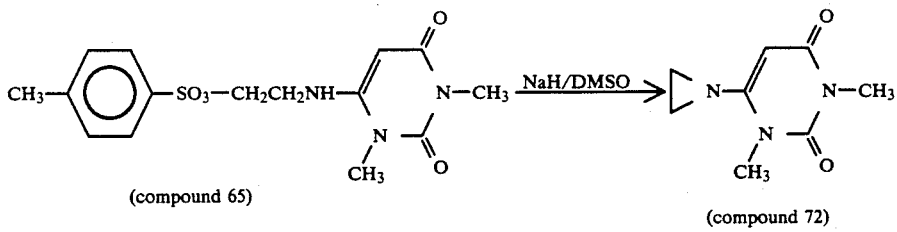

To 150 ml of an anhydrous dimethyl sulfoxide containing 47.2 g of the compound 65 obtained in Example 38-(1) was slowly added 6.24 g of sodium hydride (60% dispersion in mineral oil) at room temperature. This reaction mixture was stirred vigorously at room temperature for 5 hours, and then cooled. Afterward, a small amount of water was added thereto so as to bring reaction to an end. This solution was poured into 1 liter of water containing 70 g of potassium carbonate, and then extracted with 200 ml of chloroform three times. The combined organic layer was dried over anhydrous sodium sulfate and then concentrated, and 300 ml of ether was added to the resulting concentrate. Afterward, the solution thus obtained was allowed to stand overnight.

Next, the resulting reaction mixture was dissolved in 5 ml of ethyl acetate, and Amberlist 15 was then removed therefrom by filtration. Afterward, n-hexane was added to the filtrate.

Furthermore, the resulting solution was allowed to stand overnight, and deposited crystals were collected by filtration, washed with n-hexane, and dried under reduced pressure in order to obtain 1.5 g of 1,3-dimethyl-6-{2-[N-ethyl-2-(4-nitroanilino)ethylamino]ethylamino}-2,4(1H,3H)-pyrimidinedione.

Analytical results of the crystalline pyrimidinedione derivative thus obtained:

$^1$H-NMR (CDCl$_3$), δppm: 1.12 (t, 3H), 2.52–2.98 (m, 6H), 2.98–3.25 (m, 2H), 3.28 (s, 6H), 3.28–3.48 (m, 2H), 4.78 (s, 1H), 5.27 (m, 1H), 5.45 (m, 1H), 6.59 (d, 2H), 8.08 (d, 2H)

Furthermore, this pyrimidinedione derivative was treated with an oxalic acid/methanol solution in a usual manner to obtain 1.4 g of 1,3-dimethyl-6-{2-[N-ethyl-2-(4-nitroanilino)ethylamino]ethylamino}-2,4(1H,3H)-pyrimidinedione oxalate (compound 71).

Analytical results of the crystalline compound 71 thus obtained:

Melting point: 175.0°–176.5° C.

Values of elemental analysis (as $C_{18}H_{26}N_6O_4 \cdot (COOH)_2$)

Calcd. (%): C 50.00; H 5.87; N 17.49
Found (%): C 49.81; H 6.02; N 17.22

EXAMPLE 43

Preparation of 1,3-dimethyl-6-{2-[N-ethyl-3-(4-nitroanilino)propylamino]ethylamino}-2,4(1H,3H)-pyrimidinedione hydrochloride (compound 73)

dimethyl-6-{2-[N-methyl-3-(4-nitroanilino)propylamino]ethylamino}-2,4(1H,3H)-pyrimidinedione.

Analytical results of the crystalline pyrimidinedione derivative thus obtained:

NMR (DMSO-$d_6$), δppm: 1.05 (t, 3H), 1.6–1.9 (m, 2H), 2.4–2.8 (m, 6H), 3.0–3.4 (m, 4H), 3.1 (s, 3H), 3.25 (s, 3H), 4.65 (s, 1H), 6.4 (br, 1H), 6.6 (d, 2H), 7.2 (br, 1H), 8.0 (d, 2H)

The thus obtained crystals were treated with a hydrochloric acid/methanol solution in a usual manner to obtain 1,3-dimethyl-6-{2-[N-ethyl-3-(4-nitroanilino)propylamino]ethylamino}-2,4(1H,3H)-pyrimidinedione hydrochloride (compound 73).

Analytical results of the crystalline compound 73 thus obtained:

Values of elemental analysis (as $C_{19}H_{28}N_6O_4 \cdot 2HCl$)
Calcd. (%): C 47.80; H 6.33; N 17.60; Cl 14.85
Found (%): C 47.52; H 6.49; N 17.31; Cl 14.76

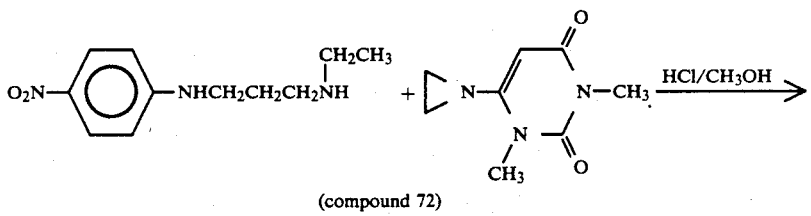

(compound 72)

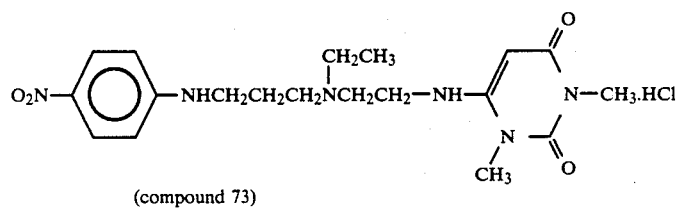

(compound 73)

The same procedure as in Example 42-(2) was repeated with the exception that N-ethyl-N'-(4-nitrophenyl)ethylenediamine was replaced with 1.45 g of N-ethyl-N'-(4-nitrophenyl)-1,3-propylenediamine as a starting material, in order to obtain crystals of 1,3-

EXAMPLE 44

Preparation of 1,3-dimethyl-6-{N-(2-hydroxyethyl)-2-[4-(4-nitrophenyl)piperazin-1-yl]ethylamino}-2,4(1H,3H)-pyrimidinedione oxalate (compound 74)

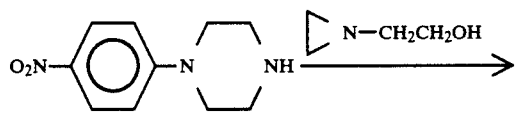

(compound 66)

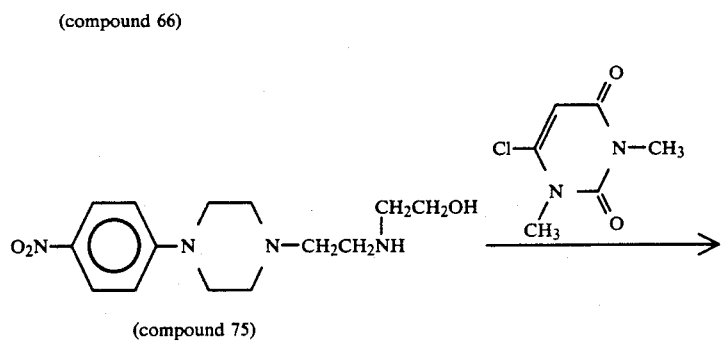

(compound 75)

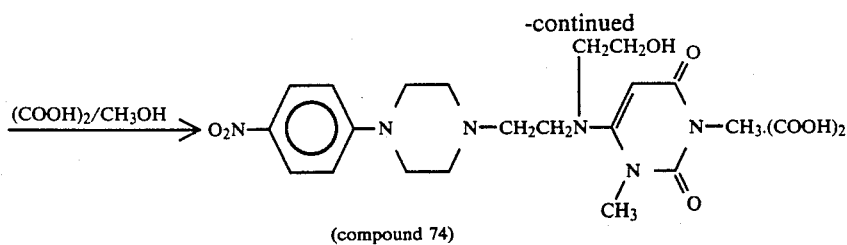

(compound 74)

(1) Preparation of 1-[2-(2-hydroxyethylamino)ethyl]-4-(4-nitrophenyl)piperazine (compound 75)

In 20 ml of chloroform was dissolved 4 g of 1-(4-nitrophenyl)piperazine (compound 66) and 0.52 ml of 1-(2-hydroxyethyl)aziridine, and the solvent was distilled off from the resulting reaction mixture under reduced pressure. To the residue was added 10 mg of Amberlist 15 (trade name; made by Rohm & Haas Co.), and the mixture was then heated with stirring at 100° C. for 3 hour. Afterward, the temperature of the reaction mixture was returned to room temperature. To the reaction mixture was added 20 ml of chloroform, and insoluble matters were then removed therefrom by filtration. The filtrate was concentrated, and the resulting residue (concentrate) was purified through a silica gel column chromatograph (chloroform/methanol=100/1 to 25/1 in terms of volume ratio), thereby preparing 1 g of 1-[2-(2-hydroxyethylamino)ethyl]-4-(4-nitrophenyl)piperazine (compound 75).

(2) Preparation of 1,3-dimethyl-6-{N-(2-hydroxyethyl)-2-[4-(4-nitrophenyl)piperazin-1-yl]ethylamino}-2,4(1H,3H)-pyrimidinedione oxalate (compound 74)

To 10 ml of ethanol were added 1.0 g of the thus obtained compound 75, 0.52 g of 6-chloro-1,3-dimethyl-2,4(1H,3H)-pyrimidinedione and 2 ml of triethylamine as starting materials, and the resulting mixture was treated in the same procedure as in Example 39-(2) to obtain 0.73 g of 1,3-dimethyl-6-{N-(2-hydroxyethyl)-2-[4-(4-nitrophenyl)piperazin-1-yl]ethylamino}-2,4(1H,3H)-pyrimidinedione.

Analytical results of the pyrimidinedione derivative thus obtained:

NMR (CDCl$_3$), δppm: 2.65 (m, 6H), 2.9–3.4 (m, 8H), 3.31 (s, 3H), 3.47 (s, 3H), 3.82 (m, 2H), 5.32 (s, 1H), 6.86 (d, 2H), 8.12 (d, 2H)

Then, 0.7 g of this pyrimidinedione derivative was further treated with an oxalic acid/methanol solution in a usual manner to obtain crystals of 0.35 g of 1,3-dimethyl-6-{N-(2-hydroxethyl)-2-[4-(4-nitrophenyl)piperazin-1-yl]ethylamino}-2,4(1H,3H)-pyrimidinedione oxalate (compound 74).

Analytical results of the crystalline compound 74 thus obtained:

Values of elemental analysis [as $C_{20}H_{28}N_6O_5 \cdot 1.5(COOH)_2 \cdot H_2O$]

Calcd. (%): C 47.18; H 5.68; N 14.35
Found (%): C 47.37; H 5.94; N 14.08

EXAMPLE 45

Preparation of tablets containing, as an effective component, 1,3-dimethyl-6-{4-[3-(4-nitroanilino)propyl]-piperazin-1-yl}-2,4(1H,3H)-pyrimidinedione hydrochloride (compound 58) which can be prepared by the process of Example 36

With 20 g of corn starch were sufficiently mixed 1 g of the above pyrimidinedione derivative hydrochloride (compound 58) and 123 g of lactose, and the mixture was further mixed with a solution prepared by dissolving 5 g of hydroxypropyl cellulose in 100 ml of water, so as to form grains, followed by drying the grains at 50° C. for 4 hours. Afterward, 1 g of magnesium stearate was added to the dried grains and then mixed sufficiently. The mixture was then formed into tablets by the use of a tableting machine, the weight of each tablet being 150 mg.

EXAMPLE 46

Preparation of capsules containing, as an effective component, 1,3-dimethyl-6-{2-[[1-(4-nitrophenyl)-piperidin-4-yl]amino]ethylamino}-2,4(1H,3H)-pyrimidinedione hydrochloride (compound 61) which can be prepared by the process of Example 37

With 25 g of corn starch were sufficiently mixed 5 g of the above pyrimidinedione derivative hydrochloride (compound 61) and 120 g of lactose, and hard capsules were filled with the resulting mixture by the use of a capsule filling machine to prepare capsules, the content of the mixture in each capsule being 150 mg.

EXAMPLE 47

Preparation of an injection containing, as an effective component, 1,3-dimethyl-6-{2-[N-methyl-N-[3-(4-nitroanilino)propyl]amino]ethylamino}-2,4(1H,3H)-pyrimidinedione hydrochloride (compound 73) which can be prepared by the process of Example 43

In distilled water for injection were dissolved 20 mg of the above pyrimidinedione derivative hydrochloride (compound 73) and 0.85 g of sodium chloride, and the total volume of the liquid was regulated to be 100 ml, thereby preparing an injection.

PHARMACOLOGICAL TEST 3

Following the same procedure as in Pharmacological Test 1, $ADP_{75}$ and ERP of the respective compounds prepared in the above examples in Table 6 were calculated. The results are set forth in Table 6.

TOXICITY TEST 3

Following the same procedure as in Toxicity Test 1, toxicity of the respective compounds prepared in the above examples in Table 7 was tested to calculate a mortality rate of mice. The results are set forth in Table 7.

Administration was made by oral administration (p.o.) in an amount of 300 mg/kg of each compound for one mouse.

TABLE 6

| | (results of pharmacological test) | | | | | | | |
|---|---|---|---|---|---|---|---|---|
| Compound No. | $APD_{75}$ (%) Dose (μg/ml) | | | | ERP (%) Dose (mg/kg, i.v.) | | | |
| | 0.3 | 1.0 | 3.0 | 10.0 | 0.1 | 0.3 | 1.0 | 3.0 |
| 58 | — | 10 | 18 | 28 | — | — | — | — |
| 61 | — | — | — | — | 8.3 | 8.3 | 8.3 | — |
| 64 | 8 | 23 | 32 | — | 21.4 | 28.6 | 28.6 | — |
| 69 | — | — | 11 | 13 | 6.7 | 6.7 | 13.3 | 20.0 |
| 71 | — | 8 | 15 | 17 | 6.7 | 7.7 | 13.4 | 16.6 |

TABLE 6-continued

| Compound No. | (results of pharmacological test) | | | | | | | |
|---|---|---|---|---|---|---|---|---|
| | APD75 (%) Dose (μg/ml) | | | | ERP (%) Dose (mg/kg, i.v.) | | | |
| | 0.3 | 1.0 | 3.0 | 10.0 | 0.1 | 0.3 | 1.0 | 3.0 |
| 73 | — | 2 | 12 | 18 | — | — | — | — |

TABLE 7

| (results of toxicity test) | |
|---|---|
| Compound Number | Mortality Rate (%) |
| 71 | 0 |

EXAMPLE 48

Preparation of 1,3-dimethyl-6-{4-[3-(2-acetyl-4-nitrophenoxy)propyl]piperazin-1-yl}-2,4(1H,3H)-pyrimidinedione oxalate (Compound 76)

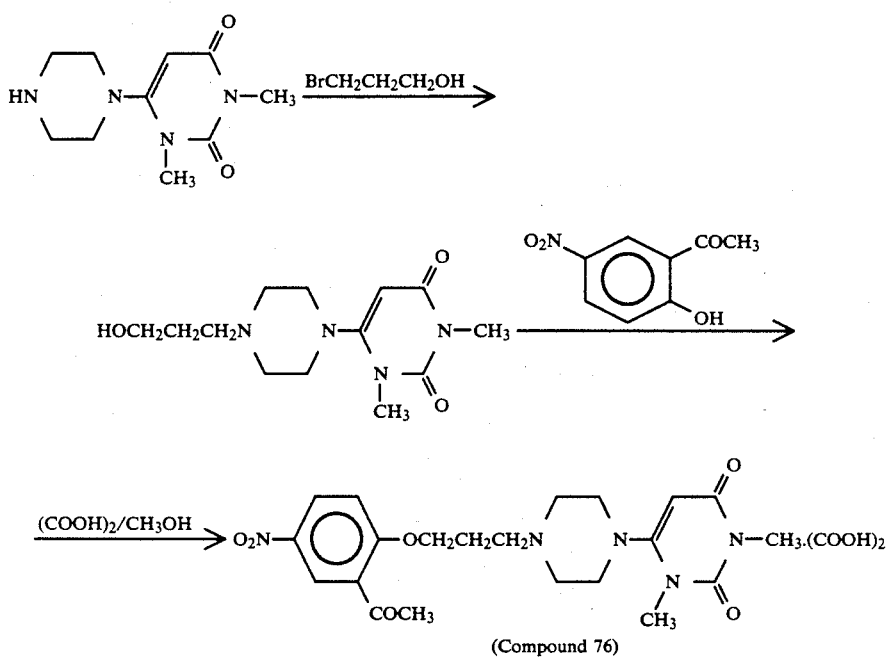

(Compound 76)

(1) Preparation of 1,3-dimethyl-6-[4-(3-hydroxypropyl)piperazin-1-yl]-2,4(1H,3H)-pyrimidinedione 14.1 g of 1,3-dimethyl-6-(1-piperazinyl)-2,4(1H,3H)-pyrimidinedione, 11.7 g of 3-bromo-1-propanol and 13 g of triethylamine were reacted by heating them under reflux for 20 hours in 250 ml of ethanol. After completion of the reaction, the reaction mixture was concentrated to dryness and the residue was dissolved in 300 ml of chloroform. The resultant solution was washed twice with 100 ml of water. After the washing, the organic layer was dried over anhydrous magnesium sulfate. The organic layer was heated under reduced pressure, whereby the solvent was distilled off to obtain 20.5 g of a reaction product in a crude form. Ether was added to the crude reaction product to crystallize it. Resulting crystals were collected by filtration, washed with chilled ether, and then dried to obtain 12.4 g of 1,3-dimethyl-6-[4-(3-hydroxypropyl)-piperazin-1-yl]-2,4(1H,3H)-pyrimidinedione (yield: 69.8%).

Analytical results of crystals of the pyrimidinedione derivative thus obtained:

Melting point: 119°–121° C.

NMR (CDCl$_3$), δppm: 1.8 (dt,2H), 2.7(m,6H), 3.02(m,4H), 3.36(s,3H), 3.43(s,3H), 3.82(t,2H), 4.34(br,1H), 5.26(s,1H).

IR$\nu_{max}^{KBr}$ (cm$^{-1}$): 3380(Br), 3180(s), 2830, 1695, 1650, 1605, 1440, 1213, 1068, 1000, 921, 760.

(2) Preparation of 1,3-dimethyl-6-{4-[3-(2-acetyl-4-nitrophenoxy)propyl]piperazin-1-yl}-2,4(1H,3H)-pyrimidinedione oxalate (Compound 76)

Into a suspension which had been obtained by mixing 0.6 g of the pyrimidinedione derivative obtained in the above procedure (1), 0.54 g of 2-hydroxy-5-nitroacetophenone and 0.69 g of triphenylphosphine in 10 ml of anhydrous tetrahydrofuran, 0.42 ml of diethyl azodicarboxylate was added dropwise under stirring at room temperature.

Next, the resulting mixture was stirred for 30 minutes at room temperature and then concentrated to dryness. The residue was purified by chromatography on a silica gel column (eluent: chloroform/methanol = 50/1 by volume), whereby 0.7 g of 1,3-dimethyl-6-{4-[3-(2-acetyl-4-nitrophenoxy)propyl]piperazin-1-yl}-2,4(1H,3H)-pyrimidinedione was obtained as an oily matter.

Analytical results of the thus-obtained pyrimidinedione derivative:

NMR (CDCl$_3$), δppm: 8.47(m,1H), 7.54(m,1H), 6.91(d,1H), 5.23(s,1H), 4.26(m,2H), 3.37(s,3H), 3.30(s,3H), 2.98(m,4H), 2.60(m,6H), 2.63(s,3H), 2.16(m,2H).

Further, the pyrimidinedione derivative was treated in an oxalic acid/methanol solution by a method known per se in the art to obtain 0.73 g of 1,3-dimethyl-6-{4-[3-(2-acetyl-4-nitrophenoxy)propyl]piperazin-1-yl}-2,4(1H,3H)-pyrimidinedione oxalate (Compound 76).

Analytical results of Compound 76 thus obtained:

Melting point: 122°–124° C. (decomposed).

IR$\nu_{max}^{KBr}$ (cm$^{-1}$): 3400, 3020, 2600, 1690, 1640, 1520, 1340, 1280, 1120, 820, 750, 700.

Elemental analysis for C$_{21}$H$_{27}$N$_5$O$_6$·(COOH)$_2$·2H$_2$O:

Calculated (%): C, 48.33; H, 5.82; N, 12.25.

Found (%): C, 48.22; H, 5.69; N, 11.93.

EXAMPLE 49

Preparation of 1,3-dimethyl-6-{4-[3-(4-acetyl-2-nitrophenoxy)propyl]piperazin-1-yl}-2,4(1H,3H)-pyrimidinedione oxalate (Compound 77)

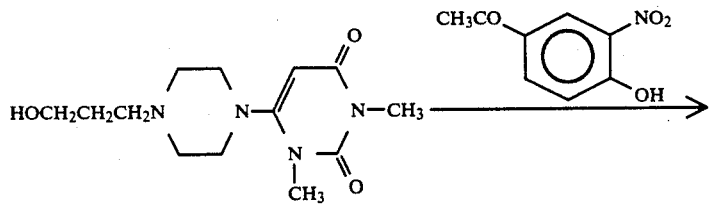

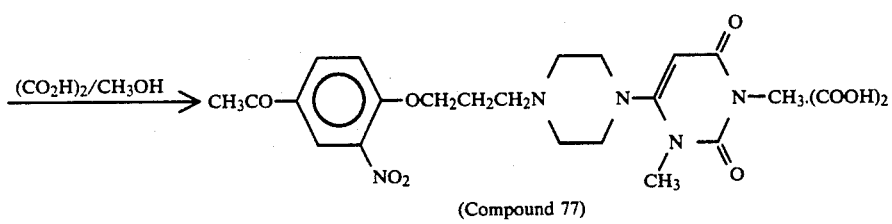

(Compound 77)

EXAMPLE 50

Preparation of 1,3-dimethyl-6-{4-[3-(4-benzoyl-2-nitrophenoxy)propyl]piperazin-1-yl}-2,4(1H,3H)-pyrimidinedione oxalate (Compound 78)

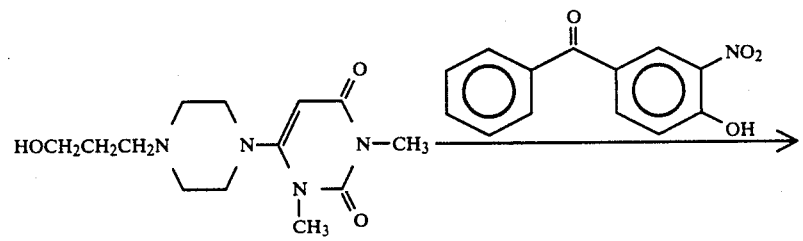

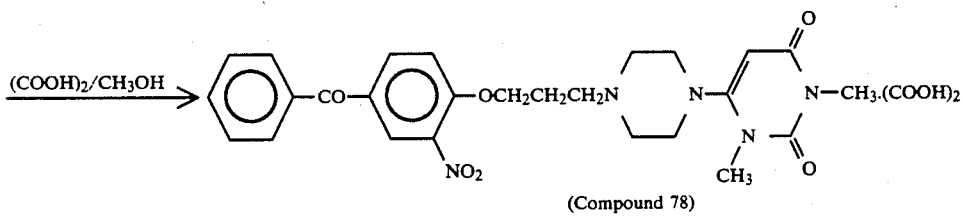

(Compound 78)

By a procedure similar to Example 48-(2) except for the use of 4-hydroxy-3-nitroacetophenone in lieu of 2-hydroxy-5-nitroacetophenone, 1,3-dimethyl-6-{4-[3-(4-acetyl-2-nitrophenoxy)propyl]piperazin-1-yl}-2,4(1H,3H)pyrimidinedione oxalate (Compound 77) was obtained.

Analytical results of the pyrimidinedione derivative (Compound 77) thus obtained:

Melting point: 119°–123° C. (decomposed).
IR$\nu_{max}^{KBr}$ (cm$^{-1}$): 3380, 2250, 1700, 1640, 1530, 1350, 1020, 760, 700.
Elemental analysis for $C_{21}H_{27}N_5O_6 \cdot (COOH)_2 \cdot 3H_2O$:
Calculated (%): C, 46.86; H, 5.98; N, 11.28.
Found (%): C, 46.79; H, 5.43; N, 11.51.

By a procedure similar to Example 48-(2) except for the use of 4-hydroxy-3-nitroacetophenone in lieu of 2-hydroxy-5-nitroacetophenone, 1,3-dimethyl-6-{4-[3-(4-benzoyl-2-nitrophenoxy)propyl]piperazin-1-yl}-2,4(1H,3H)-pyrimidinedione oxalate (Compound 78) was obtained.

Analytical results of the pyrimidinedione derivative (Compound 78) thus obtained:

Melting point: 168°–171° C. (decomposed).
IR$\nu_{max}^{KBr}$ (cm$^{-1}$): 3400, 3050, 1730, 1630, 1540, 1350, 1080, 760, 700.
Elemental analysis for $C_2H_{29}N_5O_6 \cdot (COOH)_2 \cdot H_2O$:
Calculated (%): C, 54.63; H, 5.40; N, 11.38.
Found (%): C, 54.99; H, 5.29; N, 11.30.

EXAMPLE 51

Preparation of 1,3-dimethyl-6-{4-[3-(3-acetyl-4-nitrophenoxy)propyl]piperazin-1-yl)-2,4(1H,3H)-pyrimidinedione oxalate (Compound 79)

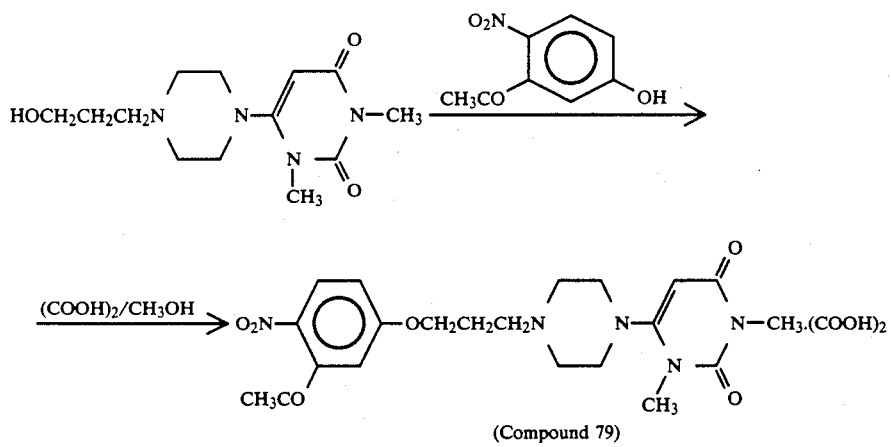

By a procedure similar to Example 48-(2) except for the use of 5-hydroxy-2-nitroacetophenone in lieu of 2-hydroxy-5-nitroacetophenone, 1,3-dimethyl-6-{4-[3-(3-acetyl-4-nitrophenoxy)propyl]piperazin-1-yl}-2,4(1H,3H)-pyrimidinedione oxalate (Compound 79) was obtained.

Analytical results of the pyrimidinedione derivative (Compound 79) thus obtained:

Melting point: 223°–224° C. (decomposed).

IR$\nu_{max}^{KBr}$(cm$^{-1}$) 3440, 3000, 2600, 1730, 1600, 1520, 1350, 1020, 810.

Elemental analysis for $C_{21}H_{27}N_5O_6\cdot(COOH)_2\cdot 2H_2O$:

Calculated (%): C, 48.33; H, 5.82; N, 12.25.

Found (%): C, 48.17; H, 5.62; N, 12.05.

EXAMPLE 52

Preparation of 1,3-dimethyl-6-{4-[3-(2-benzoyl-4-nitrophenoxy)propyl]piperazin-1-yl}-2,4(1H,3H)-pyrimidinedione oxalate (Compound 80)

none and 1.1 g of potassium hydroxide in 30 ml of water was heated under stirring at 150° C. for 5 hours.

After completion of the heating, the autoclave was allowed to cool down. The resultant reaction mixture was added with 30 ml of water, followed by the addition of hydrochloric acid to acidify the reaction mixture. Crystals precipitated upon the acidification were collected by filtration.

The thus-obtained crystals were recrystallized from ethanol to obtain 2.3 g of 2-hydroxy-5-nitrobenzophenone.

Analytical results of the crystals thus obtained:

Melting point: 125°–126° C.

NMR (CDCl$_3$), δppm: 7.21(m,2H), 7.68(m,4H), 8.41(m,2H),

IR$\nu_{max}^{KBr}$(cm$^{-1}$): 3040, 1600, 1520, 1330 1280, 1210, 1080, 960, 690.

(2) Preparation of 1,3-dimethyl-6-{4-[3-(2-benzoyl-4-nitrophenoxy)propyl]piperazin-1-yl}-2,4(1H,3H)-

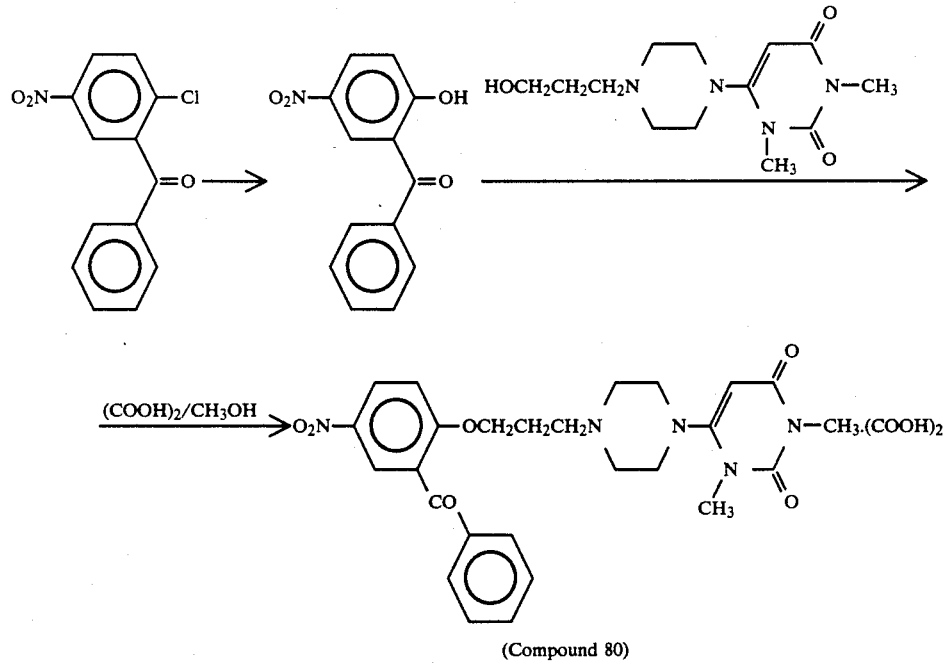

(1) Preparation of 2-hydroxy-5-nitrobenzophenone

In an autoclave, a suspension which had been obtained by suspending 3 g of 2-chloro-5-nitrobenzophepyrimidinedione oxalate (Compound 80)

By a procedure similar to Example 48-(2), 0.73 g of 2-hydroxy-5-nitrobenzophenone obtained in the above procedure (1), 0.5 g of 1,3-dimethyl-6-[4-(3-hydroxypropyl)piperazin-1-yl]-2,4(1H,3H)-pyrimidinedione, 0.58 g of triphenylphosphine and 0.34 ml of diethyl azodicarboxylate were reacted in 10 ml of anhydrous tetrahydrofuran, whereby 1,3-dimethyl-6-{4-[3-(2-benzoyl-4-nitrophenoxy)propyl]piperazin-1-yl}-2,4(1H,3H)-pyrimidinedione was obtained as a syrup-like matter (0.7 g).

Analytical results of the pyrimidine derivative thus obtained:

NMR (CDCl$_3$), δppm: 8.36(m,2H), 7.0-7.8(m,6H), 5.14(s,1H), 4.14(t,2H), 3.26(s,3H), 3.34(s,3H), 3.0 (m,4H), 2.2-2.5(m,6H), 1.9(m,2H).

Further, the pyrimidinedione derivative was treated in an oxalic acid/methanol solution by a method known per se in the art to obtain 0.71 g of 1,3-dimethyl-6-{4-[3-(2-benzoyl-4-nitrophenoxy)propyl]piperazin-1-yl}-2,4(1H,3H)-pyrimidinedione oxalate (Compound 80).

Analytical results of the pyrimidinedione derivative (Compound 80) thus obtained:

Melting point: 200°-202° C. (decomposed).

IR$\nu_{max}^{KBr}$ (cm$^{-1}$): 3450, 2910, 1690, 1650, 1510, 1330, 1280, 1150, 1080, 760, 700.

Elemental analysis for C$_{26}$H$_{29}$N$_5$O$_6$·½(COOH)$_2$·½H$_2$O:

Calculated (%): C, 57.85; H, 5.39; N, 12.49.
Found (%): C, 57.71; H, 5.54; N, 12.24.

EXAMPLE 53

Preparation of Compounds 87-92

By a procedure similar to Example 52-(1) except for the use of Compounds 81-86 of the following structural formula (1)—in which X$^1$ means the groups set out below respective—in place of 2-chloro-5-nitrobenzophenone, phenol derivatives of the below-described structural formula (I') in which X$^1$ varies respectively were obtained as Compounds 81'-86'.

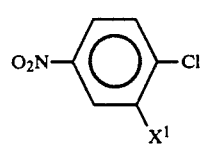

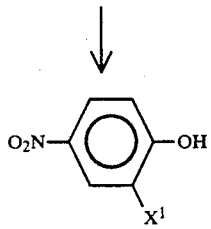

| Compound No. | X$^1$ |
|---|---|
| 81, 81' | —CO—⟨phenyl⟩—Br |

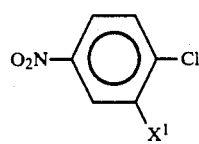

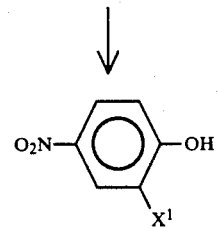

| Compound No. | X$^1$ |
|---|---|
| 82, 82' | —CO—C(=N—NH)—CH= (pyrazole) |
| 83, 83' | —CO—⟨pyrimidine, N at 1,3⟩ |
| 84, 84' | —CO—⟨pyridine, N at 3⟩ |
| 85, 85' | —CO—⟨pyridine, N at 4⟩ |
| 86, 86' | —CO—⟨pyridine, N at 2⟩ |

Analytical results of Compound 81' thus obtained:
NMR (CDCl$_3$), δppm: 8.38(m,2H), 7.70(m,4H), 7.41(m,1H),
Elemental analysis for C$_{13}$H$_8$NO$_4$Br:
Calculated (%): C, 48.47; H, 2.50; N, 4.35; Br, 24.81.
Found (%): C, 48.52; H, 2.31; N, 4.45; Br, 24.42.
Analytical results of Compound 83' thus obtained:
IR$\nu_{max}^{KBr}$ (cm$^{-1}$): 1690, 1560, 1400, 1310, 770, 750.
Analytical results of Compound 84' thus obtained:
IR$\nu_{max}^{KBr}$ (cm$^{-1}$): 1660, 1520, 1340, 1270, 1040, 730.

By a procedure similar to Example 52-(2) except that the phenol derivatives, i.e. Compounds 81'-86' were used respectively instead of 2-hydroxy-5-nitrobenzophenone, pyrimidinedione derivative oxalates (Compounds 87-92) having the following physical properties and the following structural formula (II) in which X$^1$ means the below-described groups respectively were obtained.

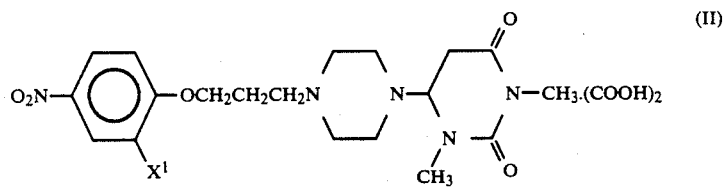

(II)

Analytical results of Compound 87 (in which $X^1$ has the same meaning as in Compound 81):
Melting point: 134°–135° C. (Decomposed).
$IR\nu_{max}^{KBr}$ (cm$^{-1}$): 2900, 1710, 1640, 1530, 1340, 840, 790.
Elemental analysis for $C_{26}H_{28}N_5O_6Br\cdot(COOH)_2\cdot 3\text{-}H_2O$:
Calculated (%): C, 46.04; H, 4.97; N, 9.59; Br, 10.94.
Found (%): C, 46.26; H, 5.16; N, 9.92; Br, 10.53.

Analytical results of Compound 88 (in which $X^1$ has the same meaning as in Compound 82):
Melting point: 171°–174° C. (Decomposed).
$IR\nu_{max}^{KBr}$ (cm$^{-1}$): 3450, 1710, 1640, 1550, 1440, 1350, 1200, 760.
Elemental analysis for $C_{23}H_{27}N_7O_6\cdot 2(COOH)_2$:
Calculated (%): C, 47.86; H, 4.61; N, 14.47;
Found (%): C, 47.38; H, 5.17; N, 14.40.

Analytical results of Compound 89 (in which $X^1$ has the same meaning as in Compound 83):
Melting point: 149°–151° C. (Decomposed).
$IR\nu_{max}^{KBR}$ (cm$^{-1}$): 2550, 1700, 1660, 1520, 1340, 850, 800.
Elemental analysis for $C_{24}H_{27}N_7O_6\cdot 2(COOH)_2\cdot 2\text{-}H_2O$:
Calculated (%): C, 45.22; H, 5.02; N, 13.19;
Found (%): C, 45.60; H, 5.18; N, 13.59.

Elemental analysis for $C_{25}H_{28}N_6O_6\cdot 2(COOH)_2\cdot 2\text{-}H_2O$:
Calculated (%): C, 48.07; H, 5.01; N, 11.60.
Found (%): C, 48.02; H, 5.05; N, 11.31.

Analytical results of Compound 91 (in which $X^1$ has the same meaning as in Compound 85):
Melting point: 104–107° C. (Decomposed).
$IR\nu_{max}^{KBr}$ (cm$^{-1}$) 2700, 1690, 1630, 1540, 1340, 1280, 800.
Elemental analysis for $C_{25}H_{28}N_6O_6\cdot 2(COOH)_2\cdot 3\text{-}H_2O$:
Calculated (%): C, 46.90; H, 5.16; N, 11.32.
Found (%): C, 46.88; H, 5.42; N, 11.38.

Analytical results of Compound 92 (in which $X^1$ has the same meaning as in Compound 86):
Melting point: Amorphous.
$IR\nu_{max}^{KBr}$ (cm$^{-1}$) 1740, 1690, 1600, 1550, 1350, 1260, 780, 700.
Elemental analysis for $C_{25}H_{28}N_6O_6\cdot 2(COOH)_2\cdot H_2O$:
Calculated (%): C, 46.29; H, 4.85; N, 11.89.
Found (%): C, 48.85; H, 4.97; N, 11.44.

EXAMPLE 54

Preparation of 1,3-dimethyl-6-{4-[2-(2-acetyl-4-nitrophenoxy)ethyl]piperazin-1-yl}-2,4(1H,3H)-pyrimidinedione oxalate (Compound 93)

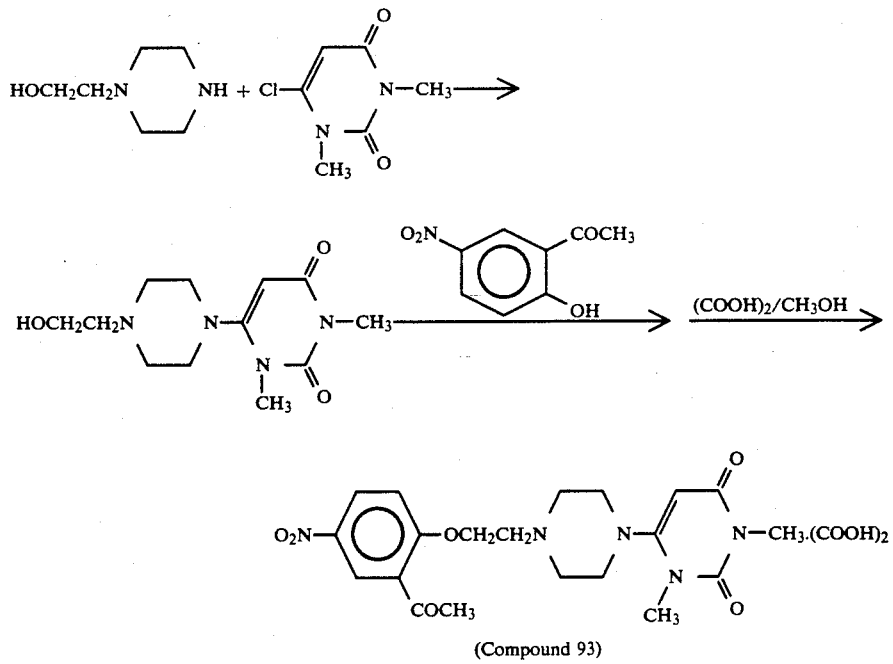

(Compound 93)

Analytical results of Compound 90 (in which $X^1$ has the same meaning as in Compound 84):
Melting point: 177°–178° C. (Decomposed).
$IR\nu_{max}^{KBr}$ (cm$^{-1}$) 2950, 1720, 1650, 1520, 1320, 1260, 860, 760.

(1) Preparation of 1,3-dimethyl-6-[4-(2-hydroxyethyl)piperazin-1-yl]-2,4(1H,3H)-pyrimidinedione 2.7 g of 6-chloro-1,3-dimethyl-2,4(1H,3H)-pyrimidinedione, 4 ml of 1-(2-hydroxyethyl)piperazine and 12 ml of triethylamine were dissolved in 70 ml of isopropanol. The resultant solution was heated under reflux for 3 hours.

After completion of the heating, the reaction mixture was allowed to cool down, the solvent was removed under reduced pressure from the reaction mixture, and the residue was dissolved in 60 ml of chloroform. The chloroform solution thus obtained was washed with water, dried over anhydrous sodium sulfate, and then concentrated to dryness under reduced pressure to obtain the reaction product in a crude form.

Next, a mixed solvent of ethanol and ethyl ether was added to the crude reaction product. Precipitated crystals were collected by filtration. Those crystals were then recrystallized from hexane/ethanol to obtain 3.72 g of 1,3-dimethyl-6-[4-(2-hydroxyethyl)piperazin-1-yl]-2,4(1H,3H)-pyrimidinedione.

Analytical results of the pyrimidinedione derivative thus obtained:

NMR (CDCl$_3$), δppm: 5.21(s,1H), 3.69(t,2H), 3.35(s,3H), 3.26(s,3H), 2.5–3.1(m,10H).

(2) Preparation of 1,3-dimethyl-6-{4-[2-(2-acetyl-4-nitrophenoxy)ethyl]piperazin-1-yl}-2,4(1H,3H)-pyrimipound to another were obtained respectively in a similar manner to Example 54-(2).

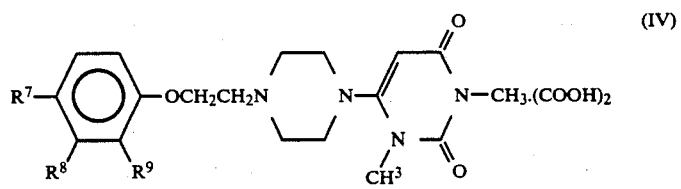

| | R$^8$ | R$^9$ | R$^7$ |
|---|---|---|---|
| Compound 94 | —H | —CO—⌬ | —NO$_2$ |
| Compound 95 | —H | —CO—⌬—Br | —NO$_2$ |
| Compound 96 | —COCH$_3$ | —H | —NO$_2$ |
| Compound 97 | —H | —NO$_2$ | —COCH$_3$ |
| Compound 98 | —H | —NO$_2$ | —CO—⌬ |

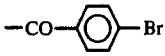

dinedione oxalate (Compound 93)

0.5 g of the pyrimidinedione derivative obtained by the above procedure (1), 0.65 g of 2-hydroxy-5-nitroacetophenone, 0.6 g of triphenylphosphine and 0.36 ml of diethyl azodicarboxylate were reacted in a similar manner to Example 48-(2) to obtain 0.65 g of 1,3-dimethyl-6-{4-[2-(2-acetyl-4-nitrophenoxy)ethyl]-piperazin-1-yl}-2,4(1H,3H)-pyrimidinedione.

Analytical results of the pyrimidinedione derivative thus obtained:

NMR (CDCl$_3$), δppm: 8.2–8.6(m,2H), 7.08(m,1H), 5.26(s,1H), 4.35(m,2H), 3.42(s,3H), 3.34(s,3H), 2.72(s,3H), 2.7–3.2(m,10H).

Next, the pyrimidinedione derivative was treated in an oxalic acid/methanol solution by a method known per se in the art to obtain 0.68 g of 1,3-dimethyl-6-{4-[2-(2-acetyl-4-nitrophenoxy)ethyl]piperazin-1-yl}-2,4(1H,3H)-pyrimidinedione oxalate (Compound 93)

Analytical results of the pyrimidinedione derivative (Compound 93) thus obtained:

Melting point: 193°–195° C. (Decomposed).

IR$\nu_{max}^{KBr}$(cm$^{-1}$) 3290, 2650, 1720, 1640, 1520, 1340, 1270, 1120, 830, 760, 700.

Elemental analysis for C$_{20}$H$_{25}$N$_5$O$_6$·(COOH)$_2$·H$_2$O:
Calculated (%): C, 48.98; H, 5.42; N, 12.98.
Found (%): C, 49.02; H, 5.22; N, 12.90.

EXAMPLE 55

Preparation of Compounds 99–103:

Using phenol derivatives (Compounds 94–98) having the below-described structural formula (III) in which R$^7$, R$^8$ and R$^9$ mean the below-described groups respectively, pyrimidinedione derivative oxalates (Compounds 99–103) having the physical properties set out below and the below-described structural formula (IV) in which R$^7$, R$^8$ and R$^9$ are different from one com- Compound 99 (R$^7$, R$^8$ and R$^9$ are as defined with respect to Compound 94):

Melting point: 160°–162° C. (decomposed).

IR$\nu_{max}^{KBr}$(cm$^{-1}$): 2530, 1700, 1640, 1520, 1340, 760, 700.

Elemental analysis for C$_{25}$H$_{27}$N$_5$O$_6$·(COOH)$_2$·2H$_2$O:
Calculated (%): C, 52.34; H, 5.37; N, 11.30.
Found (%): C, 52.14; H, 5.18; N, 11.42.

Compound 100 (R$^7$, R$^8$ and R$^9$ are as defined with respect to Compound 95):

Melting point: 136°–138° C. (decomposed).

IR$\nu_{max}^{KBr}$(cm$^{-1}$) 2600, 1700, 1600, 1530, 1340, 800, 700.

Elemental analysis for C$_{25}$H$_{26}$BrN$_5$O$_6$·(COOH)$_2$·2H$_2$O:
Calculated (%): C, 46.43; H, 4.62; N, 10.03; Br, 11.44.
Found (%): C, 46.64; H, 4.43; N, 10.30; Br, 11.25.

Compound 101 (R$^7$, R$^8$ and R$^9$ are as defined with respect to Compound 96):

Melting point: 110° C. (amorphous).

IR$\nu_{max}^{KBr}$ (cm$^{-1}$): 2990, 2550, 1700, 1630, 1520, 1320, 1180, 800.

Elemental analysis for C$_{20}$H$_{25}$N$_5$O$_6$·(COOH)$_2$·3H$_2$O:
Calculated (%): C, 45.91; H, 5.78; N, 12.17.
Found (%): C, 45.76; H, 5.54; N, 12.07.

Compound 102 (R$^7$, R$^8$ and R$^9$ are as defined with respect to Compound 97):

Melting point: 139°–141° C. (decomposed).

IR$\nu_{max}^{KBr}$(cm$^{-1}$) 3300, 2950, 1700, 1640, 1530, 1360, 1270, 800, 760.

Elemental analysis for C$_{20}$H$_{25}$N$_5$O$_6$·(COOH)$_2$·H$_2$O:
Calculated (%): C, 48.98; H, 5.42; N, 12.98.
Found (%): C, 49.08; H, 5.97; N, 12.97.

Compound 103 (R$^7$, R$^8$ and R$^9$ are as defined with respect to Compound 98):

Melting point: 133°–135° C. (decomposed).

IR$\nu_{max}^{KBr}$ (cm$^{-1}$): 3000, 2550, 1740, 1630, 1540, 1340, 1280, 760, 700.

Elemental analysis for $C_{25}H_{27}N_5O_6\cdot(COOH)_2\cdot H_2O$:
Calculated (%): C, 53.91; H, 5.19; N, 11.64.
Found (%): C, 53.66; H, 4.96; N, 11.86.

EXAMPLE 56

Preparation of 1,3-dimethyl-6-{4-<3-[2-(2-hydroxybenzoyl)-4-nitrophenoxy]propyl>piperazin-1-yl}-2,4(1H,3H)-pyrimidinedione oxalate (Compound 104)

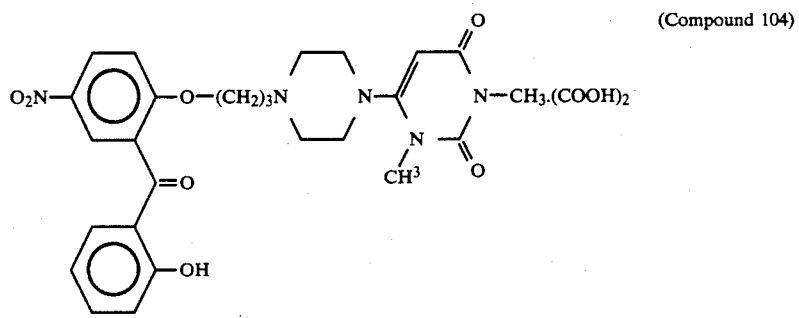
(Compound 104)

(1) Preparation of 2,2'-dihydroxy-5-nitrobenzophenone (Compound 104')

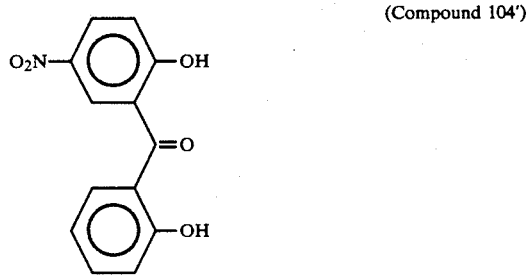
(Compound 104')

A reaction mixture, which had been obtained by suspending 3 g of 2,2'-dichloro-5-nitrobenzophenone and 1.1 g of potassium hydroxide in 30 ml of water, was heated under stirring at 150° C. for 5 hours in an autoclave.

After allowing the reaction mixture to cool down, 30 ml of water were added to the reaction mixture. Hydrochloric acid was then added to acidify the reaction mixture, and precipitated crystals were collected by filtration.

Those crystals were dried under reduced pressure to obtain 1.9 g of 2,2'-dihydroxy-5-nitrobenzophenone (Compound 104'). Those crystals were used in the following reactions without any further purification.

(2) Preparation of 1,3-dimethyl-6-{4-<3-[2-(2-hydroxybenzoyl)-4-nitrophenoxy]propyl>piperazin-1-yl}-2,4(1H,3H)-pyrimidinedione oxalate (Compound 104)

In a similar manner to Example 48-(2), 0.75 g of 2,2'-dihydroxy-5-nitrobenzophenone obtained in the above procedure (1), 0.5 g of 1,3-dimethyl-6-[4-(3-hydroxypropyl)piperazin-1-yl]-2,4(1H,3H)-pyrimidinedione, 0.58 g of triphenylphosphine and 0.34 ml of diethyl azodicarboxylate were reacted in 10 ml of anhydrous tetrahydrofuran, and the reaction mixture was treated to obtain 0.6 g of 1,3-dimethyl-6-{4-<3-[2-(2-hydroxybenzoyl)-4-nitrophenoxy]propyl>piperazin-1-yl}-2,4(1H,3H)-pyrimidinedione.

Next, the pyrimidinedione derivative was treated in an oxalic acid/methanol solution by a method known per se in the art to obtain 0.6 g of 1,3-dimethyl-6-{4-<3-[2-(2-hydroxybenzoyl)-4-nitro-phenoxy]propyl>piperazin-1-yl}-2,4(1H,3H)-pyrimidinedione oxalate (Compound 104):

Analytical results of the pyrimidinedione derivative (Compound 104) thus obtained:

Melting point: 144°-146° C. (decomposed).

IR$\nu_{max}^{KBr}$ (cm$^{-1}$): 3550, 2900, 2550, 1710, 1640, 1530, 1340, 840, 730, 700.

Elemental analysis for $C_{26}H_{29}N_5O_7\cdot2(COOH)_2\cdot H_2O$:
Calculated (%): C, 49.93; H, 4.89; N, 9.73.
Found (%): C, 49.83; H, 5.07; N, 9.43.

EXAMPLE 57

Preparation of 1,3-dimethyl-6-{4-[3-[2-(2-chlorobenzoyl)-4-nirophenoxy]propyl]piperazin-1-yl}-2,4(1H,3H)-pyrimidinedione oxalate (Compound 105)

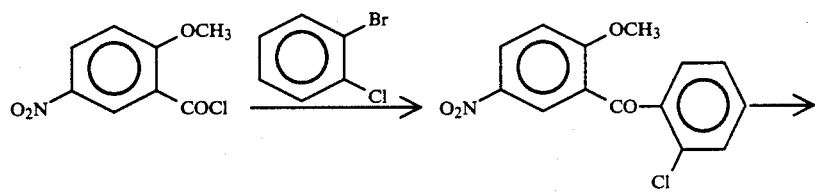

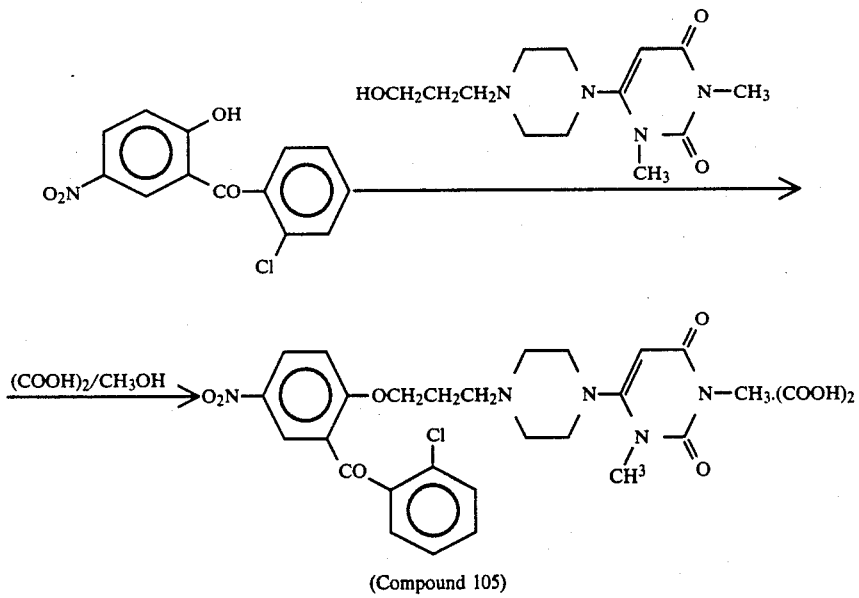

(Compound 105)

(1) Preparation of 3-(2-chlorobenzoyl)-4-methoxynitrobenzene 4.0 g of 2-methoxy-5-nitrobenzoyl chloride were dissolved in 100 ml of anhydrous tetrahydrofuran, followed by the addition of 2.72 g of 4-(N,N-dimethylamino)pyridine at room temperature. The resultant mixture was then vigorously stirred for 1 hour.

Added dropwise to the reaction mixture at −10° C. after completion of the stirring were 28 ml of a Grignard reagent which had been prepared from 3.82 g of 2-chlorobromobenzene and 0.48 g of metal magnesium in ethyl ether.

After completion of the dropwise addition, the temperature of the reaction mixture was allowed to gradually rise to room temperature over 3 hours. Water was then added to the reaction mixture, followed by concentration to dryness. Next, the residue was dissolved in 50 ml of chloroform and the solution thus obtained was washed with water. The solution was thereafter washed successively with 50 ml of a 1 N aqueous sodium hydroxide solution, 50 ml of 1 N hydrochloric acid and a saturated NaCl solution.

The thus-washed solution was dried over anhydrous sodium sulfate. The solvent was then distilled off, and the residue was was purified by chromatography on a silica gel column (eluent: chloroform/hexane=1/-50–1/20, by volume) to obtain 1.55 g of 3-(2-chlorobenzoyl)-4-methoxynitrobenzene.

Analytical results of the compound thus obtained:
NMR (CDCl$_3$), δppm: 3.80(s,2H), 6.92–7.75(m,5H), 8.28–8.69(m,2H).

(2) Preparation of 3-(2-chlorobenzoyl)-4-hydroxynitrobenzene 1.55 g of 3-(2-chlorobenzoyl)-4-methoxynitrobenzene obtained in the above procedure (1) were dissolved in 30 ml of chloroform, followed by the addition of 5.31 g of iodotrimethylsilane. The thus-obtained solution was then heated under reflux and stirring for 2 hours. The reaction mixture was allowed to cool down, washed with 30 ml of water, and then extracted twice with a 1 N aqueous sodium hydroxide solution.

Hydrochloric acid was added to the alkaline layer obtained by the above extraction, followed by extraction with chloroform. The organic layer obtained by the chloroform extraction was washed with water and dried over anhydrous sodium sulfate. The solvent was thereafter distilled off from the organic layer, thereby obtaining 0.5 g of 3-(2-chlorobenzoyl)-4-hydroxynitrobenzene in the form of a pale yellow oil.

Analytical results of the pale yellowish oily compound thus obtained:
NMR (CDCl$_3$), δppm: 7.33(d,1H,J=10.0Hz) 7.46–7.83(m,5H), 8.35(d,1H,J=2.5Hz), 8.50(dd,1H,J=2.5,10.0Hz).

(3) Preparation of 1,3-dimethyl-6-{4-<3-[2-(2-chlorobenzoyl)-4-nitrophenoxy]propyl>piperazin-1-yl}-2,4(1H,3H)-pyrimidinedione oxalate (Compound 105)

By a similar procedure to Example 48-(2) except for the use of 3-(2-chlorobenzoyl)-4-hydroxynitrobenzene obtained by the above procedure (2) in place of 2-hydroxy-5-nitroacetophenone, 0.5 g of 1,3-dimethyl-6-{4-<3-[2-(2-chlorobenzoyl)-4-nitrophenoxy]propyl>piperazin-1-yl}-2,4(1H,3H)-pyrimidinedione oxalate (Compound 105) was obtained as white crystals.

Analytical results of crystals of Compound 105 thus obtained:
Melting point: Amorphous.
IR$\nu_{max}^{KBr}$ (cm$^{-1}$): 1685, 1650, 1602, 1425, 1335, 1285, 1080,
Elemental analysis for $C_{26}H_{28}ClN_5O_6 \cdot (COOH)_2 \cdot H_2O$:
Calculated (%): C, 51.74; H, 4.96; N, 10.77; Cl, 5.45.
Found (%): C, 51.50; H, 5.11; N, 10.97; Cl, 5.71.

EXAMPLE 58

Preparation of 1,3-dimethyl-6-{4-<3-[4-nitro-2-(2-pyridinecarbonyl)phenylthio]propyl>piperazin-1-yl}-2,4(1H,3H)-pyrimidinedione oxalate (Compound 106)

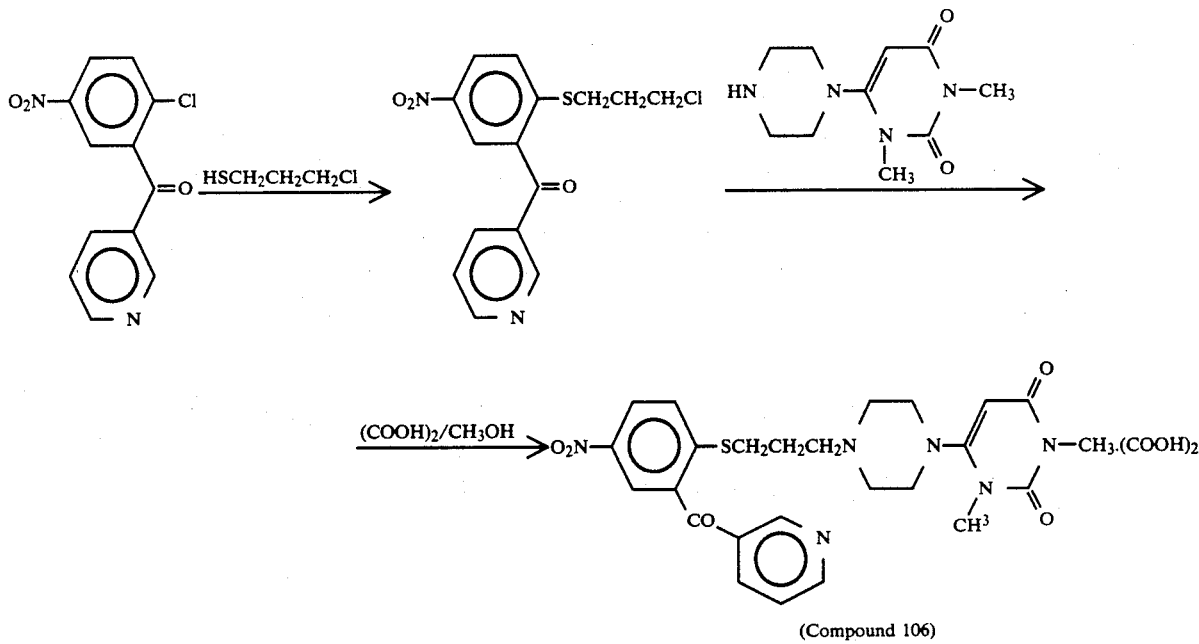

(Compound 106)

(1) Preparation of 1-chloro-3-[2-(2-pyridinecarbonyl)-4-nitrophenylthio]propane 1.58 g of 4-chloro-3-(2-pyridinecarbonyl)nitrobenzene, 0.66 g of 3-chloro-1-propanethiol and 2 ml of triethylamine were dissolved in 5 ml of dimethylsulfoxide. The resultant solution was heated under stirring at 80° C. for 3 hours.

After completion of the heating, the reaction mixture was concentrated and the concentrate thus obtained was dissolved in chloroform. The chloroform solution was washed with water and then dried over anhydrous sodium sulfate.

Next, the solvent was distilled off from the thus-dried solution. The residue was purified by chromatography on a silica gel column (eluent: chloroform) and then crystallized from a mixed solvent of hexane and ether to obtain 1.0 g of 1-chloro-3-[2-(2-pyridinecarbonyl)-4-nitrophenylthio]propane.

Analytical results of crystals of the compound thus obtained:

Elemental analysis for $C_{15}H_{13}ClN_2O_3S$:

Calculated (%): C, 53.49; H, 3.89; N, 8.32, S, 9.52; Cl, 10.53.

Found (%): C, 53.29; H, 3.79; N, 8.25; S, 9.35; Cl, 10.37.

(2) Preparation of 1,3-dimethyl-6-{4-<3-[4-nitro-2-(2-pyridinecarbonyl)phenylthio]propyl>piperazin-1-yl}-2,4(1H,3H)-pyrimidinedione oxalate (Compound 106)

0.93 g of 1-chloro-3-[2-(2-pyridinecarbonyl)-4-nitrophenylthio]propane, 0.62 g of 1,3-dimethyl-6-(piperazin-1-yl)-2,4(1H,3H)-pyrimidinedione and 2 ml of triethylamine were dissolved in 10 ml of dimethyl sulfoxide, followed by heating under stirring at 120° C for 4 hours.

After completion of the heating, the reaction mixture was allowed to cool down, the solvent was distilled off under reduced pressure from the reaction mixture, and the residue was dissolved in chloroform. The thus-obtained solution was washed with water and then dried over anhydrous sodium sulfate, followed by purification by chromatography on a silica gel column (eluent: chloroform/methanol=50/1, by volumw) to obtain 0.69 g of 1,3-dimethyl-6-{4-<3-[4-nitro-2-(2-pyridinecarbonyl)phenylthio]propyl>piperazin-1-yl}-2,4(1H,3H)-pyrimidinedione in a yellow solid form.

Analytical results of the pyrimidinedione derivative thus obtained:

Melting point: 182° C. (decomposed).

NMR (CDCl$_3$), δppm: 1.89(m,2H), 2.56(m,6H), 3.01(m,4H), 3.36(s,3H), 3.42(s,3H), 3.46(m,2H), 5.28(s,1H), 7.5–8.9(m,7H).

Elemental analysis for $C_{25}H_{28}N_6O_5S\cdot\frac{1}{2}H_2O$:

Calculated (%): C, 56.27; H, 5.48; N, 15.75; Cl, 6.01.

Found (%): C, 56.37; H, 5.36; N, 15.55; Cl, 5.79.

The pyrimidinedione derivative obtained in the yellow solid form was treated in an oxalic acid/methanol solution by a method known per se in the art to obtain 0.62 g of 1,3-dimethyl-6-{4-<3-[4-nitro-2-(2-pyridinecarbonyl)phenylthio]propyl>piperazin-1-yl}-2,4(1H,3H)-pyrimidinedione oxalate (Compound 106).

Analytical results of Compound 106 thus obtained:

Melting point: 138° C. (decomposed).

IR$\nu_{max}^{KBr}$(cm$^{-1}$) 3460, 1693, 1648, 1600, 1454, 1435, 1346, 722, 500.

Elemental analysis for $C_{25}H_{28}N_6O_5\cdot(COOH)_2\cdot\frac{1}{2}H_2O$:

Calculated (%): C, 52.00; H, 5.01; N, 13.48; S, 5.14.

Found (%): C, 51.81; H, 4,86; N, 13.24; S, 5.06.

EXAMPLE 59

Preparation of 3-methyl-6-{4-[3-(4-nitro-2-benzoyphenoxy)propyl]piperazin-1-yl}-2,4(1H,3H)-pyrimidinedione oxalate (Compound 107)

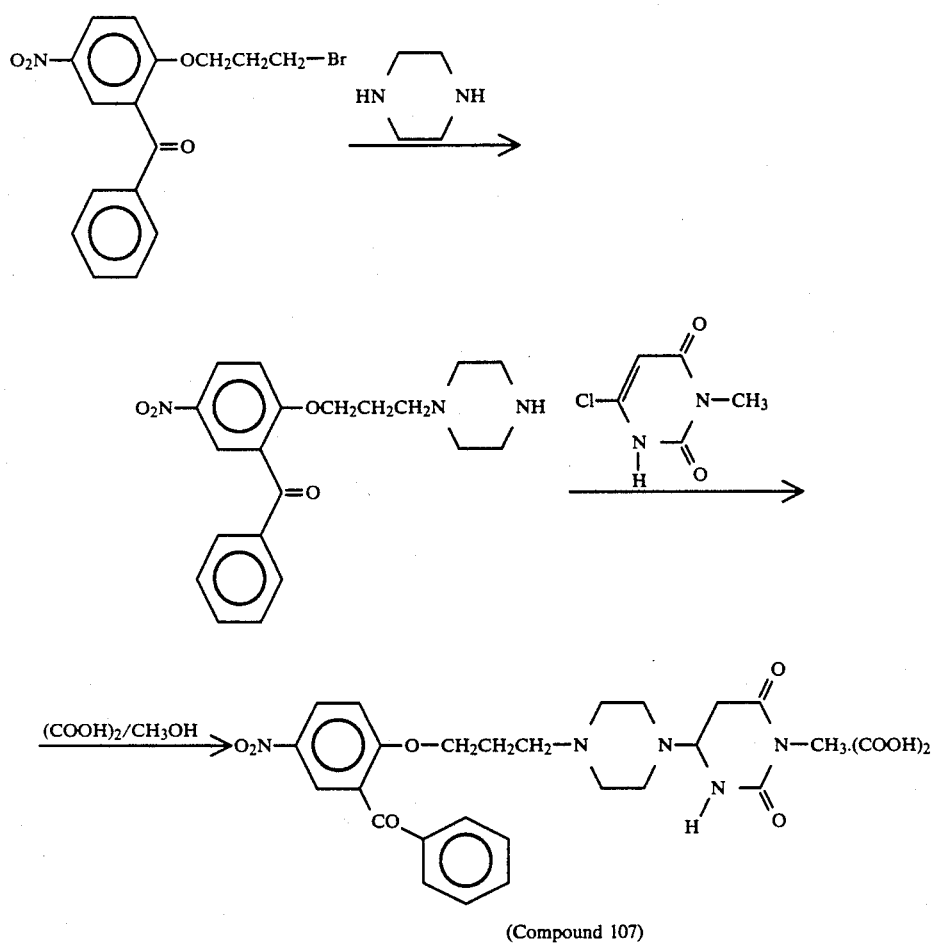

(Compound 107)

(1) Preparation of 1-[3-(2-benzoyl-4-nitrophenoxy)propyl]piperazine 3.5 g of 3-benzoyl-4-(3-bromopropyloxy)nitrobenzene and 7.8 g of piperazine were dissolved in 30 ml of chloroform. The resultant solution was heated under reflux for 4 hours.

The resultant reaction mixture was allowed to cool down, washed with water, and dried over anhydrous sodium sulfate. The solvent was thereafter distilled off from the reaction mixture and the residue was crystallized from hexane/ethanol to obtain 3.5 g of 1-[3-(2-benzoyl-4-nitrophenoxy)propyl]piperazine.

(2) Preparation of 3-methyl-6-{4-[3-(4-nitro-2-benzoylphenoxy)propyl]piperazin-1-yl}-2,4(1H,3H)-pyrimidinedione oxalate (Compound 107)

1 g of 1-[3-(2-benzoyl-4-nitrophenoxy)propyl]piperazine, 0.34 g of 6-chloro-3-methyl-2,4(1H,3H)-pyrimidinedione and 0.72 ml of triethylamine were dissolved in 3 ml of 2-propanol, followed by heating under reflux for 6 hours.

Precipitated crystals were collected by filtration from the reaction mixture and then recrystallized from isopropanol to obtain 1.9 g of 3-methyl-6-{4-[3-(4-nitro-2-benzoylphenoxy)propyl]piperazin-1-yl}-2,4(1H,3H)-pyrimidinedione.

Analytical results of the pyrimidinedione derivative thus obtained:

NMR (CDCl$_3$), δppm: 8.41(m,2H), 7.1–7.9(m,6H), 4.77(s,1H), 4.13(m,2H), 3.15(s,3H), 2.0–2.4(m,10H), 1.74(m,2H).

The pyrimidinedione derivative was next treated in an oxalic acid/methanol solution by a method known per se in the art to obtain 0.67 g of 3-methyl-6-{4-[3-(4-nitro-2-benzoylphenoxy)propyl]piperazin-1-yl}-2,4(1H,3H)-pyrimidinedione oxalate (Compound 107).

Analytical results of Compound 107 thus obtained:
Melting point: 144°–146° C. (decomposed).
IR$\nu_{max}^{KBr}$ (cm$^{-1}$): 3360, 2610, 1710, 1660, 1610, 1520, 1350, 1290, 1100, 750, 700.
Elemental analysis for $C_{25}H_{27}N_5O_6 \cdot (COOH)_2 \cdot 2H_2O$:
Calculated (%): C, 52.34; H, 5.37; N, 11.30.
Found (%): C, 51.89; H, 5.04; N, 11.23.

EXAMPLE 60

Preparation of 1,3-dimethyl-6-{2-[3-(2-benzoyl-4-nitrophenoxy)propylamino]ethylamino}-2,4(1H,3H)-pyrimidinedione oxalate (Compound 108)

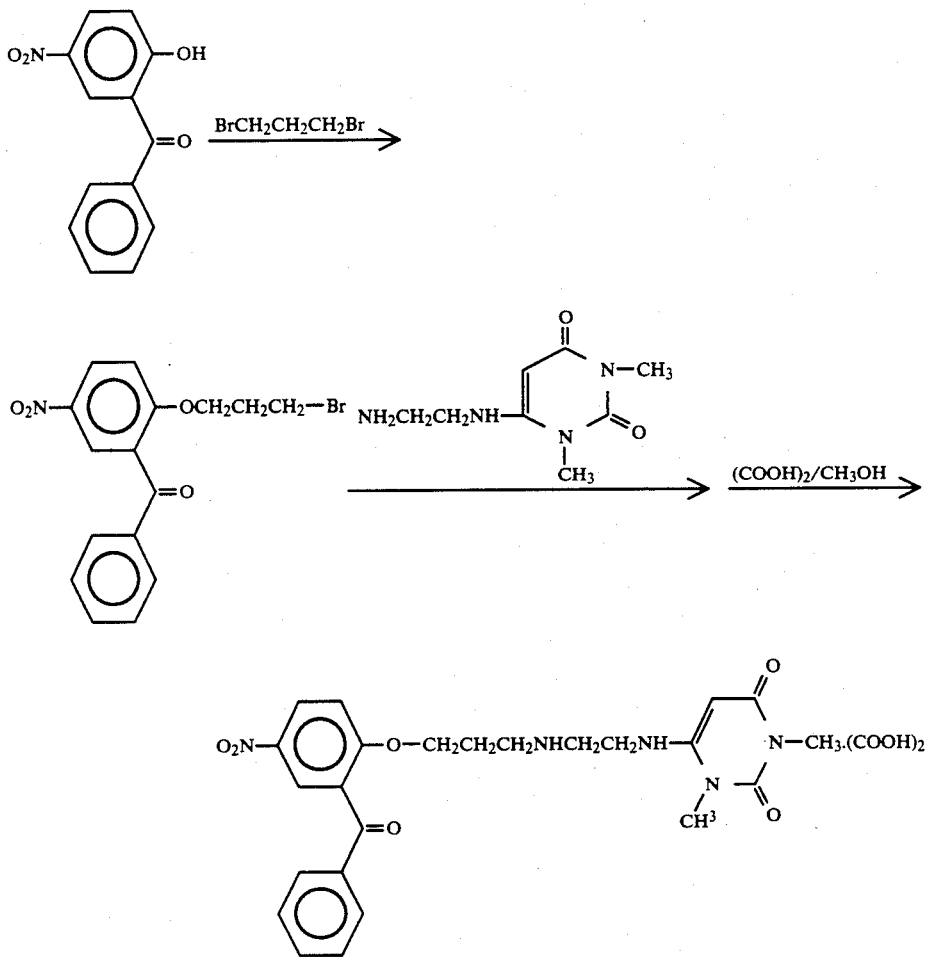

(Compound 108)

(1) Preparation of 3-(2-benzoyl-4-nitrophenoxy)propyl bromide 1.5 g of 2-hydroxy-5-nitrobenzophenone, 6 ml of 1,3-dibromopropane and 3 g of anhydrous potassium carbonate were heated and reacted under reflux for 6 hours in 10 ml of 2-butanone.

After completion of the reaction, the reaction mixture was allowed to cool down and unnecessary matters were filtered off. The filtrate was concentrated to obtain a syrup, which was purified by chromatography on a silica gel column (eluent: hexane/ethyl acetate=4/1, by volume) and then crystallized form hexane to obtain 1.0 g of 3-(2-benzoyl-4-nitrophenoxy)propyl bromide.

Analytical results of the propyl bromide derivative thus obtained:

Melting point: 86° C.

(2) Preparation of 1,3-dimethyl-6-{2-[3-(2-benzoyl-4-nitrophenoxy)propylamino]ethylamino}-2,4(1H,3H)-pyrimidinedione oxalate (Compound 108)

0.77 g of the propyl bromide derivative obtained in the above procedure (1), 0.5 g of 1,3-dimethyl-6-(2-aminoethylamino)-2,4(1H,3H)-pyrimidinedione and 0.7 ml of triethylamine were reacted at 80° C. for 4 hours in 10 ml of dimethylformamide. After distilling off the solvent from the resultant reaction mixture under reduced pressure, chloroform was added to the residue, and the solution thus formed was washed with water, dried and then concentrated to obtain a syrup.

The syrup was purified by chromatography on a silica gel column (eluent: chloroform/methanol=40/1, by volume) to obtain 0.51 g of 1,3-dimethyl-6-{2-[3-(2-benzoyl-4-nitrophenoxy)propylamino]ethylamino}-2,4(1H,3H)-pyrimidinedione.

Analytical results of the pyrimidinedione derivative thus obtained:

NMR (CDCl$_3$), δppm: 7.1–8.1(m,8H), 5.14(s,1H), 4.33(t,2H), 3.22(s,3H), 3.36(s,3H), 2.7–3.2(m,6H), 2.1(m,2H).

The pyrimidinedione derivative was next treated in an oxalic acid/methanol solution by a method known per se in the art to obtain 0.43 g of 1,3-dimethyl-6-{2-[3-(2-benzoyl-4-nitrophenoxy)propylamino]ethylamino}-2,4(1H,3H)-pyrimidinedione oxalate (Compound 108).

Analytical results of Compound 108 thus obtained:

Melting point: 111°–113° C. (decomposed).

IR$\nu_{max}^{KBr}$ (cm$^{-1}$): 3050, 1730, 1700, 1640, 1520, 1360, 770, 700.

Elemental analysis for $C_{24}H_{27}N_5O_6 \cdot (COOH)_2 \cdot 3H_2O$:

Calculated (%): C, 49.92; H, 5.69; N, 11.20.

Found (%): C, 50.11; H, 5.35; N, 11.00.

EXAMPLE 61

Preparation of 1,3-dimethyl-6-{2-[N-ethyl-3-(4-benzoyl-2-nitrophenoxy)propylamino]ethylamino}-2,4(1H,3H)-pyrimidinedione oxalate (Compound 109)

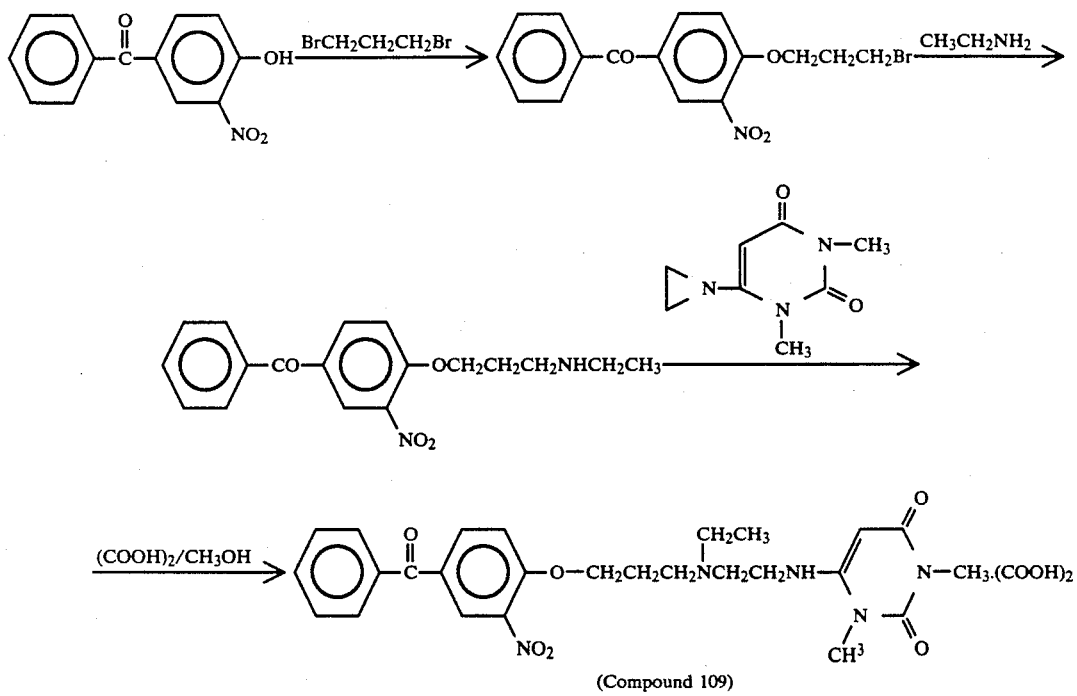

(Compound 109)

(1) Preparation of 5-benzoyl-2-(3-bromopropyloxy)-nitrobenzene 1.5 g of 4-hydroxy-3-nitrobenzophenone and 1 g of potassium carbonate were added to 5 ml of methyl ethyl ketone. The resultant mixture was heated under stirring for 30 minutes, followed by the addition of 2.0 ml of dibromopropane. The thus-obtained mixture was stirred for further 4 hours. After allowing the reaction mixture to cool down, insoluble matters were filtered off. The filtrate was then concentrated and cooled to 0° C. Under those conditions, the reaction mixture was added with 10 ml of hexane to conduct sludging. The resultant precipitate of 5-benzoyl-2-(3-bromopropyloxy)nitrobenzene was collected by filtration.

Analytical results of the precipitate:

NMR (CDCl$_3$), δppm: 7.2–8.3(m,8H), 4.40(t,2H), 3.69(t,2H), 2.47(m,2H).

2.0 g of the precipitate of 5-benzoyl-2-(3-bromopropyloxy)nitrobenzene were employed in the subsequent reaction without purification.

(2) Preparation of 1,3-dimethyl-6-{2-[N-ethyl-3-(4-benzoyl-2-nitrophenoxy)propylamino]ethylamino}-2,4(1H,3H)-pyrimidinedione oxalate (Compound 109)

1.8 g of the 5-benzoyl-2-(3-bromopropyloxy)nitrobenzene precipitate obtained in the above procedure (1) were reacted with 10 ml of ethylamine (70 wt. % of solution in water) at 70° C. for 1 hour in an autoclave. Thereafter, excess ethylamine was distilled off. The reaction mixture was added with 30 ml of chloroform and then washed twice with water.

The water-washed chloroform layer was then concentrated to obtain 2.1 g of 5-benzoyl-2-(3-ethylaminopropyloxy)nitrobenzene as a roughly-purified oily product.

1.0 g of the roughly-purified oily product, 0.4 g of 6-(1-aziridinyl)-1,3-dimethyl-2,4(1H,3H)-pyrimidinedione (Compound 6) and 0.05 g of p-toluene-sulfonic acid were reacted at 80° C. for 3 hours in a solventless state. The reaction mixture was directly subjected to chromatographic purification on a silica gel column (eluent: CHCl$_3$/CH$_3$OH=40/1, by volume), thereby obtaining 0.61 g of 1,3-dimethyl-6-{2-[N-ethyl-3-(4-benzoyl-2-nitrophenoxy)propylamino]ethylamino}-2,4(1H,3H)-pyrimidinedione.

Analytical results of the pyrimidinedione derivative thus obtained:

NMR (CDCl$_3$), δppm: 7.4–8.2(m,8H), 4.99(s,1H), 4.16(t,2H), 3.36, 3.44(s,3H), 2.4–3.0(m,8H), 2.11(m,2H), 1.10(t,3H).

The pyrimidinedione derivative was next treated in an oxalic acid/methanol solution by a method known per se in the art to obtain 0.5g of 1,3-dimethyl-6-{2-[N-ethyl-3-(4-benzoyl-2-nitrophenoxy)propylamino]ethylamino}-2,4(1H,3H)-pyrimidinedione oxalate (Compound 109).

Analytical results of Compound 109 thus obtained:
IR$\nu_{max}^{KBr}$ (cm$^{-1}$): 3400, 1690, 1620, 1530, 1360, 1250, 720, 700.

Elemental analysis for C$_2$H$_{31}$N$_5$O$_6$·(COOH)$_2$·2H$_2$O:
Calculated (%): C, 52.91; H, 5.87; N, 11.02.
Found (%): C, 52.50; H, 5.77; N, 10.92.

EXAMPLE 62

Preparation of 6-{4-[2-(2-benzoyl-4-nitrophenylthio)ethyl]piperazin-1-yl}-1,3-dimethyl-2,4(1H,3H)-pyrimidinedione oxalate (Compound 110)

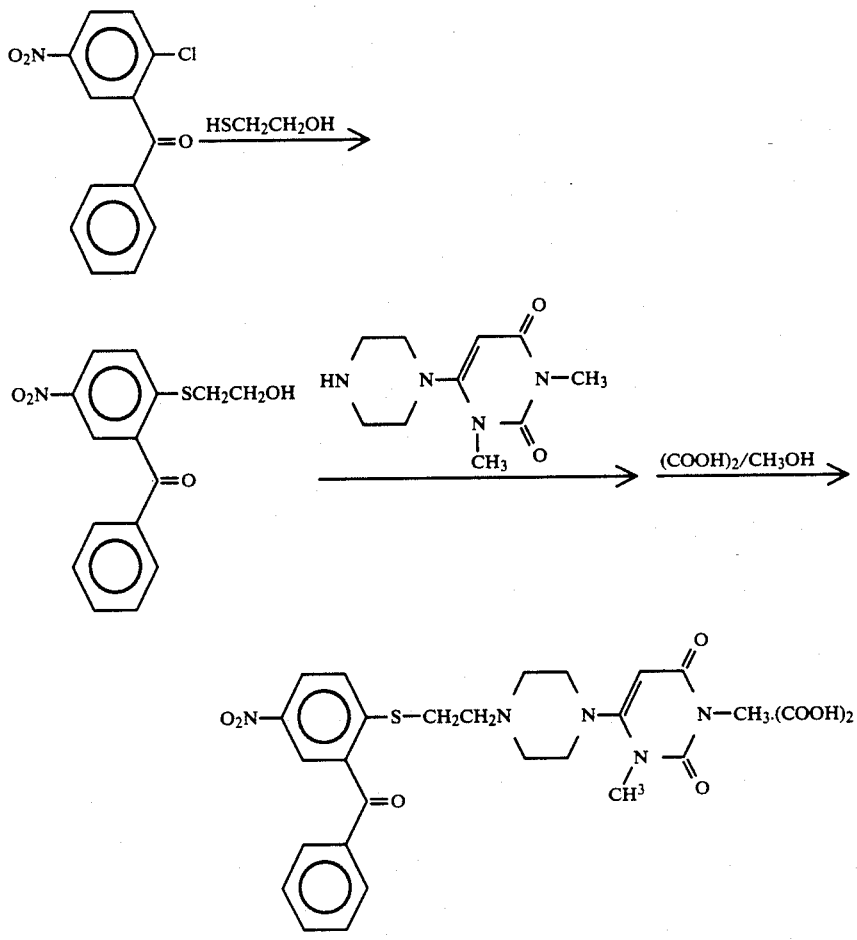

(Compound 110)

(1) Preparation of 2-(2-hydroxyethylthio)-5-nitrobenzophenone 2.0 g of 2-chloro-5-nitrobenzophenone and 2.0 g of triethylamine were dissolved in 10 ml of dimethylsulfoxide, followed by the addition of 0.63 g of 2-mercaptoethanol. The resultant mixture was heated under stirring at 80° C. for 5 hours. The reaction mixture was poured into water and then extracted with 100 ml of chloroform. After washing the extract with water and then drying it over anhydrous sodium sulfate, the solvent was distilled off under reduced pressure to obtain 2.0 g of 2-(2-hydroxyethylthio)-5-nitrobenzophenone as pale yellow crystals.

Analytical results of the benzophenone derivative thus obtained:

NMR (CDCl$_3$), δppm: 8.16–8.50(m,2H), 7.23–8.06(m,6H), 3.86(t,2H), 3.21(t,2H), 2.63(br.s,1H).

(2) Preparation of 6-{4-[2-(2-benzoyl-4-nitrophenylthio)ethyl]piperazin-1-yl}-1,3-dimethyl-2,4(1H,3H)-pyrimidinedione oxalate (Compound 110)

2.0 g of 2-(2-hydroxyethylthio)-5-nitrobenzophenone obtained in the above procedure (1) were dissolved in 20 ml of chloroform, followed by the addition of 1.6 g of triethylamine. Further, 0.91 g of methanesulfonyl chloride was added at 0° C.

After stirring the resultant mixture at 0° C. for 10 minutes, it was stirred at room temperature for further 16 hours. The reaction mixture thus obtained was diluted with 80 ml of chloroform and then poured into water. The resulting mixture was allowed to separate into layers. The organic layer was washed successively with a 1 N aqueous sodium hydroxide solution, water and saturated NaCl solution. Next, the organic layer thus washed was dried over anhydrous sodium sulfate, and the solvent was distilled off under reduced pressure to obtain 2.50 g of a mesylate as a roughly-purified product.

To a solution of the mesylate in 15 ml of dimethyl sulfoxide, 1.80 g of 1,3-dimethyl-6-(1-piperazinyl)-2,4(1H,3H)-pyrimidinedione were added. The resultant mixture was heated at 80° C. for 6 hours. The thus-obtained reaction mixture was poured into 100 ml of water in which 2.0 g of potassium carbonate were contained, and was then extracted twice with 50 ml portions of chloroform. The extracts were combined together, washed with water and then dried over anhydrous sodium sulfate. Thereafter, the solvent was distilled off under reduced pressure. The residue was purified by chromatography on a silica gel column (eluent: chloroform/methanol=50/1–25/1, by volume), thereby obtaining 2.0 g of 6-{4-[2-(2-benzoyl-4-nitrophenylthio)ethyl]piperazin-1-yl}-1,3-dimethyl-2,4(1H,3H)-pyrimidinedione as pale yellow crystals.

Analytical results of the pyrimidinedione derivative thus obtained:

NMR (CDCl ), δppm: 8.27–8.54(m,2H), 7.44–8.07(m,6H), 5.28(s,1H), 3.39(s,3H), 3.35(s,3H), 2.44–3.27(m,12H).

The pyrimidinedione derivative was next treated in an oxalic acid/methanol solution by a method known per se in the art to obtain 6-{4-[2-(2-benzoyl-4-nitrophenylthio)ethyl]piperazin-1-yl}-1,3-dimethyl-2,4(1H,3H)-pyrimidinedione (Compound 110) as white crystals.

Analytical results of Compound 110 thus obtained:
Melting point: 201.0°–202.5° C.
Elemental analysis for $C_{25}H_{27}N_5O_4S\cdot(COOH)_2$:
Calculated (%): C, 55.57; H, 5.01; N, 12.00; S, 5.49.
Found (%): C, 55.51; H, 5.55; N, 12.16; S, 5.38.

EXAMPLE 63

Production of tablets containing as an effective ingredient 1,3-dimethyl-6-(4-[3-{4-benzoyl-2-nitrophenoxy)propyl]piperazin-1-yl}-2,4-(1H,3H)-pyrimidinedione oxalate (Compound 78) available by the process of Example 50

1 g of the pyrimidinedione derivative oxalate (Compound 78), 123 g of lactose and 20 g of corn starch were finely mixed. Using a solution of 5 g of hydroxypropylcellulose in 100 ml of water, the resultant mixture was granulated. The resultant particles were dried at 50° C. for 4 hours and then mixed thoroughly with 1 g of magnesium stearate. The thus-prepared mixture was then compressed into tablets, each containing 150 mg, by a tablet machine.

EXAMPLE 64

Production of capsules containing as an effective ingredient 1,3-dimethyl-6-{4-[3-(2-benzoyl-4-nitrophenoxy)propyl]piperazin-1-yl}-2,4-(1H,3H)-pyrimidinedione oxalate (Compound 81) available by the process of Example 52

5 g of the pyrimidinedione derivative oxalate (Compound 81), 120 g of lactose and 25 g of corn starch were finely mixed. The resulting mixture was filled into hard capsules, each containing 150 mg, by a capsule filling machine.

EXAMPLE 65

Production of injection containing as an effective ingredient 1,3-dimethyl-6-{4-[3-(2-chlorobenzoyl-4-nitrophenoxy]propyl]piperazin-1-yl}-2,4-(1H,3H)-pyrimidinedione oxalate (Compound 105) available by the process of Example 57

20 mg of the pyrimidinedione derivative oxalate (Compound 105) and 0.85 g of sodium chloride were weighed. They were dissolved in distilled water for injection to give a total volume of 100 ml, thereby preparing a formulation suitable for injection.

PHARMACOLOGICAL TEST 4

Similarly to Pharmacological Test 1, the $ADP_{75}$ and ERP of each of the compounds shown in Table 8 and obtained in the corresponding examples described above were determined. The results are summarized in Table 8.

TABLE 8

| Compound No. | Result of Pharmacological Test | | | | | | |
|---|---|---|---|---|---|---|---|
| | $APD_{75}$ (%) Dose (μg/ml) | | | ERP (%) Dose (mg/kg, i.v.) | | | |
| | 1.0 | 3.0 | 10.0 | 0.1 | 0.3 | 1.0 | 3.0 |
| 76 | 16.0 | 21.0 | — | 2.4 | 4.3 | 12.6 | 16.5 |
| 78 | 19.0 | 42.0 | — | 6.7 | 13.3 | 20 | 26.7 |
| 80 | 19.0 | 30.0 | 34.0 | 2.6 | 9.7 | 21.9 | — |
| 89 | 19.0 | 30.0 | — | 5.6 | 11.1 | 11.1 | — |
| 90 | 22.0 | 31.0 | — | 20.5 | 20.5 | 14.3 | — |
| 99 | 9.0 | 22.0 | 29.0 | 9.8 | 14.7 | 23.1 | — |
| 102 | 7 | 20.0 | — | — | — | — | — |
| 104 | — | 16.0 | 25.0 | — | — | — | — |
| 105 | 11.0 | 23.0 | 28.0 | 0 | 0 | 6.3 | 6.3 |

TOXICITY TEST 4

Similarly to Toxicity Test 1, the toxicity of each of the compounds shown in Table 9 and obtained in the corresponding examples described above was tested to determine the mortality rate of mice. The results are summarized in Table 9.

Incidentally, the adminstration of each compound was conducted orally (p.o.) at a dose of 300 mg/Kg.

TABLE 9

| Compound No. | Mortality rate (%) |
|---|---|
| 77 | 0 |
| 78 | 0 |
| 80 | 0 |
| 87 | 0 |
| 100 | 0 |
| 103 | 0 |
| 105 | 0 |

EXAMPLE 66

Preparation of 1,3-dimethyl-6-{4-[3-(2-benzoyl-4-nitroanilino)propyl]piperazin-1-yl}-2,4(1H,3H)-pyrimidinedione oxalate (Compound 111)

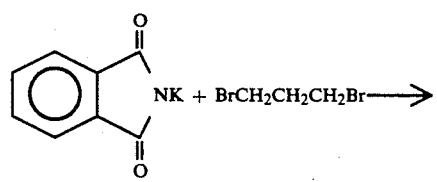

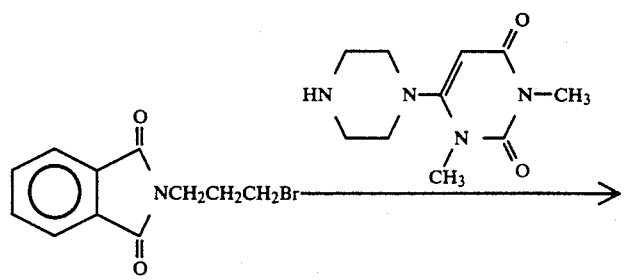

-continued

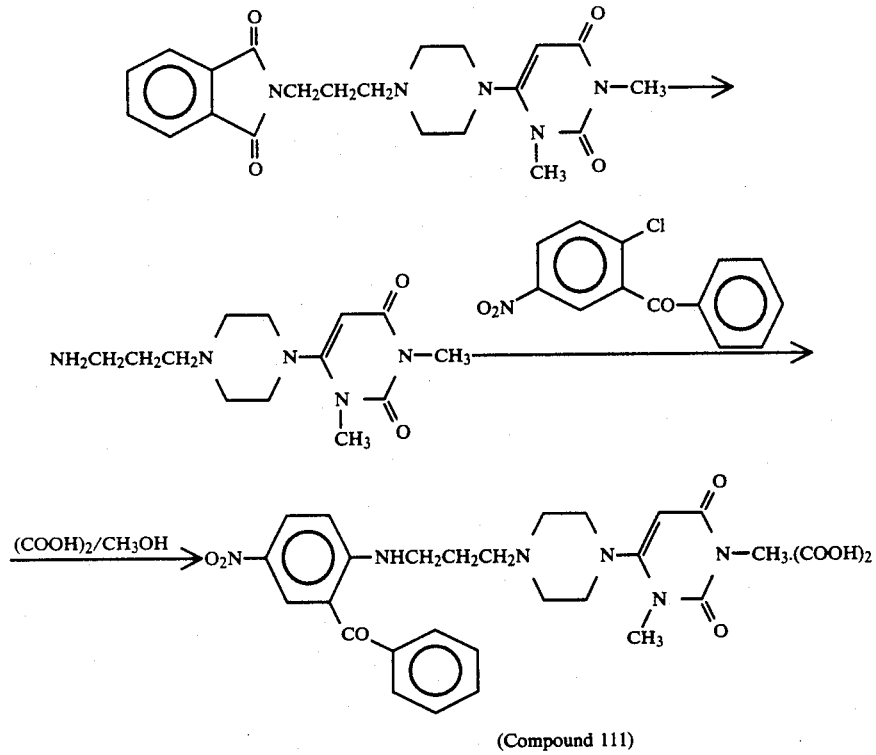

(Compound 111)

(1) Preparation of 1,3-dimethyl-6-{4-(3-aminopropyl)piperazin-1-yl}-2,4(1H,3H)-pyrimidinedione (Compound 158)

A suspension of 18.52 g of potassium phthalimide and 200 g of 1,3-dibromopropane in 100 ml of dimethylformamide was heated under stirring at 120° C. for 6 hours to react them. Insoluble matters were then filtered off from the reaction mixture and the filtrate was then concentrated to dryness under reduced pressure. The residue was washed with hexane and then recrystallized from ethanol-water. Resulting crystals were collected by filtration, washed and then dried to obtain 13.8 g of N-(3-bromopropyl)phthalimide.

A suspension which had been obtained by suspending 13.0 g of the N-(3-bromopropyl)phthalimide, 10.3 g of 1,3-dimethyl-6-(1-piperazinyl)-2,4-(1H,3H)-pyrimidinedione (Compound 157) and 20 g of triethylamine in 200 ml of dioxane was heated under reflux for 6 hours.

Further, insoluble matters were filtered off from the reaction mixture and the filtrate was concentrated to dryness under reduced pressure. The residue (dry concentrate) was recrystallized from ethyl acetate/n-hexane. Resultant crystals were collected by filtration, washed and then dried, thereby obtaining 12.5 g of 1,3-dimethyl-6-[4-(3-phthaloylaminopropyl)piperazin-1-yl]-2,4(1H,3H)-pyrimidinedione.

Next, a suspension of 12.5 g of those crystals and 6.0 g of hydrazine hydrate in 200 ml of ethanol was heated under reflux for 4 hours. After allowing the suspension to cool down, resultant insoluble matters were filtered off. The filtrate was concentrated to dryness under reduced pressure. The residue (dry concentrate) was then dissolved in water, to which dilute hydrochloric acid was added to adjust the pH to about 3. Insoluble matters formed by the pH adjustment were filtered off. After adding a large amount of potassium carbonate to the filtrate, the resultant mixture was extracted with chloroform. Subsequent to the completion of the extraction, the resulting organic layer was dried over anhydrous sodium sulfate and then heated under reduced pressure to distill off the solvent, whereby 6.80 g of 1,3-dimethyl-6-[4-(3-aminopropyl)piperazin-1-yl]-2,4(1H,3H)-pyrimidinedione (Compound 158) were obtained as a colorless syrupy substance. The syrupy substance was crystallized when allowed to stand overnight.

(2) Preparation of 1,3-dimethyl-6-{4-[3-(2-benzoyl-4-nitroanilino)propyl]piperazin-1-yl}-2,4(1H,3H)-pyrimidinedione oxalate (Compound 111):

0.9 g of 1,3-dimethyl-6-[4-(3-aminopropyl)piperazin-1-yl]-2,4(1H,3H)-pyrimidinedione and 1.0 g of 2-chloro-5-nitrobenzophenone were added to 10 ml of dimethyl sulfoxide. The resultant mixture was heated at 110° C. for 20 hours. After allowing the reaction mixture to cool down, the reaction mixture was poured into a saturated aqueous solution of sodium bicarbonate and the resulting mixture was extracted with chloroform.

An organic layer (chloroform layer) obtained by the extraction was separated, washed with water, dried over anhydrous sodium sulfate, and then concentrated to dryness. The residue was purified by chromatography on a silica gel column (eluent: chloroform/methanol=50/1-20/1, by volume), thereby obtaining 0.95 g of 1,3-dimethyl-6-{4-[3-(2-benzoyl-4-nitroanilino)propyl]piperazin-1-yl}-2,4(1H,3H)-pyrimidinedione as a yellow oily substance.

Analytical results of the oily substance of the pyrimidinedione derivative thus obtained:

NMR (CDCl$_3$), δppm: 2.04(m,2H), 2.65(m,6H), 3.04(m,4H), 3.36(s,3H), 3.42(s,3H), 3.57(t,2H), 5.30(s,1H), 6.90(d,1H), 7.69(s,5H), 8.35(dd,1H), 8.95(d,1H), 9.50(s,1H).

Further, the oily substance was treated in an oxalic acid/methanol solution by a method known per se in the art to obtain 1.0 g of 1,3- dimethyl-6-{4-[3-(2-benzoyl-4-nitroanilino)propyl]-piperazin-1-yl}-2,4(1H,3H)-pyrimidinedione oxalate (Compound 111).

Analytical results of Compound 111 thus obtained:
Melting point: Amorphous.
Elemental analysis for $C_{26}H_{30}N_6O_5 \cdot (COOH)_2$:
Calculated (%): C, 56.37; H, 5.41; N, 14.09.
Found (%): C, 56.92; H, 5.40; N, 14.20.

EXAMPLE 67

Preparation of Compounds 120–127

By a similar procedure to Example 66-(2) except for the use Compounds 112–119 having the below-described structural formula (I)—in which $R^7$, $R^8$ and $R^9$ mean the below-described groups respectively—in place of 2-chloro-5-nitrobenzophenone, pyrimidinedione derivative oxalates having the physical properties set out below and the below-described structural formula (II) in which $R^7$, $R^8$ and $R^9$ are different from one compound to another were obtained as Compounds 120–127, respectively.

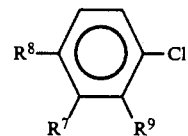

| | $R^9$ | $R^8$ | $R^7$ |
|---|---|---|---|
| Compound 118 | $-NO_2$ | 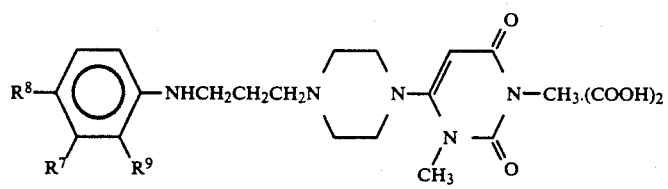 | $-H$ |
| Compound 119 | $-H$ | $-NO_2$ | $-COCH_3$ |

(structural formula II shown)

| | $R^9$ | $R^8$ | $R^7$ |
|---|---|---|---|
| Compound 112 | $-COCH_3$ | $-NO_2$ | $-H$ |
| Compound 113 | $-CO-\text{cyclopentyl}$ | $-NO_2$ | $-H$ |
| Compound 114 | $-CO-\text{(2-chlorophenyl)}$ | $-NO_2$ | $-H$ |
| Compound 115 | $-CO-\text{(2-pyridyl)}$ | $-NO_2$ | $-H$ |
| Compound 116 | $-CO-\text{(3-pyridyl)}$ | $-NO_2$ | $-H$ |
| Compound 117 | $-NO_2$ | $-COCH_3$ | $-H$ |

Compound 120 ($R^7$, $R^8$ and $R^9$ are as defined with respect to Compound 112):
Melting point: 135°–137° C. (decomposed).
$IR\nu_{max}^{KBr}(cm^{-1})$ 3300, 2550, 1720, 1630, 1560, 1320, 1250, 800, 710.
Elemental analysis for $C_{21}H_{28}N_6O_5 \cdot (COOH)_2 \cdot 2H_2O$:
Calculated (%): C, 48.42; H, 6.01; N, 14.73.
Found (%): C, 48.14; H, 5.82; N, 14.32.

Compound 121 ($R^7$, $R^8$ and $R^9$ are as defined with respect to Compound 113):
Melting point: 182°–183° C. (decomposed).
$IR\nu_{max}^{KBr}(cm^{-1})$ 3350, 2550, 1690, 1630, 1540, 1350, 1290, 1100, 810, 770.
Elemental analysis for $C_{25}H_{34}N_6O_5 \cdot (COOH)_2 \cdot 2\frac{1}{2} H_2O$:
Calculated (%): C, 50.46; H, 6.59; N, 13.08.
Found (%): C, 51.04; H, 6.77; N, 12.90.

Compound 122 ($R^7$, $R^8$ and $R^9$ are as defined with respect to Compound 114):
Melting point: Amorphous.
Elemental analysis for $C_{26}H_{29}N_6O_5Cl \cdot (COOH)_2 \cdot \frac{1}{2} H_2O$:
Calculated (%): C, 52.54; H, 5.04; N, 13.13; Cl, 5.54.
Found (%): C, 52.36; H, 5.05; N, 13.14; Cl, 5.23.

Compound 123 ($R^7$, $R^8$ and $R^9$ are as defined with respect to Compound 115)
Melting point: 151° C. (decomposed).
$IR\nu_{max}^{KBr}$ (cm$^{-1}$): 3440, 1706, 1645, 1588, 1496, 1441, 1333, 1200, 768, 722, 500.
Elemental analysis for $C_{25}H_{29}N_7O_5 \cdot 1\frac{1}{2}(COOH)_2 \cdot H_2O$:
Calculated (%): C, 50.91; H, 5.19; N, 14.84.
Found (%): C, 51.12; H, 5.10; N, 14.81.

Compound 124 ($R^7$, and $R^9$ are as defined with respect to Compound 116):
Melting point: 162°–165° C. (decomposed).
$IR\nu_{max}^{KBr}(cm^{-1})$ 3400, 1690, 1600, 1550, 1350, 1260, 1150, 780, 700.
Elemental analysis for $C_{25}H_{29}N_7O_5 \cdot 2 \cdot (COOH)_2 \cdot H_2O$:
Calculated (%): C, 48.00; H, 4.83; N, 13.06.
Found (%): C, 48.38; H, 4.92; N, 12.91.

Compound 125 (R⁷, R⁸ and R⁹ are as defined with respect to Compound 117):
Melting point: 148°–150° C. (decomposed).
IR$\nu_{max}^{KBr}$ (cm$^{-1}$): 3350, 2600, 1690, 1640, 1530, 1330, 1240, 980, 760, 700.
Elemental analysis for $C_{25}H_{34}N_6O_5 \cdot (COOH)_2 \cdot 3H_2O$:
Calculated (%): C, 50.46; H, 6.59; N, 13.08.
Found (%): C, 51.04; H, 6.77; N, 12.90.

Compound 126 (R⁷, R⁸ and R⁹ are as defined with respect to Compound 118):
Melting point: 202°614 203° C. (decomposed).
IR$\nu_{max}^{KBr}$ (cm$^{-1}$) 3560, 2550, 1700, 1610, 1530, 1320, 1280, 1110, 810, 710.
Elemental analysis for $C_{26}H_{30}N_6O_5 \cdot (COOH)_2 \cdot H_2O$:
Calculated (%): C, 54.72; H, 5.58; N, 13.67.
Found (%): C, 54.68; H, 5.21; N, 13.47.

Compound 127 (R⁷, R⁸ and R⁹ are as defined with respect to Compound 119):
Melting point: about 140° C. (amorphous).
IR$\nu_{max}^{KBr}$ (cm$^{-1}$): 3420, 2600, 1710, 1640, 1540, 1320, 1220, 1110, 810, 710.
Elemental analysis for $C_{21}H_{28}N_6O_5 \cdot COOH)_2 \cdot 2H_2O$:
Calculated (%): C, 48.24; H, 5.57; N, 14.06.
Found (%): C, 44.11; H, 5.90; N, 13.89.

EXAMPLE 68

Production of tablets containing as an effective ingredient 1,3-dimethyl-6-{4-[3-(2-benzoyl-4nitroanilino)-propyl]piperazin-1-yl}-2,4(1H,3H)-pyrimidinedione oxalate (Compound 111) available by the process of Example 66

1 g of the pyrimidinedione derivative oxalate (Compound 111), 123 g of lactose and 20 g of corn starch were finely mixed. Using a solution of 5 g of hydroxypropylcellulose in 100 ml of water, the resultant mixture was granulated. The resultant particles were dried at 50° C. for 4 hours and then mixed thoroughly with 1 g of magnesium stearate. The thus-prepared mixture was then compressed into tablets, each containing 150 mg, by a tablet machine.

EXAMPLE 69

Production of capsules containing as an effective ingredient 1,3-dimethyl-6-{4-[3-(2-acetyl-4-nitroanilino)propyl]piperazin-1-yl}-2,4(1H,3H)-pyrimidinedione oxalate (Compound 120) available by the process of Example 67

5 g of the pyrimidinedione derivative oxalate (Compound 120), 120 g of lactose and 25 g of corn starch were finely mixed. The resulting mixture was filled into hard capsules, each containing 150 mg, by a capsule filling machine.

EXAMPLE 70

Production of injection containing as an effective ingredient 1,3-dimethyl-6-{4-[3-(2-benzoyl-4-nitroanilino]propyl]piperazin-1-yl}-2,4-(1H,3H)-pyrimidinedione oxalate (Compound 111) available by the process of Example 66

20 mg of the pyrimidinedione derivative oxalate (Compound 111) and 0.85 g of sodium chloride were weighed. They were dissolved in distilled water for injection to give a total volume of 100 ml, thereby preparing a formulation suitable for injection.

PHARMACOLOGICAL TEST 5

Similarly to Pharmacological Test 1, the ADP₇₅ and ERP of each of the compounds shown in Table 10 and obtained in the corresponding examples described above were determined. The results are summarized in Table 10.

TABLE 10

| | Result of Pharmacological Test | | | | | | |
|---|---|---|---|---|---|---|---|
| | APD$_{75}$ (%) Dose (μg/ml) | | | ERP (%) Dose (mg/kg, i.v.) | | | |
| Compound No. | 1.0 | 3.0 | 10.0 | 0.1 | 0.3 | 1.0 | 3.0 |
| 111 | 13.0 | 21.0 | — | 7.7 | 10.9 | 14.0 | 21.0 |
| 120 | 16.0 | 27.0 | 29.0 | — | — | — | — |
| 125 | — | 10.0 | 21.0 | — | — | — | — |
| 126 | 23.0 | 45.0 | 48.0 | 7.0 | 14.0 | 21.0 | — |

TOXICITY TEST 5

Similarly to Toxicity Test 1, the toxicity of each of the compounds shown in Table 11 and obtained in the corresponding examples described above was tested to determine the mortality rate of mice. The results are summarized in Table 11.

Incidentally, the administration of each compound was conducted orally (p.o.) at a dose of 300 mg/Kg.

TABLE 11

| Compound No. | Mortality rate (%) |
|---|---|
| 122 | 0 |
| 126 | 0 |

EXAMPLE 71

Preparation of 1,3-dimethyl-6-{4-(2-benzoyl-4-nitrophenyl)piperazin-1-yl}-2,4(1H,3H)-pyrimidinedione oxalate (Compound 128)

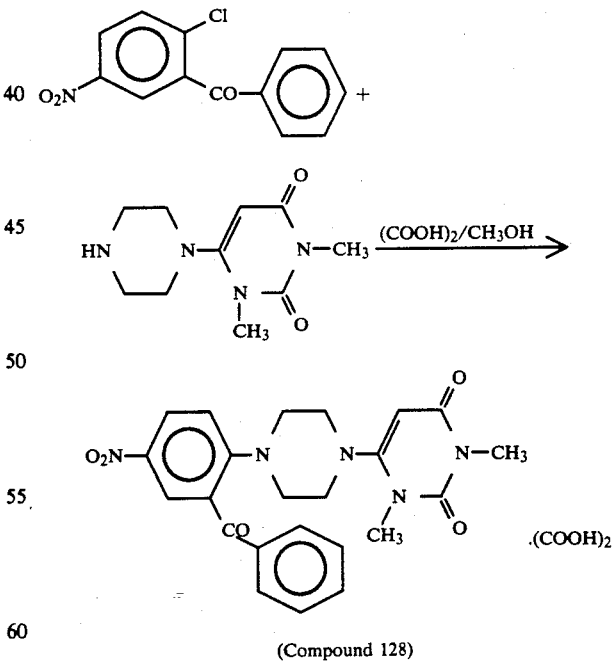

(Compound 128)

0.5 g of 1,3-dimethyl-6-(piperazin-1-yl)-2,4(1H,3H)-pyrimidinedione (Compound 157) and 0.6 g of 3-benzoyl-4-chloronitrobenzene were added to 5 ml of dimethylsulfoxide. The resultant mixture was heated at 110° C. for 20 hours. After allowing the reaction mixture to cool down, the reaction mixture was poured into a saturated aqueous solution of sodium bicarbonate and the resulting mixture was extracted with chloroform.

An organic layer (chloroform layer) obtained by the extraction was separated, washed with water, dried over anhydrous sodium sulfate, and then concentrated to dryness. The residue was purified by chromatography on a silica gel column (eluent: chloroform/methanol=50/1-20/1, by volume), thereby obtaining 0.2 g of 1,3-dimethyl-6-[4-(2-benzoyl-4-nitrophenyl)piperazin-1-yl]-2,4(1H,3H)-pyrimidinedione.

Analytical results of the pyrimidinedione derivative thus obtained:

NMR (d$_6$-DMSO), δppm: 2.64(m,2H), 3.18(m,6H), 3.28(s,3H), 3,17(s,3H), 5.00(s,1H), 7.3–8.0(m,5H), 8.2–8.6(m,3H).

Further, the pyrimidinedione derivative was treated in an oxalic acid/methanol solution by a method known per se in the art to obtain 0.18 g of 1,3-dimethyl-6-[4-(2-benzoyl-4-nitrophenyl)piperazin-1-yl]-2,4(1H,3H)-pyrimidinedione oxalate (Compound 128).

Analytical results of Compound 128 thus obtained:
Melting point: 178 179° C. (decomposed).
IR$\nu_{max}^{KBr}$ (cm$^{-1}$): 3430, 1700, 1660, 1600, 1520, 1320, 1260, 1130, 950, 860, 760, 700.
Elemental analysis for $C_{23}H_{23}N_5O_5 \cdot \frac{1}{2}(COOH)_2 \cdot \frac{1}{2} H_2O$:
Calculated (%): C, 57.25; H, 5.01; N, 13.91.
Found (%): C, 57.55; H, 4.80; N, 13.56.

EXAMPLE 72

Preparation of 1,3-dimethyl-6-{3-[4-nitro-2-(3pyridinecarbonyl)anilino]propylamino}-2,4(1H,3H)-pyrimidinedione oxalate (Compound 129)

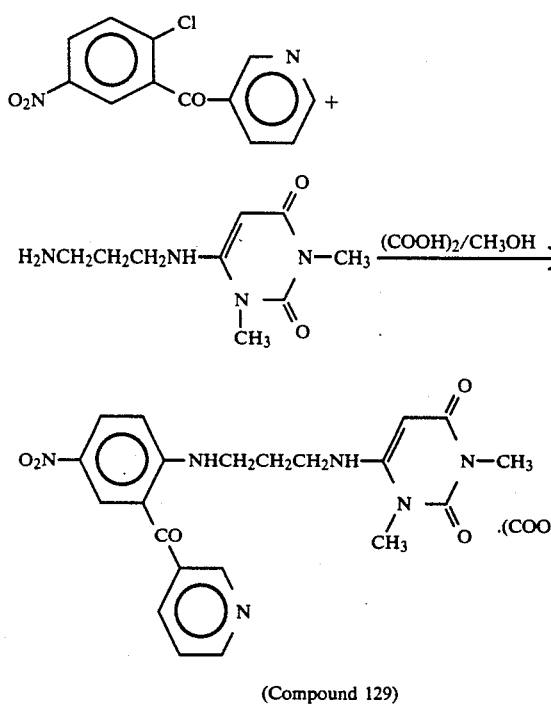

(Compound 129)

0.67 g of 4-chloro-3-(3-pyridinecarbonyl)nitrobenzene and 0.6 g of 1,3-dimethyl-6-(3-aminopropylamino)-2,4(1H,3H)-pyrimidinedione were dissolved in 3 ml of dimethylformamide, followed by the addition of 0.79 ml of triethylamine. The resultant mixture was heated under stirring at 80° C. for 5 hours.

After completion of the heating, the reaction mixture was allowed to cool down and the solvent was then distilled off. The residue was purified by chromatography on a silica gel column (eluent: chloroform/methanol=40/1, by volume) to obtain 0.39 g of 1,3-dimethyl-6-(3-[4-nitro-2-(3-pyridinecarbonyl)anilino]propylamino)-2,4(1H,3H)-pyrimidinedione as an oily substance.

Analytical results of the pyrimidinedione derivative thus obtained:

NMR (CDCl$_3$), δppm: 9.40(m,1H), 8.84(m,6H), 7.86–8.57(m,3H), 7.50(dd,1H), 6.85(d,1H), 5.90(m,1H), 4.86(s,1H), 3.23(s,3H), 3.38(s,3H), 3.40(m,4H), 2.1(m,2H).

Further, the pyrimidinedione derivative was treated in an oxalic acid/methanol solution by a method known per se in the art to obtain 0.36 g of 1,3-dimethyl-6-{3-[4-nitro-2-(3-pyridinecarbonyl)anilino]propylamino}-2,4(1H,3H)-pyrimidinedione oxalate (Compound 129).

Analytical results of Compound 129 thus obtained:
Melting point: 136°–139° C. (decomposed).
IR$\nu_{max}^{KBr}$ (cm$^{-1}$) 3350, 2550, 1690, 1640, 1550, 1330, 1260, 1110, 770, 700.
Elemental analysis for $C_{21}H_{22}N_6O_5 \cdot (COOH)_2$:
Calculated (%): C, 52.27; H, 4.58; N, 15.90.
Found (%): C, 52.25; H, 4.92; N, 15.51.

EXAMPLE 73

Preparation of 1,3-dimethyl-6-[3-(2-benzoyl-4-nitroanilino)propylamino]-2,4(1H,3H)-pyrimidinedione oxalate (Compound 130)

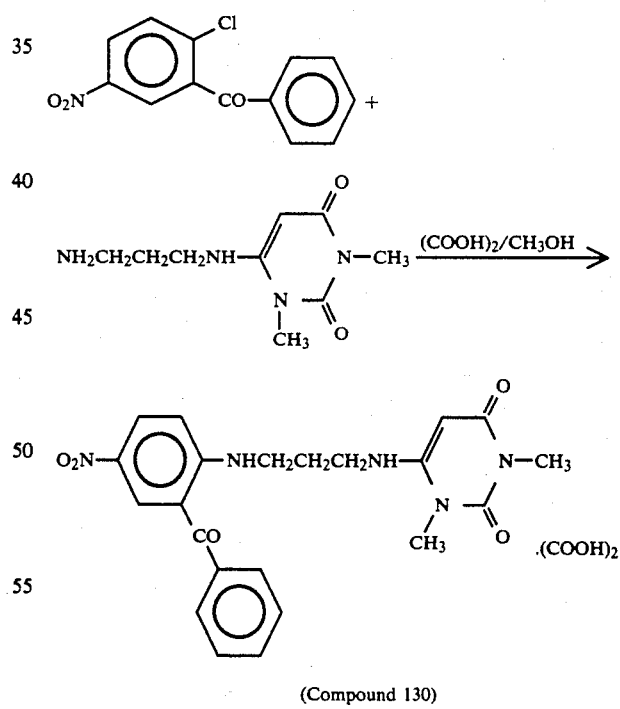

(Compound 130)

By a similar procedure to Example 72 except for the use of 3-benzoyl-4-chloronitrobenzene in place of 4-chloro-3-(3-pyridinecarbonyl)nitrobenzene, 1,3-dimethyl-6-[3-(2-benzoyl-4-nitroanilino)propylamino]-2,4(1H,3H)-pyrimidinedione oxalate (Compound 130 was obtained.

Analytical results of Compound 130 thus obtained:
Melting point: amorphous.

IR$\nu_{max}^{KBr}$(cm$^{-1}$) 3300, 1690, 1620, 1540, 1330, 1110, 990, 850, 760, 700.

Elemental analysis for $C_{22}H_{23}N_5O_5 \cdot \frac{1}{2}(COOH)_2$:
Calculated (%): C, 57.26; H, 5.01; N, 14.52.
Found (%): C, 57.16; H, 4.63; N, 14.76.

EXAMPLE 74

Preparation of 1,3-dimethyl-6-[2-(2-benzoyl-4-nitroanilino)ethylamino]-2,4(1H,3H)-pyrimidinedione oxalate (Compound 131)

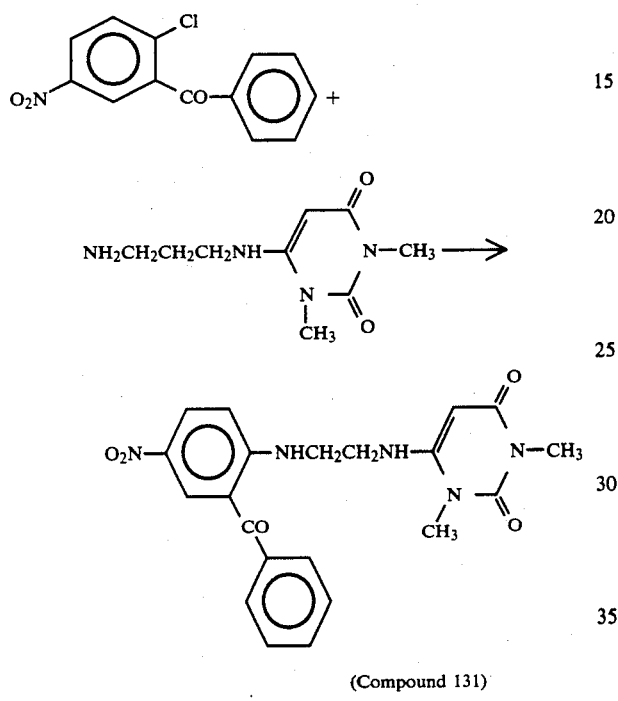

(Compound 131)

By a similar procedure to Example 73 except that 1,3-dimethyl-6-(2-aminoethylamino)-2,4(1H,3H)-pyrimidinedione was reacted in place of 1,3-dimethyl-6-(3-aminopropylamino)-2,4(1H,3H)-pyrimidinedione with 3-benzoyl-4-chloronitrobenzene, 1,3-dimethyl-6-[2-(2-benzoyl-4-nitroanilino)ethylamino]-2,4(1H,3H)-pyrimidinedione (Compound 131) was obtained.

Analytical results of Compound 131 thus obtained:
Melting point: 207°–209° C. (decomposed).
IR$\nu_{max}^{KBr}$(cm$^{-1}$) 3050, 2950, 1760, 1680, 1560, 1340, 1110, 760, 700.

Elemental analysis for $C_{21}H_{21}N_5O_5 \cdot (COOH)_2 \cdot H_2O$:
Calculated (%): C, 51.98; H, 4.74; N, 13.18.
Found (%): C, 51.81; H, 4.87; N, 12.97.

EXAMPLE 75

Preparation of 1,3-dimethyl-6-{2-[4-nitro-2-(3-pyridiencarbonyl)phenylamino]ethylamino}-2,4(1H,3H)-pyrimidinedione oxalate (Compound 132)

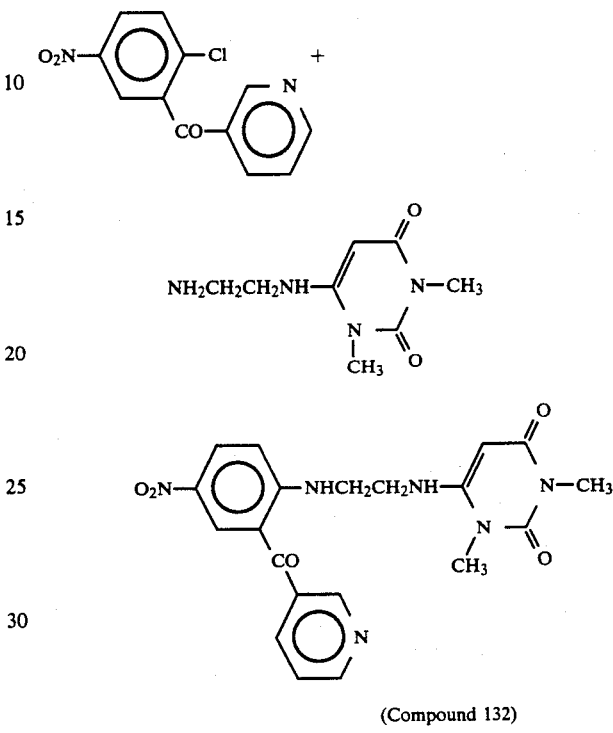

(Compound 132)

By a similar procedure to Example 72 except for the use of 1,3-dimethyl-6-(2-aminoethylamino)-2,4(1H,3H)-pyrimidinedione in place of 1,3-dimethyl-6-(3-aminopropylamino)-2,4(1H,3H)-pyrimidinedione, 1,3-dimethyl-6-{2-[4-nitro-2-(3-pyridinecarbonyl)phenylamino]ethylamino}-2,4(1H,3H)-pyrimidinedione (Compound 132) was obtained.

Analytical results of Compound 132 thus obtained:
Melting point: 148° C.
IR$\nu_{max}^{KBr}$ (cm$^{-1}$): 3380, 3200, 1692, 1630, 1587, 1333, 1265, 1155, 1115.

Elemental analysis for $C_{20}H_{20}N_6O_5 \cdot H_2O$:
Calculated (%): C, 54.30; H, 5.01; N, 19.00.
Found (%): C, 54.04; H, 4.71; N, 18.84.

EXAMPLE 76

Preparation of 1,3-dimethyl-6-(4-[2-(2-benzoyl-4-nitrophenyl)ethyl]piperazin-1-yl)-2,4(1H,3H)-pyrimidinedione oxalate (Compound 133)

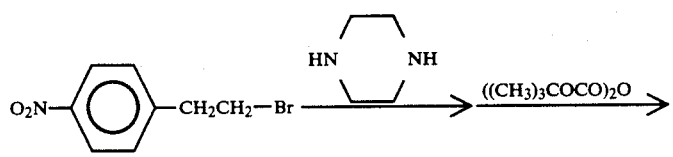

-continued

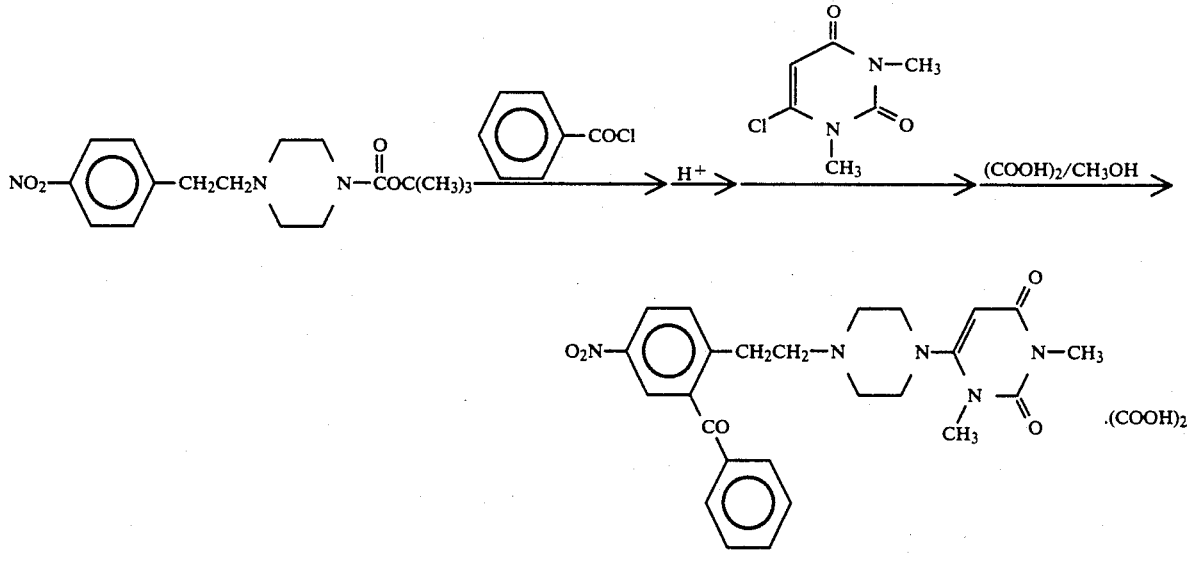

(Compound 133)

(1) Preparation of 1-[2-(4-nitrophenyl)ethyl]-4-tert-butyloxycarbonylpiperazine 1.7 g of 4-nitrophenethyl bromide and 5 g of piperazine were dissolved in 15 ml of chloroform. The resultant solution was heated under reflux for 3 hours.

After completion of the reaction, the reaction mixture was allowed to cool down and washed three times with water to remove excess piperazine from the reaction mixture. Then, the chloroform layer was separated.

Next, the solvent was removed under reduced pressure from the chloroform layer. The residue was dissolved in 15 ml of dry tetrahydrofuran, followed by the addition of 1.6 g of di-tert-butyl dicarbonate. The mixture thus obtained was stirred at room temperature for 1 hour and the solvent was distilled off from the reaction mixture.

A hexane/ethanol mixed solvent was added to the residue. The thus-precipitated crystals were collected by filtration and then recrystallized from a hexane/ethanol mixed solvent, thereby obtaining 2.4 g of 1-[2-(4-nitrophenyl)ethyl]-4-tert-butyloxycarbonylpiperazine.

Analytical results of the piperazine derivative thus obtained:

Melting point: amorphous.

NMR (CDCl$_3$), δppm: 8.14(d,2H), 7.34(d,2H), 3.41(m,4H), 2.74(m,4H), 2.43(m,4H), 1.45(s,9H).

(2) Preparation of 1,3-dimethyl-6-{4-[2-(2-benzoyl-4nitrophenyl)ethyl]piperazin-1-yl}-2,4(1H,3H)-pyrimidinedione oxalate (Compound 133)

0.8 g of 1-[2-(4-nitrophenyl)ethyl]-4-tertbutyloxycarbonylpiperazine was dissolved in 20 ml of dry tetrahydrofuran, followed by the addition of 1 ml of hexamethylphosphorus triamide. While chilling the resultant mixture at −78° C., 2.9 ml of a 1 M solution of lithium diisopropylamide in dry tetrahydrofuran were added.

Upon an elapsed tie of 1 hour after completion of the addition, the temperature of the reaction mixture was maintained at −78° C. and 0.83 ml of benzoyl chloride was then added dropwise.

After completion of the dropwise addition, the temperature of the reaction mixture was gradually raised to −30° C, at which the reaction mixture was stirred for 3 hours. The reaction mixture was then poured into ice water, followed by extraction with chloroform.

The extract was washed with water, dried over anhydrous sodium sulfate, and then concentrated under reduced pressure to obtain a syrupy substance.

The syrupy substance was dissolved in 30 ml of ethyl ether, followed by the addition of 2 ml of hydrochloric acid/dioxane (4 N). The resultant mixture was stirred at room temperature for 30 minutes.

The resultant crystals were collected by filtration and then washed with ether.

The crystals were next dissolved in 20 ml of isopropanol, to which 0.5 g of 1,3-dimethyl-6-chloro-2,4(1H,3H)-pyrimidinedione and 3 ml of triethylamine. The thus-prepared mixture was stirred under reflux for 6 hours.

After completion of the stirring, the solvent was distilled off from the reaction mixture. The residue was dissolved in chloroform. The resultant chloroform solution was washed with water, dried over anhydrous sodium sulfate, and then concentrated under reduced pressure.

The residue was purified by chromatography on a silica gel column (eluent: chloroform/methanol=50/1, by volume) to obtain 0.33 g of 1,3-dimethyl-6-{4-[2-(2-benzoyl-4-nitrophenyl)ethyl]piperazin-1-yl}-2,4(1H,3H)-pyrimidinedione.

Analytical results of the pyrimidinedione derivative thus obtained:

NMR (CDCl$_3$), δppm: 7.3–8.2(m,8H), 5.06(s,1H), 3.28(s,3H), 3.39(s,3H), 2.4–3.0(m,12H).

Next, the pyrimidinedione derivative was treated in an oxalic acid/methanol solution by a method known per se in the art to obtain 0.34 g of 1,3-dimethyl-6-{4-[2-(2-benzoyl-4-nitrophenyl)ethyl]piperazin-1-yl}-2,4(1H,3H)-pyrimidinedione oxalate (Compound 133)

Analytical results of Compound 133 thus obtained:

Melting point: 183°–185° C. (decomposed).

IR$\nu_{max}^{KBr}$ (cm$^{-1}$): 3350, 2850, 2500, 1710, 1660, 1520, 1340, 1210, 840, 800, 750, 700.

Elemental analysis for C$_{25}$H$_{27}$N$_5$O$_5$·(COOH)$_2$·H$_2$O:

Calculated (%): C, 55.38; H, 5.34; N, 11.96.

Found (%): C, 55.16; H, 5.11; N, 12.01.

EXAMPLE 77

Preparation of 1,3-dimethyl-6-{4-[(2-benzoyl-4-nitrophenyl)methyl]piperazin-1-yl}-2,4(1H,3)-pyrimidinedione oxalate (Compound 134)

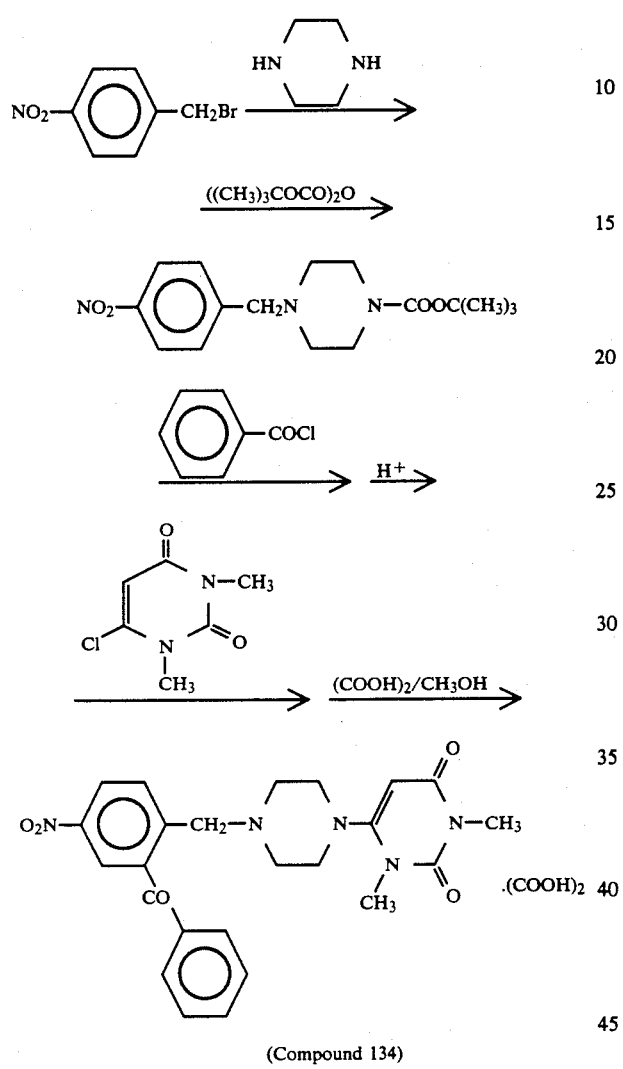

(Compound 134)

(1) Preparation of 1-[(4-nitrophenyl)methyl]-4-tert-butyloxycarbonylpiperazine:

By a similar procedure to Example 76-(1) except for the use of 1.6 g of 4-nitrobenzyl bromide in place of 4-nitrophenethyl bromide, 1.1 g of 1-[(4-nitrophenyl)-methyl]-4-tert-butyloxycarbonylpiperazine.

Analytical results of the piperazine derivative thus obtained:

NMR (CDCl₃), δppm: 8.11(d,2H), 7.44(d,2H), 2.96(m,4H), 2.73(m,4H), 1.51(s,9H).

(2) Preparation of 1,3-dimethyl-6-{4-[(2-benzoyl-4-nitrophenyl)methyl]piperazin-1-yl}-2,4(1H,3H)-pyrimidinedione oxalate (Compound 134)

In a manner similar to Example 76-(2) except for the use of 0.77 g of 1-[(4-nitrophenyl)methyl]-4-tert-butyloxycarbonylpiperazine obtained in the above procedure (1) in place of 1-[2-(4-nitrophenyl)ethyl]-4-tert-butyloxycarbonylpiperazine, 0.10 g of 1,3-dimethyl-6-{4-[(2-benzoyl-4-nitrophenyl)methyl]piperazin-1-yl}-2,4(1H,3H)-pyrimidinedione oxalate (Compound 134) was obtained.

Analytical results of Compound 134 thus obtained:

Melting point: amorphous.

IR$\nu_{max}^{KBr}$(cm$^{-1}$) 3350, 1700, 1630, 1530, 1360, 1120, 860, 760, 700.

Elemental analysis for C$_{24}$H$_{25}$N$_5$O$_5$ · ½(COOH)$_{2.3/2}$·H$_2$O:

Calculated (%): C, 56.42; H, 4.92; N, 12.65.
Found (%): C, 56.12; H, 4.77; N, 12.39.

EXAMPLE 78

Preparation of 1,3-dimethyl-6-{2-[(2-benzoyl-4-nitrophenyl)methylamino]ethylamino}-2,4-(1H,3)-pyrimidinedione oxalate (Compound 135)

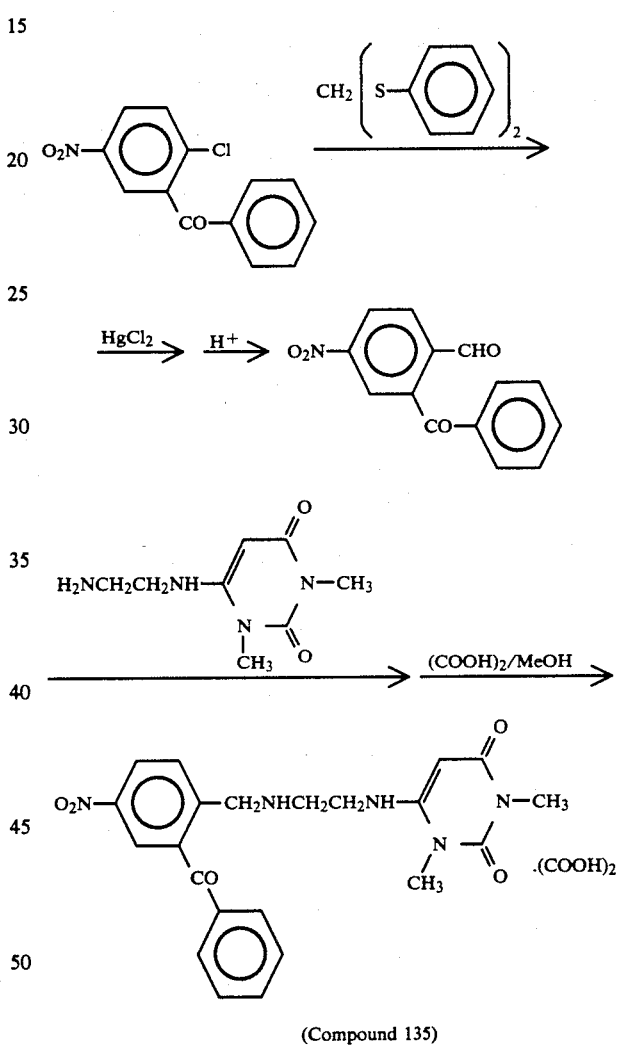

(Compound 135)

(1) Preparation of 2-benzoyl-4-nitrobenzaldehyde 3.72 g of bisthiophenylmethane were dissolved in 40 ml of tetrahydrofuran and the resultant solution was chilled to −20° C. 12 ml of n-butyl lithium (1.6 M solution in hexane) were added dropwise, followed by stirring at −20° C. for 1 hour.

After completion of the stirring, a solution of 4 g of 3-benzoyl-4-chloronitrobenzene in 20 ml of tetrahydrofuran was added dropwise while maintaining the temperature of the reaction mixture at −20° C. Subsequent to completion of the dropwise addition, they were reacted for 1 hour while controlling the temperature of the reaction mixture within a range of from −78° C. to −20° C.

After completion of the reaction, the reaction mixture was poured into water and then extracted with 400 ml of ether. The extract layer (ether layer) was washed twice with 200 ml of water and dried over anhydrous magnesium sulfate.

The solvent was next distilled off from the extract under reduced pressure and the residue was purified by chromatography on a silica gel column (eluent: hexane/ethyl acetate=10/1, by volume) to obtain an oily substance.

The oily substance was dissolved in 40 ml of acetonitrile, to which a solution of 2.0 g of mercuric chloride in 20 ml of water was added dropwise.

Subsequent to completion of the dropwise reaction, 0.1 g of p-toluenesulfonic acid was added further and was reacted at 60° C. for 4 hours.

After completion of the reaction, insoluble matters were filtered off from the reaction mixture and the filtrate was concentrated. The resultant concentrate was purified by chromatography on a silica gel column (eluent: hexane/ethyl acetate=10/1, by volume) to obtain 1.1 g of crude 2-benzoyl-4-nitrobenzaldehyde as an oily substance.

(2) Preparation of 1,3-dimethyl-6-{2-[(2-benzoyl-4-nitrophenyl)methylamino]ethylamino}-2,4(1H,3H)-pyrimidinedione oxalate (Compound 135)

A solution of 1.0 g of 1,3-dimethyl-6-(2-aminoethylamino)-2,4(1H,3H)-pyrimidinedione in 20 ml of methanol, a solution of 1.1 g of the crude product of 2-benzoyl-4-nitrobenzaldehyde in 10 ml methanol and 0.3 ml of a 4 N solution of hydrochloric acid in dioxane were separately cooled to 0° C., mixed together and then reacted at 0° C. for 1 hour.

After completion of the reaction, 0.1 g of sodium cyanoborohydride, followed by a reaction at 0°±5° C. for 3 hours.

After the reaction was completed, the reaction mixture was acidified with 1 N hydrochloric acid and then poured into ice water. The resultant mixture was rendered basic with sodium bicarbonate and then extracted twice with 50 ml portions of chloroform.

Subsequent to completion of the extraction, the chloroform layer was washed with water, dried over anhydrous magnesium sulfate and then concentrated under reduced pressure.

The thus-obtained concentrate was purified by chromatography on a silica gel column (eluent: chloroform/methanol=10/1, by volume) to obtain 0.7 g of 1,3-dimethyl-6-{2-(2-benzoyl-4-nitrophenyl)methylamino]ethylamino}-2,4(1H,3H)-pyrimidinedione as an oily substance.

Analytical results of the pyrimidinedione derivative thus obtained:

NMR (CDCl$_3$), δppm: 7.2–8.1(m,8H), 5.68(b,1H), 4.89(s,1H), 3.61(s,2H), 3.34(s,3H), 3.39(s,3H), 3.06(m,4H).

Further, 0.5 g of the pyrimidinedione derivative was treated in an oxalic acid/methanol solution by a method known per se in the art to obtain 0.11 g of 1,3-dimethyl-6-{2-[(2-benzoyl-4-nitrophenyl)methylamino]ethylamino}-2,4(1H,3H)-pyrimidinedione oxalate (Compound 135).

Analytical results of Compound 135 thus obtained:
Melting point: hygroscopic amorphous.

IR$\nu_{max}^{KBr}$ (cm$^{-1}$) 3400(br), 2700, 2550, 1700, 1620, 1530, 1340, 1120, 820, 720, 700.

Elemental analysis for $C_{22}H_{23}N_5O_5 \cdot 2(COOH)_2 \cdot 3H_2O$:
Calculated (%): C, 46.50; H, 4.95; N, 10.43.
Found (%): C, 46.82; H, 4.65; N, 10.25.

EXAMPLE 79

Preparation of 1,3-dimethyl-6-{4-[3-(4-benzoyl-2-nitrophenyl)propyl]piperazin-1-yl}-2,4(1H,3H)-pyrimidinedione hydrochloride (Compound 136)

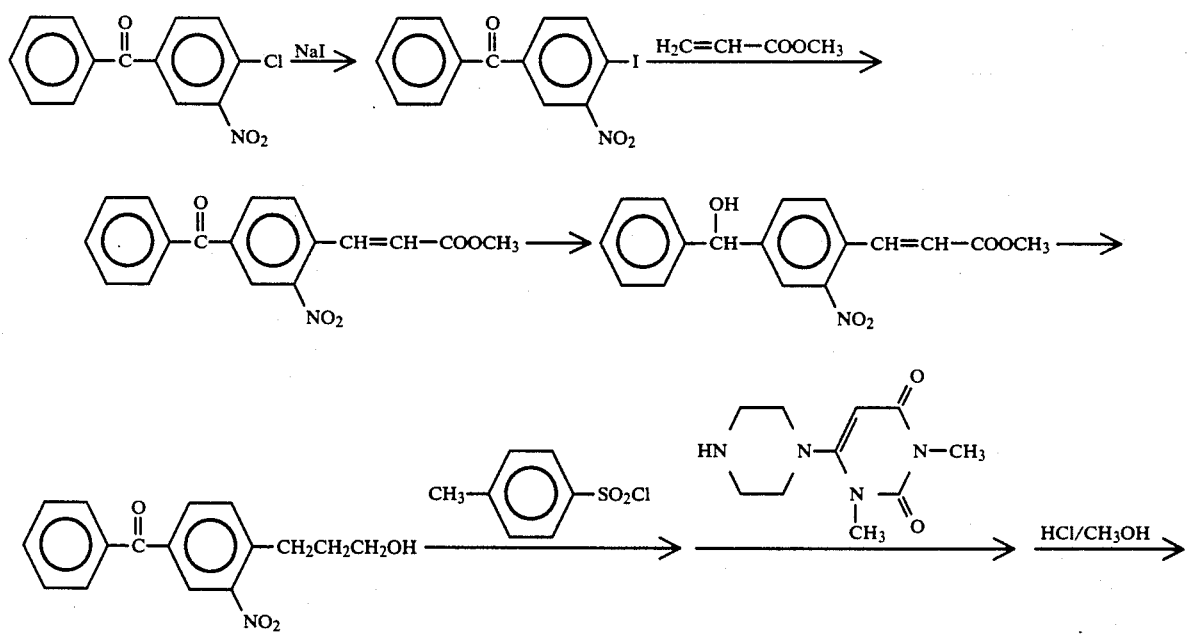

-continued

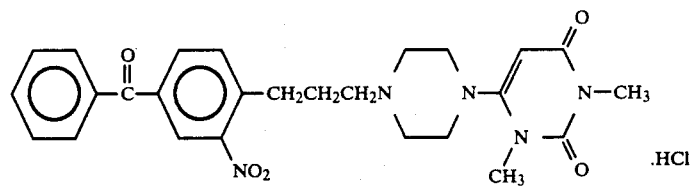

(Compound 136)

(1) Preparation of 4-iodo-3-nitrobenzophenone

A mixture of 10.44 g of 4-chloro-3-nitrobenzophenone, 60 g of sodium iodide and 60 ml of dimethylformamide was heated under reflux for 15 hours.

The reaction mixture was cooled and then poured into 800 ml of water. Precipitated crystals were collected by filtration.

The precipitated crystals were washed with water, dried under reduced pressure and then purified by chromatography on a silica gel column (eluent: chloroform/hexane=2/1-10/1, by volume), thereby obtaining 10.17 g of 4-iodo-3-nitrobenzophenone as yellow crystals.

Analytical results of the benzophenone derivative thus obtained:

NMR (CDCl$_3$), δppm: 8.35(d,1H), 8.26(d,1H), 7.40–8.10(m,6H).

(2) Preparation of methyl 4-benzoyl-2-nitrocinnamate 10.17 g of 4-iodo-3-nitrobenzophenone obtained in the above procedure (1), 4.10 g of methyl acrylate and 4.70 g of triethylamine were dissolved in 130 ml of acetonitrile and then degasified. The resultant solution was added with 0.65 g of palladium (II) acetate and heated under reflux for 6 hours under a nitrogen gas stream, whereby a reaction was conducted. After allowing the reaction mixture to cool down, the solvent was distilled off from the reaction mixture under reduced pressure. Benzene was added to the residue. The resultant solution was washed successively with water, 1 N hydrochloric acid, a saturated solution of sodium bicarbonate and a saturated NaCl solution.

The thus-washed organic layer was dried over anhydrous sodium sulfate and the solvent was then distilled off under reduced pressure. The residue was thereafter purified by chromatography on a silica gel column (eluent: chloroform) to obtain 7.12 g of methyl 4-benzoyl-2-nitrocinnamate as pale yellow crystals. Analytical results of the cinnamic acid derivative thus obtained:

NMR (CDCl$_3$), δppm: 8.43(d,1H), 7.48–8.38(m,8H), 6.51(d,1H), 3.84(s,3H).

(3) Preparation of 2-nitro-4-(α-hydroxybenzyl)cinnamic acid.

7.12 g of methyl 4-benzoyl-2-nitrocinnamate obtained in the above procedure (2) were dissolved in 120 ml of methanol, followed by the addition of 0.90 g of sodium borohydride at room temperature. After stirring the resultant mixture at the same temperature for 10 hours, a small amount of water was added to terminate the reaction.

The solvent was distilled off from the reaction mixture under reduced pressure and the residue was dissolved in benzene. The resultant solution was washed successively with 200 ml of water and 200 ml of a saturated NaCl solution.

The thus-washed organic layer was dried over anhydrous sodium sulfate and the solvent was distilled off under reduced pressure, thereby obtaining 7.12 g of methyl 2-nitro-4-(α-hydroxybenzyl)cinnamate as an pale yellow oily substance.

Further, 7.12 g of the pale yellow oily substance were dissolved in 60 ml of methanol, followed by the addition of 40 ml of a 1 N aqueous solution of potassium hydroxide at room temperature. The resultant solution was vigorously stirred for 3 hours at the same temperature. After completion of the stirring, the reaction mixture was poured into water and then neutralized with 1 N hydrochloric acid. Precipitated crystals were collected by filtration and then washed with water.

The crystals thus obtained were dried under reduced pressure to obtain 6.95 g of 2-nitro-4-(α-hydroxybenzyl)cinnamic acid in a purified form.

Analytical results of the product thus obtained in the purified form:

Elemental analysis for $C_{16}H_{13}NO_5$:

Calculated (%): C, 64.21; H, 4.38; N, 4.68.

Found (%): C, 63.79; H, 4.95; N, 4.21.

(4) Preparation of 3-(4-benzoyl-2-nitrophenyl)-1-propanol 3.54 g of 2-nitro-4-(α-hydroxybenzyl)cinnamic acid obtained in the above procedure (3), 13.38 g of hydroxyamine-O-sulfonic acid and 9.69 g of hydroxylamine sulfate were suspended in 180 ml of water. The resulting suspension was cooled and while maintaining its internal temperature at 20°–30° C., a 50% aqueous solution of sodium hydroxide (about 22 ml in total) was added dropwise thereto.

After the mixture was stirred at the same temperature for 3 hours to react them, the reaction mixture was ice-cooled. The reaction mixture was then added with 6 N sulfuric acid to acidify same, and precipitated crystals were collected by filtration. The thus-obtained crystals were washed with water and then dried under reduced pressure to obtain 3.48 g of 3-[2-nitro-4-(α-hydroxybenzyl)phenyl]propionic acid as crystals.

3.3 g of the crystals of the phenylpropionic acid derivative thus obtained were dissolved in 70 ml of tetrahydrofuran. The resultant solution was added with 1.4 ml of boran·dimethylsulfide complex, followed by stirring. Upon an elapsed time of 6 hours, 5 ml of water was added to the reaction mixture to terminate the reaction. The solvent was distilled off from the reaction mixture under reduced pressure and the residue was dissolved in 100 ml of chloroform.

The chloroform solution was washed successively with water, a 1 N aqueous solution of sodium hydroxide and a saturated saline solution. The thus-washed organic layer was dried over anhydrous sodium sulfate and the solvent was distilled off under reduced pressure to obtain 2.90 g of crude 3-[2-nitro-4-(α-hydroxybenzyl)phenyl]propanol.

2.90 g of the crude product were dissolved in 100 ml of chloroform, followed by the addition of 20 g of celite and 9.0 g of manganese dioxide. The resultant mixture was vigorously stirred for 24 hours at room temperature.

After completion of the stirring, the reaction mixture was filtered and the filtrate was concentrated to dryness to obtain 2.87 g of 3-(4-benzoyl-2-nitrophenyl)-1-propanol.

Analytical results of the phenylpropanol derivative thus obtained:

NMR (CDCl$_3$), δppm: 8.12(d,1H), 7.80(dd,1H), 7.00-7.72(m,6H). 3.64(t,2H), 3.00(t,2H), 1.92(m,2H), 1.84(brs,1H).

(5) Preparation of 1,3-dimethyl-6-{4-[3-(4-benzoyl-2-nitrophenyl)propyl]piperazin-1-yl}-2,4(1H,3H)-pyrimidinedione hydrochloride (Compound 136)

1.0 g of 3-(4-benzoyl-2-nitrophenyl)-1-propanol obtained in the above procedure(4) and 1.38 g of pyridine were dissolved in 20 ml of chloroform. The resultant mixture was added under ice-cooling with 1.34 g of p-toluenesulfonyl chloride. The resultant mixture was stirred for 10 minutes at the same temperature and for additional 16 hours at room temperature.

The thus-obtained reaction mixture was added with 2 ml of water and then stirred for 3 hours at room temperature. After addition of 50 ml of chloroform, the reaction mixture was poured into 50 ml of water. The thus-formed mixture was allowed to separate into layers. The organic layer was washed successively with 1 N hydrochloric acid, a 1 N aqueous solution of sodium hydroxide and a saturated saline solution and was then dried over anhydrous sodium sulfate. The solvent was distilled off under reduced pressure to obtain 1.51 g of 3-(4-benzoyl-2-nitrophenyl)-1-propyl p-toluenesulfonate as an oily yellow substance.

1.51 g of the oily yellow substance were dissolved in 10 ml of dimethyl sulfoxide. The resultant solution was added with 1.10 g of 1,3-dimethyl-6-(1-piperazinyl)-2,4(1H,3H)-pyrimidinedione and then heated at 80° C. for 6 hours to react them.

The resultant reaction mixture was poured into a solution which had been obtained by adding 2.0 g of potassium carbonate to 100 ml of water. The thus-prepared mixture was extracted twice with 50 ml portions of chloroform.

The organic layers separated by the two extraction operations were combined, washed with water, and then dried over anhydrous sodium sulfate. The solvent was distilled off under reduced pressure and the residue was purified by chromatography on a silica gel column (eluent: chloroform/methanol=50/1-20/1, by volume), thereby obtaining 0.92 g of 1,3-dimethyl-6-{4-[3-(4-benzoyl-2-nitrophenyl)propyl]piperazin1-yl}-2,4(1H,3H)-pyrimidinedione as pale yellow crystals.

Analytical results of the pyridine derivative thus obtained:

NMR (CDCl$_3$), δppm: 8.23(d,1H), 7.16-8.10(m,7H), 5.21(s,1H), 3.36(s,3H), 3.29(s,3H), 2.26-3.26(m,12H), 1.96(m,2H).

Next, the pyrimidinedione derivative was treated in a hydrochloric acid/methanol solution by a method known per se in the art to obtain 0.9 g of 1,3-dimethyl-6-{4-[3-(4-benzoyl-2-nitrophenyl)propyl]piperazin-1-yl}-2,4(1H,3H)-pyrimidinedione hydrochloride (Compound 136) as white crystals:

Analytical results of Compound 136 thus obtained:
Elemental analysis for C$_2$H$_{29}$N$_5$O$_5$·HCl:
Calculated (%): C, 59.14; H, 5.73; N, 13.26; Cl, 6.71.
Found (%): C, 59.56; H, 6.09; N, 13.16; Cl, 6.21.

EXAMPLE 80

Preparation of 1,3-dimethyl-6-{4-[2-(4-benzoyl-2-nitrophenyl)ethyl]piperazin-1-yl}-2,4(1H,3H)-pyrimidinedione oxalate (Compound 137)

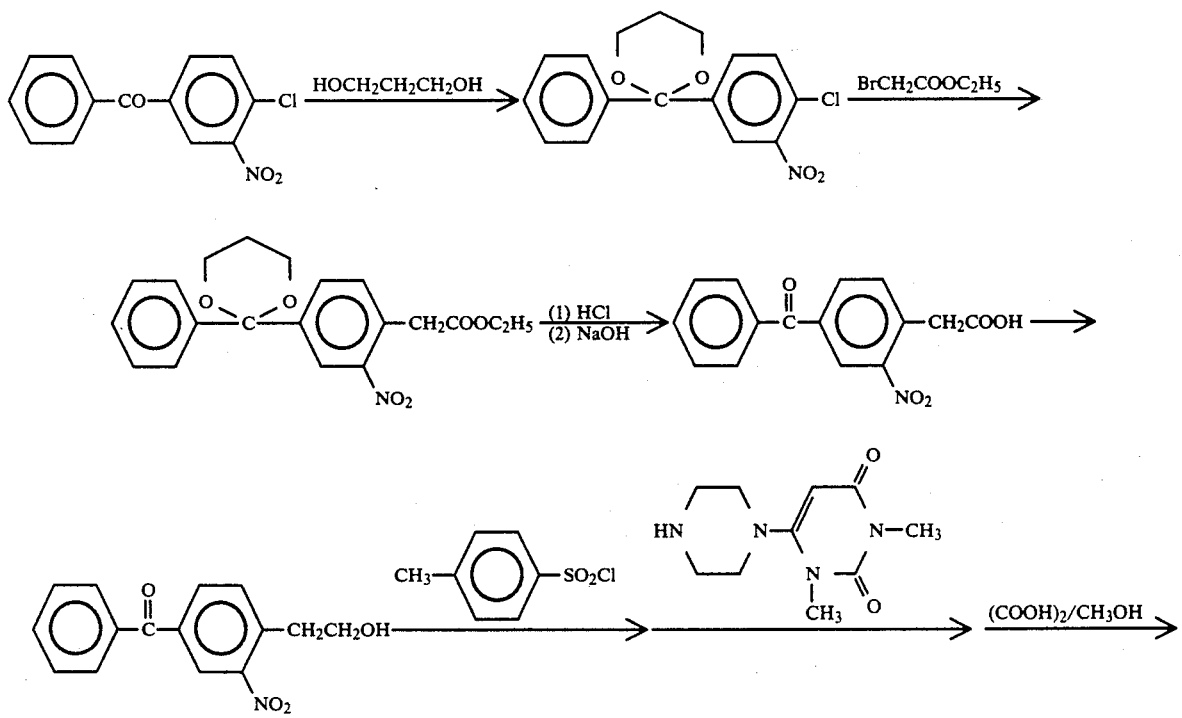

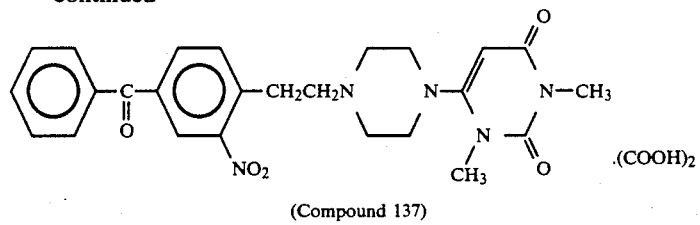

(Compound 137)

(1) Preparation of 2-(4-chloro-3-nitrophenyl)-2-phenyl-1,3-dioxane 10 g of 4-chloro-3-nitrobenzophenone, 15 ml of 1,3-propanediol and 0.5 g of camphorsulfonic acid were dissolved in 50 ml of benzene and while eliminating water by a molecular sieve ("Molecular Sieves 3A", trade name; 1/16 pellets; product of Junsei Chemical Co., Ltd.), were reacted under reflux for 12 hours.

The resultant reaction mixture was allowed to cool down, washed with a 1 N aqueous solution of sodium hydroxide, washed further with water, dried and then concentrated, thereby obtaining an oily substance.

Next, the oily substance was purified by chromatography on a silica gel column (eluent: hexane/ethyl acetate=4/1, by volume) to obtain 7.8 g of 2-(4-chloro-3-nitrophenyl)-2-phenyl-1,3-dioxane.

Analytical results of the compound thus obtained:
Elemental analysis for $C_{16}H_{13}NO_4Cl$:
Calculated (%): C, 60.29; H, 4.11; N, 4.39; Cl, 11.12.
Found (%): C, 60.09; H, 4.56; N, 4.01; Cl, 11.29.

(2) Preparation of ethyl 4-(2-phenyl-1,3-dioxan-2-yl)-2-nitrophenylacetate 5.2 g of zinc powder were suspended in a mixed solution of 10 ml of benzene and 10 ml of trimethyl borate. In a nitrogen gas atmosphere, 9 ml of ethyl bromoacetate were added dropwise at room temperature to the suspension to react them.

Upon an elapsed time of 1 hour, the reaction mixture was added further with a solution of 7.8 g of 2-(4-chloro-3-nitrophenyl)-2-phenyl-1,3-dioxane in 40 ml of benzene, 0.9 ml of dimethylformamide and 0.22 g of tris(triphenylphosphine) palladium(II) chloride. The resultant mixture was allowed to stand overnight at room temperature to react them.

Insoluble matters were then filtered off and the filtrate was concentrated. The thus-obtained filtrate was purified by chromatography on a silica gel column (eluent: hexane/ethyl acetate=3/1, by volume), thereby obtaining 4.4 g of ethyl 4-(2-phenyl-1,3-dioxan-2-yl)-2-nitrophenylacetate in an oily form.

Analytical results of the ethyl phenylacetate derivative thus obtained:
NMR (CDCl$_3$), δppm: 7.3–8.2(m,8H), 4.15(q,2H), 3.22(s,2H), 1.40(t,3H).

(3) Preparation of 4-benzoyl-2-nitrophenylacetic acid 4.4 g of ethyl 4-(2-phenyl-1,3-dioxan-2-yl)-2-nitrophenylacetate obtained in the above procedure (2) were dissolved in 30 ml of methanol, followed by the addition of 15 ml of 1 N hydrochloric acid. They were reacted under reflux for 1 hour.

After completion of the reaction, the reaction mixture was allowed to cool down and the solvent was distilled off. The residue was extracted with ether.

The organic layer obtained by the extraction was washed with water and then concentrated, whereby 3.5 g of an oily crude substance.

Next, the oily substance was dissolved in 20 ml of ethanol. The resulting solution was added with 5 ml of a 10% aqueous solution of sodium hydroxide, and they were reacted overnight at room temperature. The solvent was distilled off from the reaction mixture. The residue was added with 10 ml of water, followed by the addition of 3 N hydrochloric acid to acidify the resultant solution. Precipitated crystals were collected by filtration, thereby obtaining 2.8 g of 4-benzoyl-2-nitrophenylacetic acid.

Analytical results of the nitrophenyl acetic acid derivative thus obtained:
NMR (CDCl$_3$), δppm: 7.2–8.3(m,8H), 3.73(s,2H).

(4) Preparation of 2-(4-benzoyl-2-nitrophenyl)ethyl alcohol

A solution of 2.8 g of 4-benzoyl-2-nitrophenylacetic acid, which had been obtained in the above procedure (3), in 50 ml of tetrahydrofuran was ice-cooled, to which 2.3 ml of borane·methyl sulfide complex were added dropwise. The resultant mixture was left over.

Upon an elapsed time of 1 hour, water was added to terminate the reaction. The solvent was distilled off from the reaction mixture. The residue was added with ether and the resulting ether solution was washed with a dilute hydrogen peroxide solution.

After the washing, the ether solution was concentrated. The resulting syrup was added along with 17 g of activated manganese dioxide into 50 ml of chloroform. The mixture was vigorously stirred for 30 hours.

After completion of the stirring, manganese dioxide was filtered off from the reaction mixture and the filtrate was concentrated. The concentrate was purified by chromatography on a silica gel column (eluent: hexane/ethyl acetate=3/1, by volume), thereby obtaining 1.9 g of 2-(4-benzoyl-2-nitrophenyl)ethyl alcohol in an oily form.

Analytical results of the compound thus obtained:
NMR (CDCl$_3$), δppm: 7.2–8.3(m,8H), 4.05(t,2H), 3.11(t,2H).

(5) Preparation of 1,3-dimethyl-6-(4-[2-{4-benzoyl-2nitrophenyl)ethyl]piperazin-1-yl}-2,4(1H,3H)-pyrimidinedione oxalate (Compound 137)

1.9 g of 2-(4-benzoyl-2-nitrophenyl)ethyl alcohol obtained in the above procedure (4), 1.5 g of p-toluenesulfonyl chloride and 1.8 ml of pyridine were dissolved in 30 ml of chloroform and reacted at room temperature for 24 hours. Water was then added to the reaction mixture. After vigorously stirring the reaction mixture for 3 hours, the chloroform layer was separated, washed first with a 1 N aqueous solution of hydrochloric acid and then a 1 N aqueous solution of sodium hydroxide, washed with water, concentrated over sodium sulfate, and then concentrated to obtain a brown oily substance.

The brown oily substance, 0.6 g of 1,3-dimethyl-6-4-piperazinyl) -2,4(1H,3H)-pyrimidinedione and 3 ml of triethylamine were reacted for 6 hours under reflux in 20 ml of isopropanol.

The reaction mixture was allowed to cool down, concentrated, and then dissolved in chloroform. The resultant chloroform solution was washed with water, concentrated and then purified by chromatography on a silica gel column (eluent: chloroform/methanol=40/1, by volume), thereby obtaining 0.7 g of 1,3-dimethyl-6-{4-[2-(4-benzoyl-2-nitrophenyl)ethyl]piperazin-1-yl}-2,4(1H,3H)-pyrimidinedione in an oily form.

Analytical results of the pyrimidinedione derivative thus obtained:

NMR (CDCl$_3$), δppm: 8.01(d,1H), 7.3-7.8(m,7H), 5.12(s,1H), 4.55(m,2H), 3.22(s,3H), 3.30(s,2H), 2.6-3.3(m,10H).

Next, the oily pyrimidinedione derivative was treated in an oxalic acid/methanol solution by a method known per se in the art to obtain 0.6 g of 1,3-dimethyl-6-{4-[2-(4-benzoyl-2-nitrophenyl)ethyl]piperazin-1-yl}-2,4(1H,3H)-pyrimidinedione oxalate (Compound 137).

Analytical results of Compound 137 thus obtained:

IR$\nu_{max}^{KBr}$ (cm$^{-1}$): 2550, 1740, 1700, 1650, 1530, 1340, 1200, 1030, 830, 760, 700.

Elemental analysis for C$_{25}$H$_{27}$N$_5$O$_5$·(COOH)$_2$·3H$_2$O:
Calculated (%): C, 52.17; H,. 5.68; N, 11.27.
Found (%): C, 52.57; H, 6.01; N, 11.30.

EXAMPLE 81

Production of tablets containing as an effective ingredient 1,3-dimethyl-6-{4-[2-(2-benzoyl-4-nitrophenyl)ethyl]piperazin-1-yl}-2,4-(1H,3H)-pyrimidinedione oxalate (Compound 133) available by the process of Example 76

1 g of the pyrimidinedione derivative oxalate (Compound 133), 123 g of lactose and 20 g of corn starch were finely mixed. Using a solution of 5 g of hydroxypropylcellulose in 100 ml of water, the resultant mixture was granulated. The resultant particles were dried at 50° C. for 4 hours and then mixed thoroughly with 1 g of magnesium stearate. The thus-prepared mixture was then compressed into tablets, each containing 150 mg, by a tablet machine.

EXAMPLE 82

Production of capsules containing as an effective ingredient 1,3-dimethyl-6-[2-(2-benzoyl-4-nitroanilino)ethylamino]-2,4(1H,3H)-pyrimidinedione (Compound 131) available by the process of Example 74

5 g of the pyrimidinedione derivative oxalate (Compound 131), 120 g of lactose and 25 g of corn starch were finely mixed. The resulting mixture was filled into hard capsules, each containing 150 mg, by a capsule filling machine.

EXAMPLE 83

Production of injection containing as an effective ingredient 1,3-dimethyl-6-{3-[4-nitro-2-(3-pyridinecarbonyl)anilino]propylamino}-2,4-(1H,3H)-pyrimidinedione oxalate (Compound 129) available by the process of Example 72

20 mg of the pyrimidinedione derivative oxalate (Compound 129) and 0.85 g of sodium chloride were weighed. They were dissolved in distilled water for injection to give a total volume of 100 ml, thereby preparing a formulation suitable for injection.

PHARMACOLOGICAL TEST 6

Similarly to Pharmacological Test 1, the APD$_{75}$ and ERP of each of the compounds shown in Table 12 and obtained in the corresponding examples described above were determined. The results are summarized in Table 12.

TABLE 12

| Compound No. | Result of Pharmacological Test | | | | | | |
|---|---|---|---|---|---|---|---|
| | APD$_{75}$ (%) Dose (μg/ml) | | | ERP (%) Dose (mg/kg, i.v.) | | | |
| | 1.0 | 3.0 | 10.0 | 0.1 | 0.3 | 1.0 | 3.0 |
| 133 | — | — | — | 6.3 | 6.3 | 18.8 | — |
| 136 | 11.0 | 14.0 | — | — | 7.7 | 15.4 | 15.4 |
| 137 | 32.0 | 51.0 | — | 6.3 | 6.3 | 12.5 | 18.8 |

TOXICITY TEST 6

Similarly to Toxicity Test 1, the toxicity of each of the compounds shown in Table 13 and obtained in the corresponding examples described above was tested to determine the mortality rate of mice. The results are summarized in Table 13.

Incidentally, the administration of each compound was conducted orally (p.o.) at a dose of 300 mg/Kg.

TABLE 13

| Compound No. | Mortality rate (%) |
|---|---|
| 128 | 0 |
| 131 | 0 |
| 133 | 0 |
| 134 | 0 |

EXAMPLE 84

Preparation of 1,3-dimethyl-6-{4-[3-(3-methyl-4-nitrophenyloxy)propyl]piperazin-1-yl}-2,4-(1H,3H)-pyrimidinedione hydroxide (Compound 138)

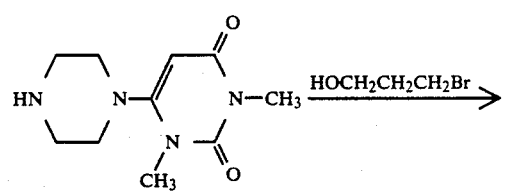

(Compound 157)

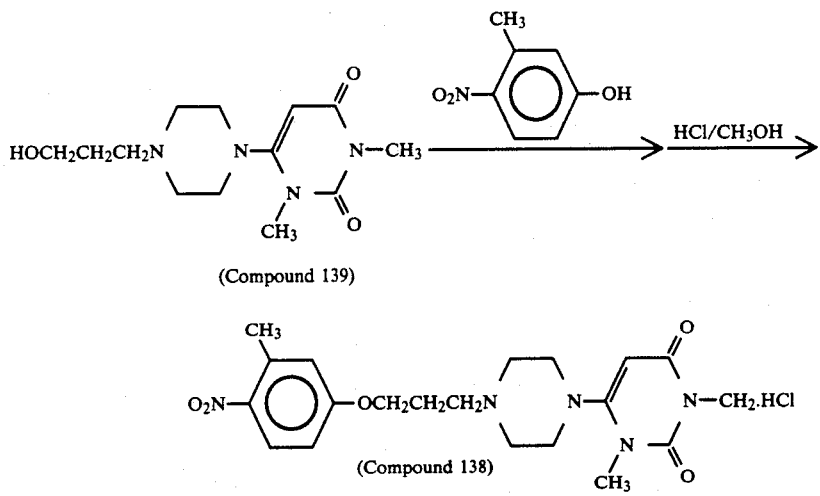

(Compound 139)

(Compound 138)

(1) Preparation of 1,3-dimethyl-6-[4-(3-hydroxypropyl)piperazin-1-yl]-2,4(1H,3H)-pyrimidinedione (Compound 139)

14.1 g of 1,3-dimethyl-6-(1-piperazinyl)-2,4(1H,3H)-pyrimidinedione (Compound 157), 11.7 g of 3-bromo-1-propanol and 13 g of triethylamine were reacted under reflux for 20 hours in 250 ml of ethanol. After completion of the reaction, the reaction mixture was concentrated to dryness. The residue was dissolved in 300 ml of chloroform. The chloroform solution was washed twice with 100 ml portions of water and the thus-washed organic layer was dried over anhydrous magnesium sulfate. The organic layer was heated under reduced pressure to distill off the solvent, whereby 20.5 g of a crude product were obtained. Ether was added to the crude product to have it crystallized. The resultant crystals were collected, washed and then dried, thereby obtaining 12.4 g of 1,3-dimethyl-6-[4-(3-hydroxylpropyl)piperazin-1-yl]-2,4(1H,3H)-pyridinedione (Compound 139) (yield: 69.8%).

Analytical results of crystals of Compound 139 thus obtained:

Melting point: 119°–121° C.

NMR (CDCl3), δppm: 1.8(d,1H), 2.7(m,6H), 3.02(m,4H), 3.36(s,3H), 3.43(s,3H), 3.82(t,2H), 4.34(br.1H), 5.26(s,1H), IRν$_{max}^{KBr}$ (cm$^{-1}$): 3380, 3180, 2830, 1695, 1650, 1605, 1440, 1213, 1068, 1000, 921, 750.

(2) Preparation of 1,3-dimethyl-6-{4-[3-(3-methyl-4-nitrophenyloxy)propyl]piperazin-1-yl}-2,4(1H,3H)-pyrimidinedione hydrochloride (Compound 138)

1.13 g of Compound 139 obtained in the above procedure, 1.21 g of triphenylphosphine and 0.70 g of 3-methyl-4-nitrophenol were suspended and mixed in 15 ml of anhydrous tetrahydrofuran. Into the resultant suspension, a solution of 0.8 g of diethyl azodicarboxylate in 10 ml of anhydrous tetrahydrofuran was added at room temperature.

After stirring the resultant mixture for 10 minutes, it was concentrated to dryness. The residue was purified by chromatography on a silica gel column (eluent: methanol/ethyl acetate = 1/15–1/7, by volume), thereby obtaining 0.92 g of 1,3-dimethyl-6-{4-[3-(3-methyl-4-nitrophenyloxy)propyl]piperazin-1-yl}-2,4(1H,3H)-pyrimidinedione.

Analytical results of crystals of the pyrimidinedione derivative thus obtained:

Melting point: 178.5°–181° C.

Elemental analysis for C20H27N5O5:

Calculated (%): C, 57.54; H, 6.52; N, 16.78.

Found (%): C, 57.30; H, 6.56; N, 16.64.

NMR (CDCl3), δppm: 1.9–2.3(m,2H), 2.6–2.8(m,9H), 3.0–3.2(m,4H), 3.44(s,3H), 3.54(s.3H), 4.28(t,2H), 5.44(s,1H), 7.0–7.16(m,2H), 8.40(d,1H).

Next, 0.80 g of 1,3-dimethyl-6-{4-[3-(3-methyl-4-nitrophenyloxy)propyl]-piperazin-1-yl}-2,4(1H,3H)-pyrimidinedione was treated in an HCl/methanol solution by a method known per se in the art to obtain 0.60 g of 1,3-dimethyl-6-{4-[3-(3-methyl-4-nitrophenyloxy)propyl]piperazin-1-yl}-2,4(1H,3H)-pyrimidinedione hydrochloride (Compound 138).

Analytical results of Compound 138 thus obtained:

Melting point: 224° C. (decomposed).

Elemental analysis for C20H27N5O5·HCl·2H2O:

Calculated (%): C, 49.03; H, 6.58; N, 14.29; Cl, 7.24.

Found (%): C, 48.82; H, 6.88; N, 14.18; Cl, 7.31.

EXAMPLE 85

Preparation of 1,3-dimethyl-6-{4-[3-(4-chloro-2-nitrophenoxy)propyl]piperazin-1-yl}-2,4(1H,3H)-pyrimidinedione hydrochloride (Compound 140)

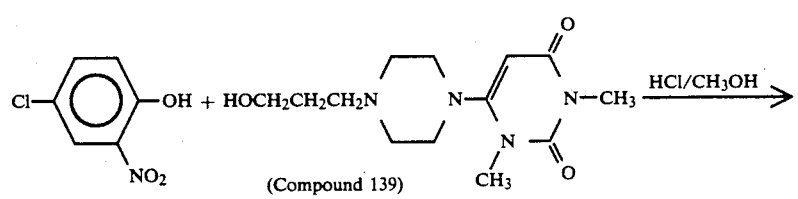

(Compound 139)

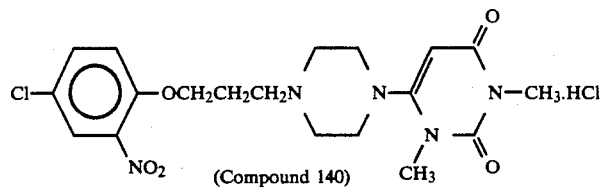

(Compound 140)

0.80 g of 4-chloro-2-nitrophenol, 1.13 g of 1,3-dimethyl-6-[4-(3-hydroxypropyl)piperazin-1-yl]-2,4(1H,3H)-pyrimidinedione (Compound 139) and 1.21 g of triphenylphosphine were suspended in 15 ml of anhydrous tetrahydrofuran, followed by the addition of 0.80 g of diethyl azodicarboxylate. The resultant mixture was treated in a similar manner to Example 84-(2), thereby obtaining 1.43 g of 1,3-dimethyl-6-{4-[3-(4-chloro-2-nitrophenyloxy)propyl]piperazin-1-yl}-2,4(1H,3H)-pyrimidinedione as crystals.

Analytical results of crystals of the pyrimidinedione derivative thus obtained:

Melting point: 162°–163° C.

Elemental analysis for $C_{19}H_{24}N_5O_5Cl \cdot \frac{1}{2}H_2O$:

Calculated (%): C, 51.07; H, 5.64; N, 15.67; Cl, 7.93.
Found (%): C, 51.11; H, 5.68; N, 15.64; Cl, 7.94.

NMR (CDCl$_3$), δppm 1.8–2.2(m,2H), 2.4–2.8(m,6H), 2.8–3.04(m,4H), 3.2–3.4(m,2H), 3.52(s,3H), 3.80(s,3H), 4.18(t,2H), 5.20(s,1H), 7.20(d,1H), 7.45(dd,1H). 7.81(d,1H).

Next, 1.2 g of the pyrimidinedione derivative were treated in a 15% HCl/methanol solution by a method known per se in the art to obtain 1.13 g of 1,3-dimethyl-6-{4-[3-(4-chloro-2-nitrophenyloxy)propyl]piperazin-1-yl}-2,4(1H,3H)-pyrimidinedione hydrochloride (Compound 140).

Analytical results of Compound 140 thus obtained:

Melting point: 271° C. (decomposed).

Elemental analysis for $C_{19}H_{24}N_5O_5Cl \cdot HCl$:

Calculated (%): C, 48.11; H, 5.31; N, 14.76; Cl, 14.95.
Found (%): C, 47.80; H, 5.33; N, 14.62; Cl, 14.86.

EXAMPLE 86

Preparation of 1,3-dimethyl-6-{4-[3-(2-chloro-4-nitrophenyloxy)propyl]piperazin-1-yl}-2,4(1H,3H)-pyrimidinedione hydrochloride (Compound 141)

pyrimidinedione (Compound 139) and 3.62 g of triphenylphosphine were suspended in 70 ml of anhydrous tetrahydrofuran, followed by the addition of 2.4 g of diethyl azodicarboxylate. The resultant mixture was treated in a similar manner to Example 84-(2), thereby obtaining 2.5 g of pale yellow crystals. Those crystals were recrystallized from ethanol so that 2.07 g of 1,3-dimethyl-6-{4-[3-(2-chloro-4-nitrophenyloxy)propyl]piperazin-1-yl}-2,4(1H,3H)-pyrimidinedione were obtained as crystals.

Analytical results of crystals of the pyrimidinedione derivative thus obtained:

Melting point: 133°–134° C.

Elemental analysis for $C_{19}H_{24}N_5O_5Cl$:

Calculated (%): C, 52.12; H, 5.52; N, 15.99; Cl, 8.10.
Found (%): C, 51.99; H, 5.72; N, 15.70; Cl, 8.06.

NMR (CDCl$_3$), δppm: 1.8–2.3(m,2H), 2.3–3.1(m,10H), 3.33(s,3H), 3.41(s,3H), 4.24(t,2H), 5.26(s,1H), 7.0–8.4(m,3H).

Next, 0.5 g of the pyrimidinedione derivative was treated in a 15% HCl/methanol solution by a method known per se in the art to obtain 0.5 g of 1,3-dimethyl-6-{4-[3-(2-chloro-4-nitrophenyloxy)propyl]piperazin-1-yl}-2,4(1H,3H)-pyrimidinedione hydrochloride (Compound 141).

Analytical results of Compound 141 thus obtained:

Melting point: 115°–120° C.

Elemental analysis for $C_{19}H_{24}N_5O_5Cl \cdot HCl \cdot H_2O$:

Calculated (%): C, 46.35; H, 5.53; N, 14.22; Cl, 14.40.
Found (%): C, 46.25; H, 5.29; N, 14.46; Cl, 14.69.

IR$\nu_{max}^{KBr}$ (cm$^{-1}$): 1700, 1345, 1285, 1200, 1130, 1055, 900, 830, 750.

EXAMPLE 87

Preparation of 1,3-dimethyl-6-{4-[3-(4-methanesulfonamido-2-nitrophenyloxy)propyl]piperazin-1-yl}-

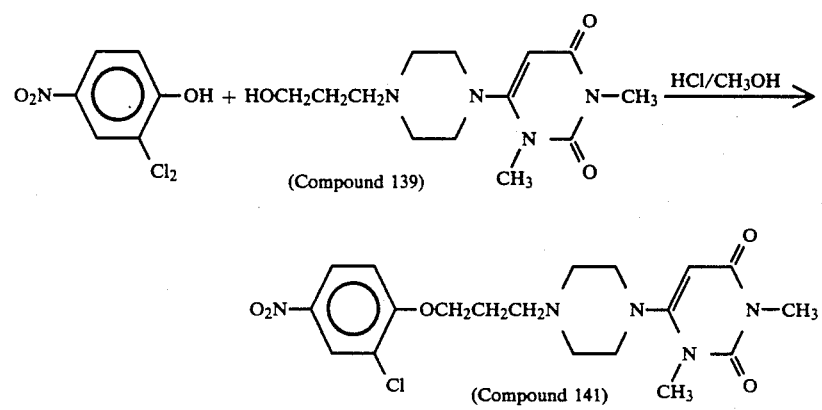

2.4 g of 2-chloro-4-nitrophenol, 3.38 g of 1,3-dimethyl-6-[4-(3-hydroxypropyl)piperazin-1-yl]-2,4(1H,3H)-

2,4(1H,3H)-pyrimidinedione hydrochloride (Compound 142)

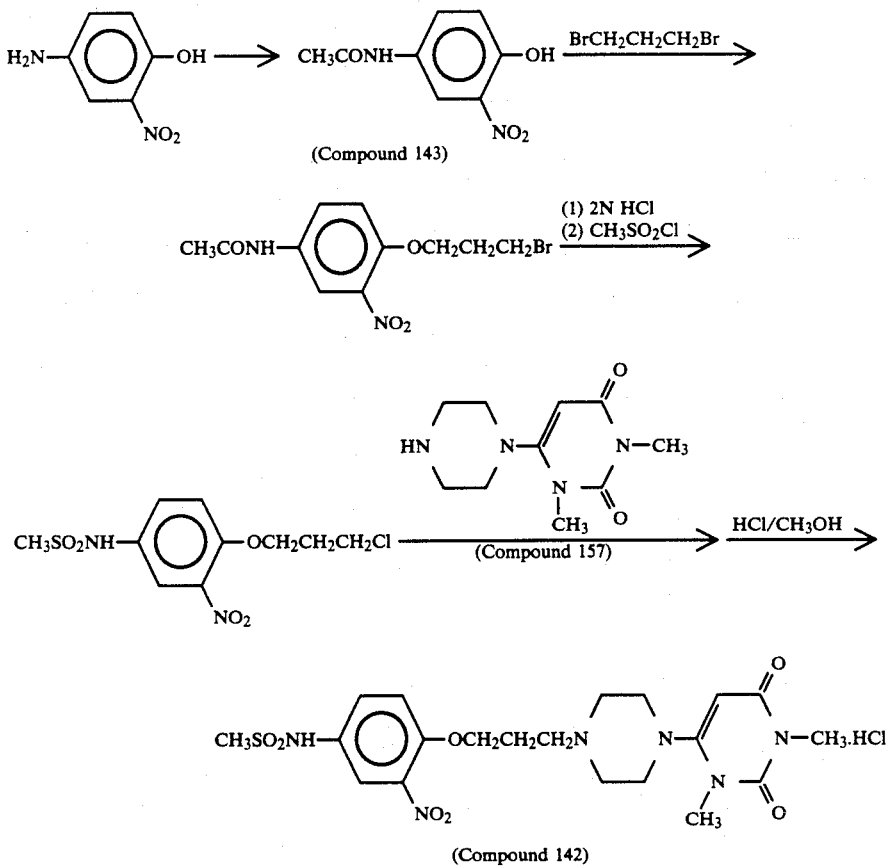

(Compound 142)

(1) Preparation of 4-acetamido-2-nitrophenol (Compound 143)

10.1 g of 4-amino-2-nitrophenol were dissolved in 80 ml of acetic acid, followed by the addition of 6.7 g of acetic anhydride over 5 minutes. After stirring the resultant mixture for 1 hour, the solvent was distilled off under reduced pressure. Water was added to the residue, whereby a solid of a dark brown color precipitated. The solid was collected by filtration. The solid was washed with water and then recrystallized from water-containing ethanol, thereby obtaining 10.2 g of 4-acetamido-2-nitrophenol (Compound 143) as crystals.

Analytical results of crystals of Compound 143 thus obtained:

Melting point: 158°–159° C.

(2) Preparation of 3-(4-acetamido-2-nitrophenyloxy)-propyl bromide

A mixture consisting of 10.2 g of 4-acetamido-2-nitrophenol (Compound 143) obtained by the above procedure, 13.9 g of potassium carbonate, 100 ml of methyl ethyl ketone and 40.2 g of 1,3-dibromopropane was reacted under reflux for 6 hours. Insoluble matters were filtered off from the reaction mixture and the filtrate was concentrated under reduced pressure. The residue was dissolved in chloroform. The chloroform solution was washed with water and then dried over anhydrous magnesium sulfate. The solvent was distilled off under reduced pressure. The residue was then purified by chromatography on a silica gel column (eluent: chloroform/methanol=100/1, by volume), followed by recrystallization from dichloromethane-hexane to obtain 5.2 g of 3-(4-acetamido-2-nitrophenyloxy)propyl bromide as crystals.

Analytical results of crystals of the propyl bromide derivative thus obtained:

Melting point: 134° C.

Elemental analysis for $C_{11}H_{13}N_2O_3Br$:

Calculated (%): C, 41.66; H, 4.13; N, 8.83; Br, 25.13.

Found (%): C, 41.84; H, 4.35; N, 8.92; Br, 24.73.

(3) Preparation of 3-(4-methanesulfonamido-2-nitrophenyloxy)propyl chloride 1.0 g of 3-(4-acetamido-2-nitrophenyloxy)propyl bromide obtained by the above procedure was suspended in 15 ml of 2 N hydrochloric acid. After heating the resultant mixture under reflux for 30 minutes, 10 ml of acetic acid were added, followed by heating under reflux for additional 4 hours. The reaction mixture was concentrated under reduced pressure and water was added to the residue. Sodium carbonate was added to the resultant aqueous mixture to adjust the pH to 7–8. The aqueous mixture was then extracted with chloroform.

The extract was dried over anhydrous sodium sulfate. The drying agent was filtered off. The filtrate was added with 1 ml of pyridine. A solution of 0.5 g of mesyl chloride in 5 ml of chloroform was added dropwise under ice-cooling. After stirring the thus-obtained mixture for 2 hours under ice-cooling, it was stirred at room temperature for 2 hours and then extracted twice with a 2 N solution of sodium hydroxide. The resultant aqueous layer was washed with chloroform. This aqueous layer was acidified with 6 N hydrochloric acid and then extracted with ethyl acetate. The extract was concentrated under reduced pressure and the residue was recrystallized from ethanol, thereby obtaining 0.7 g of 3-(4-methanesulfonamido-2-nitrophenyloxy)propyl chloride as crystals.

Analytical results of crystals of the propyl chloride derivative thus obtained:
Elemental analysis for $C_{10}H_{13}ClN_2O_5S$:
Calculated (%): C, 38.90 H, 4.24; N, 9.07; Cl, 11.49; S, 10.38.
Found (%): C, 38.90; H, 4.30; N, 8.94; Cl, 10.72; S, 10.03.

(4) Preparation of 1,3-dimethyl-6-{4-[3-(4-methanesulfonamido-2-nitrophenyloxy)propyl]piperazin-1-yl}-2,4(1H,3H)-pyrimidinedione hydrochloride (Compound 142)

Analytical results of crystals of Compound 142 thus obtained:
Melting point: 239° C.
Elemental analysis for $C_{20}H_{28}N_6O_7S \cdot HCl \cdot \frac{1}{2}H_2O$:
Calculated (%): C, 44.32; H, 5.58; N, 15.51; Cl, 6.54; S, 5.92.
Found (%): C, 44.30; H, 5.58; N, 15.45; Cl, 6.96; S., 5.94.

EXAMPLE 88

Preparation of 1,3-dimethyl-6-{4-[3-(4-acetamido-2-nitrophenyloxy)propyl]piperazin-1-yl}-2,4(1H,3H)-pyrimidinedione hydrochloride (Compound 144)

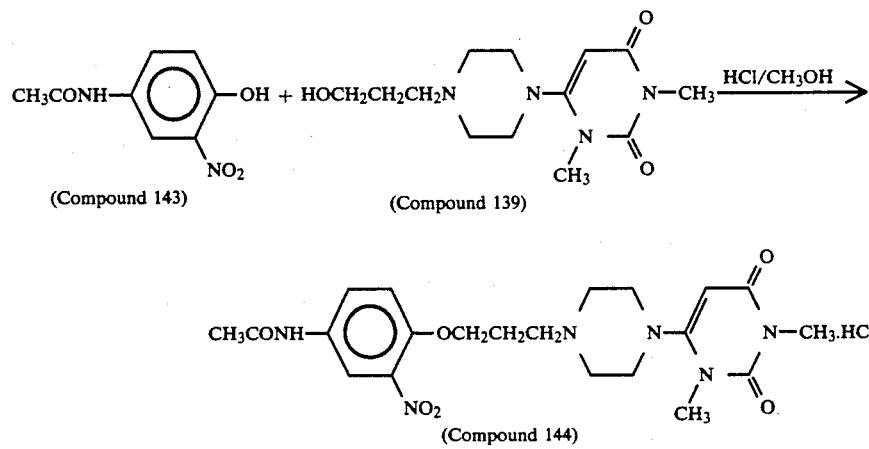

0.31 g of 3-(4-methanesulfonamido-2-nitrophenyloxy)propyl chloride, 0.22 g of 1,3-dimethyl-6-(1-piperazinyl)-2,4(1H,3H)-pyrimidinedione (Compound 157) and 0.5 ml of triethylamine were dissolved under heat in 10 ml of ethanol to give a uniform solution. The solvent was distilled off under reduced pressure. After heating the residue at 110° C. for 2 hours, 10 ml of n-butanol were added and the resulting mixture was heated under stirring at 110° C. for 5 hours. The reaction mixture was concentrated under reduced pressure and the residue was dissolved in a dilute aqueous solution of sodium hydroxide. The thus-prepared solution was washed with chloroform. The water layer was then adjusted to pH 1-2 with dilute hydrochloric acid, washed with ethyl acetate, and then added with sodium hydrogencarbonate to raise the pH to 7-8. Precipitated insoluble matters were collected by filtration. The thus-collected substance was dried under reduced pressure and then dissolved in methanol. 15% HCl/methanol was added to convert it into the hydrochloride by a method known per se in the art, thereby obtaining 0.2 g of 1,3-dimethyl-6-{4-[3-{4-methanesulfonamido-2-nitrophenyloxy)propyl]piperazin-1-yl}-2,4(1H,3H)-pyrimidinedione hydrochloride (Compound 142 as crystals.

2.71 g of 4-acetamido-2-nitrophenol (Compound obtained in Example 87-(1), 3.38 g of 1,3-dimethyl-6-[4-(3-hydroxypropyl)piperazin-1-yl]-2,4(1H,3H)-pyrimidinedione (Compound 139) and 3.62 g of triphenylphosphine were suspended in 70 ml of anhydrous tetrahydrofuran, followed by the addition of 2.4 g of diethyl azodicarboxylate. The thus-prepared mixture was treated in a similar manner to Example 84-(2), thereby obtaining 2.7 g of pale yellow crystals. 2.0 g of the crystals were treated in a 15% HCl/methanol solution by a method known per se in the art to obtain 2.5 g of 1,3-dimethyl-6-{4-[3-(4-acetamido-2-nitrophenyloxy)-propyl]piperazin-1-yl}-2,4(1-yl}-2,4-(1H,3H)-pyrimidinedione hydrochloride (Compound 144).

Analytical results of Compound 144 thus obtained:
Melting point: 228.5°-230° C.
Elemental analysis for $C_{21}H_{28}N_6O_6 \cdot HCl$:
Calculated (%): C, 50.76; H, 5.88; N, 16.91; Cl, 7.13.
Found (%): C, 50.67; H, 6.27; N, 17.07; Cl, 6.81.

EXAMPLE 89

Preparation of 1,3-dimethyl-6-{4-[3-(2-hydroxy-5-nitrophenyloxy)propyl]piperazin-1-yl}-2,4(1H,3H)-pyrimidinedione hydrochloride (Compound 145)

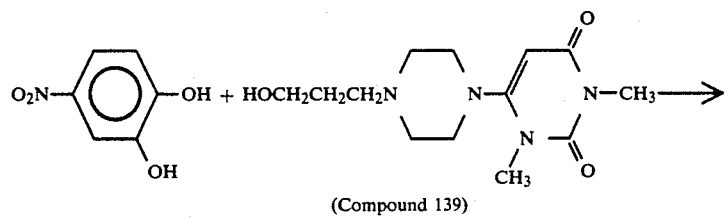

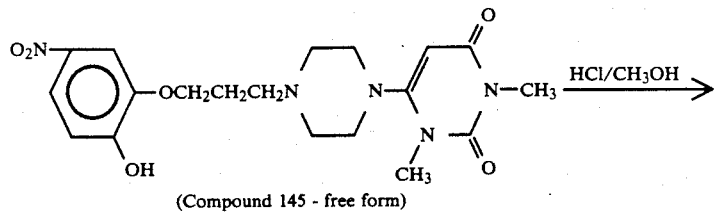

(Compound 145 - free form)

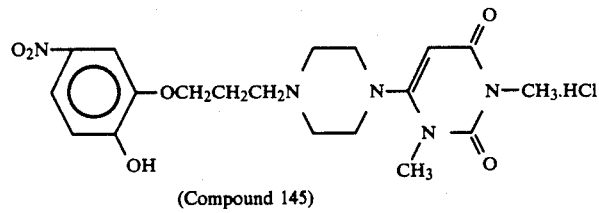

(Compound 145)

0.63 g of 2-nitrocatechol, 1.0 g of 1,3-dimethyl-6-[4-(3-hydroxypropyl)piperazin-1-yl]-2,4(1H,3H)-pyrimidinedione (Compound 139) and 1.06 g of triphenylphosphine were suspended in 15 ml of anhydrous tetrahydrofuran, followed by the addition of 0.71 g of diethyl azodicarboxylate. The thus-prepared mixture was treated in a similar manner to Example 84-(2), thereby obtaining 0.65 g of pale yellow crystals. The crystals were recrystallized form ethanol to obtain 0.55 g of 1,3-dimethyl-6-{4-[3-(2-hydroxy-5-nitrophenyloxy)propyl]piperazin-1-yl}-2,4(1H,3H)-pyrimidinedione (Compound 145—free form) as crystals.

Analytical results of crystals of the pyrimidinedione derivative thus obtained:

Melting point: 171°–173° C.

Elemental analysis for $C_{19}H_{25}N_5O_5$:

Calculated (%): C, 54.40; H, 6.00; N, 16.69.

Found (%): C, 54.40; H, 6.28; N, 16.48.

NMR (CDCl$_3$), δppm: 1.9–2.2(m,2H), 2.6–3.2(m,10H), 3.2(m,10H), 3.3(s,3H), 3.4(s,3H), 4.1(t,2H), 5.24(s,1H), 6.88–7.08(m,1H), 7.60–7.80(m,2H).

IR$v_{max}^{KBr}$ (cm$^{-1}$): 1700, 1620, 1500, 1340, 1285, 1280, 1140, 990, 870.

Next, 0.5 g of the pyrimidinedione derivative were treated in a 20% HCl/methanol solution by a method known per se in the art to obtain 0.5 g of 1,3-dimethyl-6-{4-[3-(2-hydroxy-5-nitrophenyloxy)propyl]piperazin-1-yl}-2,4(1H,3H)-pyrimidinedione hydrochloride (Compound 145) as crystals.

Analytical results of crystals of Compound 145 thus obtained:

Melting point: 246°–249° C.

Elemental analysis for $C_{19}H_{25}N_5O_5 \cdot HCl \cdot 2H_2O$:

Calculated (%): C, 46.39; H, 6.15; N, 14.24; Cl, 7.21.

Found (%): C, 46.83; H, 5.97; N, 14.55; Cl, 7.77.

EXAMPLE 90

Preparation of 1,3-dimethyl-6-{4-[3-(2-allyloxy-5-nitrophenyloxy)propyl]piperazin-1-yl}-2,4(1H,3H)-pyrimidinedione hydrochloride (Compound 146)

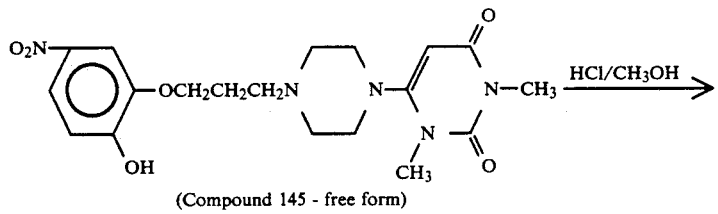

(Compound 145 - free form)

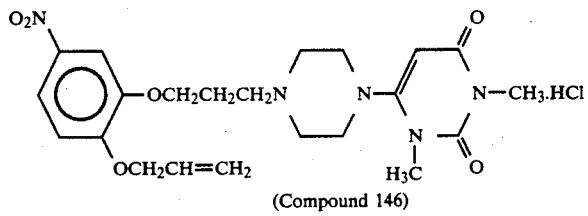

(Compound 146)

1 g of 1,3-dimethyl-6-{4-[3-(2-hydroxy-5-nitrophenyloxy)propyl]piperazin-1-yl}-2,4(1H,3H)-pyrimidinedione (Compound 145—free form), 0.31 g of allyl bromide and 0.36 g of potassium carbonate were suspended in 10 ml of dry acetone and heated under reflux for 5 hours. The reaction mixture was poured into 60 ml of water and then extracted three times with 30 ml portions of chloroform. The extract was washed first with a 0.5 N aqueous solution of sodium hydroxide and then with water. The chloroform solution was dried over anhydrous sodium sulfate. The solvent was distilled off under reduced pressure and the residue was purified by chromatography on a silica gel column (eluent: chloroform/methanol=20/1, by volume). The resulting oily substance was crystallized from ethanol, thereby obtaining 0.78 g of 1,3-dimethyl-6-{4-[3-(2-allyloxy-5-nitrophenyloxy)propyl]piperazin-1-yl}-2,4(1H,3H)-pyrimidinedione as crystals.

Analytical results of crystals of the pyrimidinedione derivative thus obtained:

Melting point: 120°-121° C.

NMR (CDCl$_3$), δppm: 2.08(t,2H), 2.5-3.0(m,10H), 3.3(s,3H), 3.36(s,3H), 4.16(t,2H), 4.5-4.7(m,2H), 5.2(s,1H), 5.16-5.6(m,2H), 5.8-6.24(m,1H), 6.9(d,1H), 7.68-7.92(m,2H).

IR$\nu_{max}^{KBr}$ (cm$^{-1}$): 1690, 1630, 1510, 1330, 1280, 1000.

Next, 0.5 g of the pyrimidinedione derivative was treated in a 20% HCl/methanol solution by a method known per se in the art to obtain 0.5 g of 1,3-dimethyl-6-{4-[3-(2-allyloxy-5-nitrophenyloxy)propyl]piperazin-1-yl}-2,4(1H,3H)-pyrimidinedione hydrochloride (Compound 146) as crystals.

Analytical results of Compound 146 thus obtained:
Melting point: 161.5°-180° C.

EXAMPLE 91

Preparation of 1,3-dimethyl-6-{4-[3-(4-methylthio-2-nitrophenyloxy)propyl]piperazin-1-yl}-2,4(1H,3H)-pyrimidinedione hydrochloride (Compound 147)

ylthio-2-nitrophenyloxy)propyl]piperazin-1-yl}-2,4(1H,3H)-pyrimidinedione as crystals.

Analytical results of crystals of the pyrimidinedione derivative thus obtained:

NMR (CDCl$_3$), δppm: 1.9-2.2(m,2H), 2.48(s,3H), 2.4-2.7(m,6H), 2.8-3.0(m,4H), 3.28(s,3H), 3.36(s,3H), 4.14(m,2H), 5.16(s,1H), 7.0(d,1H), 7.36(dd,1H), 7.62(d,1H).

Next, 0.5 g of the pyrimidinedione derivative were treated in a 20% HCl/methanol solution by a method known per se in the art to obtain 0.4 g of 1,3-dimethyl-6-{4-[3-(4-methylthio-2-nitrophenyloxy)propyl]piperazin-1-yl}-2,4(1H,3H)-pyrimidinedione hydrochloride (Compound 147) as crystals.

Analytical results of crystals of Compound 147 thus obtained:
Melting point: 224°-226° C.
Elemental analysis for C$_{20}$H$_{27}$N$_5$O$_5$S·HCl:
Calculated (%): C, 49.43; H, 5.81; N, 14.41; Cl, 7.30; S, 6.60.

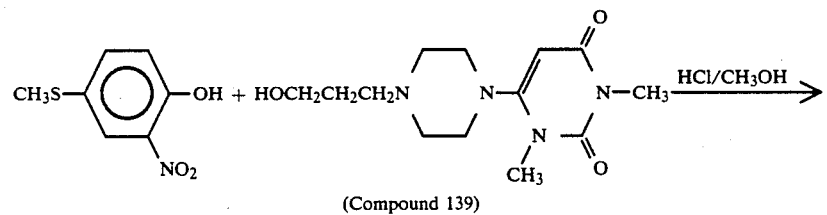

(Compound 139)

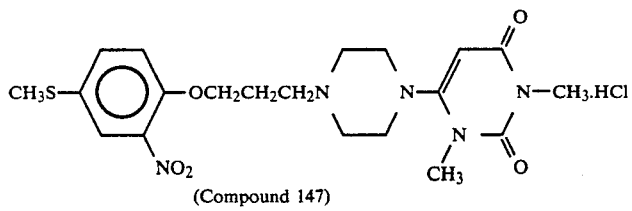

(Compound 147)

1.5 g of 4-methylthio-2-nitrophenol, 2.0 g of 1,3-dimethyl-6-[4-(3-hydroxypropyl)piperazin-1-yl]-2,4(1H,3H)-pyrimidinedione (Compound 139) and 2.2 g of triphenylphosphine were suspended in 30 ml of anhydrous tetrahydrofuran, followed by the addition of 1.35 ml of diethyl azodicarboxylate. The thus-prepared mixture was treated in a similar manner to Example 84-(2), thereby obtaining 2.9 g of 1,3-dimethyl-6-{4-[3-(4-meth- Found (%): C, 49.20; H, 5.97; N, 14.28; Cl, 7.23; S, 6.84.

EXAMPLE 92

Preparation of 1,3-dimethyl-6-{4-<3-[2-(α-hydroxybenzyl)-4-nitrophenyloxy]propyl>piperazin-1-yl}-2,4(1H,3H)-pyrimidinedione oxalate (Compound 148)

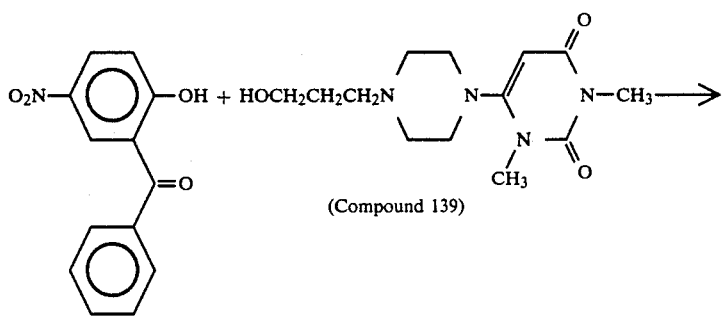

(Compound 139)

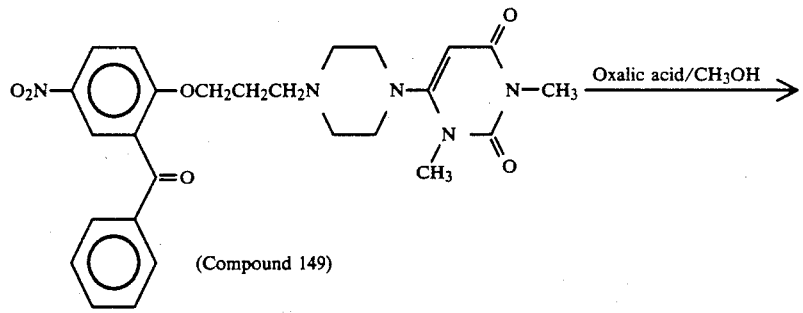

(Compound 149)

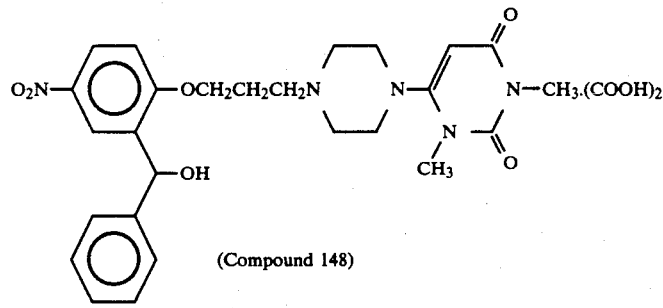

(Compound 148)

(1) Preparation of 1,3-dimethyl-6-{4-[3-(2-benzoyl-4-nitrophenyloxy)propyl]piperazin-1-yl}-2,4(1H,3H)-pyrimidinedione (Compound 149)

3.74 g of 2-benzoyl-4-nitrophenol, 3.5 g of 1,3-dimethyl-6-[4-(3-hydroxypropyl)piperazin-1-yl]-2,4(1H,3H)-pyrimidinedione (Compound 139) and 3.3 g of triphenylphosphine were suspended in 50 ml of anhydrous tetrahydrofuran, followed by the addition of 2.40 ml of diethyl azodicarboxylate. The thus-prepared mixture was treated in a similar manner to Example 84-(2), thereby obtaining 3.9 g of 1,3-dimethyl-6-{4-[3-(2-benzoyl-4-nitrophenyloxy)propyl]piperazin-1-yl}-2,4(1H,3H)-pyrimidinedione (Compound 149 as crystals.

Analytical results of crystals of the pyrimidinedione derivative (Compound 149) thus obtained:

NMR (CDCl$_3$), δppm: 1.9–2.2(m,2H), 2.4–2.7(m,6H), 2.8–3.0(m,4H), 3.26(s,3H), 3.36(s,3H), 4.14(m,2H), 5.14(s,1H), 7.0–7.8(m,8H), 8.36(d,2H).

(2) Preparation of 1,3-dimethyl-6-{4-<3-[2-(α-hydroxybenzyl)-4-nitrophenyloxy]propyl>piperazin-1-yl}-2,4(1H,3H)-pyrimidinedione oxalate (Compound 148)

0.2 g of the pyrimidinedione derivative (Compound 149) obtained in the above procedure and 15 mg of sodium borohydride were dissolved in ethanol. The resultant solution was stirred at room temperature for 6 hours. The reaction mixture was poured into water and then extracted with chloroform. The chloroform layer was washed with water and then dried over anhydrous sodium sulfate. The solvent was distilled off and the residue was purified by chromatography on a silica gel column (eluent: chloroform/methanol=40/1, by volume), thereby obtaining 0.15 g of 1,3-dimethyl-6-{4-<3-[2-(α-hydroxybenzyl)-4-nitrophenyloxy]propyl>piperazin-1-yl}-2,4(1H,3H)-pyrimidinedione.

Analytical results of crystals of the pyrimidinedione derivative thus obtained:

NMR (CDCl$_3$), δppm: 2.0(m,2H), 2.5–2.9(m,10H), 3.26(s,3H), 3.37(s,3H), 4.11(m,2H), 5.16(s,1H), 6.04(s,1H), 6.88(d,1H), 8.14(dd,1H), 8.52(d,1H).

Next, 0.15 g of the pyrimidinedione derivative was treated in an oxalic acid/methanol solution by a method known per se in the art to obtain 0.15 g of 1,3-dimethyl-6-{4-<3-[2-(α-hydroxybenzyl)-4-nitrophenyloxy]-propyl>piperazin-1-yl}-2,4(1H,3H)-pyrimidinedione oxalate (Compound 148) as crystals.

Analytical results of crystals of Compound 148 thus obtained:

Melting point: 111°–115° C.
Elemental analysis for C$_{26}$H$_{31}$N$_5$O$_6$·(COOH)$_2$·2H$_2$O:
Calculated (%): C, 52.91; H, 5.87; N, 11.02.
Found (%): C, 52.74; H, 5.65; N, 10.94;
IRν$_{max}^{KBr}$ (cm$^{-1}$): 3460, 1700, 1640, 1610, 1510, 1340, 760, 700.

EXAMPLE 93

Preparation of 1,3-dimethyl-6-{4-[3-(3-trifluoromethyl-4-nitrophenyloxy)propyl]piperazin-1-yl}-2,4(1H,3H)-pyrimidinedione oxalate (Compound 150)

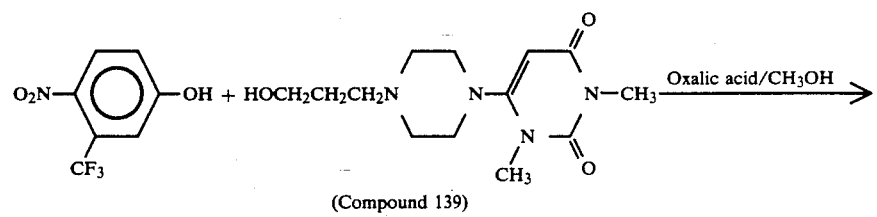

(Compound 139)

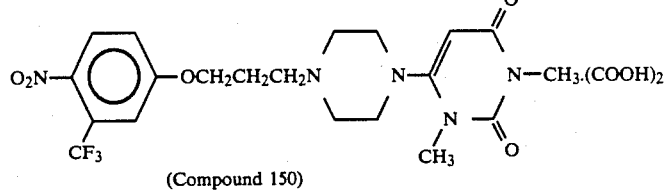

(Compound 150)

1.9 g of 4-nitro-3-trifluoromethylphenol, 2.25 g of 1,3-dimethyl-6-[4-(3-hydroxypropyl)piperazin-1-yl]-2,4(1H,3H)-pyrimidinedione (Compound 139) and 2.41 g of triphenylphosphine were suspended in 60 ml of anhydrous tetrahydrofuran, followed by the addition of 1.6 g of diethyl azodicarboxylate. The thus-prepared mixture was treated in a similar manner to Example 84-(2), thereby obtaining 3.50 g of pale yellow crystals. The crystals were recrystallized from ethanol to obtain 3.31 g of 1,3-dimethyl-6-{4-[3-(3-trifluoromethyl-4-nitrophenyloxy)propyl]piperazin-1-yl}-2,4(1H,3H)-pyrimidinedione as crystals.

Analytical results of crystals of the pyrimidinedione derivative thus obtained:

NMR (CDCl₃), δppm: 1.9-2.2(m,2H), 2.5-2.75(m,6H), 2.9-3.1(m,4H), 3.3(s,3H), 3.4(s,3H), 4.15(t,2H), 5.3(s,1H), 7.1-7.4(m,2H), 8.15(d,1H).

Next, 3.2 g of the pyrimidinedione derivative were treated in an oxalic acid/methanol solution by a method known per se in the art to obtain 3.22 g of 1,3-dimethyl-6-{4-[3-(3-trifluoromethyl-4-nitrophenyloxy)propyl]-piperazin-1-yl}-2,4(1H,3H)-pyrimidinedione oxalate (Compound 150) as crystals.

Analytical results of crystals of Compound 150 thus obtained:

Melting point: 187°-189° C.

Elemental analysis for C₂₀H₂₄F₃N₅O₅·(COOH)₂:

Calculated (%): C, 47.06; H, 4.67; N, 12.47; F, 10.15.

Found (%): C, 47.51; H, 5.24; N, 12.67; F, 10.49.

EXAMPLE 94

Preparation of 1,3-dimethyl-6-{4-[3-(2-methoxycarbonyl-4-nitrophenyloxy)propyl]piperazin-1-yl}-2,4(1H,3H)-pyrimidinedione oxalate (Compound 151)

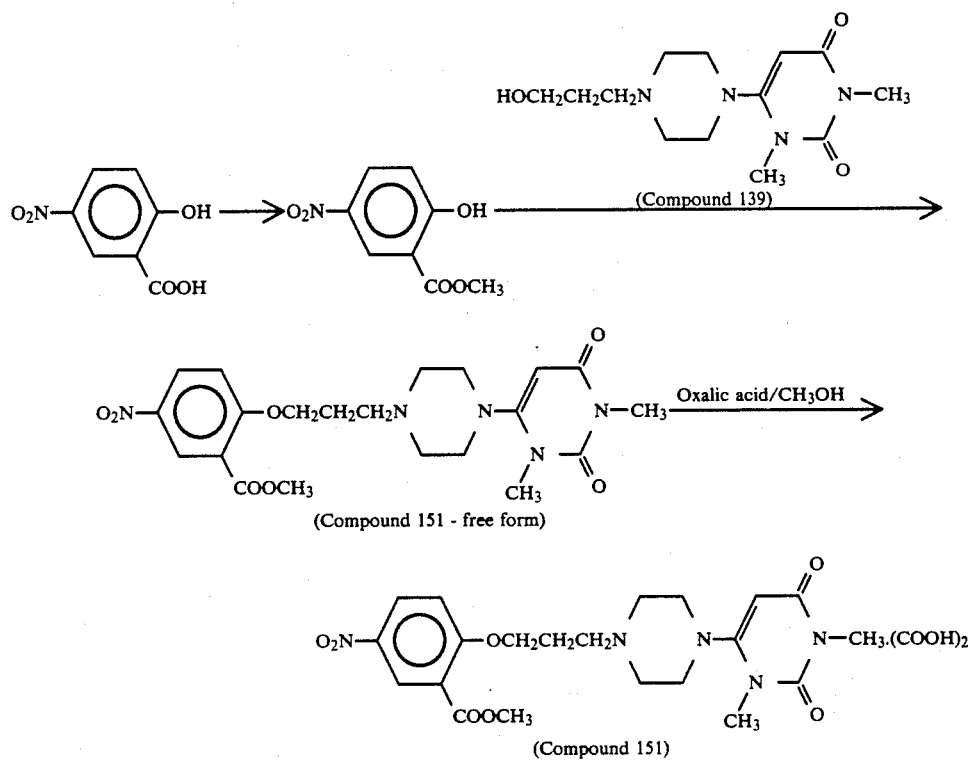

(1) Preparation of methyl 5-nitrosalicylate 80 ml of methanol and 10 g of concentrated sulfuric acid were added to 5 g of 5-nitrosalicylic acid. The resultant mixture was heated under stirring for 8 hours while distilling methanol off. The solvent was then distilled off under reduced pressure and the residue was dissolved in chloroform. The resultant chloroform solution was washed with water and then concentrated to dryness. The resultant residue was purified by chromatography on a silica gel column (eluent: chloroform), followed by recrystallization from chloroform-ether to obtain 5.1 g of methyl 5-nitrosalicylate as crystals.

Analytical results of crystals of methyl 5-nitrosalicylate thus obtained:

Melting point: 114°-116° C.

(2) Preparation of 1,3-dimethyl-6-{4-[3-(2-methoxycarbonyl-4-nitrophenyloxy)propyl]piperazin-1-yl}-2,4(1H,3H)-pyrimidinedione oxalate (Compound 151)

2.96 g of methyl 5-nitrosalicylate obtained by the above procedure, 4.23 g of 1,3-dimethyl-6-[4-(3-hydroxypropyl)piperazin-1-yl]-2,4(1H,3H)-pyrimidinedione (Compound 139) and 3.93 g of triphenylphosphine were suspended in 50 ml of anhydrous tetrahydrofuran, followed by the addition of 2.6 g of diethyl azodicarboxylate. The thus-prepared mixture was treated in a similar manner to Example 84-(2), thereby obtaining 6.5 g of pale yellow crystals. The crystals were recrystallized from methanol to obtain 5.74 g of 1,3-dimethyl-6-{4-[3-(2-methoxycarbonyl-4-nitrophenyloxy)propyl]piperazin-1-yl}-2,4(1H,3H)-pyrimidine-dione (Compound 151—free form) as crystals.

Analytical results of crystals of the pyrimidinedione derivative (Compound 151—free form) thus obtained:

Melting point: 145°–146° C.

NMR (CDCl$_3$), δppm: 1.8–2.2(m,2H), 2.4–3.0(m,10H), 3.27(s,3H), 3.36(s,3H), 3.87(s,3H), 4.17(t,2H), 5.24(s,1H), 7.0–8.7(m,2H).

Next, 5.5 g of the pyrimidinedione derivative were treated in an oxalic acid/methanol solution by a method known per se in the art to obtain 5.6 g of 1,3-dimethyl-6-{4-[3-(2-methoxycarbonyl-4-nitrophenyloxy)propyl]-piperazin-1-yl}-2,4(1H,3H)-pyrimidinedione oxalate (Compound 151) as crystals.

Analytical results of crystals of Compound 151 thus obtained:

Melting point: 186°–187° C. (decomposed).

Elemental analysis for $C_{21}H_{27}N_5O_7 \cdot (COOH)_2 \cdot CH_3OH$:

Calculated (%): C, 47.92; H, 5.86; N, 11.64.

Found (%): C, 47.74; H, 5.66; N, 11.43.

$IR\nu_{max}^{KBr}$ (cm$^{-1}$): 1655, 1520, 1345, 1200, 1130, 1080, 820, 765, 750.

EXAMPLE 95

Preparation of 1,3-dimethyl-6-{4-[3-(2-carboxy-4-nitrophenyloxy)propyl]piperazin-1-yl}-2,4(1H,3H)-pyrimidinedione oxalate (Compound 152)

pyrimidinedione (Compound 151—free form) were dissolved in 200 ml of methanol, followed by the addition of 100 ml of a 1.5 N aqueous solution of sodium hydroxide. The resultant mixture was stirred at 60° C. for 30 minutes. The reaction mixture was allowed to cool down, neutralized with dilute hydrochloric acid, and then concentrated to a total volume of 50 ml under reduced pressure. The concentrate was ice-cooled and precipitated crystals were collected by filtration, thereby obtaining 1.16 g of 1,3-dimethyl-6-{4-[3-(2-carboxy-4-nitrophenyloxy)propyl]piperazin-1-yl}-2,4(1H,3H)-pyrimidinedione.

Analytical results of crystals of the pyrimidinedione derivative thus obtained:

Melting point: 155°–158° C.

NMR (DMSO-d6), δppm: 1.8–2.3(m,2H), 2.4–3.2(m,10H), 3.13(s,3H), 3.27(s,3H), 4.2(t,2H), 5.2(s,1H), 7.3–8.5(m,3H).

Next, 1.0 g of the pyrimidinedione derivative was treated in an oxalic acid/methanol solution by a method known per se in the art to obtain 0.9 g of 1,3-dimethyl-6-{4-[3-(2-carboxy-4-nitrophenyloxy)propyl]piperazin-1-yl}-2,4(1H,3H)-pyrimidinedione oxalate (Compound 152) as crystals.

Analytical results of crystals of Compound 152 thus obtained:

Melting point: 191°–193° C. (decomposed).

Elemental analysis for $C_{20}H_{25}N_5O_7 \cdot (COOH)_2 \cdot H_2O$:

Calculated (%): C, 47.57; H, 5.26; N, 12.61.

Found (%): C, 47.85; H, 5.32; N, 12.49.

$IR\nu_{max}^{KBr}$ (cm$^{-1}$): 1700, 1650, 1500, 1345, 1290, 1135, 1075, 760, 750.

EXAMPLE 96

Preparation of 1,3-dimethyl-6-{4-[3-(2-amino-4-nitro-

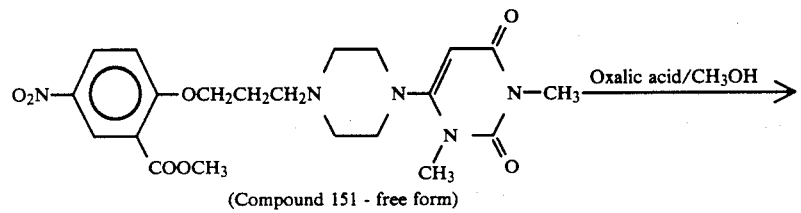

(Compound 151 - free form)

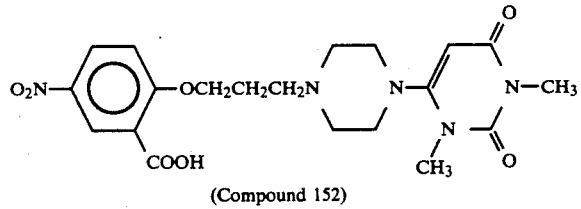

(Compound 152)

1.38 g of 1,3-dimethyl-6-{4-[3-(2-methoxycarbonyl-4-nitrophenyloxy)propyl]piperazin-1-yl}-2,4(1H,3H)-phenyloxy)propyl]piperazin-1-yl}-2,4(1H,3H)-pyrimidinedione oxalate (Compound 153)

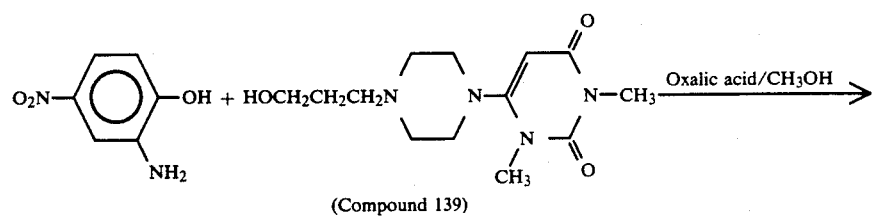

(Compound 139)

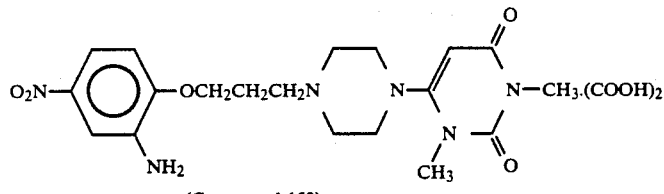

(Compound 153)

1.54 g of 2-amino-4-nitrophenol, 2.82 g of 1,3-dimethyl-6-[4-(3-hydroxypropyl)piperazin-1-yl]-2,4(1H,3H)-pyrimidinedione (Compound 139) and 2.88 g of triphenylphosphine were suspended in 20 ml of anhydrous tetrahydrofuran, followed by the addition of 1.92 g of diethyl azodicarboxylate. The thus-prepared mixture was stirred for 1 hour at room temperature and a precipitate was collected by filtration. The precipitate was washed with chloroform-ether to obtain 1.44 g of crystals. The crystals were recrystallized from ethanol-chloroform, thereby obtaining 0.6 g of 1,3-dimethyl-6-{4-[3-(2-amino-4-nitrophenyloxy)propyl]piperazin-1-yl}-2,4(1H,3H)-pyrimidinedione as crystals.

Analytical results of crystals of the pyrimidinedione derivative thus obtained:
Melting point: 188° C.
NMR (DMSO-d6), δppm: 1.9–2.0(m,2H), 2.4–3.0(m,10H), 3.1(s,3H), 3.24(s,3H), 4.08(m,2H), 5.15(s,1H), 5.35(br.2H), 6.8–7.5(m,3H).

Next, 0.2 g of the pyrimidinedione derivative was treated in an oxalic acid/methanol solution by a method known per se in the art to obtain 0.21 g of 1,3-dimethyl-6-{4-[3-(2-amino-4-nitrophenyloxy)propyl]piperazin-1-yl}-2,4(1H,3H)-pyrimidinedione oxalate (Compound 153) as crystals.

Analytical results of crystals of Compound 153 thus obtained:
Melting point: 145° C.
Elemental analysis for $C_{19}H_{26}N_6O_5 \cdot (COOH)_2$:
Calculated (%): C, 49.60; H, 5.55; N, 16.53.
Found (%): C, 49.53; H, 5.96; N, 16.49.
$IR\nu_{max}^{KBr}$ (cm$^{-1}$); 3430, 3340, 2940, 1690, 1650, 1510, 1435, 1340, 1290, 1235, 1075.

EXAMPLE 97

Preparation of 1,3-dimethyl-6-{4-[3-(4-methoxycarbonyl-2-nitrophenyloxy)propyl]piperazin-1-yl}-2,4(1H,3H)-pyrimidinedione oxalate (Compound 154)

0.84 g of methyl 4-hydroxy-3-nitrobenzoate, 0.8 g of 1,3-dimethyl-6-[4-(3-hydroxypropyl)piperazin-1-yl]-2,4(1H,3H)-pyrimidinedione (Compound 139) and 0.88 g of triphenylphosphine were suspended in 14 ml of anhydrous tetrahydrofuran, followed by the addition of 0.54 g of diethyl azodicarboxylate. The thus-prepared mixture was treated in a similar manner to Example 84-(2), thereby obtaining 1.1 g of 1,3-dimethyl-6-{4-[3-(4-methoxycarbonyl-2-nitrophenyloxy)propyl]piperazin-1-yl}-2,4(1H,3H)-pyrimidinedione as an oily substance.

Analytical results of the pyrimidinedione derivative thus obtained:
NMR (CDCl3), δppm: 2.1(m,2H), 2.3–3.0(m,10H), 3.3(s,3H), 3.4(s,3H), 3.95(s,3H), 4.3(t,2H), 5.25(s,1H), 7.25(d,1H), 8.27(dd,1H), 8.61(d,1H).

Next, 1.0 g of the pyrimidinedione derivative was treated in an oxalic acid/methanol solution by a method known per se in the art to obtain 1.0 g of 1,3-dimethyl-6-{4-[3-(4-methoxycarbonyl-2-nitrophenyloxy)propyl]piperazin-1-yl}-2,4(1H,3H)-pyrimidinedione oxalate (Compound 154) as crystals.

Analytical results of crystals of Compound 154 thus obtained:
Melting point: 190°–193° C. (decomposed).
Elemental analysis for $C_{21}H_{27}N_5O_7 \cdot 619$ (COOH)$_2 \cdot 3H_2O$:
Calculated (%): C, 45.62; H, 5.83; N, 11.57.
Found (%): C, 45.92; H, 5.21; N, 11.84.
$IR\nu_{max}^{KBr}$ (cm$^{-1}$): 2900, 2500, 1740, 1720, 1700, 1640, 1620, 1530, 1340, 800.

EXAMPLE 98

Preparation of 1,3-dimethyl-6-{4-[3-(2-cyano-4-nitrophenyloxy)propyl]piperazin-1-yl}-2,4(1H,3H)-pyrimidinedione oxalate (Compound 155)

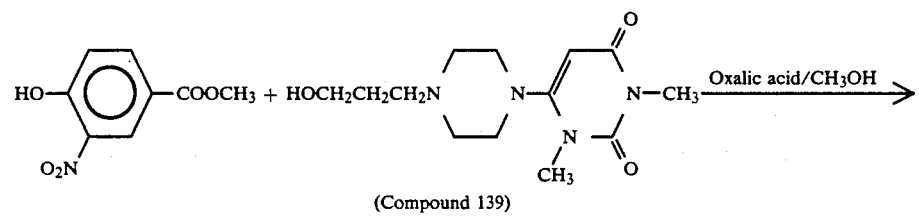

(Compound 139)

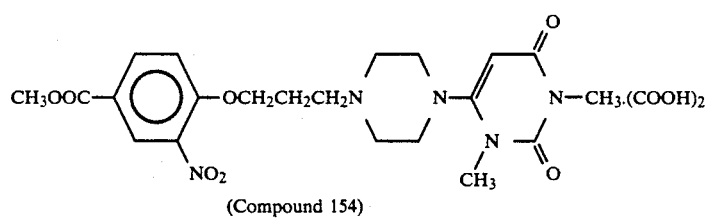

(Compound 154)

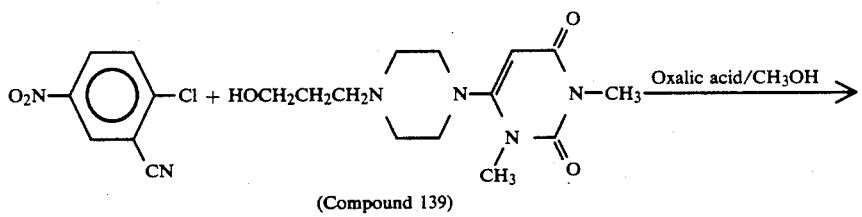

(Compound 139)

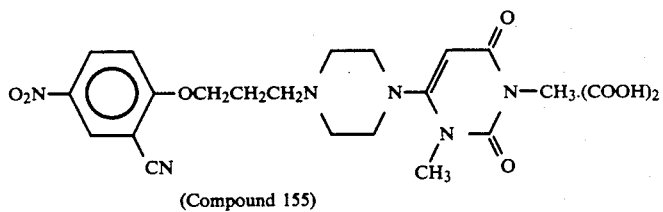

(Compound 155)

0.82 g of 2-chloro-5-nitrobenzonitrile, 1.0 g of 1,3-dimethyl-6-[4-(3-hydroxypropyl)piperazin-1-yl]-2,4(1H,3H)-pyrimidinedione (Compound 139) and 0.22 g of sodium hydride were reacted at 0° C. for 1 hour in 5 ml of dimethylformamide. Water was then added. Precipitated crystals were collected by filtration and washed with water. The thus-obtained crystals were dried in vacuum, thereby obtaining 0.9 g of 1,3-dimethyl-6-{4-[3-(2-cyano-4-nitrophenyloxy)propyl]piperazin-1-yl}-2,4(1H,3H)-pyrimidinedione.

Analytical results of crystals of the pyrimidinedione derivative thus obtained:

NMR (CDCl$_3$), δppm: 2.1(m,2H), 2.6–3.0(m,10H), 3.3(s,3H), 3.35(s,3H), 4.6(t,2H), 5.1(s,1H), 7.5(d,1H), 8.6(m,2H).

Next, 0.9 g of the pyrimidinedione derivative was treated in an oxalic acid/methanol solution by a method known per se in the art to obtain 0.87 g of 1,3-dimethyl-6-{4-[3-(2-cyano-4-nitrophenyloxy)propyl]piperazin-1-yl}-2,4(1H,3H)-pyrimidinedione oxalate (Compound 155) as crystals.

Analytical results of crystals of Compound 155 thus obtained:

Melting point: 191°–193° C. (decomposed).

Elemental analysis for $C_{20}H_{24}N_6O_5 \cdot (COOH)_2 \cdot 3H_2O$:
Calculated (%): C, 46.15; H, 5.63; N, 14.68.
Found (%): C, 45.89; H, 5.38; N, 14.29.

IR$\nu_{max}^{KBr}$ (cm$^{-1}$): 2200, 1680, 1630, 1600, 1580, 1520, 1340, 840.

EXAMPLE 99

Preparation of 1,3-dimethyl-6-{4-[3-(2-cyano-4-nitroanilino)propyl]piperazin-1-yl}-2,4(1H,3H)-pyrimidinedione oxalate (Compound 156)

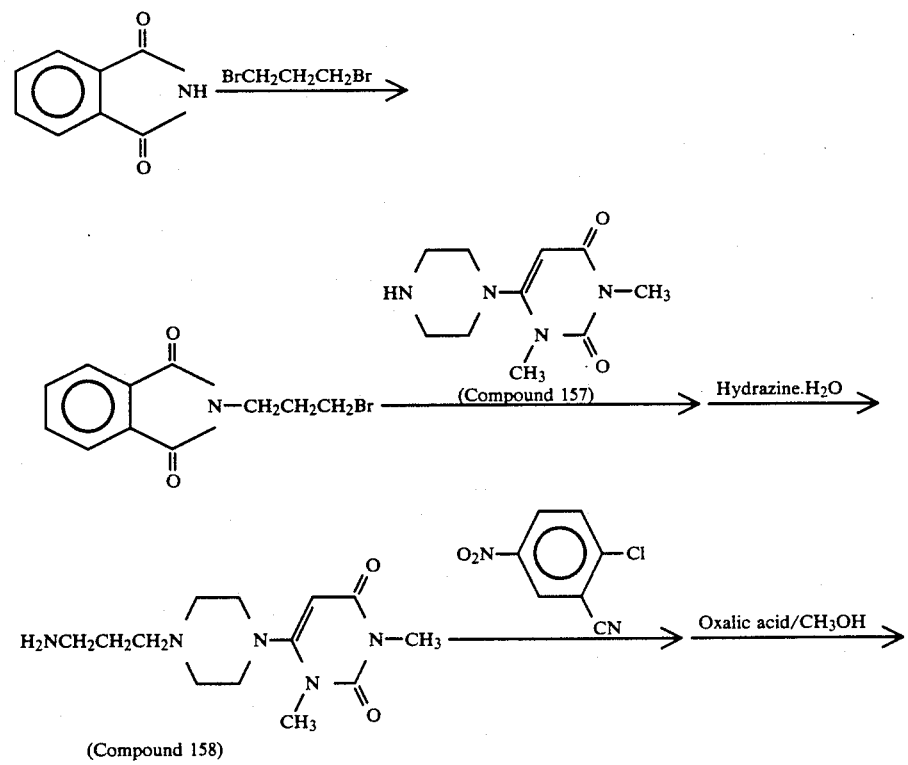

(Compound 158)

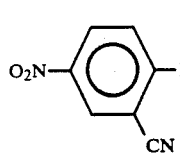 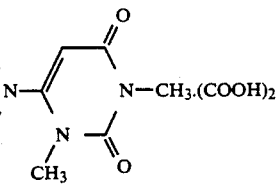

(Compound 156)

(1) Preparation of 1,3-dimethyl-6-[4-(3-aminopropyl)-piperazin-1-yl]-2,4(1H,3H)-pyrimidinedione (Compound 158)

A solution in which 18.52 g of potassium phthalimide and 200 g of 1,3-dibromopropane were suspended in 100 ml of dimethylformamide was heated under stirring at 120° C. for 6 hours, so that potassium phthalimide and 1,3-dibromopropane were reacted. Next, insoluble matters were filtered off from the reaction mixture and the filtrate was concentrated to dryness under reduced pressure. The residue was washed with hexane and then recrystallized from ethanol-water. Crystals thus obtained were collected by filtration, washed and then dried, thereby obtaining 13.8 g of N-(3-bromopropyl)phthalimide.

Next, 13.0 g of N-(3-bromopropyl)phthalimide, 10.3 g of 1,3-dimethyl-6-(1-piperazinyl)-2,4(1H,3H)-pyrimidinedione (Compound 157) and 20 g of triethylamine were suspended in 200 ml of dioxane. The suspension was thereafter heated under reflux for 6 hours.

Further, insoluble matters were filtered off from the reaction mixture and the filtrate was concentrated to dryness under reduced pressure. The residue (dry concentrate) was recrystallized from ethyl acetate/n-hexane. Resultant crystals were collected by filtration, washed and then dried, thereby obtaining 1.25 g of 1,3-dimethyl-6-[4-(3-phthaloylaminopropyl)piperazin-1-yl]-2,4(1H,3H)-pyrimidinedione.

12.5 g of the crystals and 6.0 g of hydrazine hydrate were next suspended in 200 ml of ethanol. The suspension was heated for 4 hours under reflux. After allowing the suspension to cool down, resultant insoluble matters were filtered off. The filtrate was concentrated to dryness under reduced pressure. Then, the residue (dry concentrate) was dissolved in water, to which dilute hydrochloric acid was added to adjust the pH to about 3. Insoluble matters formed upon the pH adjustment were filtered off. The filtrate was added with a large amount of potassium carbonate and then extracted with chloroform. After completion of the extraction, the resultant organic layer was dried over anhydrous sodium sulfate and then heated under reduced pressure to distill the solvent off, whereby 6.80 g of 1,3-dimethyl-6-[4-(3-aminopropyl)piperazin1-yl]-2,4(1H,3H)-pyrimidinedione (Compound 158) were obtained as a colorless syrupy substance. The syrupy substance was crystallized when allowed to stand overnight.

Analytical results of crystals of Compound 158 thus obtained:

Melting point: 85°–88° C. NMR (CDCl$_3$), δppm: 1.58(br.2H), 1.66(m,2H), 2.48(t,2H), 2.59(m,4H), 2.78(t,2H), 2.97(m,4H), 3.32(s,3H), 3.38(s,3H), 5.24(s,1H).

(2) Preparation of 1,3-dimethyl-6-{4-[3-(2-cyano-4-nitroanilino)propyl]piperazin-1-yl}-2,4(1H,3H)-pyrimidinedione oxalate (Compound 156)

0.3 g of Compound 158 obtained beforehand, 0.3 g of 2-chloro-5-nitrobenzonitrile and 0.31 ml of trtiethylamine were stirred at 80° C. for 1 hour in 5 ml of dimethylformamide. The reaction mixture was concentrated under reduced pressure and the residue was purified by chromatography on a silica gel column (eluent: chloroform/methanol=40/1, by volume), thereby obtaining 0.4 g of 1,3-dimethyl-6-{4-[3-(2-cyano-4-nitroanilino)propyl]piperazin-1-yl}-2,4(1H,3H)-pyrimidinedione.

Analytical results of the pyrimidinedione derivative thus obtained:

NMR (CDCl$_3$), δppm: 2.0(m,2H), 2.6–3.3(m,12H), 3.35(s,3H), 3.45(s,3H), 5.33(s,1H), 7.28(m,1H), 8.4–8.6(m,2H).

Next, 0.4 g of the pyrimidinedione derivative was treated in an oxalic acid/methanol solution by a method known per se in the art to obtain 0.41 g of 1,3-dimethyl-6-{4-[3-(2-cyano-4-nitroanilino)propyl]piperazin-1-yl}-2,4(1H,3H)pyrimidinedione oxalate (Compound 156) as crystals.

Analytical results of crystals of Compound 156 thus obtained:

Melting point: 156°–158° C. (decomposed).
Elemental analysis for C$_{20}$H$_{25}$N$_7$O$_4$·(COOH)$_2$·H$_2$O:
Calculated (%): C, 49.41%; H, 5.43; N, 17.94.
Found (%): C, 49.34; H, 5.46; N, 18.31.
IR$\nu_{max}^{KBr}$ (cm$^{-1}$): 3300, 2250, 2200, 1530, 1340, 1160, 800, 750, 700.

EXAMPLE 100

Preparation of 1,3-dimethyl-6-{4-[3-(2-chloro-4-nitroanilino)propyl]piperazin-1-yl}-2,4(1H,3H)-pyrimidinedione oxalate (Compound 159)

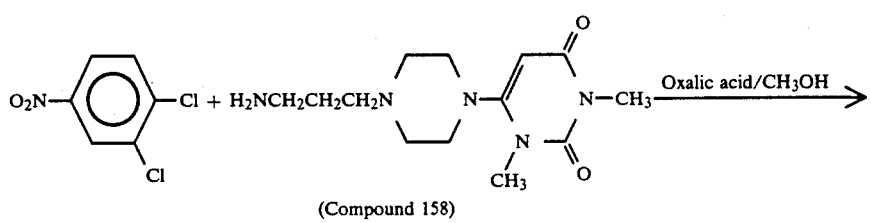

(Compound 158)

-continued

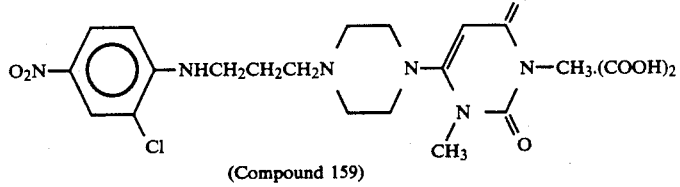
(Compound 159)

A mixture consisting of 0.4 g of Compound 158 obtained in Example 99-(1), 0.4 g of 3,4-dichloro-nitrobenzene, 0.43 ml of triethylamine and 6 ml of dimethylformamide was treated in a manner similar to Example 99-(2), thereby obtaining 0.55 g of 1,3-dimethyl-6-{4-[3-(2-chloro-4-nitroanilino)propyl]piperazin-1-yl}-2,4(1H,3H)-pyrimidinedione.

Analytical results of crystals of the pyrimidinedione derivative thus obtained:

NMR (CDCl$_3$), δppm: 2.0(m,2H), 2.5–3.3(m,10H), 3.28(s,3H), 3.39(s,3H), 5.23(s,1H), 6.77(m,1H), 8.11(m,1H), 8.20(m,1H).

Next, 0.5 g of the pyrimidinedione derivative was treated in an oxalic acid/methanol solution by a method known per se in the art to obtain 0.53 g of 1,3-dimethyl-6-{4-[3-(2-chloro-4-nitroanilino)propyl]piperazin-1-yl}-2,4(1H,3H)-pyrimidinedione oxalate (Compound 159) as crystals.

Analytical results of crystals of Compound 159 thus obtained:

Melting point: 153°–155° C. (decomposed).

Elemental analysis for C$_{19}$H$_{25}$ClN$_6$O$_4$·(COOH)$_2$·2½H$_2$O:

Calculated (%): C, 44.10; H, 5.64; N, 14.69; Cl, 6.20.
Found (%): C, 44.14; H, 5.20; N, 14.63; Cl, 6.13.

IRν$_{max}^{KBr}$ (cm$^{-1}$): 2250, 1690, 1640, 1630, 1590, 1530, 1330, 800, 740.

EXAMPLE 101

Preparation of 1,3-dimethyl-6-{4-[3-(2-methoxy-5-nitrophenyloxy)propyl]piperazin-1-yl}-2,4(1H,3H)-pyrimidinedione hydrochloride (Compound 160)

0.9 g of 2-methoxy-5-nitrophenol, 1.0 g of 1,3-dimethyl-6-[4-(3-hydroxypropyl)piperazin-1-yl]-2,4(1H,3H)-pyrimidinedione (Compound 139) and 1.1 g of triphenylphosphine were suspended in 20 ml of anhydrous tetrahydrofuran, followed by the addition of 0.67 ml of diethyl azodicarboxylate. The thus-prepared mixture was treated in a similar manner to Example 84-(2), thereby obtaining 1.2 g of 1,3-dimethyl-6-{4-[3-(2-methoxy-5-nitrophenyloxy)propyl]piperazin-1-yl}-2,4(1H,3H)-pyrimidinedione as an oily substance.

Analytical results of the pyrimidinedione derivative thus obtained:

NMR (CDCl$_3$), δppm: 2.15(m,2H), 2.5–3.2(m,10H), 3.3(s,3H), 3.4(s,3H), 3.97(s,3H), 4.23(t,2H), 5.26(s,1H), 6.96(d,1H), 7.86(m,2H).

Next, 1.1 g of the pyrimidinedione derivative was treated in a 10% HCl/methanol solution by a method known per se in the art to obtain 1.17 g of 1,3-dimethyl-6-{4-[3-(2-methoxy-5-nitrophenyloxy)propyl]piperazin-1-yl}-2,4(1H,3H)-pyrimidinedione hydrochloride (Compound 160) as crystals.

Analytical results of crystals of Compound 160 thus obtained:

Melting point: 158°–162° C. (decomposed).

Elemental analysis for C$_{20}$H$_{27}$N$_5$O$_6$·HCl·H$_2$O:

Calculated (%): C, 49.23; H, 6.20; N, 14.35; Cl, 7.27.
Found (%): C, 49.04; H, 6.28; N, 14.26; Cl, 7.54.

IRν$_{max}^{KBr}$ (cm$^{-1}$): 3400, 2950, 1660, 1620, 1540, 1350, 1260, 1010, 810, 770.

EXAMPLE 102

Preparation of 1,3-dimethyl-6-{4-[3-(2-allyloxy-4-nitrophenyloxy)propyl]piperazin-1-yl}-2,4(1H,3H)-pyrimidinedione hydrochloride (Compound 161)

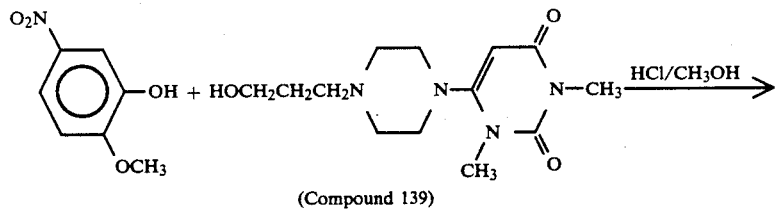
(Compound 139)

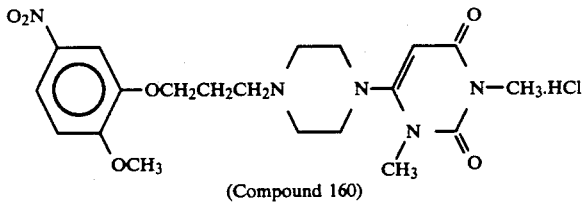
(Compound 160)

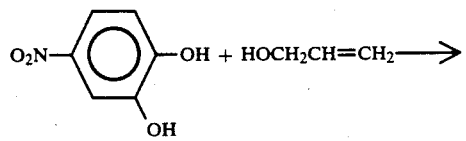

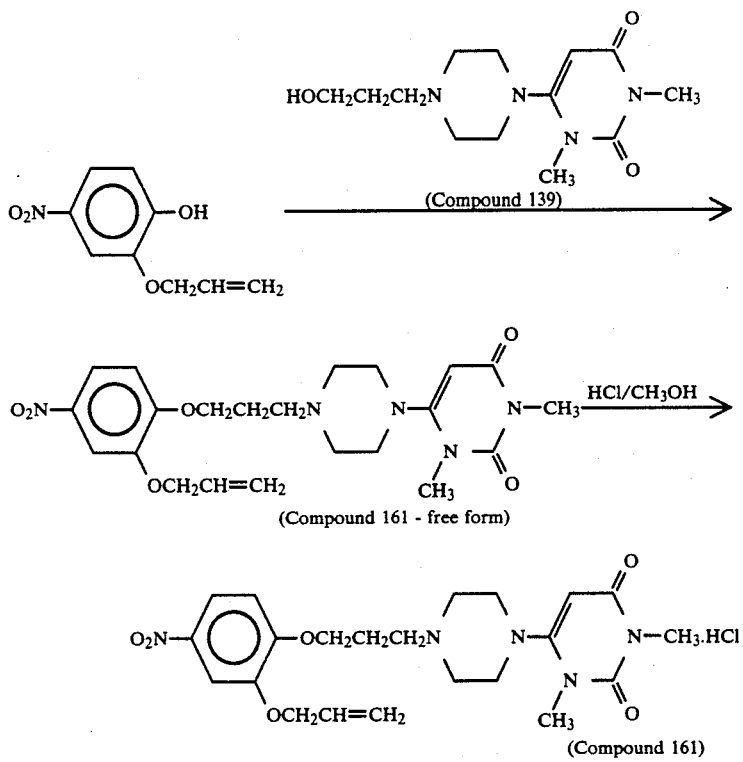

(1) Preparation of 2-allyloxy-4-nitrophenol 1.7 g of 4-nitrochatechol, 0.74 ml of allyl alcohol and 2.4 g of triphenylphosphine were suspended in 40 ml of anhydrous tetrahydrofuran, followed by the addition of 1.5 ml of diethyl azodicarboxylate. The resultant mixture was stirred at room temperature for 11 hours, followed by the addition of 5 g of silica gel. The thus-prepared mixture was concentrated under reduced pressure. The residue was purified by chromatography on a silica gel column (eluent: hexane/ethyl acetate=3/1, by volume), thereby obtaining 1.5 g of 2-allyloxy-4-nitrophenol as an oily substance.

Analytical results of the phenol derivative thus obtained:

NMR (CDCl$_3$), δppm: 4.76(m,2H), 5.22(m,1H), 5.35(m,1H), 5.96(m,1H), 6.99(d,1H), 7.91(m,2H).

(2) Preparation of 1,3-dimethyl-6-{4-[3-(2-allyloxy-4-nitrophenyloxy)propyl]piperazin-1-yl}-2,4(1H,3H)-pyrimidinedione hydrochloride (Compound 161)

1.5 g of 2-allyloxy-4-nitrophenol, 1.0 g of 1,3-dimethyl-6-[4-(3-hydroxypropyl)piperazin-1-yl]-2,4(1H,3H)-pyrimidinedione (Compound 139) and 1.1 g of triphenylphosphine were suspended in 20 ml of anhydrous tetrahydrofuran, followed by the addition of 0.67 ml of diethyl azodicarboxylate. The thus-prepared mixture was treated in a similar manner to Example 84-(2), thereby obtaining 1.1 g of 1,3-dimethyl-6-{4-[3-(2-allyloxy-4-nitrophenyloxy)propyl]piperazin-1-yl}-2,4(1H,3H)-pyrimidinedione (Compound 161—free form) as an oily substance.

Analytical results of the pyrimidinedione derivative (Compound 161—free form) thus obtained:

NMR (CDCl$_3$), δppm: 2.1(m,2H), 2.5–3.3(m,10H), 3.35(s,3H), 3.43(s,3H), 4.76(m,2H), 5.3(s,1H), 5.6(m,2H), 6.15(m,1H), 7.0(m,1H), 7.8(m,2H).

Next, 0.5 g of the pyrimidinedione derivative was treated in a 10% HCl/methanol solution by a method known per se in the art to obtain 0.4 g of 1,3-dimethyl-6-{4-[3-(2-allyloxy-4-nitrophenyloxy)propyl]piperazin-1-yl}-2,4(1H,3H)-pyrimidinedione hydrochloride (Compound 161) as crystals.

Analytical results of crystals of Compound 161 thus obtained:

Melting point: 134°–136° C. (decomposed).

Elemental analysis for C$_{22}$H$_{29}$N$_5$O$_6$·HCl·2½H$_2$O:

Calculated (%): C, 48.84; H, 6.52; N, 12.95; Cl, 6.55.
Found (%): C, 48.97; H, 6.27; N, 12.74; Cl, 6.75.

IR$\nu_{max}^{KBr}$ (cm$^{-1}$): 3350, 2900, 1700, 1640, 1510, 1340, 1280, 1090, 810, 760.

EXAMPLE 103

Preparation of 1,3-dimethyl-6-{4-[3-(2-hydroxy-4-nitrophenyloxy)propyl]piperazin-1-yl}-2,4(1H,3H)-pyrimidinedione hydrochloride

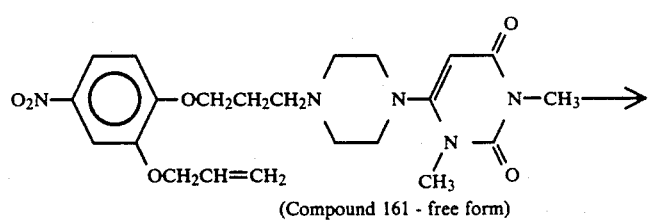

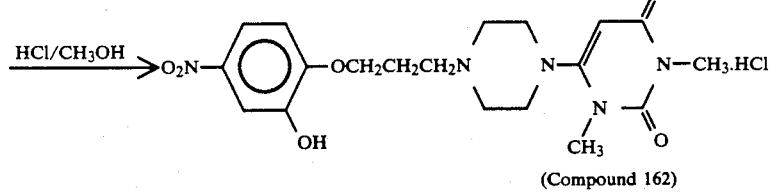

(Compound 162)

0.6 g of 1,3-dimethyl-6-{4-[3-(2-allyloxy-4-nitrophenyloxy)propyl]piperazin-1-yl}-2,4(1H,3H)-pyrimidinedione (Compound 161—free form) was dissolved in 10 ml of methanol, followed by the addition of 0.1 g of 10% Pd/activated carbon, 0.1 g of p-toluenesulfonic acid monohydrate and 2 ml of water. The resultant mixture was heated for 15 hours under stirring and reflux. After allowing the reaction mixture to cool down, insoluble matters were filtered off and the filtrate was concentrated. The residue was purified by chromatography on a silica gel column (eluent: chloroform/methanol=50/1, by volume), thereby thereby obtaining 0.4 g of 1,3-dimethyl-6-{4-[3-(2-hydroxy-4-nitrophenyloxy)propyl]piperazin-1-yl}-2,4(1H,3H)-pyrimidinedione.

Analytical results of the pyrimidinedione derivative thus obtained:

NMR (CDCl$_3$), δppm: 2.15(m,2H), 2.7–3.3(m,10H), 3.34(s,3H), 3.43(s,3H), 4.13(t,2H), 5.34(s,1H), 7.0(m,1H), 8.03(m,2H).

Next, 0.4 g of the pyrimidinedione derivative was treated in a 10% HCl/methanol solution by a method known per se in the art to obtain 0.33 g of 1,3-dimethyl-6-{4-[3-(2-hydroxy-4-nitrophenyloxy)propyl]piperazin-1-yl}-2,4(1H,3H)-pyrimidinedione hydrochloride (Compound 162) as amorphous powder.

Analytical results of amorphous powder of Compound 162 thus obtained:

Elemental analysis for $C_{19}H_{25}N_5O_6 \cdot HCl \cdot 1\frac{1}{2}H_2O$:
Calculated (%): C, 47.26; H, 6.05; N, 14.05; Cl, 7.34.
Found (%): C, 47.53; H, 6.21; N, 13.75; Cl, 7.59.
IR$\nu_{max}^{KBr}$ (cm$^{-1}$): 3350, 1680, 1630, 1530, 1340, 1220, 1000, 750, 710.

EXAMPLE 104

Preparation of 1,3-dimethyl-6-{4-[3-(2-benzylamino-4-nitrophenyloxy)propyl]piperazin-1-yl}-2,4(1H,3H)pyrimidinedione oxalate (Compound 163)

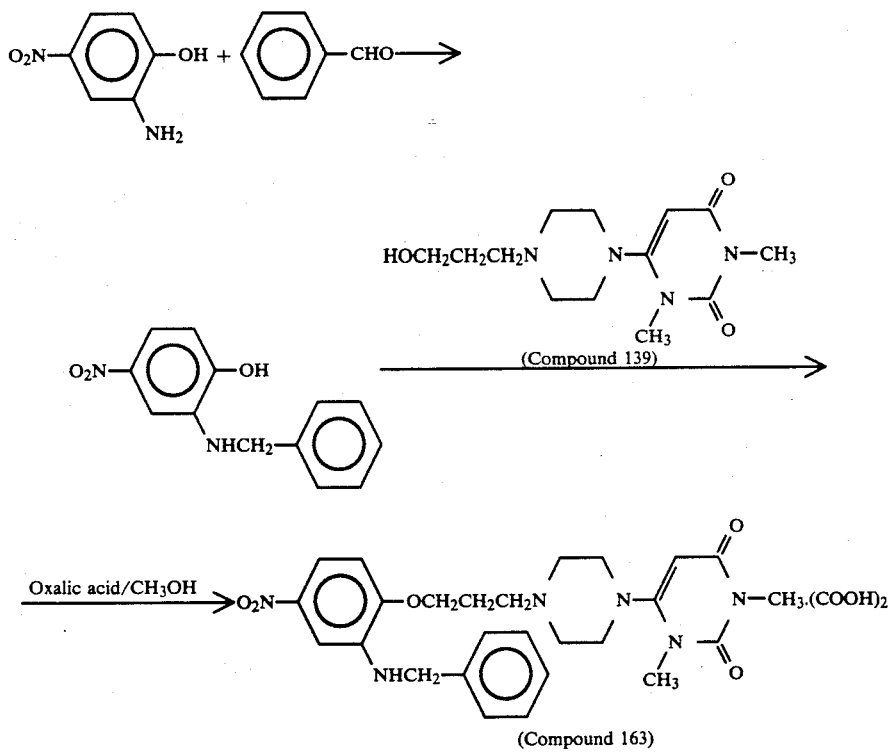

(Compound 163)

(1) Preparation of 2-benzylamino-4-nitrophenol 4.4 g of 2-amino-4-nitrophenol, 5.2 g of benzaldehyde and 0.4 g of p-toluenesulfonic acid monohydrate were dissolved in 300 ml of benzene. The resultant mixture was heated under reflux for 5 hours while removing water. The solvent was distilled off under reduced pressure and hexane is added to the residue. Precipitated crystals were collected by filtration to obtain 6.6 g of crystals. The crystals were dissolved in 55 ml of dimethylformamide, followed by the addition of 2.2 g of sodium borohydride under ice-cooling. The resultant mixture was stirred at the same temperature for 2 hours. Ether was added to the reaction mixture. The resultant ether solution was washed with water and then dried over anhydrous sodium sulfate. The solvent was distilled off to obtain 4.2 g of 2-benzylamino-4-nitrophenol. This product was provided for the subsequent reaction without purification.

Analytical results of 2-benzylamino-4-nitrophenol thus obtained:
NMR (CDCl$_3$), δppm: 4.5(s,2H), 6.8-7.0(d,1H), 7.3-7.6(m,2H), 7.4(s,1H).

(2) Preparation of 1,3-dimethyl-6-{4-[3-(2-benzylamino-4-nitrophenyloxy)propyl]piperazin-1-yl}-2,4(1H,3H)pyrimidinedione oxalate (Compound 163)

0.7 g of 2-benzylamino-4-nitrophenol, 0.8 g of 1,3-dimethyl-6-[4-(3-hydroxypropyl)piperazin-1-yl]-2,4(1H,3H)-pyrimidinedione (Compound 139) and 0.9 g of triphenylphosphine were suspended in 20 ml of anhydrous tetrahydrofuran, followed by the addition of 0.65 g of diethyl azodicarboxylate. The thus-prepared mixture was treated in a similar manner to Example 84-(2), thereby obtaining 0.93 g of 1,3-dimethyl-6-{4-[3-(2-benzylamino-4-nitrophenyloxy)propyl]piperazin-1yl}-2,4(1H,3H)-pyrimidinedione as crystals.

Analytical results of the pyrimidinedione derivative thus obtained:
NMR (CDCl$_3$), δppm: 2.05(m,2H), 2.6(m,6H), 2.95(m,4H), 3.3(s,3H), 3.35(s,3H), 4.15(t,2H), 4.35(d,2H), 4.8(m,1H), 5.25(s,1H), 6.75(d,1H), 7.2-7.45(m,1H), 7.35(s,5H), 7.6(m,1H).

Next, 0.8 g of the pyrimidinedione derivative was treated in an oxalic acid/methanol solution by a method known per se in the art to obtain 0.81 g of 1,3-dimethyl-6-{4-[3-(2-benzylamino-4-nitrophenyloxy)propyl]piperazin-1-yl}-2,4(1H,3H)-pyrimidinedione oxalate (Compound 163) as crystals.

Analytical results of crystals of Compound 163 thus obtained:
Elemental analysis for C$_{26}$H$_{32}$N$_6$O$_5$·(COOH)$_2$·½H$_2$O:
Calculated (%): C, 55.35; H, 5.81; N, 13.83.
Found (%): C, 55.73; H, 5.78; N, 13.87.

EXAMPLE 105

Preparation of 1,3-dimethyl-6-{4-[3-(2-methoxy-4-nitrophenyloxy)propyl]piperazin-1-yl}-2,4(1H,3H)-pyrimidinedione hydrochloride (Compound 164)

filtration, followed by dissolution in water. The thus-prepared solution was neutralized with 6 N hydrochloric acid and crystals thus precipitated were collected by filtration. The crystals were dissolved in chloroform. The resultant solution was washed with water and dried over anhydrous sodium sulfate. By concentrating the chloroform layer under reduced pressure, 4.5 g of 2-methoxy-4-nitrophenol were obtained as crystals.

Analytical results of 2-methoxy-4-nitrophenol thus obtained:
Melting point: 102°-103° C.

(2) Preparation of 1,3-dimethyl-6-{4-[3-(2-methoxy-4-nitrophenyloxy)propyl]piperazin-1-yl}-2,4(1H,3H)-pyrimidinedione hydrochloride (Compound 164)

0.68 g of 2-methoxy-4-nitrophenol, 1.0 g of 1,3-dimethyl-6-[4-(3-hydroxypropyl)piperazin-1-yl]-2,4(1H,3H)-pyrimidinedione (Compound 139) and 1.1 g of triphenylphosphine were suspended in 20 ml of anhydrous tetrahydrofuran, followed by the addition of 0.71 g of diethyl azodicarboxylate. The thus-prepared mixture was treated in a similar manner to Example 84-(2), followed by recrystallization from methanol, whereby 1.35 g of 1,3-dimethyl-6-{4-[3-(2-methoxy-4-nitrophenyloxy)propyl]piperazin-1-yl}-2,4(1H,3H)-pyrimidinedione as crystals.

Analytical results of the pyrimidinedione derivative thus obtained:
NMR (CDCl$_3$), δppm: 1.9-3.3(m,12H), 3.43(s,3H), 3.5(s,3H), 4.06(s,3H), 4.26(t,2H), 5.35(s,1H), 7.05(d,1H), 7.8-8.15(m,2H).

Next, 1.3 g of the pyrimidinedione derivative was treated in a 10%HCl/methanol solution by a method known per se in the art to obtain 1.17 g of 1,3-dimethyl-6-{4-[3-(2-methoxy-4-nitrophenyloxy)propyl]piperazin-1-yl}-2,4(1H,3H)-pyrimidinedione hydrochloride (Compound 164) as crystals.

Analytical results of crystals of Compound 164 thus obtained:
Melting point: 135°-138° C.
Elemental analysis for C$_{20}$H$_{27}$N$_5$O$_6$·HCl·1½H$_2$O:
Calculated (%): C, 48.34; H, 6.29; N, 14.09; Cl, 7.13.
Found (%): C, 48.20; H, 6.61; N, 14.27; Cl, 7.38.

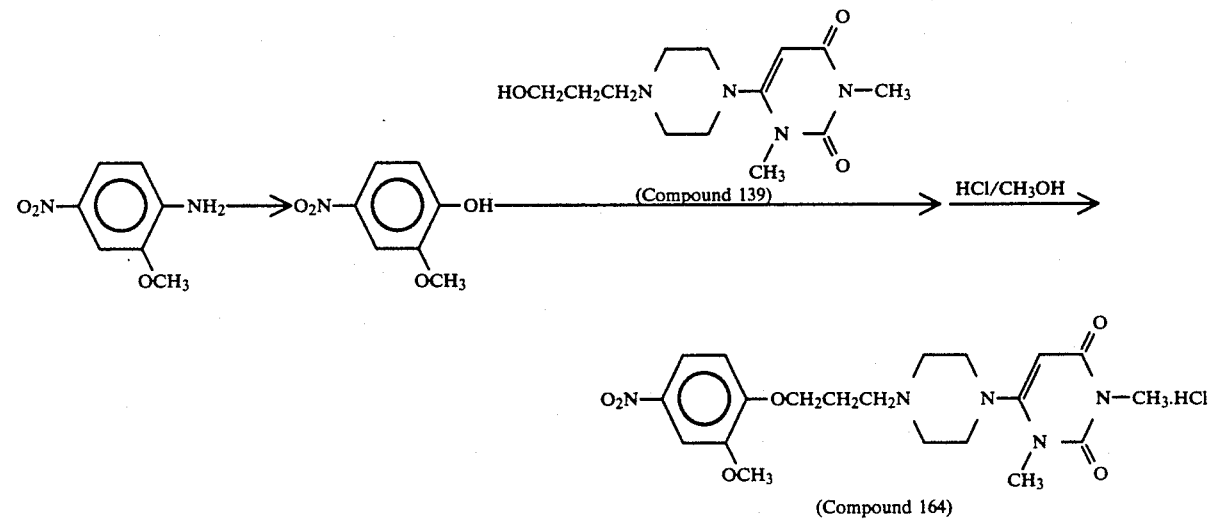

(1) Preparation of 2-methoxy-4-nitrophenol
50 g of 2-amino-5-nitroanisole, 50 g of sodium hydroxide were dissolved in 450 ml of water. The resultant mixture was heated under reflux for 3 hours and then ice-cooled. Precipicated crystals were collected by

EXAMPLE 106

Preparation of 1,3-dimethyl-6-{4-[3-(2,6-dichloro-4-nitrophenyloxy)propyl]piperazin-1-yl}-2,4(1H,3H)-pyrimidinedione hydrochloride (Compound 165)

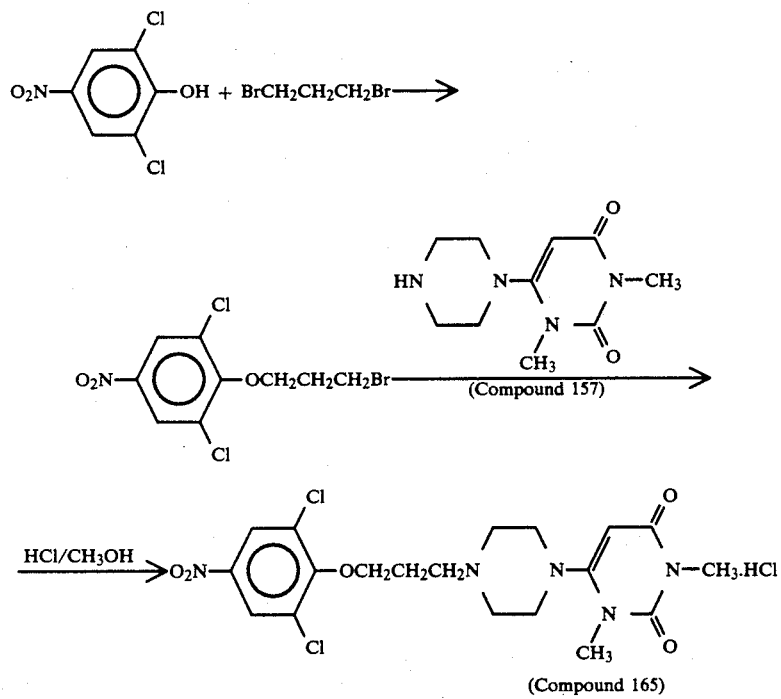

(Compound 165)

(1) Preparation of 1-bromo-3-(2,6-dichloro-4-nitrophenyloxy)propane

A mixture of 4.16 g of 2,6-dichloro-4-nitrophenol, 40.4 g of 1,3-dibromopropane, 2.76 g of potassium carbonate and 2.46 g of potassium t-butoxide was heated under reflux for 4 hours in 50 ml of methyl ethyl ketone. The reaction mixture was allowed to cool down and insoluble matters were filtered off. The filtrate was concentrated under reduced pressure. The residue was dissolved in chloroform. The thus-prepared chloroform solution was washed with water, and the chloroform was then distilled off. The residue was purified by chromatography on a silica gel column (eluent: chloroform/hexane=4/1, by volume) to obtain 6.24 g of 1-bromo-3-(2,6-dichloro-4-nitrophenyloxy)propane. This compound was employed in the next reaction without any further purification.

(2) Preparation of 1,3-dimethyl-6-{4-[3-(2,6-dichloro-4-nitrophenyloxy)propyl]piperazin-1-yl}-2,4(1H,3H)-pyrimidinedione hydrochloride (Compound 165)

4.94 g of 1-bromo-3-(2,6-dichloro-4-nitrophenyloxy)propane obtained by the above procedure, 3.36 g of 1,3-dimethyl-6-(1-piperazinyl)-2,4(1H,3H)-pyrimidinedione (Compound 157) and 4 ml of triethylamine were dissolved in 100 ml of dioxane. The thus-prepared mixture was heated for 2 hours under stirring and reflux. The reaction mixture was allowed to cool down and then filtered to remove insoluble matters. The filtrate was concentrated to dryness under reduced pressure and the residue was dissolved in chloroform. The resultant chloroform solution was washed with water and the solvent was distilled off. The residue was purified by chromatography on a silica gel column (eluent: chloroform/methanol=100/0-2, by volume), followed by recrystallization from ethanol, whereby 3.57 g of 1,3-dimethyl-6-{4-[3-(2,6-dichloro-4-nitrophenyloxy)propyl]-piperazin-1-yl}-2,4(1H,3H)-pyrimidinedione as crystals.

Analytical results of the pyrimidinedione derivative thus obtained:

NMR (CDCl$_3$), δppm: 1.95-2.25(m,2H), 2.5-2.8(m,6H), 2.9-3.1(m,4H), 3.3(s,3H), 3.4(s,3H), 4.2(t,2H), 5.35(s,1H), 8.25(s,2H).

Next, 0.5 g of the pyrimidinedione derivative was treated in a 10%HCl/methanol solution by a method known per se in the art to obtain 0.45 g of 1,3-dimethyl-6-{4-[3-(2,6-dichloro-4-nitrophenyloxy)propyl]piperazin-1-yl}-2,4(1H,3H)-pyrimidinedione hydrochloride (Compound 165) as crystals.

Analytical results of crystals of Compound 165 thus obtained:

Melting point: 200°-202° C.
Elemental analysis for $C_{19}H_{23}Cl_2N_5O_5 \cdot HCl \cdot \frac{1}{4}H_2O$:
Calculated (%): C, 44.46; H, 4.81; N, 13.64; Cl, 20.72.
Found (%): C, 44.47; H, 4.87; N, 13.55; Cl, 20.73.

EXAMPLE 107

Production of tablets containing as an effective ingredient 1,3-dimethyl-6-{4-[3-(4-chloro-2-nitrophenyloxy)propyl]piperazin-1-yl}-2,4(1H,3H)-pyrimidinedione hydrochloride (Compound 140) available by the process of Example 85

1 g of the pyrimidinedione derivative hydrochloride (Compound 140), 123 g of lactose and 20 g of corn starch were finely mixed. Using a solution of 5 g of hydroxypropylcellulose in 100 ml of water, the resultant mixture was granulated. The resultant particles were dried at 50° C. for 4 hours and then mixed thoroughly with 1 g of magnesium stearate. The thus-prepared mixture was then compressed into tablets, each containing 150 mg, by a tablet machine.

EXAMPLE 108

Production of capsules containing as an effective ingredient 1,3-dimethyl-6-{4-[3-(2-chloro-4-nitrophenyloxy)propyl]piperazin-1-yl}-2,4(1H,3H)-pyrimidinedione hydrochloride (Compound 141) available by the process of Example 86

5 g of the pyrimidinedione derivative hydrochloride (Compound 141), 120 g of lactose and 25 g of corn starch were finely mixed. The resulting mixture was filled into hard capsules, each containing 150 mg, by a capsule filling machine.

EXAMPLE 109

Production of injection containing as an effective ingredient 1,3-dimethyl-6-{4-[3-(4-methanesulfonamido-2-nitrophenyloxy)propyl]piperazin-1-yl}-2,4(1H,3H)-pyrimidinedione hydrochloride (Compound 142) available by the process of Example 87

20 mg of the pyrimidinedione derivative hydrochloride (Compound 142) and 0.85 g of sodium chloride were weighed. They were dissolved in distilled water for injection to give a total volume of 100 ml, thereby preparing a formulation suitable for injection.

PHARMACOLOGICAL TEST 7

Similarly to Pharmacological Test 1, the $ADP_{75}$ and ERP of each of the compounds shown in Table 14 and obtained in the corresponding examples described above were determined. The results are summarized in Table 14.

TABLE 14

| | Result of Pharmacological Test | | | | | | |
|---|---|---|---|---|---|---|---|
| | Effects to duration time of myocardinal action potential $APD_{75}$ (%) Dose (µg/ml) | | | Effects to refractory period of ventricular muscle ERP (%) Dose (mg/kg, i.v.) | | | |
| Compound No. | 1.0 | 3.0 | 10.0 | 0.1 | 0.3 | 1.0 | 3.0 |
| 140 | 6 | 17 | 29 | 0 | 3.55 | 3.55 | — |
| 141 | 27 | 41 | — | 0 | 2.1 | 2.1 | 15 |
| 145 | 7 | 16 | 23 | 0 | 6.7 | 6.7 | 20 |
| 147 | 14 | 18 | — | 0 | 0 | 0 | — |
| 150 | — | 16 | — | 0 | 0 | 6.3 | 6.3 |
| 153 | 20 | 25 | — | 6.1 | 9.1 | 18.3 | — |
| 154 | 9 | 12 | 20 | 0 | 0 | 5.9 | 11.8 |
| 161 | 26 | 39 | — | 0 | 6.7 | 6.7 | 6.7 |
| 162 | 19 | 41 | 60 | 0 | 0 | 0 | 0 |
| 164 | — | 8 | 12 | 0 | 7.7 | 15.4 | 15.4 |

TOXICITY TEST 7

Similarly to Toxicity Test 1, the toxicity of each of the compounds shown in Table 15 and obtained in the corresponding examples described above was tested to determine the mortality rate of mice. The results are summarized in Table 15.

Incidentally, the administration of each compound was conducted orally (p.o.) at a dose of 300 mg/Kg.

TABLE 15

| Results of Toxicity Test on Novel Pyrimidine Derivative Compounds | |
|---|---|
| Compound No. | Mortality rate (%) |
| 141 | 0 |
| 145 | 0 |
| 147 | 0 |
| 148 | 0 |
| 161 | 0 |

EXAMPLE 110

Preparation of 1,3-dimethyl-6-{2-[N-methoxycarbonylmethyl-3-(4-nitroanilino)propylamino]ethylamino}-2,4(1H,3H)-pyrimidinedione hydrochloride (Compound 166)

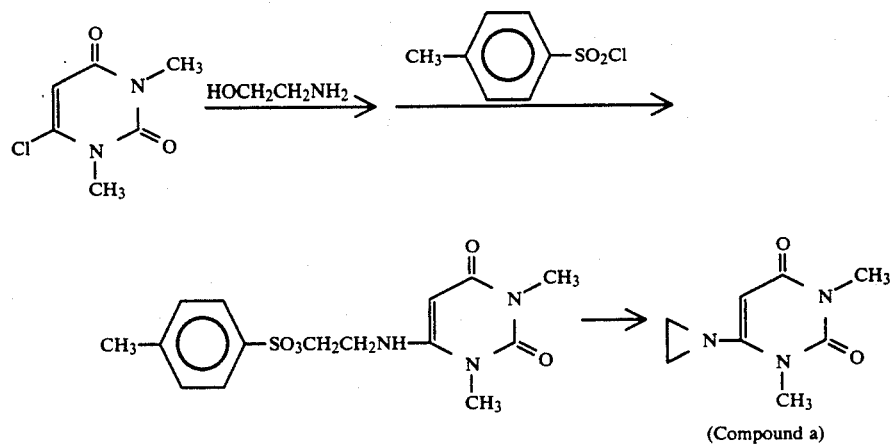

(Compound a)

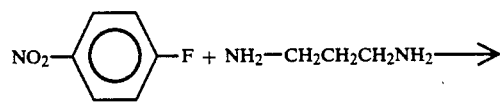

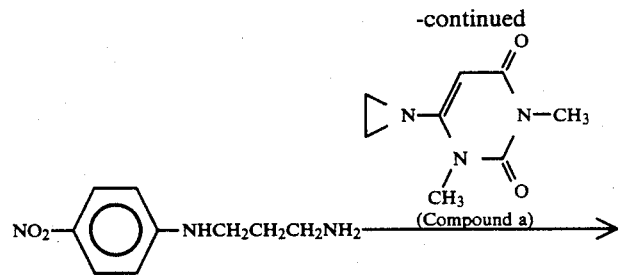

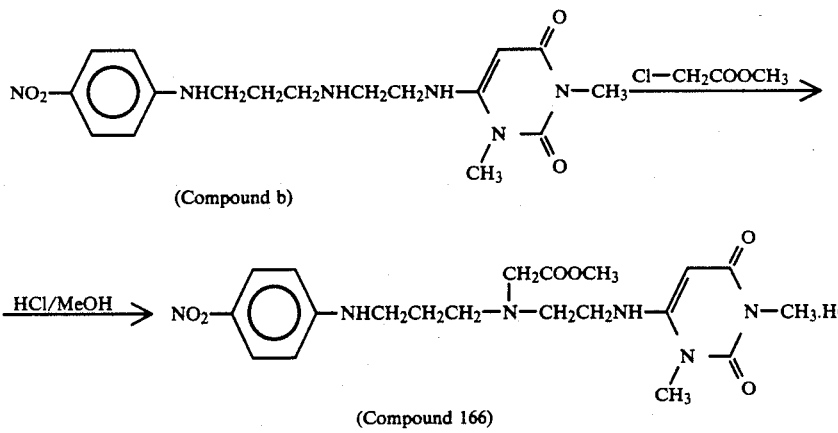

(Compound 166)

(1) Preparation of 1,3-dimethyl-6-[2-(p-toluenesulfonyloxy)ethylamino]-2,4(1H,3H)-pyrimidinedione 35.0 g of 2-aminoethanol were heated to 90° C. and then removed from an oil bath. 50.0 g of 6-chloro-1,3-dimethyl-2,4-(1H,3H)-pyrimidinedione were then added to react them to each other. The addition was conducted at such a rate that the reaction temperature was maintained within the range of 90°–110° C. After completion of the addition, the reaction mixture was stirred for 10 minutes, followed by the addition of 300 ml of dioxane/methanol (=10/1, by volume). The resultant mixture was allowed to stand overnight. Crystals thus obtained were washed with a small amount of dioxane and then dried to obtain 49.0 g of 1,3-dimethyl-6-(2-hydroxyethylamino)-2,4-(1H,3H)-pyrimidinedione as white crystals.

Next, a suspension of 49.0 g of the white crystals in 200 ml of pyridine was chilled to −5° C., to which 40.0 g of p-toluenesulfonyl chloride were added at a rate slow enough to maintain the reaction temperature below 5° C. To eliminate cloudiness from the reaction mixture, 51.0 g of p-toluenesulfonyl chloride were used additionally.

The reaction mixture was poured into 1.5 l of ice water in which 70 g of $K_2CO_3$ were contained. The thus-obtained mixture was allowed to stand overnight. Resulting crystals were collected by filtration, washed with water, and then dried under reduced pressure, thereby obtaining 50.5 g of 1,3-dimethyl-6-[2-(p-toluenesulfonyloxy)ethylamino]-2,4(1H,3H)-pyrimidinedione as pale yellow crystals.

Analytical results of crystals of the pyrimidinedione derivative thus obtained:

Melting point: 146.0°–149.0° C.

$IR\nu_{max}^{KBr}$ (cm$^{-1}$): 3270, 1682, 1615, 1550, 1480, 1435, 1360, 1190, 1178, 1010, 903, 780.

(2) Preparation of 6-(1-aziridinyl)-1,3-dimethyl-2,4(1H,3H)-pyrimidinedione (Compound a)

To a solution of 47.2 g of 1,3-dimethyl-6-[2-(p-toluenesulfonyloxy)ethylamino-2,4(1H,3H)-pyrimidinedione, which had been obtained in the above procedure, in 150 ml of anhydrous dimethylsulfoxide, 6.24 g of 60% oil-base sodium hydride were gradually added at room temperature. The resultant mixture was vigorously stirred at room temperature for 5 hours and then cooled. A small amount of water was added to terminate the reaction. The thus-obtained mixture was poured into 1 l of water which contained 70 g of potassium carbonate. The resultant mixture was extracted 3 times with 200 ml portions of chloroform. The extracts were combined into an organic layer. The organic layer was dried over anhydrous sodium sulfate and then concentrated. The concentrate thus prepared was added with 300 ml of ether and the resulting solution was allowed to stand overnight.

Pale yellow crystals which had precipitated by while the solution was allowed to stand overnight were collected by filtration, washed with ether and then dried under reduced pressure, whereby 15.2 g of 6-(1-aziridinyl)-1,3-dimethyl-2,4(1H,3H)-pyrimidinedione (Compound a) were obtained.

Analytical results of crystals of Compound a thus obtained:

Melting point: 126.0°–126.5° C.

$IR\nu_{max}^{KBr}$ (cm$^{-1}$): 1705, 1650, 1612, 1470, 1440, 1305, 1160, 783, 490.

$^1$H-NMR (CDCl$_3$), δppm: 2.34(s,4H), 3.35(s,3H), 3.56(s,3H), 5.25(s,1H).

(3) Preparation of 1,3-dimethyl-6-{2-[3-(4-nitroanilino)propylamino]ethylamino}-2,4(1H,3H)-pyrimidinedione (Compound b)

2.8 g of 4-nitrofluorobenzene were heated to 80° C. in 29.6 g of propylenediamine and then stirred for 1 hour at the same temperature. The reaction mixture was poured into water and precipitated crystals were collected by filtration, thereby obtaining 3.6 g of N-(4-nitrophenyl)propylenediamine as crystals.

After dissolving 1.2 g of N-(4-nitrophenyl)propylenediamine and 1.1 g of 6-(1-aziridinyl)-1,3- dimethyl-2,4(1H,3H)-pyrimidinedione (Compound a), which were obtained in the above procedure (2), in 5 ml of chloroform, the resultant mixture was concentrated under reduced pressure. The residue was added with 10 mg of "Amberlist 15" (trade name; product of Rohm & Hass Co.) and stirred at 80° C. for 1 hour. The thus-obtained mixture was dissolved in 20 ml of chloroform and "Amberlist 15" was filtered off. The filtrate was washed with water and dried over anhydrous sodium salfate. The solvent was then distilled off under reduced pressure to obtain 1,3-dimethyl-6-{2-[3-(4-nitroanilino)-propylamino]ethylamino}-2,4(1H,3H)-pyrimidinedione (Compound b) in a crude form. Although the reaction product obtained by the above procedure contained impurities, it was provided for the next reaction without purification.

(4) Synthesis of 1,3-dimethyl-6-{2-[N-methoxycarbonylmethyl-3-(4-nitroanilino)propylamino]ethylamino}-2,4(1H,3H)-pyrimidinedione hydrochloride (Compound 166)

1.5 g of 1,3-dimethyl-6-{2-[3-(4-nitroanilino)-propylamino]ethylamino}-2,4(1H,3H)-pyrimidinedione (Compound b) obtained in the above procedure (3) were dissolved in 12 ml of DMSO, followed by the addition of 1.2 g of methyl chloroacetate and 1.5 ml of triethylamine. The resultant mixture was stirred at 50° C. for 2 hours, dissolved in chloroform, washed with water and then dried over anhydrous sodium sulfate. The solvent was thereafter distilled off under reduced pressure. The residue was purified by chromatography on a silica gel column (eluent: chloroform/methanol=30/1, by volume), thereby obtaining 1.8 g of 1,3-dimethyl-6-{2-[N-methoxycarbonylmethyl-3-(4-nitroanilino)propylamino]ethylamino}-2,4(1H,3H)-pyrimidinedione.

Analytical results of crystals of the pyrimidinedione derivative thus obtained:
NMR (DMSO-d6), δppm: 1.70(m,2H), 2.6–2.9(m,4H), 2.95–3.4(m,4H), 3.25(s,3H), 3.3(s,3H), 3.45(s,2H), 3.65(s,3H), 4.6(s,1H), 6.45(m,1H), 6.6(d,2H), 7.2(m,1H), 7.95(d,2H).

Further, 1.5 g of the pyrimidinedione derivative were treated in an HCl/methanol solution by a method known per se in the art to obtain 1.4 g of 1,3-dimethyl-6-{2-[N-methoxycarbonylmethyl-3-(4-nitroanilino)-propylamino]ethylamino}-2,4(1H,3H)-pyrimidinedione hydrochloride (Compound 166) as amorphous powder.

Elemental analysis for $C_{20}H_{28}N_6O_6 \cdot HCl \cdot H_2O$:
Calculated (%): C, 47.76; H, 6.21; N, 16.71; Cl, 7.05.
Found (%): C, 47.06; H, 5.91; N, 16.05; Cl, 7.58.

EXAMPLE 111

Preparation of 1,3-dimethyl-6-{2-[N-(2-acetoxyethyl)-3-(4-nitrophenyl)propylamino]ethylamino}-2,4(1H,3H)-pyrimidinedione oxalate (Compound 167)

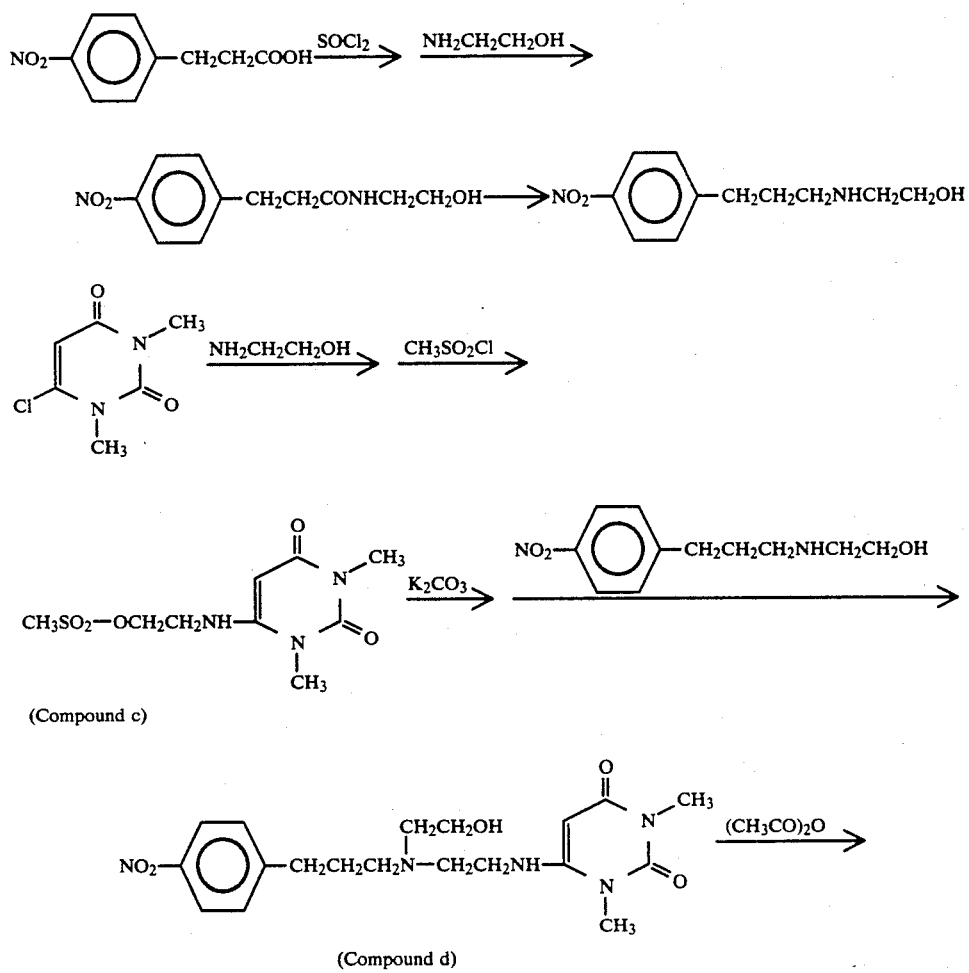

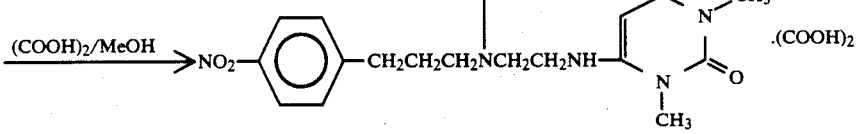

(Compound 167)

(1) Preparation of N-(2-hydroxyethyl)-3-(4-nitrophenyl)propionamide 60 g of 3-(4-nitrophenyl)propionic acid were suspended in 360 ml of chloroform, followed by the addition of 2.25 g of dimethylformamide. The thus-prepared reaction mixture was heated at 50°–60° C., to which 33.5 ml of thionyl chloride were gradually added dropwise. After the dropwise addition, the resultant mixture was heated under reflux for 1 hour, the solvent was distilled off under reduced pressure, and the resultant oily substance was dissolved in 150 ml of chloroform. The chloroform solution was added dropwise under ice cooling into a solution which had been formed by dissolving 28.2 g of ethanolamine and 42.5 g of potassium carbonate in 450 ml of water. After completion of the dropwise addition, the resultant mixture was stirred for 1 hour. Precipitated crystals were collected by filtration and then recrystallized from 1 of ethyl acetate, thereby obtaining 56.1 g of N-(2-hydroxyethyl)-3-(4-nitrophenyl)propionamide as crystals.

Melting point: 122°–125° C.

(2) Preparation of N-(2-hydroxyethyl)-3-(4-nitrophenyl)propylamine 50 g of N-(2-hydroxyethyl)-3-(4-nitrophenyl)propionamide obtained in the above procedure and 31.8 g of sodium borohydride were suspended in 500 ml of tetrahydrofuran, followed by the dropwise addition of 50.5 g of acetic acid under ice-cooling. After completion of the dropwise addition, the resultant mixture was heated under reflux for 2 hours. It was again ice-cooled, followed by the dropwise addition of 500 ml of water. 4 N hydrochloric acid was added to adjust the pH to 5–6 and tetrahydrofuran was distilled off under reduced pressure. The resultant aqueous solution was added with 425 ml of 4 N hydrochloric acid and the mixture thus prepared was heated at 60°–70° C. for 1 hour under stirring. The reaction mixture was allowed to cool down to room temperature and washed with chloroform. The resultant aqueous solution was adjusted to pH 11 with a 16% aqueous solution of sodium hydroxide and then extracted twice with 500 ml portions of chloroform. The chloroform extracts were combined together and then concentrated under reduced pressure. The residue was crystallized from 900 ml of toluene, thereby obtaining 38.6 g of N-(2-hydroxyethyl)-3-(4-nitrophenyl)propylamine as crystals.

Melting point: 82.5°–84.5° C.

(3) Preparation of 1,3-dimethyl-6-(2-methanesulfonyloxyethylamino)-2,4(1H,3H)-pyrimidinedione (Compound c)

52.4 g of 6-chloro-1,3-dimethyl-2,4(1H,3H)-pyrimidinedione were dissolved in 280 ml of pyridine, followed by the addition of 45.5 g of triethylamine and 21.3 g of aminoethanol. The thus-prepared mixture was heated under reflux at 90° C. for 4 hours. The reaction mixture was ice-cooled and while maintaining the internal temperature at 0°–4° C., 55.8 g of methanesulfonyl chloride were added dropwise. The resultant mixture was stirred for 3 hours at the same temperature. 1.2 l of methanol were added, followed by stirring for additional 2 hours. Crytals precipitated in the reaction mixture were collected by filtration and then recrystallized from 3.5 l of methanol, thereby obtaining 70.0 g of 1,3-dimethyl-6-(2-methanesulfonyloxyethylamino)-2,4(1H,3H)-pyrimidinedione (Compound c) as crystals.

Melting point: 169°–170° C.

(4) Preparation of 1,3-dimethyl-6-{2-[N-(2-hydroxyethyl)-3-(4-nitrophenyl)propylamino]ethylamino}-2,4(1H,3H)-pyrimidinedione (Compound d)

20.2 g of 1,3-dimethyl-6-(2-methanesulfonyloxyethylamino)-2,4(1H,3H)-pyrimidinedione (Compound c), which had been synthesized in the above procedure (3), and 15.1 g of potassium carbonate were suspended in 300 ml of acetonitrile. The resultant mixture was heated under reflux for 4 hours. Insoluble matters were filtered off, and the filtrate was concentrated under reduced pressure to the total volume of about 60 ml, followed by the addition of 18 g of N-(2-hydroxyethyl)-3-(4-nitrophenyl)propylamine obtained in the above procedure (2), 36 ml of DMF and 0.69 g of p-toluenesulfonic acid monohydrate. Under reduced pressure, acetonitrile was distilled off. The residue was heated under stirring at 80° C. for 2 hours. The reaction mixture was cooled to room temperature, to which 900 ml of 0.1 N hydrochloric acid were added to dissolve insoluble matters. Thereafter, a 0.5 M aqueous solution of potassium carbonate was added to render the mixture alkaline. The thus-prepared mixture was stirred at room temperature for 3 hours. Precipitated crystals were collected by filtration, dried and then recrystallized from ethanol, thereby obtaining 26.6 g of 1,3-dimethyl-6-{2-[N-(2-hydroxyethyl)-3-(4-nitrophenyl)propylamino]ethylamino}-2,4(1H,3H)-pyrimidinedione (Compound d) as crystals.

Melting point: 125°–126° C.

(5) Preparation of 1,3-dimethyl-6-{2-[N-(2-acetoxyethyl)-3-(4-nitrophenyl)propylamino]ethylamino}-2,4-(1H,3H)-pyrimidinedione oxalate (Compound 167)

1.6 g of 1,3-dimethyl-6-{2-[N-(2-hydroxyethyl)-3-(4-nitrophenyl)propylamino]ethylamino}-2,4(1H,3H)-pyrimidinedione (Compound d) and 0.8 g of acetic anhydride were dissolved in 5 ml of pyridine. The resultant mixture was stirred at room temperature for 24 hours and then at 60° C. for 1 hour. The reaction mixture was poured into water and extracted with chloroform. The extract was washed with water and then concentrated. The residue was purified by chromatography on a silica gel column (eluent: chloroform/methanol=25/1–10/1, by volume), thereby obtaining 1.65 g of 1,3-dimethyl-6-{2-[N-(2-acetoxyethyl)-3-(4-nitrophenyl)propylamino]ethylamino}-2,4(1H,3H)-pyrimidinedione as crystals.

Analytical results of crystals of the pyrimidinedione derivative thus obtained:

Melting point: 90.5°–92.0° C.

NMR (CDCl$_3$), δppm: 1.85 (m,2H), 2.15(s,3H), 2.5–3.3(m,10H), 3.26(s,3H), 3.37(s,3H), 4.3(t,2H), 4.78(s,1H), 7.2–8.2(m,4H).

Further, 1.5 g of the pyrimidinedione derivative were treated in an oxalic acid/methanol solution by a method known per se in the art to obtain 1.6 g of 1,3-dimethyl-6-{2-[N-(2-acetoxyethyl)-3-(4-nitrophenyl)-propylamino]ethylamino}-2,4(1H,3H)-pyrimidinedione oxalate (Compound 167) as crystals.

Analytical results of crytals of Compound 167 thus obtained:

Elemental analysis for $C_{21}H_{29}N_5O_6 \cdot (COOH)_2 \cdot H_2O$:
Calculated (%): C, 49.73; H, 5.99; N, 12.61.
Found (%): C, 50.22; H, 5.75; N, 12.98.

EXAMPLE 112

Preparation of 1,3-dimethyl-6-{2-[N-(2-benzoyloxyethyl)-3-(4-nitrophenyl)propylamino]ethylamino}-2,4(1H,3H)-pyrimidinedione oxalate (Compound 168)

zoyloxyethyl)-3-(4-nitrophenyl)propylamino]ethylamino}-2,4(1H,3H)-pyrimidinedione were obtained.

Analytical results of the pyrimidinedione derivative thus obtained:

NMR (CDCl$_3$), δppm: 1.93 (m,2H), 2.5–3.4(m,10H), 3.29(s,3H), 3.38(s,3H), 4.45(t,2H), 4.77(s,1H), 7.0–8.2(m,9H).

Further, 1.5 g of the pyrimidinedione derivative were treated in an oxalic acid/methanol solution by a method known per se in the art to obtain 1.4 g of 1,3-dimethyl-6-{2-[N-(2-benzoyloxyethyl)-3-(4-nitro phenyl)-propylamino]ethylamino}-2,4(1H,3H)-pyrimidinedione oxalate (Compound 168) as crystals.

Analytical results of crytals of Compound 168 thus obtained:

Elemental analysis for $C_{26}H_{31}N_5O_6 \cdot (COOH)_2 \cdot H_2O$:
Calculated (%): C, 54.45: H, 5.71: N, 11.34.
Found (%): C, 54.90; H, 5.55; N, 11.55.

EXAMPLE 113

Preparation of 1,3-dimethyl-6-{2-<N-[2-(4-fluorobenzoyloxy)ethyl]-3-(4-nitrophenyl)-propylamino>ethylamino}-2,4(1H,3H)-pyrimidinedione oxalate (Compound 169)

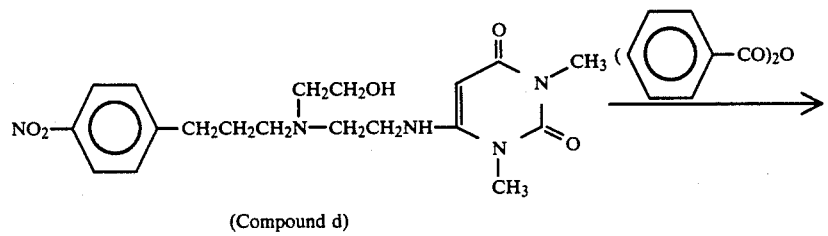

(Compound d)

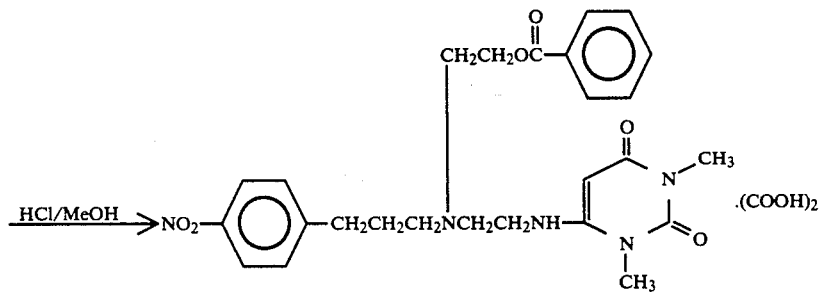

(Compound 168)

In a similar manner to Example 111-(5) except for the use of 1.6 g of benzoic anhydride in place of acetic anhydride, 1.85 g of 1,3-dimethyl-6-{2-[N-(2-ben-

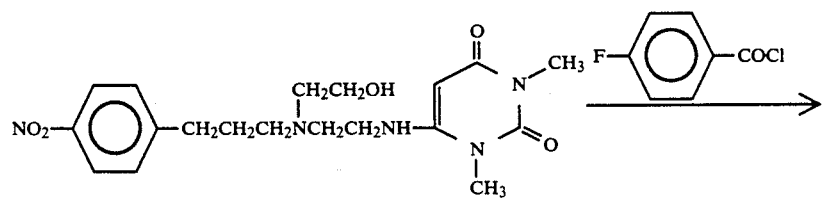

-continued

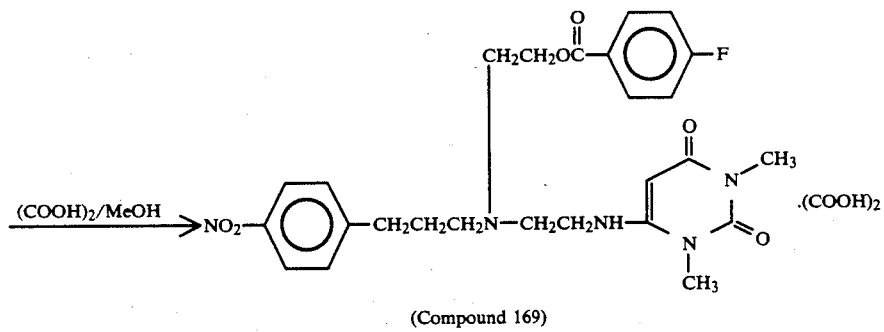

(Compound 169)

1.0 g of 1,3-dimethyl-6-{2-[N-(2-hydroxyethyl)-3-(4-nitrophenyl)propylamino]ethylamino}-2,4(1H,3H)-pyrimidinedione (Compound d), which had been obtained in Example 111-(4), and 0.8 g of p-fluorobenzoyl chloride were dissolved in 5 ml of pyridine. The resultant mixture was stirred at room temperature for 12 hours, poured into water, and then extracted with chloroform. The extract was washed with water and then concentrated. The residue was purified by chromatography on a silica gel column (eluent: chloroform/methanol=40/1, by volume), thereby obtaining 1.0 g of 1,3-dimethyl-6-{2-<N-[2-(4-fluorobenzoyloxy)ethyl]-3-(4-nitrophenyl)propylamino>ethylamino}-2,4(1H,3H)-pyrimidinedione.

Analytical results of crystals of the pyrimidinedione derivative thus obtained:

NMR (CDCl$_3$), δppm: 1.9–3.1(m,12H), 3.29(s,1H), 3.38(s,3H), 4.59(t,2H), 4.78(s,1H), 7.1–8.0(m,8H).

Further, 0.95 g of the pyrimidinedione derivative was treated in an oxalic acid/methanol solution by a method known per se in the art to obtain 1.07 g of 1,3-dimethyl-6-{2-<N-[2-(4-fluorobenzoyloxy)ethyl]-3-(4-nitrophenyl)propylamino>ethylamino}-2,4(1H,3H)-pyrimidinedione oxalate (Compound 169) as crystals.

Analytical results of crytals of Compound 169 thus obtained:

Melting point: 96°–99° C. (decomposed).
Elemental analysis for C$_{26}$H$_{30}$N$_5$O$_6$F·(COOH)$_2$·2H$_2$O:
Calculated (%): C, 51.45; H, 5.55; N, 10.71.

Found (%): C, 51.82; H, 5.40; N, 10.82.
IRν$_{max}$$^{KBr}$ (cm$^{-1}$): 3350, 2950, 1740, 1700, 1620, 1530, 1330, 1000, 850, 760.

EXAMPLE 114

Preparation of 1,3-dimethyl-6-{2-<N-[2-(4-methoxybenzoyloxy)ethyl]-3-(4-nitrophenyl)propylamino>ethylamino}-2,4(1H,3H)-pyrimidinedione oxalate (Compound 170)

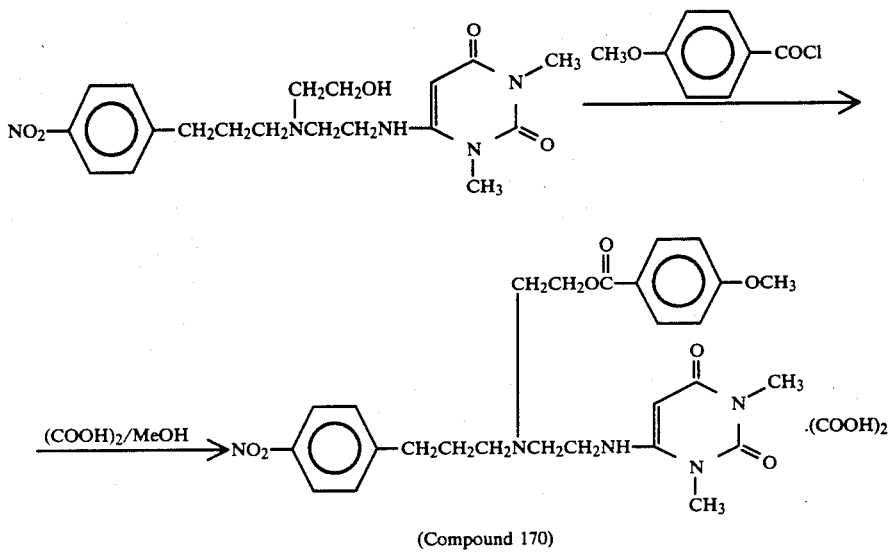

(Compound 170)

In a similar manner to Example 113 except for the use of 0.63 g of p-methoxybenzoyl chloride instead of p-fluorobenzoyl chloride, 1.1 g of 1,3-dimethyl-6-{2-<N-[2-(4-methoxybenzoyloxy)ethyl]-3-(4-nitrophenyl)propylamino>ethylamino}-2,4(1H,3H)-pyrimidinedione were obtained.

Analytical results of the pyrimidinedione derivative thus obtained:

NMR (CDCl$_3$), δppm: 2.0(m,2H), 2.4–3.0(m,10H), 3.31(s,3H), 3.42(s,3H), 3.50(s,3H), 4.4(t,2H), 4.77(s,1H), 5.31(br,1H), 7.18(m,4H), 8.0(m,4H).

Further, 1.0 g of the pyrimidinedione derivative were treated in an oxalic acid/methanol solution by a method known per se in the art to obtain 1.05 g of 1,3-dimethyl-6-{2-<N-[2-(4-methoxybenzoyloxy)ethyl]-3-(4-nitrophenyl)propylamino>ethylamino}-2,4(1H,3H)-pyrimidinedione oxalate (Compound 170) as crystals.

Analytical results of crytals of Compound 170 thus obtained:

Elemental analysis for C$_{27}$H$_{33}$N$_5$O$_7$·(COOH)$_2$·½H$_2$O:
Calculated (%): C, 54.54; H, 5.68; N, 10.97.

Found (%): C, 54.21; H, 5.99; N, 10.92.

IR$\nu_{max}^{KBr}$ (cm$^{-1}$): 3300, 2950, 1690, 1600, 1520, 1350, 1250, 1020, 850, 760.

EXAMPLE 115

Preparation of 1,3-dimethyl-6-{2-[N-(2-methoxyethyl)-3-(4-nitrophenyl)propylamino]ethylamino}-2,4(1H,3H)-pyrimidinedione oxalate (Compound 171)

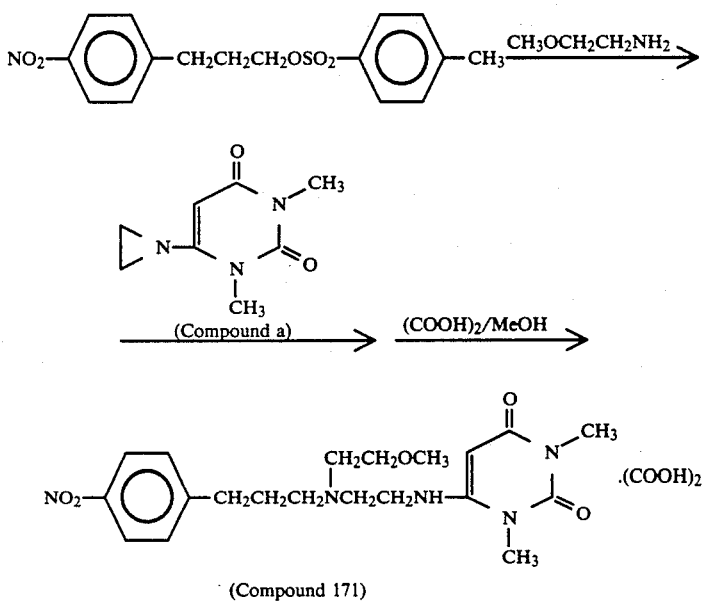

(Compound 171)

A mixture consisting of 1 g of 3-(4-nitrophenyl)propyl p-toluenesulfonate, 6.5 ml of 2-methoxyethylamine and 5 ml of dioxane was heated under reflux for 3 hours, followed by the addition of 100 ml of chloroform. The resultant mixture was washed with water and then dried over anhydrous sodium sulfate. The thus-prepared chloroform solution was added with 10 mg of p-toluenesulfonic acid and 0.54 g of 6-(1-aziridinyl)-1,3-dimethyl-2,4(1H,3H)-pyrimidinedione (Compound a) obtained in Example 110-(2), followed by the distillation of the solvent under reduced pressure. The mixture was then heated at 80° C. for 2 hours and then cooled down to the room temperature. The thus-obtained mixture was directly subjected to chromatographic purification on a silica gel column (eluent: chloroform/methanol=40/1, by volume), thereby obtaining 0.82 g of 1,3-dimethyl-6-{2-[N-(2-methoxyethyl)-3-(4-nitrophenyl)propylamino]ethylamino}-2,4(1H,3H)-pyrimidinedione as an oily substance.

Analytical results of the pyrimidinedione thus obtained:

NMR (CDCl$_3$), δppm: 1.9(m,2H), 2.4–3.6(m,12H), 3.23(s,3H), 3.30(s,3H), 3.33(s,3H), 4.71(s,1H), 5.74(br,1H), 7.19(d,2H), 8.03(d,2H).

Further, 0.80 g of the pyrimidinedione derivative was treated in an oxalic acid/methanol solution by a method known per se in the art to obtain 0.85 g of 1,3-dimethyl-6-{2-[N-(2-methoxyethyl)-3-(4-nitrophenyl)-propylamino]ethylamino}-2,4(1H,3H)-pyrimidinedione oxalate (Compound 171) as crystals.

Analytical results of crytals of Compound 171 thus obtained:

Elemental analysis for C$_{20}$H$_{29}$N$_5$O$_5$·(COOH)$_2$·H$_2$O:
Calculated (%): C, 50.09; H, 6.31; N, 13.28.
Found (%): C, 50.14; H, 6.39; N, 13.30.

IR$\nu_{max}^{KBr}$ (cm$^{-1}$): 3300, 3000, 1680, 1630, 1510, 1430, 1350, 1200, 770, 700.

EXAMPLE 116

Preparation of 1,3-dimethyl-6-{2-[N-benzyl-3-(4-nitrophenyl)propylamino]ethylamino}-2,4(1H,3H)-pyrimidinedione oxalate (Compound 172)

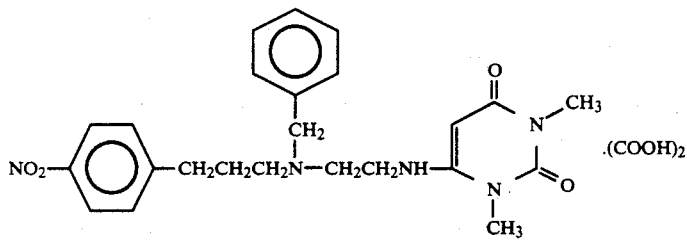

(Compound 172)

In a similar manner to Example 115 except for the use of 0.36 ml of benzylamine instead of 2-methoxyethylamine and the addition of 1 ml of triethylamine, 1.6 g of 1,3-dimethyl-6-{2-[N-benzyl-3-(4-nitrophenyl)-propylamino]ethylamino}-2,4(1H,3H)-pyrimidinedione were obtained.

Analytical results of crystals of the pyrimidinedione derivative thus obtained:

NMR (CDCl$_3$), δppm: 2.0(m,2H), 2.4–3.3(m,8H), 3.21(s,3H), 3.25(s,3H), 3.58(s,2H), 4.67(s,1H), 5.22(br,1H), 7.22(d,2H), 7.30(s,5H), 8.03(d,2H).

Further, 1.50 g of the pyrimidinedione derivative were treated in an oxalic acid/methanol solution by a method known per se in the art to obtain 1.55 g of 1,3-dimethyl-6-{2-[N-benzyl-3-(4-nitrophenyl)-propylamino]ethylamino}-2,4(1H,3H)-pyrimidinedione oxalate (Compound as crystals.

Analytical results of crytals of Compound 172 thus obtained:

Elemental analysis for C$_{24}$H$_{29}$N$_5$O$_4$·(COOH)$_2$·½H$_2$O:
Calculated (%): C, 56.72; H, 5.86; N, 12.72.
Found (%): C, 56.41; H, 5.82; N, 12.24.

IRν$_{max}^{KBr}$ (cm$^{-1}$): 3300, 2950, 1680, 1630, 1540, 1340, 1200, 770, 700.

EXAMPLE 117

Preparation of 1,3-dimethyl-6-{2-[N-(t-butoxycarbonyl)-3-(4-nitrophenyl)propylamino]ethylamino}-2,4(1H,3H)-pyrimidinedione (Compound 173)

(1) Preparation of 3-(4-nitrophenyl)propylamine

A solution of 21 g of 3-(4-nitrophenyl)propionyl chloride in 30 ml of chloroform was added dropwise into a mixture of 75 ml of concentrated aqueous ammonia and 75 ml of ice water. The resultant mixture was then stirred for 2 hours under ice-cooling. The resultant precipitate was collected by filtration, dried in air and recrystallized from ethyl acetate, thereby obtaining 13.7 g of 3-(4-nitrophenyl)propanamide.

10.0 g of the amide compound and 9.5 g of sodium borohydride were suspended in 250 ml of dioxane, followed by the dropwise addition of 15 ml of acetic acid. The resultant mixture was stirred for 10 hours under reflux. The reaction mixture was added with 10 ml of methanol and then concentrated to dryness. The residue was dissolved in chloroform. The solution thus obtained was washed with water and then concentrated to dryness, thereby obtaining 6.0 g of 3-(4-nitrophenyl)-propylamine as an oily substance. This compound was provided for the next reaction without any further purification.

NMR (CDCl$_3$), δppm: 1.9(m,2H), 2.4–3.0(m,4H), 6.70(br,2H), 8.31(d,2H), 8.10(d,2H).

(2) Preparation of 1,3-dimethyl-6-{2-[N-(t-butoxycarbonyl)-3-(4-nitrophenyl)propylamino]ethylamino}-2,4(1H,3H)-pyrimidinedione (Compound 173)

6.0 g of 3-(4-nitrophenyl)propylamine obtained in the above procedure (1) and 3.98 g of 6-(1-aziridinyl)-1,3-dimethyl-2,4(1H,3H)-pyrimidinedione (Compound a) obtained in Example 110-(2) were dissolved in 50 ml of chloroform, and the resultant mixture was concentrated

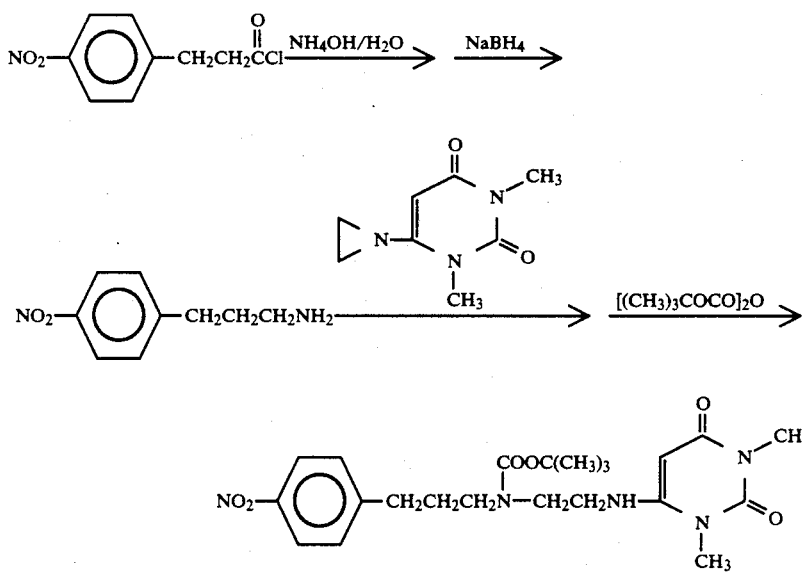

(Compound 173)

to dryness under reduced pressure. The residue was added with 50 mg of p-toluenesulfonic acid monohydrate and the mixture thus prepared was stirred at 90° C. for 2 hours. The mixture was dissolved in 60 ml of tetrahydrofuran, followed by the addition of 3.0 g of di-tert-butyldicarbonate. The thus-obtained mixture was stirred at room temperature for 1 hour and then concentrated. The residue was purified by chromatography on a silica gel column (eluent: chloroform/methanol=40/1, by volume), thereby obtaining 5.0 g of 1,3-dimethyl-6-{2-[N-(t-butoxycarbonyl)-3-(4-nitrophenyl)propylamino]ethylamino}-2,4(1H,3H)-pyrimidinedione (Compound 173) as crystals.

Analytical results of Compound 173 thus obtained:
Melting point: 111°–112° C.
NMR (CDCl$_3$), δppm: 1.51(s,9H), 1.9(m,2H), 2.5–3.0(m,6H), 3.3–3.4(m,2H), 3.28(s,3H), 3.36(s,3H), 4.68(s,1H), 6.54(br,1H), 7.39(d,2H), 8.20(d,2H).
Elemental analysis for $C_{22}H_{31}N_5O_6$:
Calculated (%): C, 57.25; H, 6.77; N, 15.17.
Found (%): C, 57.29; H, 6.76; N, 15.13.

EXAMPLE 118

Preparation of 1,3-dimethyl-6-{2-[N-(4-methoxybenzyl)-3-(4-nitrophenyl)propylamino]ethylamino}-2,4(1H,3H)-pyrimidinedione oxalate (Compound 174)

volume) of ethanol and ether, thereby obtaining 3.9 g of 1,3-dimethyl-6-{2-[3-(4-nitrophenyl)propylamino]ethylamino}-2,4(1H,3H)-pyrimidinedione hydrochloride (Compound e).

Analytical results of crystals of Compound e thus obtained:
Melting point: 230°–231° C. (decomposed).
Elemental analysis for $C_{17}H_{23}N_5O_4 \cdot 2HCl \cdot H_2O$:
Calculated (%): C, 45.14; H, 6.02; N, 15.48; Cl, 15.68.
Found (%): C, 45.31; H, 5.87; N, 15.54; Cl, 15.67.

(2) Preparation of 1,3-dimethyl-6-{2-[N-(4-methoxybenzyl)-3-(4-nitrophenyl)propylamino]ethylamino}-2,4(1H,3H)-pyrimidinedione oxalate (Compound 174)

1.4 g of 1,3-dimethyl-6-{2-[3-(4-nitrophenyl)propylamino]ethylamino}-2,4(1H,3H)-pyrimidinedione hydrochloride (Compound e) were dissolved in 5 ml of water, followed by the addition of potassium carbonate to render the solution alkaline. The solution was then extracted with chloroform. The thus-obtained chloroform solution was concentrated to dryness, followed by the addition of 0.6 g of p-methoxybenzyl bromide, 3 ml of triethylamine and 20 ml of isopropanol. The resultant mixture was heated for 8 hours under reflux. The solvent was distilled off under reduced pressure and the residue was directly subjected to chromatographic purification on a silica gel (eluent: chloroform/me-

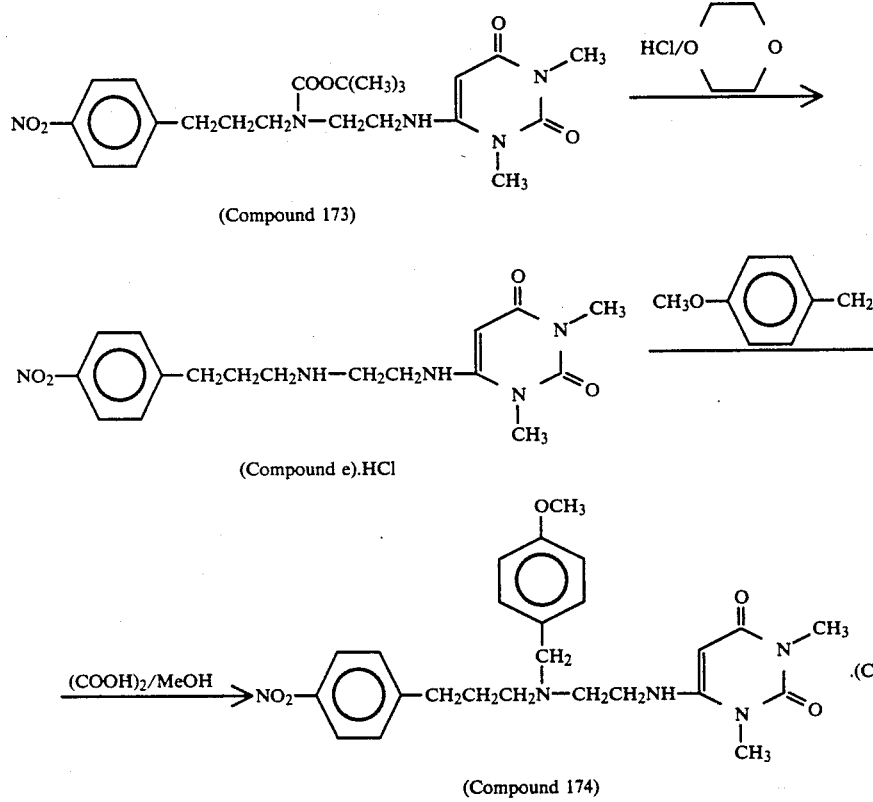

(Compound 173)

(Compound e).HCl (Compound 174)

(1) Preparation of 1,3-dimethyl-6-{2-[3-(4-nitrophenyl)propylamino]ethylamino}-2,4(1H,3H)-pyrimidinedione hydrochloride (Compound e)

30 ml of 0.5 N HCl/dioxane were added to 4.9 g of 1,3-dimethyl-6-{2-[N-(t-butoxycarbonyl)-3-(4-nitrophenyl)propylamino]ethylamino}-2,4(1H,3H)-pyrimidinedione (Compound 173). The resultant mixture was stirred at room temperature for 24 hours. Precipitated crystals were collected by filtration and then washed with a chilled solvent consisting of a 1:2 mixture (by thanol=40/1, by volume), thereby obtaining 0.55 g of 1,3-dimethyl-6-{2-[N-(4-methoxybenzyl)-3-(4-nitrophenyl)propylamino]ethylamino}-2,4(1H,3H)-pyrimidinedione.

Analytical results of the pyrimidinedione derivative thus obtained:

NMR (CDCl₃), δppm: 2.0(m,2H), 2.5-3.1(m,8H), 3.24(s,3H), 3.30(s,3H), 3.64(s,2H), 4.59(s,1H), 5.16(m,1H), 7.16(m,4H), 7.94(m,4H).

Further, 0.52 g of the pyrimidinedione derivative was treated in an oxalic acid/methanol solution by a method known per se in the art to obtain 0.54 g of 1,3-dimethyl-6-{2-[N-(4-methoxybenzyl)-3-(4-nitrophenyl)-propylamino]ethylamino}-2,4(1H,3H)-pyrimidinedione oxalate (Compound 174) as crystals.

Analytical results of crytals of Compound 174 thus obtained:

Melting point: 104°-106° C. (decomposed).

IR$\nu_{max}^{KBr}$ (cm⁻¹): 3300, 2950, 1710, 1700, 1630, 1520, 1340, 1250, 1070, 770, 700.

Elemental analysis for $C_{25}H_{31}N_5O_5$·(COOH)₂·1.5-H₂O:

Calculated (%): C, 54.18; H, 6.06; N, 11.70.
Found (%): C, 54.74; H, 5.97; N, 11.37.

EXAMPLE 119

Preparation of 1,3-dimethyl-6-{2-[N-ethoxycarbonylmethyl-3-(4-nitrophenyl)propylamino]ethylamino}-2,4(1H,3H)-pyrimidinedione oxalate (Compound 175)

propylamino]ethylamino}-2,4(1H,3H)-pyrimidinedione was obtained.

Analytical results of crystals of the pyrimidinedione derivative thus obtained:

NMR (CDCl₃), δppm: 1.30(t,3H), 1.9(m,2H), 2.4-3.0(m,6H), 3.0-3.4(m,4H), 3.3(s,3H), 3.5(s,3H), 4.22(q,2H), 4.74(s,1H), 7.31(d,2H), 8.12(d,2H).

Further, 0.7 g of the pyrimidinedione derivative was treated in an oxalic acid/methanol solution by a method known per se in the art to obtain 0.72 g of 1,3-dimethyl-6-{2-[N-ethoxycarbonylmethyl-3-(4-nitrophenyl)-propylamino]ethylamino}-2,4(1H,3H)-pyrimidinedione oxalate (Compound 175) as crystals.

Analytical results of crytals of Compound 175 thus obtained:

Melting point: 148°-149° C. (decomposed).

IR$\nu_{max}^{KBr}$ (cm⁻¹): 2930, 2450, 1730, 1700, 1600, 1540, 1340, 1250, 1200, 850, 750.

Elemental analysis for $C_{21}H_{29}N_5O_6$·(COOH)₂·½H₂O:
Calculated (%): C, 50.55; H, 5.90; N, 12.81.
Found (%): C, 50.89; H, 5.81; N, 12.62.

EXAMPLE 120

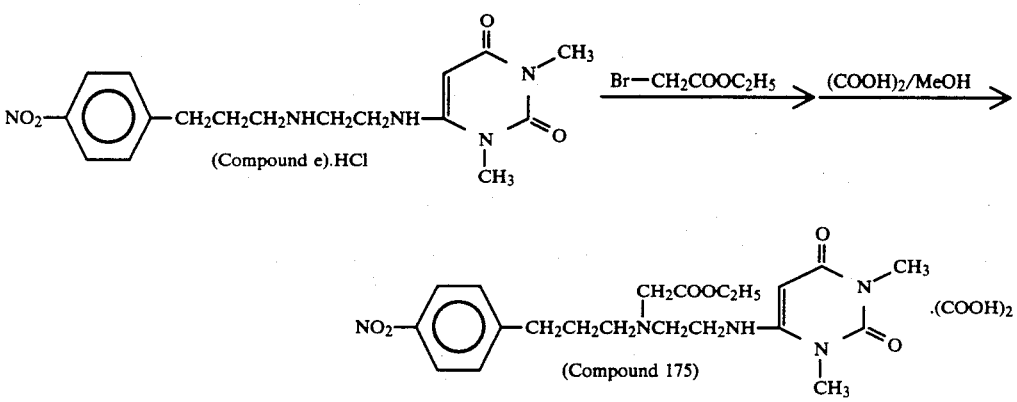

In a similar manner to Example 118-(2) except for the use of 0.4 ml of ethyl bromoacetate in place of p-methoxybenzyl bromide, 0.77 g of 1,3-dimethyl-6-{2-[N-(2-ethoxycarbonylmethyl-3-(4-nitrophenyl)-

Preparation of 1,3-dimethyl-6-{N-(2-phenylethyl)-2-[3-(4-nitrophenyl)propylamino]ethylamino}-2,4(1H,3H)-pyrimidinedione hydrochloride (Compound 176)

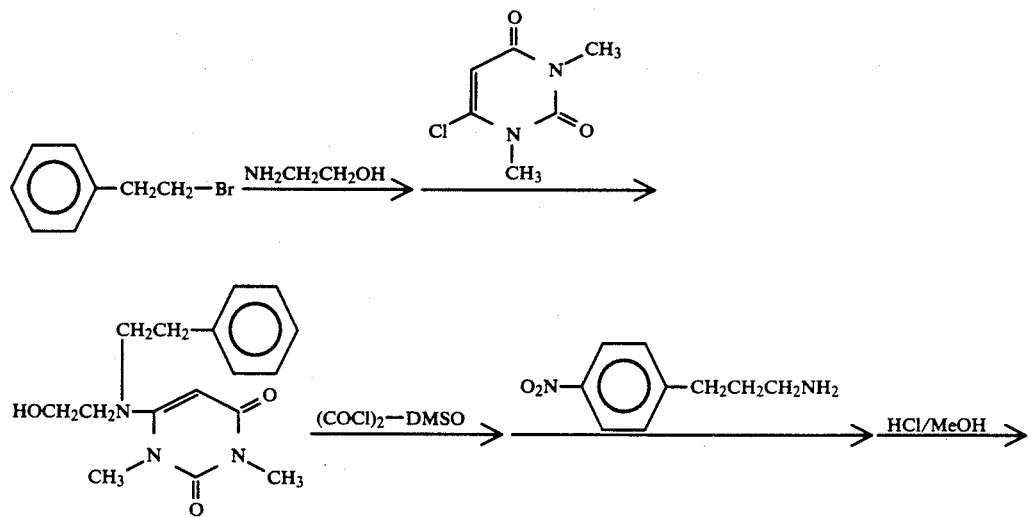

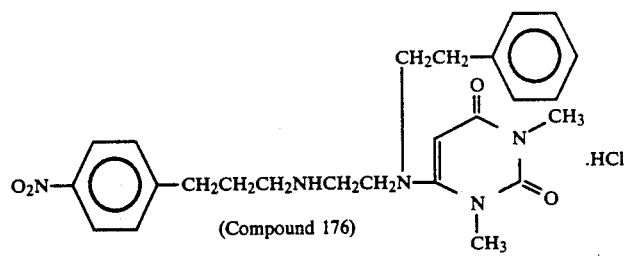

(Compound 176)

(1) Preparation of 1,3-dimethyl-6-[N-(2-hydroxethyl)-2-phenylethylamino]-2,4(1H,3H)-pyrimidinedione A mixture consisting of 3 ml of phenethyl bromide, 13 ml of ethanolamine and 15 ml of isopropanol was heated for 2 hours under reflux. After allowing the reaction mixture to cool down, 50 ml of chloroform were added. The thus-prepared mixture was washed with water and then concentrated to obtain an oily substance. To the oily substance, 3.5 g of 6-chloro-1,3-dimethyl-2,4(1H,3H)-pyrimidinedione and 3.3 ml of triethylamine were added. The resultant mixture was dissolved in 15 ml of dimethylformamide and stirred at 110° C. for 4 hours. The solution was cooled down to room temperature, followed by the addition of 150 ml of chloroform. The resultant chloroform solution was washed with water and then concentrated to obtain an oily substance. By crystallizing the oily substance from ether, 4.1 g of 1,3-dimethyl-6-[N-(2-hydroxyethyl)-2-phenylethylamino]-2,4(1H,3H)-pyrimidinedione were obtained as crystals.

Analytical results of crystals of the pyrimidinedione derivative thus obtained:

Melting point: 77°-78° C.

NMR (CDCl$_3$), δppm: 2.4–3.2(m,6H), 3.18(s,3H), 3.22(s,3H), 3.50(t,2H), 5.28(s,1H), 7.18(br,5H).

Elemental analysis for $C_{16}H_{21}N_3O_3$:

Calculated (%): C, 63.35; H, 6.98; N, 13.85.

Found (%): C, 63.01; H, 6.78; N, 13.91.

(2) Preparation of 1,3-dimethyl-6-{N-(2-phenylethyl)-2-[3-(4-nitrophenyl)propylamino]ethylamino}-2,4(1H,3H)-pyrimidinedione hydrochloride (Compound 176)

0.26 ml of oxalyl chloride was dissolved in ml of dichloromethane. The resultant mixture was chilled to −78° C., followed by the dropwise addition of a solution of 0.21 ml of dimethylsulfoxide in 5 ml of dichloromethane. The thus-prepared mixture was stirred for 15 minutes at the same temperature, followed by the dropwise addition of a solution of 0.6 g of 1,3-dimethyl-6-[N-(2-hydroxyethyl)-2-phenylethylamino]-2,4(1H,3H)-pyrimidinedione in 10 ml of dichloromethane. The mixture was stirred for further 15 minutes. After adding 0.84 ml of triethylamine, the mixture was gradually cooled to room temperature and then stirred for 5 minutes. 30 ml of chloroform were added. The mixture thus obtained was washed with water and then dried over anhydrous sodium sulfate. The solvent was distilled off under reduced pressure to obtain 0.51 g of an oily substance.

The oily substance was dissolved in 10 ml of methanol, followed by the addition of 0.72 g of 3-(4-nitrophenyl)propylamine obtained in Example 117-(1) and 0.5 ml of 4 N-HCl/dioxane. The resulting mixture was stirred at room temperature for 30 minutes and 1 g of sodium cyanoborohydride was added in several small portions. After stirring the mixture at room temperature for 12 hours, 1 N hydrochloric acid was added to acidify the reaction mixture. Methanol was distilled off and potassium carbonate was added to neutralize the residue. The thus-prepared solution was extracted with chloroform and the chloroform layer was concentrated to dryness. The residue was purified by chromatography on a silica gel column (eluent: chloroform/methanol=40/1, by volume), thereby obtaining 0.2 g of 1,3-dimethyl-6-{N-(2-phenylethyl)-2-[3-(4-nitrophenyl)propylamino]ethylamino}-2,4(1H,3H)-pyrimidinedione.

Analytical results of crystals of the pyrimidinedione derivative thus obtained:

NMR (CDCl$_3$), δppm: 1.9(m,2H), 2.6–3.6(m,12H), 3.18(s,3H), 3.26(s,3H), 5.28(s,1H), 7.18(br,5H), 7.30(d,2H), 8.09(d,2H).

Further, 0.19 g of the pyrimidinedione derivative was treated in a 1 N-HCl/methanol solution by a method known per se in the art to obtain 0.12 g of 1,3-dimethyl-6-{N-(2-phenylethyl)-2-[3-(4-nitrophenyl)propylamino]ethylamino}-2,4(1H,3H)-pyrimidinedione hydrochloride (Compound 176) as crystals.

Analytical results of crystals of Compound 176 thus obtained:

Elemental analysis for $C_{25}H_{31}N_5O_4 \cdot HCl \cdot 3H_2O$:

Calculated (%): C, 54.00; H, 6.89; N, 12.59; Cl, 6.38.

Found (%): C, 53.81; H., 6.74; N, 12.11; Cl, 5.91.

IR$\nu_{max}^{KBr}$ (cm$^{-1}$): 3420, 2610, 1700, 1600, 1620, 1550, 1320, 1010, 820, 780, 750.

EXAMPLE 121

Preparation of 1,3-dimethyl-6-{2-[N-allyl-3-(4-nitrophenyl)propylamino]ethylamino}-2,4(1H,3H)-pyrimidinedione oxalate (Compound 177)

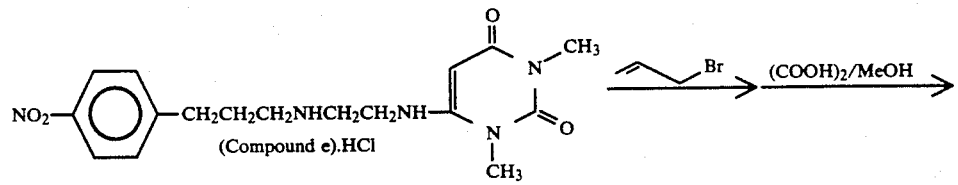

-continued

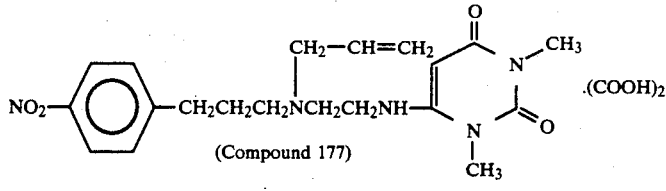
(Compound 177)

In a similar manner to Example 118-(2) except for the use of 0.38 ml of allyl bromide in place of p-methoxybenzyl bromide, 0.9 g of 1,3-dimethyl-6-{2-N-allyl-3-(4-nitrophenyl)propylamino]ethylamino}-2,4(1H,3H)-pyrimidinedione was obtained.

Analytical results of crystals of the pyrimidinedione derivative thus obtained:
Melting point: 109°-111° C.
NMR (CDCl$_3$), δppm: 2.0(m,2H), 2.5-3.1(m,10H), 3.26(s,3H), 3.34(s,3H), 4.75(s,1H), 5.16(m,2H), 5.63(m,1H), 7.25(d,2H), 8.04(d,2H).

Further, 0.80 g of the pyrimidinedione derivative was treated in an oxalic acid/methanol solution by a method known per se in the art to obtain 0.75 g of 1,3-dimethyl-6-{2-[N-allyl-3-(4-nitrophenyl)propylamino]ethylamino}-2,4(1H,3H)-pyrimidinedione oxalate (Compound as crystals.

Analytical results of crytals of Compound 177 thus obtained:
Melting point: 85°-90° C.
Elemental analysis for C$_{20}$H$_{27}$N$_5$O$_4$·(COOH)$_2$·$\frac{1}{2}$H$_2$O:
Calculated (%): C, 50.96; H, 6.22; N, 13.51.
Found (%): C, 51.30; H, 6.26; N, 13.24.
IR$\nu_{max}^{KBr}$ (cm$^{-1}$): 3250, 2940, 1690, 1620, 1540, 1340, 1160, 990, 850, 770, 700.

EXAMPLE 122

Preparation of 1,3-dimethyl-6-{2-[N-propargyl-3-(4-nitrophenyl)proylamino]ethylamino}-2,4(1H,3H)-pyrimidinedione oxalate (Compound 178)

Further, 0.80 g of the pyrimidinedione derivative was treated in an oxalic acid/methanol solution by a method known per se in the art to obtain 0.75 g of 1,3-dimethyl-6-{2-[N-propargyl-3-(4-nitrophenyl)propylamino]ethylamino}-2,4(1H,3H)-pyrimidinedione oxalate (Compound 178) as crystals.

Analytical results of crytals of Compound 178 thus obtained:
Melting point: 170°-172° C.
Elemental analysis for C$_{20}$H$_{25}$N$_5$O$_4$·(COOH)$_2$·$\frac{1}{2}$H$_2$O:
Calculated (%): C, 53.01; H, 5.66; N, 14.05.
Found (%): C, 53.31; H, 5.63; N, 14.18.
IR$\nu_{max}^{KBr}$ (cm$^{-1}$): 3250, 2600, 1640, 1620, 1530, 1340, 770, 700.

EXAMPLE 123

Production of tablets containing as an effective ingredient 1,3-dimethyl-6-{2-[N-(2-acetoxyethyl)-3-(4-nitrophenyl)propylamino]ethylamino}-2,4-(1H,3H)-pyrimidinedione oxalate (Compound 167) available by the process of Example 111

1 g of the pyrimidinedione derivative oxalate (Compound 167), 123 g of lactose and 20 g of corn starch were finely mixed. Using a solution of 5 g of hydroxypropylcellulose in 100 ml of water, the resultant mixture was granulated. The resultant particles were dried at 50° C. for 4 hours and then mixed thoroughly with 1 g of magnesium stearate. The thus-prepared mixture was then compressed into tablets, each containing 150 mg, by a tablet machine.

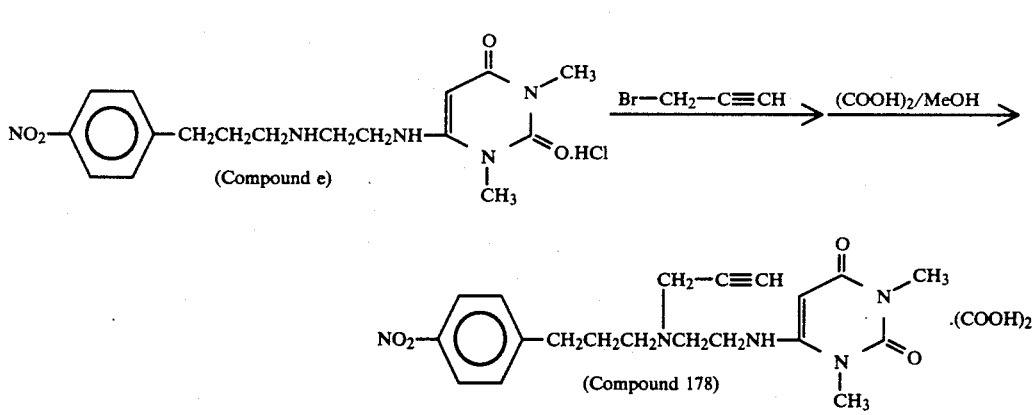

In a similar manner to Example 118-(2) except for the use of 0.37 ml of propargyl bromide in place of p-methoxybenzyl bromide, 0.85 g of 1,3-dimethyl-6-{2-[N-propargyl-3-(4-nitrophenyl)propylamino]ethylamino}-2,4(1H,3H)-pyrimidinedione was obtained.

Analytical results of crystals of the pyrimidinedione derivative thus obtained:
Melting point: 156°-157° C.
NMR (CDCl$_3$), δppm: 1.9(m,2H), 2.23(m,1H), 2.4-3.1(m,10H), 3.25(s,3H), 3.34(s,3H), 4.73(s,1H), 5.22(br,1H), 7.27(d,2H), 8.04(d,2H).

EXAMPLE 124

Production of capsules containing as an effective ingredient 1,3-dimethyl-6-{2-[N-benzyl-3-(4-nitrophenyl)propylamino]ethylamino}-2,4(1H,3H)-pyrimidinedione oxalate (Compound 172) available by the process of Example 116

5 g of the pyrimidinedione derivative oxalate (Compound 172), 120 g of lactose and 25 g of corn starch were finely mixed. The resulting mixture was filled into hard capsules, each containing 150 mg, by a capsule filling machine.

EXAMPLE 125

Production of injection containing as an effective ingredient 1,3-dimethyl-6-{2-[N-ethoxycarbonylmethyl-3-(4-nitrophenyl)propylamino]ethyl-2,4(1H,3H)-pyrimidinedione oxalate (Compound 175) available by the process of Example 119

20 mg of the pyrimidinedione derivative oxalate (Compound 175) and 0.85 g of sodium chloride were weighed. They were dissolved in distilled water for injection to give a total volume of 100 ml, thereby preparing a formulation suitable for injection.

PHARMACOLOGICAL TEST 8

Similarly to Pharmacological Test 1, the $ADP_{75}$ and ERP of each of the compounds shown in Table 16 and obtained in the corresponding examples described above were determined. The results are summarized in Table 16.

TABLE 16

| | Results of Pharmacological Test | | | | | | |
|---|---|---|---|---|---|---|---|
| | $APD_{75}$ (%) | | | ERP (%) | | | |
| Compound | Dose (μg/ml) | | | Dose (mg/kg, i.v.) | | | |
| No. | 1.0 | 3.0 | 10.0 | 0.1 | 0.3 | 1.0 | 3.0 |
| 166 | 8 | 18 | — | 6.7 | 6.7 | 6.7 | 6.7 |
| 167 | 16 | 21 | 26 | 8 | 8 | 15 | 15 |
| 168 | 48 | 55 | 68 | 6 | 12 | 18 | 18 |
| 171 | 19 | 23 | 38 | — | — | — | — |
| 175 | 8 | 16 | — | — | — | — | — |

TOXICITY TEST 8

Similarly to Toxicity Test 1, the toxicity of each of the compounds shown in Table 17 and obtained in the corresponding examples described above was tested to determine the mortality rate of mice. The results are summarized in Table 17.

Incidentally, the administration of each compound was conducted orally (p.o.) at a dose of 300 mg/Kg.

TABLE 17

| Compound No. | Mortality rate (%) |
|---|---|
| 165 | 0 |
| 166 | 0 |
| 167 | 0 |
| 175 | 0 |

EXAMPLE 126

Preparation of 6-{2-[N-(2-hydroxyethyl)-3-(4-nitrophenyl) propylamino]ethylamino}-1,3,5-trimethyl-2,4(1H,3H)-pyrimidinedione hydrochloride.

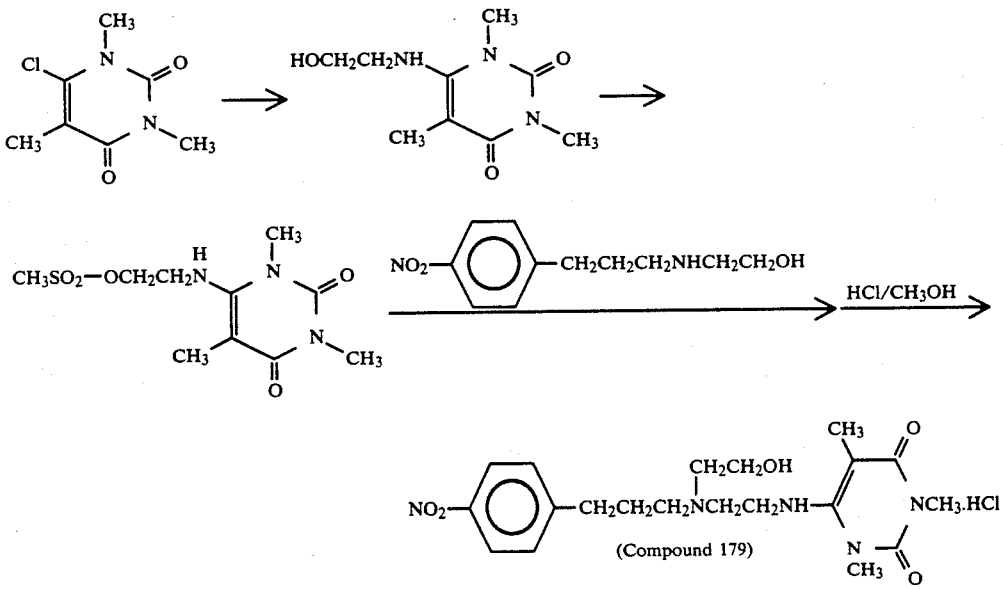

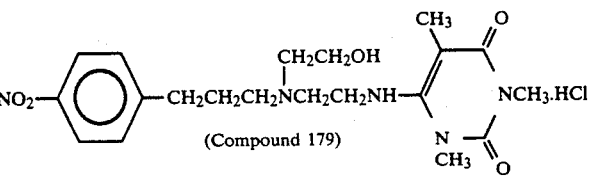

(1) Preparation of 6-(2-hydroxyethylamino)-1,3,5-trimethyl-2,4(1H,3H)-pyrimidinedione 6-chloro-1,3,5-trimethyl-2,4(1H,3H)-pyrimidinedione (3.4 g) was suspended in 30 ml of isopropanol, and the suspension was added with 1.26 ml of ethanolamine and 3.8 ml of triethylamine and then the resultant mixture was refluxed for 3 hours. The reaction mixture was allowed to stand overnight at room temperature, and thereafter crystals formed were collected by filtration, washed with water and then recrystallized using a water-ethanol solution (1:1, v/v), thereby 2.9 g of 6-(2-hydroxyethylamino)-1,3,5-trimethyl-2,4(1H,3H)-pyrimidinedione being obtained.

Results of analysis of the pyrimidinedione derivative thus obtained:

Melting point: 159°–160° C.

NMR (CDCl$_3$), δppm: 4.71 (t,2H ), 3.55 (m, 2H), 3.21 (s, 3H), 3.39 (s, 3H), 1.93 (s, 3H)

Elemental analysis: $C_9H_{15}N_3O_3$

Calculated (%): C, 50.69; H, 7.09; N, 19.71

Analyzed (%): C, 50.89; H, 7.11; H, 19.90

(2) Preparation of 6-(2-methanesulfonyloxyethylamino)-1,3,5-trimethyl-2,4(1H,3H)-pyrimidinedione 6-{2-hydroxyethylamino)-1,3,5-trimethyl-2,4(1H,3H)-pyrimidinedione (2.9 g) was dissolved in 20 ml of pyridine and added with 1.20 ml of methanesulfonyl chloride drop by drop at 0° C. After the reaction at 0° C. for 4 hours, the reaction mixture was poured into 10 ml of ice water and then subjected to chloroform extraction. The extract was washed with water, dried over sodium sulfate anhydrous, concentrated in vacuo. The resultant oily substance was subjected to silica gel column chromatograph (chloroform/methanol=30:1, v/v) for purification. Thus, 3.0 g of 6-(2-methanesulfonyloxylamino)-1,3,5-trimethyl-2,4-(1H,3H)-pyrimidinedione was obtained.

Results of analysis of the pyrimidinedione derivative thus obtained:

NMR (CDCl₃), δppm: 5.02 (t,2H), 3.48 (m, 2H), 3.30 (s, 3H), 3.41 (s, 3H), 2.14 (s, 3H), 1.99(s, 3H)

Elemental analysis: $C_{10}H_{17}N_3O_5S$
Calculated (%): C, 41.23; H, 5.88; H, 14.42; S, 11.01
Analyzed (%): C, 40.97; H, 5.91; N, 14.65; S, 11.07

(3) Preparation of 6-{2-[N-(2-hydroxyethyl)-3-(4-nitrophenyl)propylamino]ethylamino}-1,3,5-trimethyl-2,4(1H,3H)-pyrimidinedione hydrochloride (compound 179)

thylamino}-1,3,5-trimethyl-2,4(1H,3H)-pyrimidinedione hydrochloride (compound 179), was obtained.

Results of the analysis of the compound 179 thus obtained:

IRνKBr max (cm⁻¹): 3300, 2640, 1690, 1590, 1550, 1340, 1220, 930, 750, 700

Elemental analysis: $C_{20}H_{29}N_5O_5$ HCl $H_2O$
Calculated (%): C, 50.68; H, 6.81; N, 14.78; Cl, 7.48
Analyzed (%): C, 51.22; H, 6.94; N, 14.29; Cl, 7.73

EXAMPLE 127

Preparation of 1,3-dimethyl-6-{2-[N-(2-hydroxethyl)-3-(4-nitrophenyl)propylamino]ethylamino}-5-nitro-2,4(1H,3H)-pyrimidinedione hydrochloride (compound 180)

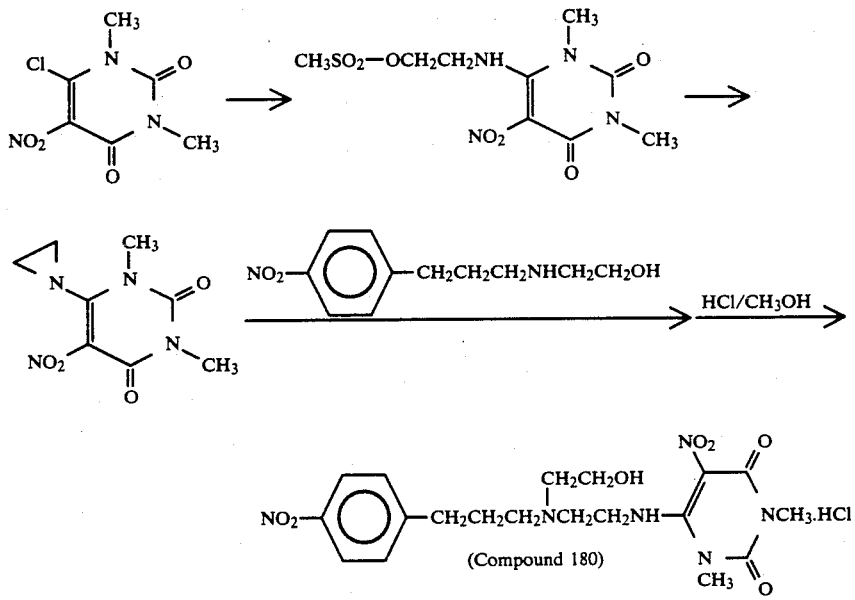

6-(2-methanesulfonyloxyethylamino)-1,3,5-trimethyl-2,4(1H,3H)-pyrimidinedione (3.0 g) was dissolved in 36 ml of acetonitrile, added with 2.1 g potassium carbonate and then allowed to react under heating with reflux for 6 hours. After the reaction, the reaction mixture was allowed to stand overnight at room temperature. Insoluble materials were removed by filtration and the filtrate was made to 100 ml by addition of acetonitrile. A portion of 10 ml was taken, and 0.23 g of N-(2-hydroxyethyl)-3-(4-nitrophenyl)propylamine and 50 mg of p-toluenesulfonic acid monohydrate was dissolved in this portion. The solution was concentrated in vacuo and the resultant oily substance was allowed to react at 80° C. for 6 hours. The reaction mixture was then subjected to silica gel column chromatograph (chloroform/methanol=40:1, v/v) for purification. Thus, 0.29 g of 6-{2-[N-(2-hydroxethyl)-3-(4-nitrophenyl)propylamino]ethylamino}-1,3,5-trimethyl-2,4(1H,3H)-pyrimidinedione was obtained.

Results of the analysis of the pyrimidinedione derivative thus obtained:

NMR (CDCl₃), δppm: 8.05 (d, 2H), 7.30 (d, 2H), 4.32 (m, 2H), 3.25 (s, 3H), 3.31 (s, 3H), 2.6–3.1(m, 10H), 2.06 (s, 3H), 1.9 (m, 2H)

Next, this pyrimidinedione derivative was treated with HCl/methanol in an ordinary method and thereby 0.12 g of a hygroscopic amorphous compound, 6-{2-[N-(2-hydroxyethyl)-3-(4-nitrophenyl)propylamino]e-

(1) Preparation of 6-(2-methanesulfonyloxyethylamino)-1,3-dimethyl-5-nitro-2,4(1H,3H)-pyrimidinedione 6-chloro-1,3-dimethyl-5-nitro-2,4(1H,3H)-pyrimidinedione (4.0 g) was dissolved in a solution of 13 ml of dichloromethane and added to a solution of 1.26 ml of ethanolamine and 3.8 ml of triethylamine in dichloromethane (13 ml) gradually drop by drop at 0° C. The reaction was carried out at 0° C. for 1 hour; the reaction mixture was allowed to stand at room temperature for 5 hours.

The reaction mixture was again cooled down to 0° C. and added with 3.8 ml of triethylamine and with 2.28 ml of methanesulfonyl chloride drop by drop. After the reaction at 0° C. for 5 hours, 30 ml of ice water was added, and the mixture was stirred vigorously for 30 minutes. The dichloromethane layer fraction was removed, and the water layer fraction was subjected to extraction with chloroform. The extract combined with the organic layer fraction was washed with water, dried over sodium sulfate anhydrous and then concentrated in vacuo. The resultant oily substance was subjected to silica gel column chromatograph (chloroform/methanol=30:1 (v/v)) for purification. Thus, 5.8 g of 6-(2-methanesulfonyloxyethylamino)-1,3-dimethyl-5-nitro-2,4(1H,3H)-pyrimidinedione was obtained.

Results of the analysis of the pyrimidinedione derivative thus obtained:

NMR (CDCl₃), δppm: 5.12 (t, 2H), 3.44 (s, 3H), 3.22 (m, 2H), 3.16 (s, 3H)

(2) Preparation of 6-(aziridin-1-yl)-1,3-dimethyl-5-nitro-2,4(1H,3H)-pyrimidinedione 6-(2-methanesulfonyloxyethylamino)-1,3-dimethyl-5-nitro-2,4(1H,3H)-pyrimidinedione (5.8 g) was dissolved in 70 ml of acetonitrile and added with 3.8 g of potassium carbonate. The reaction was carried out under heating with reflux for 3 hours. The reaction mixture as cooled down to room temperature; insoluble materials were removed by filtration. The filtrate was concentrated to a volume of 20 ml, added with 100 ml of ether and then stored refrigerated for 2 days. Crystals formed were collected by filtration and washed with hexane; thus 1.0 g of a powdery compound, 6-aziridin-1-yl)-1,3-dimethyl-5-nitro-2,4(1H,3)-pyrimidinedione, was obtained.

Results of the analysis of the pyrimidinedione derivative thus obtained:

NMR CDCl₃, δppm: 3.37 (s, 3H), 3.18 (s, 3H), 2.1–2.2 (m, 4)

(3) Preparation of 1,3-dimethyl-6-{2-[N-(2-hydroxethyl)-3-(4-nitrophenyl)propylamino]ethylamino}-5-nitro-2,4(1H,3H)-pyrimidinedione hydrochloride (compound 180)

An oily substance obtained by dissolving 1.0 g of 6-(aziridin-1-yl)-1,3-dimethyl-5-nitro-2,4(1H,3H)-pyrimidinedione, 0.99 g of N-(2-hydroxethyl)-3-(4-nitrophenyl)propylamine and 50 mg of p-toluenesulfonic acid in 1.0 ml of dimethylformamide was allowed to react at 90° C. for 3 hours. The reaction mixture was cooled down to room temperature, added with 10 ml of water and then vigorously stirred. Crystals formed were collected by filtration, dissolved in chloroform and then subjected to silica gel chromatograph (chloroform/methanol=40:1 (v/v)) for purification. Thus, 0.44 g of 1,3-dimethyl-6-{2-[N-(2-hydroxyethyl)-3-(4-nitrophenyl)propylamino]ethylamino}-5-nitro-2,4(1H,3H)-pyrimidinedione (a free form of compound 180) was obtained.

Results of the analysis of the pyrimidinedione derivative thus obtained:

NMR (CDCl₃), δppm: 8.01 (d, 2H), 7.31 (d, 2H), 3.66 (t,2H) 3.45 (s, 3H), 3.35 (s, 3H), 2.6–3.6 (m, 10H), 2.0(m, 2H)

Next, this pyrimidinedione derivative was treated with HCl/methanol in an ordinary method; thus 0.11 g of a hygroscopic amorphous compound, 1,3-dimethyl-6-{2-[N-(2-hydroxyethyl)-3-(4-nitrophenyl)propylamino]ethylamino}-5-nitro-2,4(1H,3H)-pyrimidinedione hydrochloride (compound 180), was obtained.

Results of the analysis of the compound 180 thus obtained:

IRνKBr max (cm⁻¹): 3300, 2550, 1700, 1650, 1530, 1350, 1110, 930, 750

Elemental analysis: $C_{19}H_{26}N_6O_7$ HCl 3H₂O
Calculated (%): C, 42.19; H, 6.15; N, 15.54; Cl, 6.55
Analyzed (%): C, 41.79; H, 6.41; N, 14.83; Cl, 6.02

EXAMPLE 128

Preparation of tablets containing, as an active ingredient, 1,3-dimethyl-6-{2-[N-(2-hydroxethyl)-3-(4-nitrophenyl)propylamino]ethylamino}-5-nitro-2,4(1H,3H)-pyrimidinedione (free form of compound 180), which can be obtained by the method of Example 127.

Said pyrimidinedione derivative (free form of compound 180) (1 g), 123 g of lactose and 20 g of corn starch were thoroughly mixed. The mixture was mixed in an aqueous solution of 5 g of hydroxypropylcellulose (100 ml) was granulated and dried at 50° C. for 4 hours. The granules were thoroughly blended with 1 g of magnesium stearate and then compressed into tablets using a tablet machine with a pressure of 150 mg/tablet.

EXAMPLE 129

Production of capsules containing, as an active ingredient, 6-{2-[N-(2-hydroxyethyl)-3-(4-nitrophenyl)propylamino]ethylamino}-1,3,5-trimethyl-2,4(1H,3H)-pyrimidinedione hydrochloride (compound 179), which can be obtained by the method of Example 126.

Said pyrimidinedione hydrochloride derivative (compound 179) (5 g), 120 g of lactose and 25 g of corn starch were thoroughly mixed, and the resultant mixture was formulated into hard capsules (150 mg per capsule) using a capsule filling machine.

EXAMPLE 130

Production of an injection containing, as an active ingredient, 1,3-dimethyl-6-{2-[N-(2-hydroxyethyl)-3-4-nitrophenyl)propylamino]ethylamino}-5-nitro-2,4(1H,3H)-pyrimidinedione hydrochloride (compound 180) which can be obtained by the method of Example 127

Said pyrimidinedione derivative hydrochloride (compound 180) (20 mg) and 0.85 g of sodium chloride were dissolved in an appropriate amount of distilled water for injection to total the volume 100 ml and thus formulated into an injection.

PHARMACOLOGICAL TEST EXAMPLE 9

A pharmacological tests with the compound 180 obtained by the method of Example 127 was carried out in the same manner as described in Pharmacological test 1. As a result, the $ADP_{75}$ values as shown in Table 18 were obtained.

TABLE 18

| | $ADP_{75}$ (%) Concentration (μg/ml) | | | |
|---|---|---|---|---|
| Compound No. | 0.3 | 1.0 | 3.0 | 10.0 |
| 180 | — | 11 | 20 | 26 |

EXAMPLE 131

Preparation of 1,3-dimethyl-6-{4-<3-[2-nitro-4-(2-pyridinecarbonyl)phenoxy]propyl>piperazin-1-yl}-2,4(1H,3H)-pyrimidinedione oxalate (compound 181)

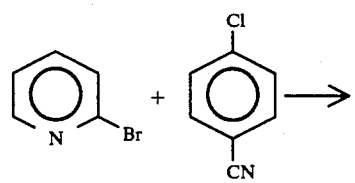

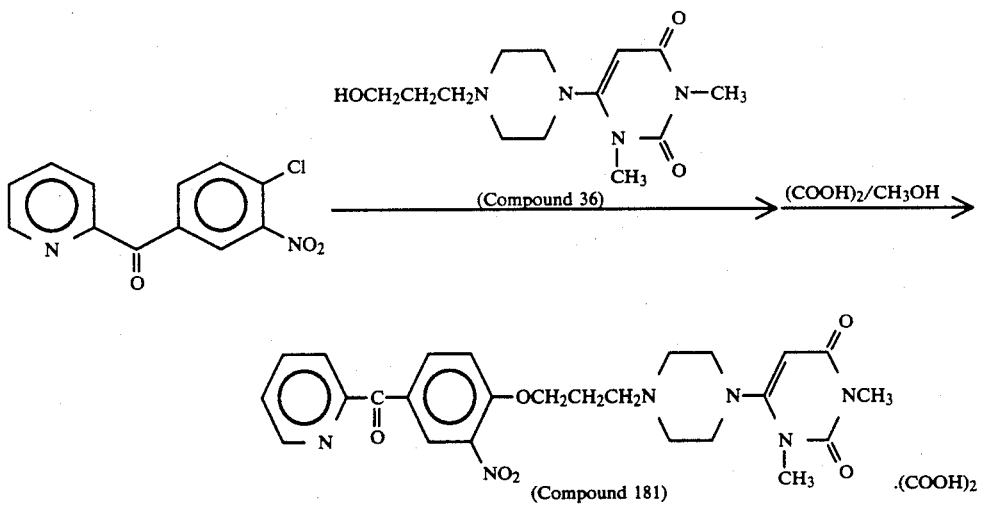

(1) Preparation of 2-chloro-5-(2-pyridinecarbonyl) nitrobenzene 2-bromopyridine (3.3 ml) was dissolved in 30 ml of ether and added with 22.1 ml of butyllithium (1.6 M, in hexane) drop by drop at −30° C. To this mixture were added a solution of 5.0 g of 4-chlorobenzonitrile in ether (10 ml) drop by drop at the same temperature. The reaction mixture was stirred for 1 hour and then poured into ice water. Ether was removed in vacuo. The resultant water-layer fraction was acidified by adding 6 N HCl, stirred at 100° C. for 1 hour, cooled, alkalized by adding sodium hydroxide and then extracted with ether. The resultant ether-layer fraction was concentrated and the oil thus obtained was dissolved in 10 ml of fuming sulfuric acid at 0° C. To this solution, added 1.2 ml of fuming nitric acid drop by drop and the resultant solution was stirred at the same temperature for 1 hour. The reaction mixture was poured into ice water and crystals formed were collected by filtration. The crystals were further recrystallized using ethanol, and 3.6 g of crystalline 2-chloro-5-(2-pyridinecarbonyl)nitrobenzene was thus obtained.

(2) Preparation of 1,3-dimethyl-6-{4-<3-[2-nitro-4-(2-pyridinecarbonyl)phenoxy]propyl>piperazin-1-yl}-2,4(1H,3H)-pyrimidinedione oxalate (compound 181)

Sodium hydride (60% dispersion in mineral oil) (0.17 g) was washed with hexane to remove oil and added with 8 ml of DMF.

The mixture was cooled down to 0° C. added with 1.0 g of 1,3-dimethyl-6-[4-(3-hydroxypropyl)>piperazin-1-yl]-2,4(1H,3H)-pyrimidinedione (compound 36) and stirred for 30 minutes. To this mixture was added 1.1 g of 2-chloro-5-(2-pyridinecarbonyl)nitrobenzene, and the resultant mixture was stirred for 1 hour. The reaction mixture was poured into ice water and crystals formed were collected by filtration, washed with water, dried and 1.0 g of 1,3-dimethyl-6-{4-<3-[2-nitro-4-(2-pyridinecarbonyl)phenoxy]propyl>piperazin-1-yl}-2,4(1H,3H)-pyrimidinedione in an amorphous powder form was thus obtained.

Results of the analysis of the pyrimidinedione derivative thus obtained:

NMR (CDCl$_3$), δppm: 2.1 (m, 2H), 2.4–3.1 (m, 10H), 3.25 (s, 3H), 3.34 (s, 3H), 4.28(t, 2H), 5.14 (s, 1H), 7.1–8.9 m, 7)

Next, this pyrimidinedione derivative (0.98 g) was treated with an oxalic acid/methanol solution in the ordinary method; thus 0.76 g of crystals of 1,3-dimethyl-6-{4-<3-[2-nitro-4-(2-pyridinecarbonyl)phenoxy]propyl>piperazin-1-yl}-2,4(1H,3H)-pyrimidinedione oxalate (compound 181) was obtained.

Results of the analysis of the compound 181 thus obtained:

IRνKBr max (cm$^{-1}$): 3450, 2500, 1700, 1650, 1600, 1520, 1310, 1280, 800, 740, 700

Elemental analysis: $C_{25}H_{28}N_6O_6$ (COOH)$_2$2H$_2$O
Calculated (%): C, 51.10; H, 5.40; N, 13.24;
Analyzed (%): C, 51.32; H, 5.40; N, 13.15

EXAMPLE 132

Preparation of 1,3-dimethyl-6-{2-[N-(3-hydroxypropyl)-3-(4-nitrophenyl)propylamino]ethylamino}-2,4(1H,3H)-pyrimidinedione oxalate (compound 182)

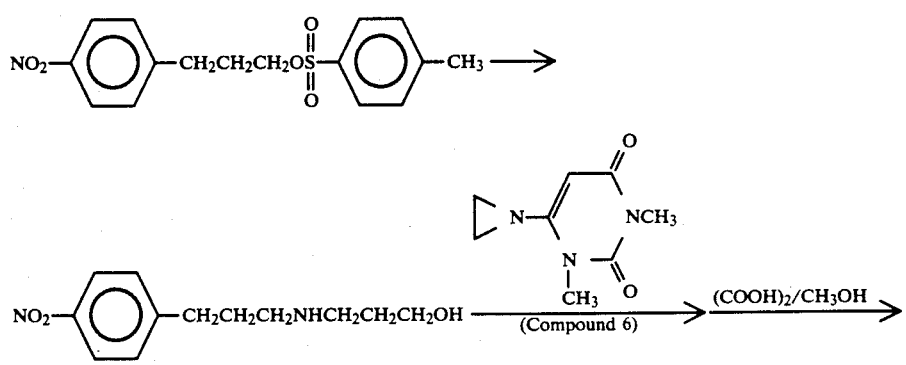

-continued

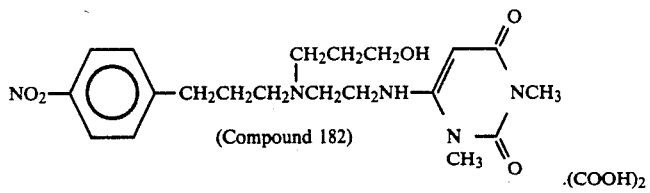
(Compound 182)

(1) Preparation of N-(3-hydroxypropyl)-3-(4-nitrophenyl)propylamine 3-(4-nitrophenyl)propyl p-toluenesulfonate (1 g) and 4.1 ml of 3-hydroxypropylamine were dissolved in 10 ml of dioxane and the solution was stirred at 80° C. for 30 minutes. To the solution was added 100 ml of water and 100 ml of chloroform, and the mixture was thoroughly mixed for separation. The chloroform-layer fraction was taken, washed with water and then dried over sodium sulfate anhydrous. The solvent was removed in vacuo and 0.7 g of an oil of N-(3-hydroxypropyl)-3-(4-nitrophenyl)propylamine was obtained.

Results of the analysis of the amine derivative thus obtained:

NMR (CDCl$_3$), δppm: 1.9–2.1 (m, 4H), 2.8–3.2 (m, 6H), 4.18 (t, 2H), 7.62 (d, 2H), 8.01 (d, 2H)

(2) Preparation of 1,3-dimethyl-6-{2-[N-(3-hydroxypropyl)-3-(4-nitrophenyl)propylamino]ethylamino}-2,4(1H,3H)-pyrimidinedione oxalate (compound 182)

N-(3-hydroxypropyl)-3-(4-nitrophenyl)propylamine (0.7 g), 0.53 g of 6-(1-aziridinyl)-1,3-dimethyl-2,4(1H,3H)-pyrimidinedione (compound 6) and 50 mg of p-toluene-sulfonic acid monohydrate were dissolved in 30 ml of acetonitrile, and then the solvent was removed in vacuo. The resultant oil was allowed to react at 80° C. for 3 hours and subjected to silica gel column chromatograph (chloroform/methanol=40:1 (v/v)) for purification: 0.68 g of 1,3-dimethyl-6-{2-[N-(3-hydroxypropyl)-3-(4-nitrophenyl)propylamino]ethylamino}-2,4(1H,3H)-pyrimidinedione was thus obtained.

Results of the analysis of the pyrimidinedione derivative thus obtained:

NMR (CDCl$_3$), δppm: 1.7 (m, 4H), 2.4–3.1 (m, 8H), 3.21 (s, 3H), 3.34 (s, 3H), 3.70 (br, 2H), 4.0 (m, 2H), 4.71 (s, 1H), 5.81 (br, 1H), 7.25 (d, 2H), 8.06 (d, 2H)

Next, this pyrimidinedione derivative (0.65 g) was treated with an oxalic acid/methanol solution in the ordinary method; thus 0.62 g of crystalline 1,3-dimethyl-6-{2-[N-(3-hydroxypropyl)-3-(4-nitrophenyl)propylamino]ethylamino}-2,4(1H,3H)-pyrimidinedione oxalate (compound 182) was obtained.

Results of the analysis of the compound 182 thus obtained:

IRνKBr max (cm$^{-1}$): 3300, 1690, 1620, 1540, 1410, 1330, 1050, 850, 770, 740, 690

Elemental analysis: $C_{20}H_{29}N_5O_5$ (COOH)$_2$ H$_2$O
Calculated (%): C, 50.09; H, 6.31; N, 13.28
Analyzed (%): C, 50.37; H, 6.25; N, 12.79

EXAMPLE 133

Preparation of 1,3-dimethyl-6-{2-[N-(1-methylethyl)-3-(4-nitrophenyl)propylamino]ethylamino}-2,4(1H,3H)-pyrimidinedione oxalate (compound 183)

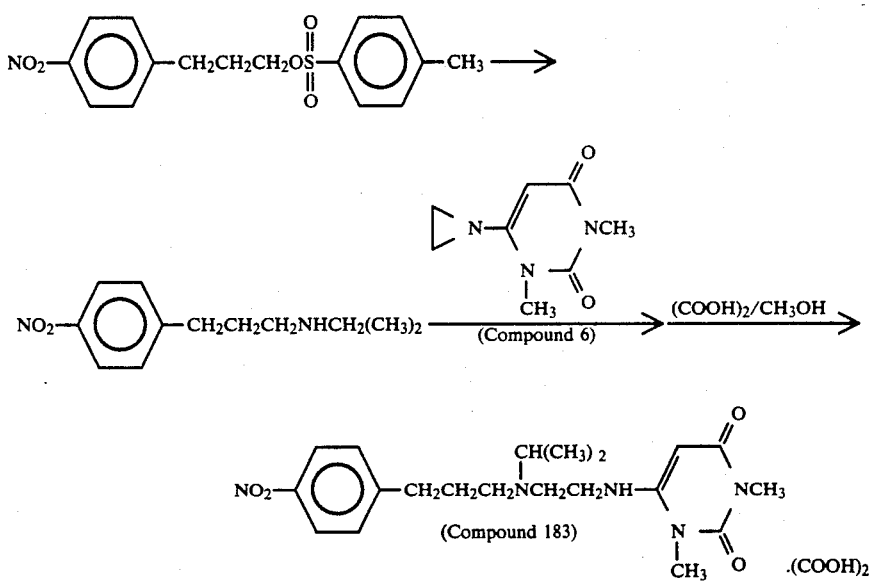
(Compound 183)

(1) Preparation of N-(1-methylethyl)-3-(4-nitrophenyl)propylamine 3-(4-nitrophenyl)propyl p-toluenesulfonate (1 g) and 5 ml of isopropylamine were dissolved in 15 ml of dioxane, and the solution was stirred under heating with reflux for 4 hours. To the solution were added 100 ml of water and 100 ml of chloroform, and the mixture was thoroughly mixed for extraction. The chloroform-layer fraction was taken, washed with water and dried over sodium sulfate anhydrous. The solvent was removed in vacuo, and thus 0.61 g of an oil of N-(1-methylethyl)-3-(4-nitrophenyl)propylamine was obtained.

Results of the analysis of the amine derivative thus obtained:

NMR (CDCl₃), δppm: 1.22 (d, 6H), 2.0 (m, 2H), 2.9-3.3 (m, 5H), 7.28(d, 2H), 8.09 (d, 2H)

(2) Preparation of 1,3-dimethyl-6-{2-[N-(1-methylethyl)-3-(4-nitrophenyl)propylamino]ethylamino}-2,4(1H,3H)-pyrimidinedione oxalate (compound 183)

N-(1-methylethyl)-3-(4-nitrophenyl)propylamine (0.6 g), 0.5 g of 6-(1-aziridinyl)-1,3-dimethyl-2,4(1H,3H)-pyrimidinedione (compound 6) and 50 mg of p-toluenesulfonic acid monohydrate was dissolved in 30 ml acetonitrile, and then the solvent was removed in vacuo. The resultant oil was allowed to react at 80° C. for 3 hours and subjected to silica gel column chromatograph (chloroform/methanol=40:1 (v/v)) for purification. Thus, 1.0 g of 1,3-dimethyl-6-{2-[N-(1-methylethyl)-3-(4-nitrophenyl)propylamino]ethylamino}-2,4(1H,3H)-pyrimidinedione was obtained.

Results of the analysis of the pyrimidinedione derivative thus obtained:

NMR (CDCl₃), δppm: 1.45(d, 6H), 2.0 (m, 2H), 3.29 (s, 3H), 3.40 (s, 3H), 2.5-3.1 (m, 7H), 3.8-4.1 (m, 4H), 4.80 (s, 1H), 5.5 (m, 1H) 7.31 (d, 2H), 8.00 (d, 2H)

This pyrimidinedione derivative (0.95 g) was treated with an oxalic acid/methanol solution in the ordinary method; thus 0.88 g of crystals of 1,3-dimethyl-6-{2-[N-(1-methylethyl)-3-(4-nitrophenyl)propylamino]ethylamino}-2,4(1H,3H)-pyrimidinedione oxalate (compound 183) was obtained.

Results of the analysis of the compound 183 thus obtained:

IRνKBr max (cm⁻¹): 3250, 2600, 1700, 1640, 1590, 1510, 1330, 1220, 760, 750, 700

Elemental analysis: C₂₀H₂₉N₅O₄ 1.5(COOH)₂ 0.5H₂O
Calculated (%): C, 50.45; H, 6.08; N, 12.79
Analyzed (%): C, 50.25; H, 5.81; N, 12.52

EXAMPLE 134

Preparation of 1,3-dimethyl-6-{2-[N-(2-hydroxy-1-methylethyl)-3-(4-nitrophenyl)propylamino]ethylamino}-2,4(1H,3H)-pyrimidinedione hydrochloride (compound 187)

(1) Preparation of N-(2-hydroxy-1-methylethyl)3-(4-nitrophenyl)propionamide 3-(4-nitrophenyl)propionic acid (5 g) was suspended in 40 ml of thionychloride, and the suspension was stirred under heating with reflux for 2 hours. Excessive thionylchloride was removed in vacuo and the oil thus obtained was dissolved in 15 ml of chloroform.

Separately, 3.8 g of 2-amino-1-propanol and 3.5 go f potassium carbonate were dissolved in 35 ml water, and the resultant solution was cooled down to 0° C. and added drop by drop with the chloroform solution which had been obtained previously. The mixture was stirred maintaining at 5° C. for 1 hour. Crystals formed were collected by filtration and washed with water. Furthermore, the crystals were recrystallized using an ethyl acetate/chloroform (1:1 (v/v)), and thus 3.46 g of crystalline N-(2-hydroxy-1-methylethyl)-3-(4-nitrophenyl)propionamide was obtained.

Results of the analysis of the amine derivative thus obtained:

Melting point: 174° C.

(2) Preparation of N-(2-hydroxy-1-methylethyl)-3-(4-nitrophenyl)propylamine

N-(2-hydroxy-1-methylethyl)-3-(4-nitrophenyl) propionamide obtained in (1) above (3.4 g) and sodium borohydride (2.1 g) was suspended in 32 ml of THF. To the mixture was added drop by drop with a solution of 3.3 g acetic acid in THF (32 ml). The mixture was stirred under heating with reflux for 10 hours. The reaction mixture was then cooled down to 5° C., added with 20 ml of methanol, stirred for 30 minutes and then concentrated by drying. To the resultant residue was added 50 ml of 1N-HCl and 50 ml of chloroform, and the mixture was vigorously stirred. The mixture was allowed to stand for extraction then fractionated. The water-layer friction was alkalinized with sodium hydroxide and extracted with chloroform. The chloroform-layer fraction was washed with water, dried over sodium sulfate anhydrous and then concentrated by drying; thus, 2.96 g of an oily compound, N-(2-hydroxy-1-methylethyl)-3-(4-nitrophenyl)propylamine, was obtained. This was used for the following reaction without further purification.

(3) Preparation of 1,3-dimethyl-6-{2-[N-(3-hydroxy-1-methyl)-3-(4-nitrophenyl)propylamino]ethylamino}-

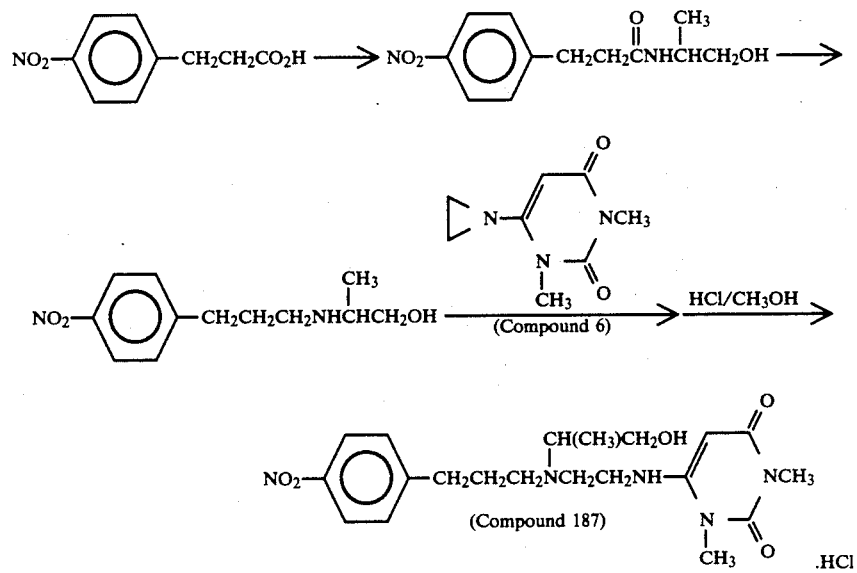

2,4(1H,3H)-pyrimidinedione hydrochloride (compound 187)

N-(2-hydroxy-1-methylethyl)-3-(4-nitrophenyl) propylamine (2.2 g) obtained in (2) above, 1.6 g of 6-(1-aziridinyl)-1,3-dimethyl-2,4(1H,3H)-pyrimidinedione (compound 6) and 0.1 g of p-toluenesulfonic acid monohydrate were dissolved in 100 ml of acetonitrile, and then the solvent was removed in vacuo. The resultant oil was allowed to react at 80° C. for 3 hours, and subjected to silica gel column chromatograph (chloroform/methanol=40:1 (v/v)) for purification; thus, 3.0 g of 1,3-dimethyl-6-{2-[N-(2-hydroxy-1-methylethyl)-3-(4-nitrophenyl)propylamino]ethylamino}-2,4(1H,3H)-pyrimidinedione was obtained.

Results of the analysis of the pyrimidinedione derivative thus obtained:

NMR (CDCl$_3$), δppm: 1.04 (d, 3H), 1.9 (m, 2H), 2.5-3.0 (m, 9H), 3.28 (s, 3H), 3.40 (s, 3H), 4.13 (m, 2H), 4.69 (s, 1H), 6.47 (m, 1H), 7.29 (d, 2H), 8.06 (d, 2H)

This pyrimidinedione derivative (2.95 g) was treated with a HCl/methanol solution in the ordinary method; thus 3.02 g of crystalline 1,3-dimethyl-6-{2-[N-(2-hydroxy-1-methylethyl)-3-(4-nitrophenyl)-propylamino]ethylamino}-2,4(1H,3H)-pyrimidinedione hydrochloride (compound 187) was obtained.

Results of the analysis of the compound 187 thus obtained:

Melting point: 154°-155° C.

IRνKBr max (cm$^{-1}$): 3250, 2900, 1690, 1600, 1550, 1340, 1240, 1060, 840, 760, 700

EXAMPLE 135

Preparation of 1,3-dimethyl-6-[4-(3-methyl-4-nitrobenzylpiperazin-1-yl]-2,4(1H,3)-pyrimidinedione hydrochloride (compound 188)

(1) Preparation of 3-methyl-4-nitrobenzyl chloride 3-methyl-4-nitrobenzylalcohol (2 g) and 0.2 ml of DMF were dissolved in 20 ml of toluene. The solution was added with 1 ml of thionyl chloride and stirred under heating with reflux for 3 hours. The reaction mixture was concentrated and thus 2.2 g of an oil, 3-methyl-4-nitrobenzyl chloride, was obtained. This compound was used for the following reaction without further purification.

(2) Preparation of 1,3-dimethyl-6-[4-(3-methyl-4-nitrobenzyl)piperazin-1-yl]-2,4(1H,3H)-pyrimidinedione chloride (compound 188)

3-methyl-4-nitrobenzyl chloride (2.2 g) obtained in (1) above, 2.2 g of 1,3-dimethyl-6-(piperazin-1-yl}-2,4(1H,3H)-pyrimidinedione (compound 2) and 4.1 ml of triethylamine were dissolved in 40 ml of isopropanol, and the solution was stirred under heating with reflux for 2.5 hours. After the reaction, the solvent was removed in vacuo, and the residue was dissolved in 50 ml of chloroform. The chloroform solution was washed with water and dried over sodium sulfate anhydrous and then the solvent was removed in vacuo; thereby 2.76 g of crystalline 1,3-dimethyl-6-[4-(3-methyl-4-nitrobenzyl)piperazin-1-yl]-2,4(1H,3H)-pyrimidinedione was obtained.

Results of the analysis of the pyrimidinedione derivative thus obtained:

Melting point: 162°-164° C.

NMR (CDCl$_3$), δppm: 2.5-3.3 (m, 8H), 2.61 (s, 3H), 3.26 (s, 3H), 3.36 (s, 3H), 3.61 (br, 2H), 5.15 (s, 1H), 7.35 (m, 2H), 7.87 (d, 1H)

This pyrimidinedione derivative (2.4 g) was treated with a hydrochloric acid/methanol solution by the ordinary method; thus 2.34 g of crystalline 1,3-dimethyl-6-[4-(3-methyl-4-nitrobenzyl)piperazin-1-yl]-2,4(1H,3H)-pyrimidinedione hydrochloride (compound 188) was obtained.

Results of the analysis of the compound 188 thus obtained:

IRνKBr max (cm$^{-1}$): 3360, 2540, 1690, 1640, 1520, 1440, 1340, 1200, 980, 840, 760, 700

Elemental analysis: C$_{18}$H$_{23}$N$_5$O$_4$ HCl H$_2$O

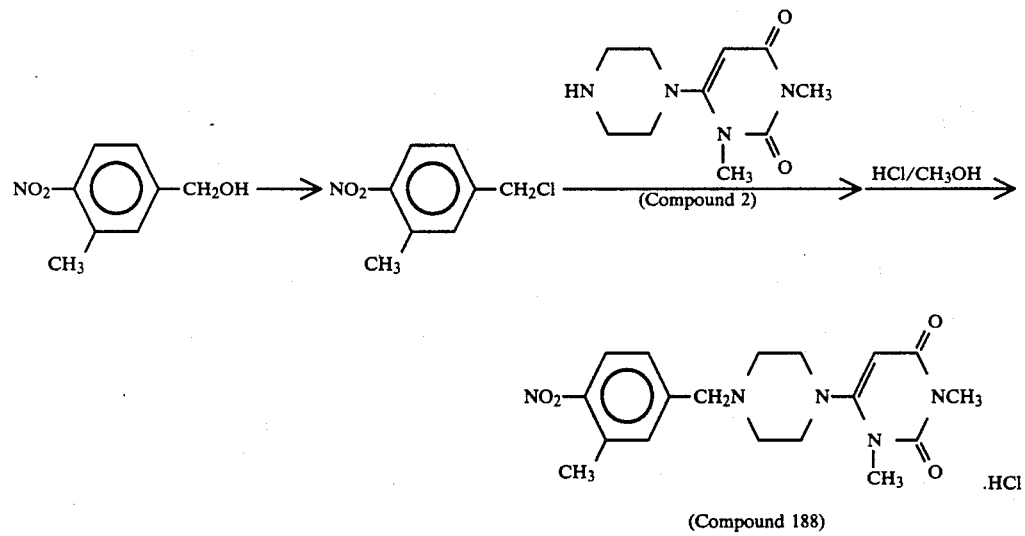

(Compound 188)

Calculated (%): C, 50.52; H, 6.12; N, 16.36; Cl, 8.28
Analyzed (%): C, 50.87; H, 6.64; N, 16.44; Cl, 7.68

EXAMPLE 136

Preparation of 1,3-dimethyl-6-{2-[N-(2-hydroxyethyl)-3-(4-benzoyl-2-nitrophenoxy)propylamino]ethylamino}-2,4(1H,3H)-pyrimidinedione oxalate (compound 189)

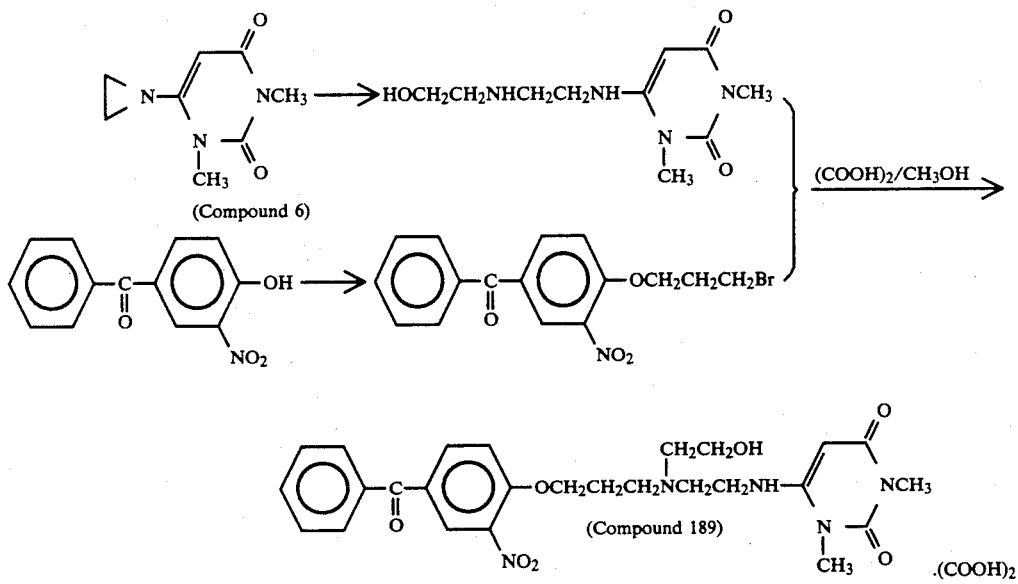

(1) Preparation of 1,3-dimethyl-6-{2-(2-hydroxethylamino) ethylamino}-2,4(1H,3H)-pyrimidinedione 6-(1-aziridinyl)-1,3-dimethyl-2-4(1H,3H)-pyrimidinedione (compound 6) (0.81 g), 1 ml of ethanolamine and 50 mg of p-toluenesulfonic acid monohydrate were dissolved in 200 ml of acetonitrile and then the solvent was removed in vacuo. The resultant oil was allowed to react at 90° C. for 3 hours. The reaction mixture was cooled down to room temperature and then dissolved by adding ethanol. Ether was added to this solution for crystallization. The crystals formed were collected by filtration and further recrystallized using an ethanol/ether mixed solvent; thereby 1.02 g of crystalline 1,3-dimethyl-6-{2-(2-hydroxethylamino)ethylamino}-2,4(1H,3H)-pyrimidinedione was obtained.

Results of the analysis of the crystals of the pyrimidinedione derivative

Melting point: 146°–148° C.

(2) Preparation of 4-(3-bromopropyloxy)-3-nitrobenzophenone 4-hydroxy-3-nitrobenzophenone (2.5 g) and 7.1 g of potassium carbonate were suspended in 15 ml methylethylketone. The suspension was stirred under heating with reflux for 30 minutes, added with 1,3-dibromopropane and then heated with reflux for 6 hours. The reaction mixture was cooled down to room temperature, and insoluble substances were removed by filtration. The filtrate was then concentrated, and the resultant precipitate was subjected to silica gel column chromatograph (hexane/ethyl acetate=3.1 (v/v)) for purification; thereby 2.08 g of an oil, 4-(3-bromopropyloxy)-3-nitrobenzophenone, was obtained.

NMR (CDCl$_3$), δppm: 2.40(m, 2H), 3.66 (t, 2H), 4.39 (t, 2H), 7.13–8.34 (m, 8H)

(3) Preparation of 1,3-dimethyl-6-{2-[N-(2-hydroxethyl)-3-(4-benzoyl-2-nitrophenoxy)propylamino]ethylamino)-2,4(1H,3H)-pyrimidinedione oxalate (compound 189)

A mixture of 0.67 g of 1,3-dimethyl-6-{2-(2-hydroxyethylamino)ethylamino}-2,4(1H,3H)-pyrimidinedione obtained in (1) above, 1.0 g of 4-(3-bromopropyloxy)-3-nitrobenzophenone obtained in (2) above, 1.5 ml of triethylamine and 3 ml of DMF were stirred under heating at 100° C. for 1 hour. The mixture was cooled down to room temperature, added with 50 ml chloroform, washed with water and then dried over anhydrous sodium sulfate. The solvent an ethanol/ether mixed solvent; 0.59 g of crystalline 1,3-dimethyl-6-{2-[N-(2-hydroxyethyl)-3-(4-benzoyl-2-nitrophenoxy)-propylamino]ethylamino}-2,4(1H,3H)-pyrimidinedione was thus obtained.

Results of the analysis of the pyrimidinedione derivative thus obtained:

Melting point: 180°–181° C.

NMR (CDCl$_3$/DMSO-d6=1/1, v/v), δppm: 2.0 (m, 2H), 2.6–3.1 (m, 8H), 3.21 (s, 3H), 3.34 (s, 3H), 3.67 (t, 2H), 4.39 (t, 2H), 4.58 (s, 1H), 6.25 (br, 1H), 7.31 (d, 1H), 7.5–8.1 (m, 6H), 8.26 (d, 1H)

This pyrimidinedione derivative (0.55 g) was treated with an oxalic acid/methanol solution in the ordinary method; 0.62 g of crystalline 1,3-dimethyl-6-{2-[N-(2-hydroxyethyl)-3-(4-benzoyl-2-nitrophenoxy) propylamino]ethylamino}-2,4(1H,3H)-pyrimidinedione oxalate (compound 189) was thus obtained.

Results of the analysis of the compound 189 thus obtained:

Melting point: 144°–147° C. (Decomposed)

IRνKBr max (cm$^{-1}$): 3300, 2590, 1720, 1680, 1630, 1530, 1340, 1280, 1070, 780, 710

Elemental analysis: $C_{26}H_{31}N_5O_7(COOH)_2 \cdot 0.5H_2O$

Calculated (%): C, 53.84; H, 5.49; N, 11.21;

Analyzed (%): C, 53.88; H, 5.26; N, 11.27

EXAMPLE 137

Preparation of 1,3-dimethyl-6-{2-[N-(2-hydroxyethyl)-3-(3-methoxy-4-nitrophenyl)propylamino]ethylamino}-2,4(1H,3H)-pyrimidinedione oxalate (compound 190)

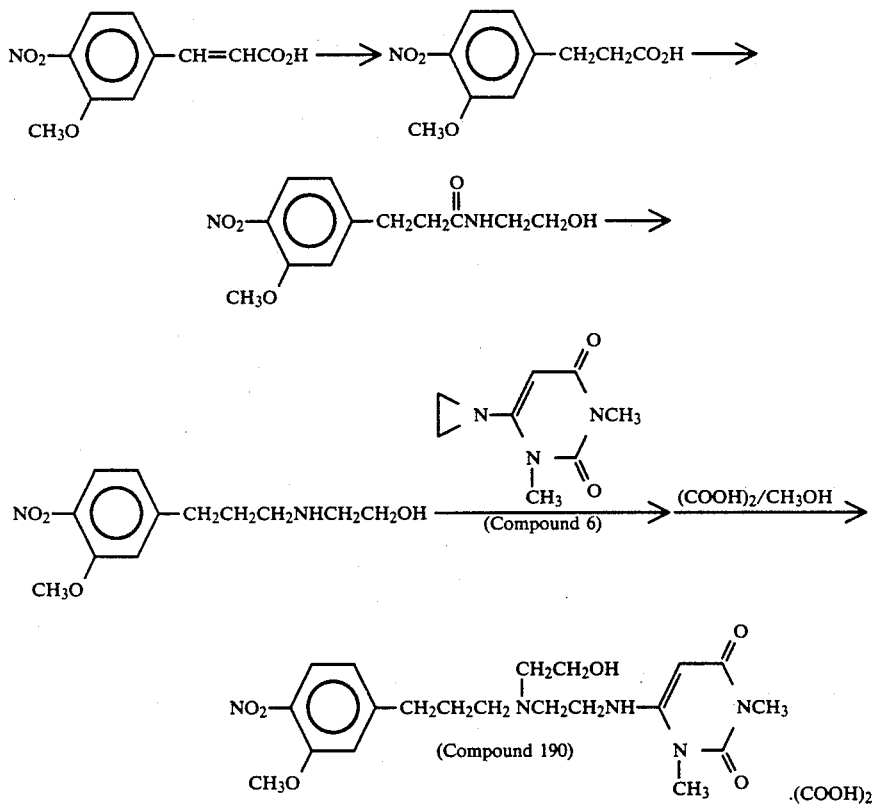

(1) Preparation of 3-(3-methoxy-4-nitrophenyl)propionic acid 3-methoxy-4-nitrocinnamic acid (6.2 g) and 12.3 g of hydroxyamine sulfate were dissolved in 250 ml of water. To the solution was added 7.1 g of sodium hydroxide, and further alternately added a solution of 18 g of sodium hydroxide in water (27 ml) and 19.2 g of hydroxyamine-o-sulfonic acid little by little, maintaining the pH at 9. The mixture was stirred at 5° C. for 6 hours and then insoluble substances were removed by filtration. The resultant filtrate was cooled on ice and was added with 6 N sulfuric acid to adjust the pH to 2. Crystals formed were collected by filtration, washed with water and dried; 1.27 g of crystalline 3-(3-methoxy-4-nitrophenyl)propionic acid was thus obtained.

Results of the analysis of the crystalline propionic acid derivative thus obtained:

Melting point: 137°–139° C.

(2) Preparation of N-(2-hydroxyethyl)-3-(3-methoxy-4-nitrophenyl)propanamide 3-(3-methoxy-4-nitrophenyl)propionic acid obtained in (1) above (1.2 g) was suspended in 20 ml of thionyl chloride. The suspension was stirred for 2 hours under heating with reflux and then the solvent was removed. The resultant residue was dissolved in 3 ml of chloroform.

Separately, 0.51 g of ethanolamine and 0.78 g of potassium carbonate were dissolved in 8 ml of water, and the resultant solution was cooled down to 0° C. and added drop by drop with the chloroform solution which had been obtained previously. The mixture was vigorously for 1 hour at the temperature maintained at 0° C. Crystals formed were collected by filtration, washed with water and dried. Furthermore, the crystals were recrystallized using an ethyl acetate solution and thus 1.14 g of crystalline N-(2-hydroxyethyl)-3-(3-methoxy-4-nitrophenyl)propanamide was obtained.

Results of the analysis of the crystalline amide thus obtained:

Melting point: 155° C. (Decomposed)

(3) Preparation of N-(2-hydroxyethyl)-3-(3-methoxy-4-nitrophenyl)propylamine

Sodium borohydride (0.78 g) was suspended in 12 ml of THF. To this suspension were added 1.1 g of N-(2-hydroxyethyl)-3-(3-methoxy-4-nitrophenyl)propanamide obtained in (2) above, and further added little by little 1.2 ml of acetic acid. The mixture was stirred until bubbling stopped and then stirred under heating with reflux for 10 hours. The mixture was cooled down to room temperature and added with 10 ml of methanol little by little. The solvent was removed in vacuo. The residue was added with 20 ml of chloroform and then extracted with a 1N-HCl solution. The extracted acidic water phase was alkalinized by adding sodium hydroxide on ice and extracted with chloroform. The chloroform-layer fraction was washed with a saturated sodium chloride solution and dried over anhydrous sodium sulfate, and chloroform was removed; thereby 0.72 g of an oily compound, N-(2-hydroxyethyl)-3-(3-methoxy-4-nitrophenyl)propylamine, was obtained. This compound was used for the following reaction without further purification.

(4) Preparation of 1,3-dimethyl-6-{2-[N-(2-hydroxyethyl)-3-(3-methoxy-4-nitrophenyl)propylamino]ethylamino}-2,4(1H,3H)-pyrimidinedione oxalate (compound 190)

6-(1-aziridinyl)-1,3-dimethyl-2,4(1H,3H)-pyrimidinedione (compound 6) (0.45 g), 0.7 g of N-(2-hydroxyethyl)-3-(3-methoxy-4-nitrophenyl)propylamine and 50 mg of p-toluenesulfonic acid monohydrate was dissolved in 25 ml of acetonitrile and then the solvent was removed in vacuo. The resultant oil was allowed to react at 80° C. for 3 hours and then subjected to silica gel column chromatograph (chloroform/methanol=40/1, v/v) for purification; thereby 0.38 g of an oil, 1,3-dimethyl-6-{2-[N-(2-hydroxethyl)-3-(3-methoxy-4-nitrophenyl)propylamino]ethylamino}-2,4(1H,3H)-pyrimidinedione, was obtained.

Results of the analysis of the pyrimidinedione derivative thus obtained:

NMR (CDCl$_3$) δppm: 1.9 (m, 2H), 2.4–3.8 (m, 12H), 3.20 (s, 3H), 3.33 (s, 3H), 3.83 (s, 3H), 4.63 (s, 1H), 6.11 (m, 1H), 6.75 (m, 2H), 7.26 (m, 1H)

This pyrimidinedione derivative (0.33 g) was treated with an oxalic acid/methanol solution in the ordinary method; 0.22 g of an amorphous powder of 1,3-dimethyl-6-{2-[N-(2-hydroxyethyl)-3-(3-methoxy-4-nitrophenyl)propylamino]ethylamino}-2,4(1H,3H)-pyrimidinedione oxalate (compound 190) was thus obtained.

Results of the analysis of the compound 190 thus obtained:

IR$\nu$KBr max (cm$^{-1}$): 3300, 2550, 1690, 1640, 1540, 1350, 1280, 760, 700

Elemental analysis: C$_{20}$H$_{29}$N$_5$O$_6$ 2(COOH)$_2$ 2H$_2$O
Calculated (%): C, 44.24; H, 5.72; N, 10.75
Analyzed (%): C, 43.93; H, 5.85; N, 11.10

EXAMPLE 138

Production of 1,3-dimethyl-6-{2-[N-(2-diethylamino)ethyl-3-(4-nitrophenyl)propylamino]ethylamino}-2,4(1H,3H)-pyrimidinedione oxalate (Compound 191)

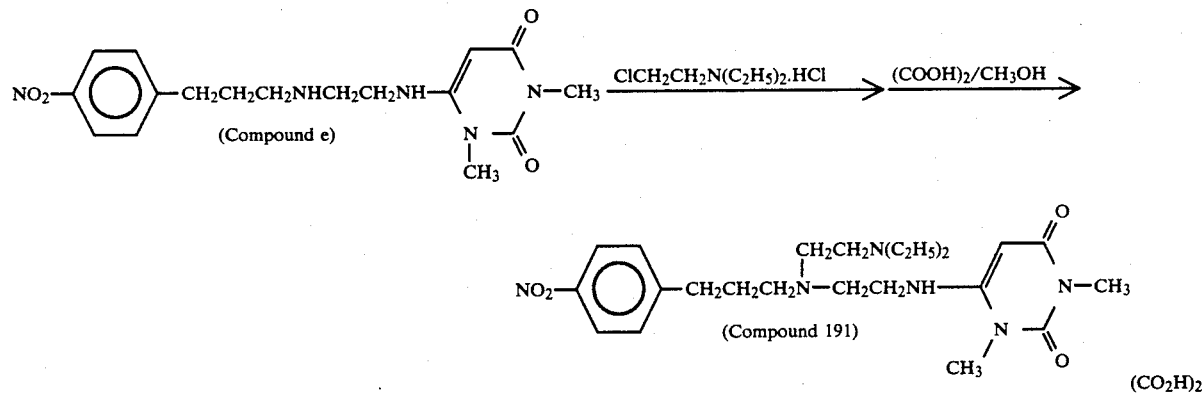

First, 1.4 g of 1,3-dimethyl-6-{2-[3-(4-nitrophenyl)propylamino]ethylamino}-2,4(1H,3H)-pyrimidinedione hydrochloride (Compound e) was dissolved with 5 ml of water, followed by the addition of K$_2$CO$_3$ to render the solution alkaline.

The resulting solution was then extracted with CHCl$_3$. The combined layers were concentrated in vacuo, followed by the addition of 1.0 g of 2-diethylamino ethylchloride, 3 ml of triethylamine and 20 ml of isopropanol.

The reaction mixture was refluxed for 10 hours. Solvent was removed in vacuo, and then the resulting residue was directly purified by a silica gel chromatography (eluent: CHCl$_3$/CH$_3$OH=20/1, by volume) thereby obtaining 0.6 g of 1,3-dimethyl-6-{2-[N-diethylamino)ethyl-3-(4-nitrophenyl)propylamino}-2,4(1H,3H)-pyrimidinedione.

Further, 0.6 g of the pyrimidinedione derivative was treated with an oxalic acid/methanol solution by a method known per se in the art to obtain 0.52 g of 1,3-dimethyl-6-{2-[N-(2-diethylamino)ethyl-3-(4-nitrophenyl)propylamino]ethylamino}-2,4(1H,3H)-pyrimidinedione (Compound 191) as pale yellow crystals.

Analytical results of crystals of compound 191 thus obtained:

Melting point: 197°–199° C.
IR$\nu_{max}^{KBr}$(cm$^{-1}$): 3000, 2950, 1720, 1700, 1600, 1340, 852, 700

What is claimed is:

1. A pyrimidinedione compound of the formula (1)

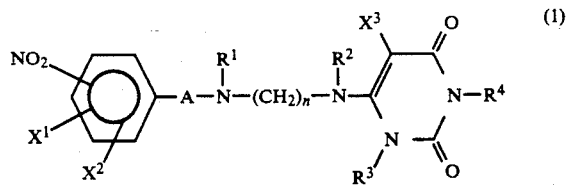

in which A represents —(CH$_2$)$_m$—, —B—(CH$_2$)$_k$—, —D—(CH$_2$)$_l$—,

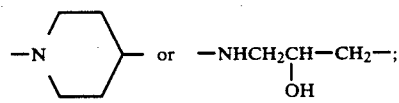

B represents an oxygen or a sulfur atom,

D represents

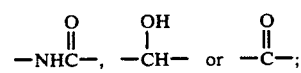

R$^1$ and R$^2$ each independently represent a hydrogen atom, a lower alkyloxycarbonyl group, an unsaturated lower alkyl group or a lower alkyl group, any one of the hydrogen atoms of said alkyl groups may be substituted by a group selected from the group consisting of a hydroxy group; a lower monoalkylamino group; a lower dialkylamino group; a lower alkyloxy group; a lower alkanoyloxy group; a benzoyloxy group; a benzoyloxy group substituted by a halogen atom or a lower alkyloxy group;

a phenyl group; a phenyl group substituted by a halogen atom or a lower alkyloxy group; and a lower alkyloxycarbonyl group, or R¹ and R² may be so linked as to make an alkylene chain and thus form a heterocyclic structure;

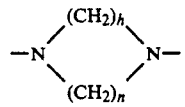

where h is 2 or 3 and n is 2 or 3;

R³ and R⁴ each independently represent a hydrogen atom or a lower alkyl group;

X¹ and X² each independently represent a hydrogen atom, —CO—R⁶, a halogen atom, a lower alkyl group, a halogen-substituted lower alkyl group, a hydroxy group, a lower alkyloxy group, a lower alkylthio group, a lower alkyloxycarbonyl group, a carboxy group, a cyano group, an amino group, a lower alkanoyloxy group, a lower alkanoylamino group, a lower alkylsulfonamido group, a lower mono- or di-alkylamino group, a phenyl-substituted lower alkylamino group or an unsaturated lower alkyloxy group;

X³ represents a hydrogen atom, a nitro group, a methyl group or a cyano group; R⁵ represents a hydrogen atom, a lower alkanoyl group, a lower alkylsulfonyl group or a lower alkyl group, or R¹ and R⁵ may be so linked as to make an alkylene chain and thus form a heterocyclic structure;

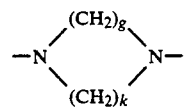

where g is 2 or 3 and k is 2, 3 or 4;

R⁶ represents a lower alkyl group, a C₅-C₆ cycloalkyl group or a phenyl group, said phenyl group may be substituted by either one or two of groups selected from the group consisting of a halogen atom, a lower alkyl group, a hydroxy group and a lower alkyloxy group, or a heterocyclic ring;

n represents an integral number 2 or 3; m represents an integral number, 0, 1, 2, 3, or 4; k represents an integral number, 2, 3 or 4; and l represents an integral number, 0, 1, 2, 3 or 4.

2. A pyrimidinedione compound as set forth in claim 1, of the formula (2)

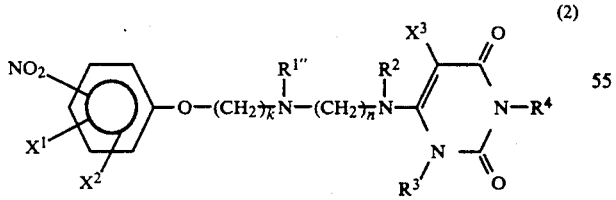

in which R¹''' and R² each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoylamino and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group), or R¹''' and R² may be so linked as to make an alkylene chain and thus form a heterocyclic structure;

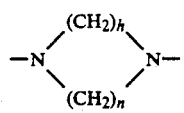

where h is 2 or 3 and n is 2 or 3;

R³ and R⁴ each independently represent a hydrogen atom or a lower alkyl group;

X¹ and X² each independently represent a hydrogen atom, —CO—R⁶, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

X³ represents a hydrogen atom, nitro, methyl or cyano group;

R⁶ represents a lower alkyl, C₅-C₆ cycloalkyl, phenyl, group (said phenyl group may be substituted by either one or two of substituting groups selected from the group consisting of a halogen atom, a lower alkyl group, hydroxy group and lower alkyloxy group), or a heterocyclic ring;

n represents an integral number 2 or 3; and k represents an integral number, 2, 3 or 4.

3. The pyrimidinedione compound as set forth in claim 1, of the formula (3)

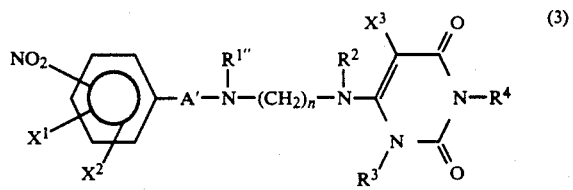

in which A' represents —(CH₂)ₘ—, —B'—(CH₂)ₖ— or wherein

B' represents an oxygen or sulfur atom, or

R¹''' and R² each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group), or R¹''' and R² may be so linked as to make an alkylene chain and thus form a heterocyclic structure;

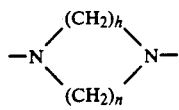

where h is 2 or 3 and n is 2 or 3;

$R^3$ and $R^4$ each independently represent a hydrogen atom or a lower alkyl group;

$X^1$ and $X^2$ each independently represent a hydrogen atom, $-CO-R^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

$R^3$ represents a hydrogen atom, nitro, methyl or cyano group;

$R^{5'}$ represents a hydrogen atom, a lower alkanoyl, lower alkylsulfonyl or lower alkyl group;

$X^6$ represents a lower alkyl, $C_5$–$C_6$ cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

n represents an integral number, 2 or 3; m represents an integral number, 0, 1, 2, 3 or 4; and k represents an integral number, 2, 3 or 4.

4. The pyrimidinedione compound as set forth in claim 1, of the formula (4)

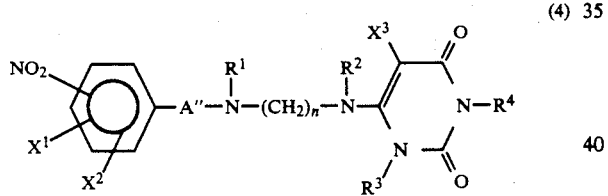
(4)

in which A" represents $-B''-(CH_2)_k-$, or

wherein B" represents an oxygen or sulfur atom or

$R^1$ and $R^2$ each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group), or $R^1$ and $R^2$ may be so linked as to make an alkylene chain and thus form a heterocyclic structure;

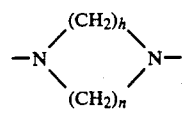

where h is 2 or 3 and n is 2 or 3;

$R^3$ and $R^4$ each independently represent a hydrogen atom or a lower alkyl group;

$X^1$ and $X^2$ each independently represent a hydrogen atom, $-CO-R^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

$X^3$ represents a hydrogen atom, nitro, methyl or cyano group;

$R^5$ represents a hydrogen atom, a lower alkanoyl, lower alkylsulfonyl or lower alkyl group, or $R^1$ and $R^5$ may be so linked as to make an alkylene chain and thus form a heterocyclic structure;

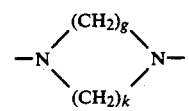

where g is 2 or 3 and k is 2, 3 or 4;

$R^6$ represents a lower alkyl, $C_5$–$C_6$ cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

n represents an integral number, 2 or 3; and k represents an integral number, 2, 3 or 4.

5. The pyrimidinedione compound as set forth in claim 1, of the formula (5)

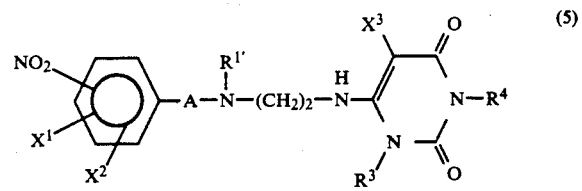
(5)

in which A represents $-(CH_2)_m-$, $-B-(CH_2)_k-$, $-D-(CH_2)_l-$,

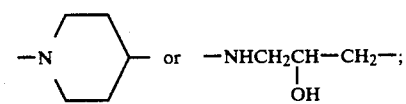

wherein

B represents an oxygen or sulfur atom,

D represents

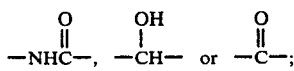

R$^{1'}$ represents a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group);

R$^3$ and R$^4$ each independently represent a hydrogen atom or a lower alkyl group;

X$^1$ and X$^2$ each independently represent a hydrogen atom, —CO—R$^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

X$^3$ represents a hydrogen atom, nitro, methyl or cyano group;

R$^5$ represents a hydrogen atom, a lower alkanoyl, lower alkylsulfonyl or lower alkyl group, or R$^{1'}$ and R$^5$ may be so linked as to make an alkylene chain and thus form a heterocyclic structure;

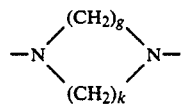

where g is 2 or 3 and k is 2, 3 or 4;

R$^6$ represents a lower alkyl, C$_5$-C$_6$ cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

m represents an integral number, 0, 1, 2, 3 or 4; k represents an integral number, 2, 3, or 4; and l represents an integral number, 0, 1, 2, 3 or 4.

6. The pyrimidinedione compound as set forth in claim 1, of the formula (6)

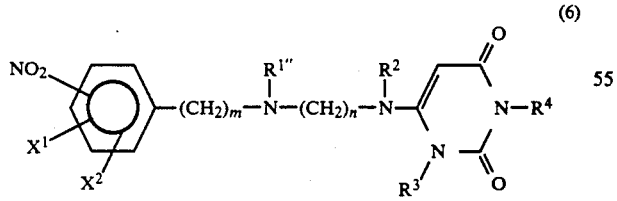

in which R$^{1''}$ and R$^2$ each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group, and a lower alkyloxycarbonyl group), or R$^{1''}$ and R$^2$ may be so linked as to make an alkylene chain and thus form a heterocyclic structure;

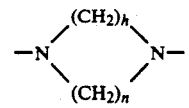

where h is 2 or 3 and n is 2 or 3;

R$^3$ and R$^4$ each independently represent a hydrogen atom or a lower alkyl group;

X$^1$ and X$^2$ each independently represent a hydrogen atom, —CO—R$^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

R$^6$ represents a lower alkyl, cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

n represents an integral number, 2 or 3; and m represents an integral number, 0, 1, 2, 3 or 4.

7. The pyrimidinedione compound as set forth in claim 1, of the formula (7)

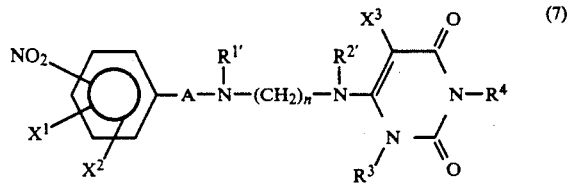

in which A represents —(CH$_2$)$_m$—, —B—(CH$_2$)$_k$—, —D—(CH$_2$)$_l$—,

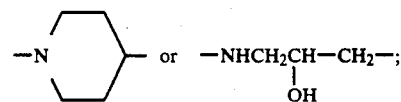

wherein

B represents an oxygen or sulfur atom

D represents

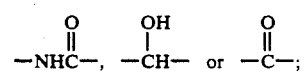

R$^{1'}$ and R$^{2'}$ each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group);

$R^3$ and $R^4$ each independently represent a hydrogen atom or a lower alkyl group;

$X^1$ and $X^2$ each independently represent a hydrogen atom, —CO—$R^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyloxy group;

$X^3$ represents a hydrogen atom, nitro, methyl or cyano group;

$R^5$ represents a hydrogen atom, a lower alkanoyl, lower alkylsulfonyl or lower alkyl group, or $R^{1'}$ and $R^5$ may be so linked as to make an alkylene chain and thus form a heterocyclic structure;

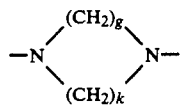

where g is 2 or 3 and k is 2, 3 or 4;

$R^6$ represents a lower alkyl, $C_5$-$C_6$ cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

n represents an integral number, 2 or 3; m represents an integral number, 0, 1 2, 3 or 4; k represents an integral number, 2, 3 or 4; and l represents an integral number, 0, 1, 2, 3 or 4.

8. The pyrimidinedione compound as set forth in claim 1, of the formula (8)

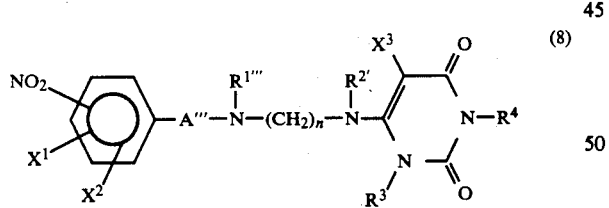

in which A''' represents —(CH₂)ₘ—, —B'''—(CH₂)ₖ—, —D—(CH₂)ₗ—,

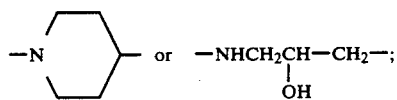

wherein

B''' represents an oxygen or sulfur atom,

D represents

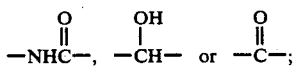

$R^{1'''}$ and $R^{2'}$ each independently represent a hydrogen atom, a lower alkyloxycarbonyl, unsaturated lower alkyl or lower alkyl group (any one of the hydrogen atoms of said alkyl groups may be substituted by a substituting group selected from the group consisting of a hydroxy, lower monoalkylamino, lower dialkylamino, lower alkyloxy, lower alkanoyloxy and benzoyloxy groups; a benzoyloxy group substituted by a halogen atom or a lower alkyloxy group; a phenyl group; a phenyl group substituted by a halogen atom or a lower alkyloxy group; and a lower alkyloxycarbonyl group);

$R^3$ and $R^4$ each independently represent a hydrogen atom or a lower alkyl group;

$X^1$ and $X^2$ each independently represent a hydrogen atom, —CO—$R^6$, a halogen atom, a lower alkyl, halogen-substituted lower alkyl, hydroxy, lower alkyloxy, lower alkylthio, lower alkyloxycarbonyl, carboxyl, cyano, amino, lower alkanoyloxy, lower alkanoylamino, lower alkylsulfonamido, lower mono- or di-alkylamino, phenyl-substituted lower alkylamino or unsaturated lower alkyl group;

$X^3$ represents a hydrogen atom, nitro, methyl or cyano group;

$R^{5'}$ represents a hydrogen atom, a lower alkanoyl, lower alkylsulfonyl or lower alkyl group;

$R^6$ represents a lower alkyl, cycloalkyl, phenyl group (said phenyl group may be substituted by either one or two of substituting groups selected from the group consisting of a halogen atom, a lower alkyl group, hydroxy group and lower alkyloxy group), or a heterocyclic ring;

n represents an integral number, 2 or 3; m represents an integral number, 0, 1, 2, 3 or 4; k represents an integral number, 2, 3 or 4; and l represents an integral number, 0, 1, 2, 3 or 4.

9. A pharmaceutically acceptable acid addition salt of the pyrimidinedione derivative as set forth in claim 1.

10. A pharmaceutical composition for the treatment of cardiac arrythmias comprising an antiarrythmic effective amount of the compound of claim 1 or a pharmaceutically acceptable acid addition salt thereof, together with a pharmaceutically acceptable carrier or diluent.

11. A pharmaceutical composition of claim 10, containing from about 0.02 weight percent to about 3.3 weight percent of the compound of claim 1.

12. A method of treating cardic arrythmias comprising administering to a person in need of same an effective amount of the compound of claim 1 or an acid addition salt of the compound of claim 1.

* * * * *